United States Patent
Fader et al.

(10) Patent No.: US 9,315,499 B2
(45) Date of Patent: Apr. 19, 2016

(54) CYTOMEGALOVIRUS INHIBITOR COMPOUNDS

(71) Applicants: Lee Fader, New Milford, CT (US); Olivier Lepage, Laval (CA); Murray Bailey, Pierrefonds (CA); Pierre Louis Beaulieu, Rosemere (CA); Francois Bilodeau, Laval (CA); Rebekah J. Carson, Mascouche (CA); André Giroux, Ste-Anne-de-Bellevue (CA); Cédrickx Godbout, Attenweiler (DE); Benoît Moreau, Newton, MA (US); Julie Naud, Blainville (CA); Mathieu Parisien, Laval (CA); Martin Poirier, Blainville (CA); Maude Poirier, Pennington, NJ (US); Simon Surprenant, Montreal (CA); Carl Thibeault, Mascouche (CA)

(72) Inventors: Lee Fader, New Milford, CT (US); Olivier Lepage, Laval (CA); Murray Bailey, Pierrefonds (CA); Pierre Louis Beaulieu, Rosemere (CA); Francois Bilodeau, Laval (CA); Rebekah J. Carson, Mascouche (CA); André Giroux, Ste-Anne-de-Bellevue (CA); Cédrickx Godbout, Attenweiler (DE); Benoît Moreau, Newton, MA (US); Julie Naud, Blainville (CA); Mathieu Parisien, Laval (CA); Martin Poirier, Blainville (CA); Maude Poirier, Pennington, NJ (US); Simon Surprenant, Montreal (CA); Carl Thibeault, Mascouche (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/390,243

(22) PCT Filed: Apr. 3, 2013

(86) PCT No.: PCT/US2013/035055
§ 371 (c)(1),
(2) Date: Oct. 2, 2014

(87) PCT Pub. No.: WO2013/152063
PCT Pub. Date: Oct. 10, 2013

(65) Prior Publication Data
US 2015/0158861 A1 Jun. 11, 2015

Related U.S. Application Data

(60) Provisional application No. 61/620,752, filed on Apr. 5, 2012.

(51) Int. Cl.
C07D 471/04 (2006.01)
A61K 31/4375 (2006.01)
C07D 519/00 (2006.01)
A61K 31/496 (2006.01)
A61K 31/5513 (2006.01)
A61K 31/506 (2006.01)
A61K 31/553 (2006.01)
A61K 31/4985 (2006.01)
A61K 31/5377 (2006.01)
A61K 31/541 (2006.01)
A61K 31/501 (2006.01)
A61K 45/06 (2006.01)
C12N 7/00 (2006.01)

(52) U.S. Cl.
CPC .......... *C07D 471/04* (2013.01); *A61K 31/4375* (2013.01); *A61K 31/496* (2013.01); *A61K 31/4985* (2013.01); *A61K 31/501* (2013.01); *A61K 31/506* (2013.01); *A61K 31/5377* (2013.01); *A61K 31/541* (2013.01); *A61K 31/553* (2013.01); *A61K 31/5513* (2013.01); *A61K 45/06* (2013.01); *C07D 519/00* (2013.01); *C12N 7/00* (2013.01); *C12N 2710/16163* (2013.01)

(58) Field of Classification Search
None
See application file for complete search history.

(56) References Cited

U.S. PATENT DOCUMENTS

2002/0007066 A1* 1/2002 Vaillancourt ........ C07D 471/04
546/122

FOREIGN PATENT DOCUMENTS

WO 0170742 A1 9/2001
WO 0174816 A1 10/2001

OTHER PUBLICATIONS

International Search Report for PCT/US2013/035055 filed Apr. 3, 2013.
Falardeau, Guy et al. "Substituted 1,6-Naphthyridines as Human Cytomegalovirus Inhibitors: Conformational Requirements" Bioorganic & Medicinal Chemistry Letters, (2000) vol. 10, pp. 2769-2770.
Vaillancourt, Valerie A. et al. "Naphthalene Carboxamides as Inhibitors of Human Cytomegalovirus DNA Polymerase" Bioorganic & Medicinal Chemistry Letters (2000) vol. 10, pp. 2079-2081.

* cited by examiner

Primary Examiner — Timothy R Rozof
(74) Attorney, Agent, or Firm — Michael P. Morris; Usha R. Patel

(57) ABSTRACT

Compounds of Formula (I) wherein n, m, $R^1$, $R^2$, $R^3$, $R^4$, R5 and R6 are defined herein, are useful for the treatment of cytomegalovirus disease and/or infection.

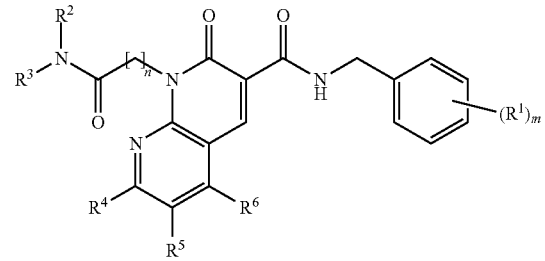

(I)

21 Claims, No Drawings

CYTOMEGALOVIRUS INHIBITOR COMPOUNDS

RELATED APPLICATIONS

This application is the national phase entry under 35 U.S.C. §371 of International Application No. PCT/US2013/035055, filed Apr. 3, 2013, which claims priority to U.S. Provisional Application Ser. No. 61/620,752, filed Apr. 5, 2012, which are hereby incorporated by reference in their entireties.

FIELD OF THE INVENTION

The present invention relates to 1,8-naphthyridin-2(1H)-one analogs and their use as inhibitors of human cytomegalovirus (CMV) DNA polymerase, pharmaceutical compositions containing such analogs, and methods of using these analogs in the treatment and prevention of CMV disease and/or infection.

BACKGROUND OF THE INVENTION

CMV, a β-herpes virus, is a frequent and ubiquitous virus that affects all populations, worldwide, including adults and children with normal or compromised immune systems. The current therapies approved for the treatment of CMV include Valganciclovir, Ganciclovir, Cidofovir and Foscarnet. Each of these therapies inhibit CMV DNA polymerase, a protein encoded by the UL54 gene, which is an enzyme essential for viral replication (*PNAS* 2003, 100(24), 14223-14228 and WO 2005/012545).

SUMMARY OF THE INVENTION

The present invention provides a novel series of compounds having inhibitory activity against CMV DNA polymerase.

Further objects of this invention arise for the one skilled in the art from the following description and the examples.

Representative embodiments of the compound aspect of the invention are described below and throughout the specification.

In one embodiment the invention provides a compound of Formula (I):

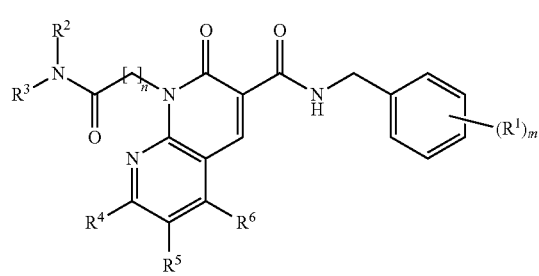

(I)

wherein
m is 1, 2 or 3;
n is 1, 2 or 3;
$R^1$ is halo, —CN, $(C_{1-6})$alkyl, OH, —O—$(C_{1-6})$alkyl, $(C_{1-6})$haloalkyl or nitro;
$R^2$ is H or $(C_{1-6})$alkyl optionally substituted with halo, —CN, $(C_{1-6})$alkyl, $(C_{1-6})$haloalkyl, —$(C_{3-7})$cycloalkyl, —O—$(C_{1-6})$alkyl, OH, —$NH_2$, —NH$(C_{1-6})$alkyl or —N$((C_{1-6})$alkyl$)_2$;

$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;

or $R^2$ and $R^3$, together with the N to which they are attached, are linked to form a heterocyclyl or heteroaryl; wherein each said heterocyclyl and heteroaryl are optionally mono-, di-, or tri-substituted with $R^{32}$;

$R^{32}$ is each independently selected from the group consisting of $R^{33}$, halo, oxo, —CN, OH, SH, —COOH, —O—$(C_{1-6})$alkyl, —S—$(C_{1-6})$alkyl, $(C_{3-7})$cycloalkyl, $(C_{1-6})$haloalkyl, —C(=O)—$(C_{1-6})$alkyl, —C(=O)—O—$(C_{1-6})$alkyl, —$SO_2NH_2$, —$SO_2$—NH$(C_{1-6})$alkyl, —$SO_2$—N$((C_{1-6})$alkyl$)_2$, —SO$(C_{1-6})$alkyl, —$SO_2(C_{1-6})$alkyl, —C(=O)—$NH_2$, —C(=O)—NH$(C_{1-6})$alkyl, —C(=O)—N$((C_{1-6})$alkyl$)_2$, —C(=O)—NH—$SO_2(C_{1-6})$alkyl, —$SO_2$—NH—C(=O)—$(C_{1-6})$alkyl, —$NH_2$, —NH$(C_{1-6})$alkyl, —N$((C_{1-6})$alkyl$)_2$, —NH$(C_{3-7})$cycloalkyl, —N$((C_{1-6})$alkyl$)(C_{3-7})$cycloalkyl, —NH—C(=O)$(C_{1-6})$alkyl, —NH—C(=O)—O$(C_{1-6})$alkyl, heterocyclyl (optionally substituted with $(C_{1-6})$alkyl) and (heteroaryl optionally substituted with $(C_{1-6})$alkyl);

$R^{33}$ is $(C_{1-6})$alkyl optionally mono- or di-substituted with OH, —O—$(C_{1-6})$alkyl, —$NH_2$, —NH$(C_{1-6})$alkyl or —N$((C_{1-6})$alkyl$)_2$;

$R^4$, $R^5$ and $R^6$ are each independently selected from the group consisting of halo, —CN, nitro, $R^{42}$, —C(=O)—$R^{42}$, —C(=O)O$R^{42}$, —O$R^{42}$, —S$R^{42}$, —SO$R^{42}$, —$SO_2R^{42}$, —N$(R^{43})R^{42}$, —$(C_{1-6})$alkyl-N$(R^{43})R^{42}$, —C(=O)—N$(R^{43})R^{42}$, —N$(R^{43})$—C(=O)$R^{42}$, —N$(R^{43})$—C(=O)—O$R^{42}$, —O—C(=O)—N$(R^{43})R^{42}$, —C(=O)—N(H)—$SO_2R^{42}$, —$SO_2$—N(H)—C(=O)$R^{42}$, —N$(R^{43})$—$SO_2R^{42}$ and —$SO_2$—N$(R^{43})R^{42}$;

$R^{42}$ is each independently selected from the group consisting of H, $(C_{1-6})$alkyl, $(C_{2-6})$alkenyl, $(C_{2-6})$alkynyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, alkenyl, alkynyl, cycloalkyl, aryl, heterocyclyl and heteroaryl, either alone or in combination with another radical, is optionally substituted with 1 to 3 substituents each independently selected from the group consisting of: oxo, halo, —CN, OH, —COOH, —O—$(C_{1-6})$alkyl, —S—$(C_{1-6})$alkyl, $(C_{3-7})$cycloalkyl, —O—$(C_{3-7})$cycloalkyl, $(C_{1-6})$haloalkyl, —C(=O)—O—$(C_{1-6})$alkyl, —$SO_2NH_2$, —$SO_2$—NH$(C_{1-6})$alkyl, —$SO_2$—N$((C_{1-6})$alkyl$)_2$, —SO$(C_{1-6})$alkyl, —$SO_2(C_{1-6})$alkyl, —C(=O)—$NH_2$, —C(=O)—NH$(C_{1-6})$alkyl, —C(=O)—N$((C_{1-6})$alkyl$)_2$, —$NH_2$, —NH$(C_{1-6})$alkyl, —N$((C_{1-6})$alkyl$)_2$, —NH—C(=O)$(C_{1-6})$alkyl, —NH—C(=O)—O$(C_{1-6})$alkyl, —C(=O)—N(H)—$SO_2(C_{1-6})$alkyl, —$SO_2$—N(H)—C(=O)$(C_{1-6})$alkyl, and $(C_{1-6})$alkyl optionally mono- or di-substituted with OH, —O—$(C_{1-6})$alkyl, —S—$(C_{1-6})$alkyl, —SO$(C_{1-6})$alkyl, —$SO_2(C_{1-6})$alkyl, —$NH_2$, —NH$(C_{1-6})$alkyl, —N$((C_{1-6})$alkyl$)_2$, —C(=O)-heterocyclyl, —C(=O)-heteroaryl, aryl, heterocyclyl or heteroaryl;

$R^{43}$ is H, $(C_{1-6})$haloalkyl or $(C_{1-6})$alkyl optionally mono- or di-substituted with OH, —O—$(C_{1-6})$alkyl, or —O—$(C_{3-7})$cycloalkyl;

or a salt thereof.

Another embodiment of the invention provides a compound as described above, or a pharmaceutically acceptable salt thereof, wherein n is 1 or 2.

Another embodiment of the invention provides a compound as described above, or a pharmaceutically acceptable salt thereof, wherein n is 1.

Another embodiment of the invention provides a compound as described above, or a pharmaceutically acceptable salt thereof, wherein $R^1$ is F, Cl, Br, —CN, $(C_{1-3})$alkyl, OH, —O—$(C_{1-3})$alkyl, $(C_{1-3})$haloalkyl or nitro.

Another embodiment of the invention provides a compound as described above, or a pharmaceutically acceptable salt thereof, wherein $R^1$ is F, Cl, Br, —CN, OH or —O—$(C_{1-3})$alkyl.

Another embodiment of the invention provides a compound as described above, or a pharmaceutically acceptable salt thereof, wherein m is 1 or 2.

Another embodiment of the invention provides a compound as described above, or a pharmaceutically acceptable salt thereof, wherein m is 1.

Another embodiment of the invention provides a compound as described above, or a pharmaceutically acceptable salt thereof, wherein $R^2$ is H or $(C_{1-6})$alkyl;
- $R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;
- or $R^2$ and $R^3$, together with the N to which they are attached, are linked to form a heterocyclyl; wherein said heterocyclyl is optionally mono-, di-, or tri-substituted with $R^{32}$;
- $R^{32}$ is each independently selected from the group consisting of $R^{33}$, halo, oxo, —CN, OH, —COOH, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);
- $R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

Another embodiment of the invention provides a compound as described above, or a pharmaceutically acceptable salt thereof, wherein $R^2$ and $R^3$, together with the N to which they are attached, are linked to form a heterocyclyl; wherein said heterocyclyl is optionally mono-, di-, or tri-substituted with $R^{32}$;
- $R^{32}$ is each independently selected from the group consisting of $R^{33}$, halo, oxo, —CN, OH, —COOH, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);
- $R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

Another embodiment of the invention provides a compound as described above, or a pharmaceutically acceptable salt thereof, wherein $R^2$ and $R^3$, together with the N to which they are attached, are linked to form a heterocyclyl; wherein each said heterocyclyl is optionally mono- or di-substituted with $R^{32}$;
- $R^{32}$ is each independently selected from the group consisting of $R^{33}$, halo, oxo, —CN, OH, $(C_{1-6})$haloalkyl, heterocyclyl (optionally substituted with $(C_{1-6})$alkyl) and heteroaryl (optionally substituted with $(C_{1-6})$alkyl);
- $R^{33}$ is $(C_{1-6})$alkyl optionally mono- or di-substituted with OH or —O—$(C_{1-6})$alkyl.

Another embodiment of the invention provides a compound as described above, or a pharmaceutically acceptable salt thereof, wherein $R^4$, $R^5$ and $R^6$ are each independently selected from the group consisting of halo, —CN, nitro, $R^{42}$, —OR$^{42}$, —SR$^{42}$, —SOR$^{42}$, —SO$_2$R$^{42}$, —N(R$^{43}$)R$^{42}$, —$(C_{1-3})$alkyl-N(R$^{43}$)R$^{42}$, —C(=O)—N(R$^{43}$)R$^{42}$, —N(R$^{43}$)—C(=O)R$^{42}$ and —N(R$^{43}$)—SO$_2$R$^{42}$;
- $R^{42}$ is each independently selected from the group consisting of H, $(C_{1-6})$alkyl, $(C_{2-6})$alkenyl, —$(C_{1-3})$alkyl-$(C_{3-7})$cycloalkyl, —$(C_{1-3})$alkyl-aryl, —$(C_{1-3})$alkyl-heterocyclyl, —$(C_{1-3})$alkyl-heteroaryl, $(C_{3-7})$cycloalkyl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of: oxo, halo, —CN, OH, —COOH, —O—$(C_{1-3})$alkyl, $(C_{1-3})$haloalkyl, —SO$_2$NH$_2$, —SO$_2$—NH$(C_{1-3})$alkyl, —SO$_2$—N$((C_{1-3})$alkyl$)_2$, —NH$_2$, —NH$(C_{1-3})$alkyl, —N$((C_{1-3})$alkyl$)_2$, —NH—C(=O)$(C_{1-3})$alkyl and $(C_{1-6})$alkyl optionally mono- or di-substituted with OH, —O—$(C_{1-6})$alkyl, —S—$(C_{1-3})$alkyl, —SO$(C_{1-3})$alkyl, —SO$_2(C_{1-3})$alkyl, —C(=O)-heterocyclyl, —C(=O)-heteroaryl, aryl, heterocyclyl or heteroaryl;
- $R^{43}$ is H, $(C_{1-3})$haloalkyl or $(C_{1-3})$alkyl optionally mono- or di-substituted with OH or —O—$(C_{1-3})$alkyl.

Another embodiment of the invention provides a compound as described above, or a pharmaceutically acceptable salt thereof, wherein $R^4$, $R^5$ and $R^6$ are each independently selected from the group consisting of $R^{42}$ and —N(R$^{43}$)R$^{42}$;
- $R^{42}$ is each independently selected from the group consisting of H, $(C_{1-6})$alkyl, —$(C_{1-3})$alkyl-heterocyclyl, —$(C_{1-3})$alkyl-heteroaryl, heterocyclyl and heteroaryl, wherein each said alkyl, heterocyclyl and heteroaryl, either alone or in combination with another radical, is optionally substituted with 1 to 2 substituents each independently selected from the group consisting of: halo, oxo, —CN, OH, —COOH, —O—$(C_{1-3})$alkyl, $(C_{1-3})$haloalkyl, —SO$_2$NH$_2$, —SO$_2$—NH$(C_{1-3})$alkyl, —SO$_2$—N$((C_{1-3})$alkyl$)_2$, —NH$_2$, —NH$(C_{1-3})$alkyl, —N$((C_{1-3})$alkyl$)_2$, —NH—C(=O)$(C_{1-3})$alkyl and $(C_{1-6})$alkyl;
- $R^{43}$ is H or $(C_{1-3})$alkyl optionally mono- or di-substituted with OH or —O—$(C_{1-3})$alkyl.

Another embodiment of the invention provides a compound as described above, or a pharmaceutically acceptable salt thereof, wherein two of $R^4$, $R^5$ and $R^6$ are H; and one of $R^4$, $R^5$ and $R^6$ are each independently selected from the group consisting of $R^{42}$ and —N(R$^{43}$)R$^{42}$;
- $R^{42}$ is each independently selected from the group consisting of H, $(C_{1-6})$alkyl, —$(C_{1-3})$alkyl-heterocyclyl, —$(C_{1-3})$alkyl-heteroaryl, heterocyclyl and heteroaryl, wherein each said alkyl, heterocyclyl and heteroaryl, either alone or in combination with another radical, is optionally substituted with 1 to 2 substituents each independently selected from the group consisting of: halo, oxo, —CN, OH, —COOH, —O—$(C_{1-3})$alkyl, $(C_{1-3})$ haloalkyl, —SO$_2$NH$_2$, —SO$_2$—NH(C$_{1-3}$)alkyl, —SO$_2$—N((C$_{1-3}$)alkyl)$_2$, —NH$_2$, —NH(C$_{1-3}$)alkyl, —N((C$_{1-3}$)alkyl)$_2$, —NH—C(=O)(C$_{1-3}$)alkyl and (C$_{1-6}$)alkyl;

R$^{43}$ is H or (C$_{1-3}$)alkyl optionally mono- or di-substituted with OH or —O—(C$_{1-3}$)alkyl.

Another embodiment of the invention provides a compound as described above, or a pharmaceutically acceptable salt thereof, as a medicament.

Also within the scope of this invention is the use of a compound of formula (I), or a pharmaceutically acceptable salt thereof, for the manufacture of a medicament for the treatment or prevention of CMV disease and/or infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a CMV infection in a human being having or at risk of having the infection.

The invention also provides the use of a pharmaceutical composition as described hereinabove for the treatment of CMV disease in a human being having or at risk of having the disease.

Another aspect of the invention involves a method of treating or preventing CMV disease and/or infection in a human being by administering to the human being an anti-CMV virally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat CMV disease and/or infection; and packaging material comprising a label which indicates that the composition can be used to treat disease and/or infection by CMV; wherein the composition comprises a compound of formula (I) according to this invention or a pharmaceutically acceptable salt thereof.

Still another aspect of this invention relates to a method of inhibiting the replication of CMV comprising exposing the virus to an effective amount of the compound of formula (I), or a salt thereof, under conditions where replication of CMV is inhibited.

Further included in the scope of the invention is the use of a compound of formula (I), or a salt thereof, to inhibit the replication of CMV.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, C$_{1-6}$-alkyl means an alkyl group or radical having 1 to 6 carbon atoms. In general, for groups comprising two or more subgroups, the first named subgroup is the radical attachment point, for example, the substituent "—C$_{1-3}$-alkyl-aryl" means an aryl group which is bound to a C$_{1-3}$-alkyl-group, with the C$_{1-3}$-alkyl group bound to the core. Unless specifically stated otherwise, for groups comprising two or more subgroups, the substituent may be attached to either subgroup. Substituents contemplated in the context of a specific molecule or fragment thereof are those which give rise to chemically stable compounds, such as are recognized by those skilled in the art.

In case a compound of the present invention is depicted in the form of a chemical name and as a formula in case of any discrepancy the formula shall prevail. An asterisk or the designation, ----, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "C$_{1-n}$-alkyl", wherein n is an integer from 2 to n, either alone or in combination with another radical denotes an acyclic, saturated, branched or linear hydrocarbon radical with 1 to n C atoms. For example the term C$_{1-3}$-alkyl embraces the radicals H$_3$C—, H$_3$C—CH$_2$—, H$_3$C—CH$_2$—CH$_2$— and H$_3$C—CH(CH$_3$)—.

The term "C$_{2-n}$-alkenyl", is used for a group as defined in the definition for "C$_{1-n}$-alkyl" with at least two carbon atoms, if at least two of those carbon atoms of said group are bonded to each other by a double bond.

The term "C$_{2-n}$-alkynyl", is used for a group as defined in the definition for "C$_{1-n}$-alkyl" with at least two carbon atoms, if at least two of those carbon atoms of said group are bonded to each other by a triple bond.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or S(O)$_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms and all spiro, bridged and fused systems. Thus, the term "heterocyclyl" or "heterocyclyl" includes the following exemplary structures which are not depicted as radicals as each form may be attached through a covalent bond to any atom so long as appropriate valences are maintained:

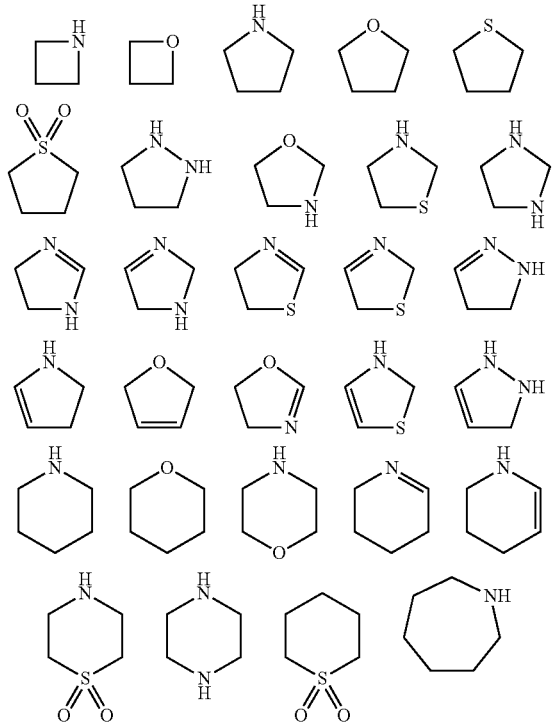

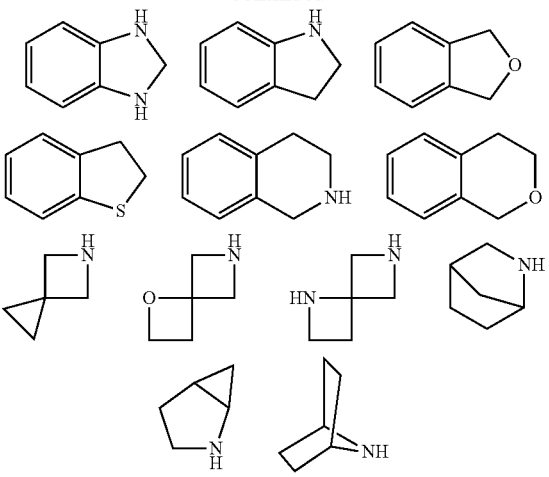

The term "heteroaryl" means a mono- or polycyclic-ring system containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms and all spiro, bridged and fused systems. Thus, the term "heteroaryl" includes the following exemplary structures which are not depicted as radicals as each form may be attached through a covalent bond to any atom so long as appropriate valences are maintained:

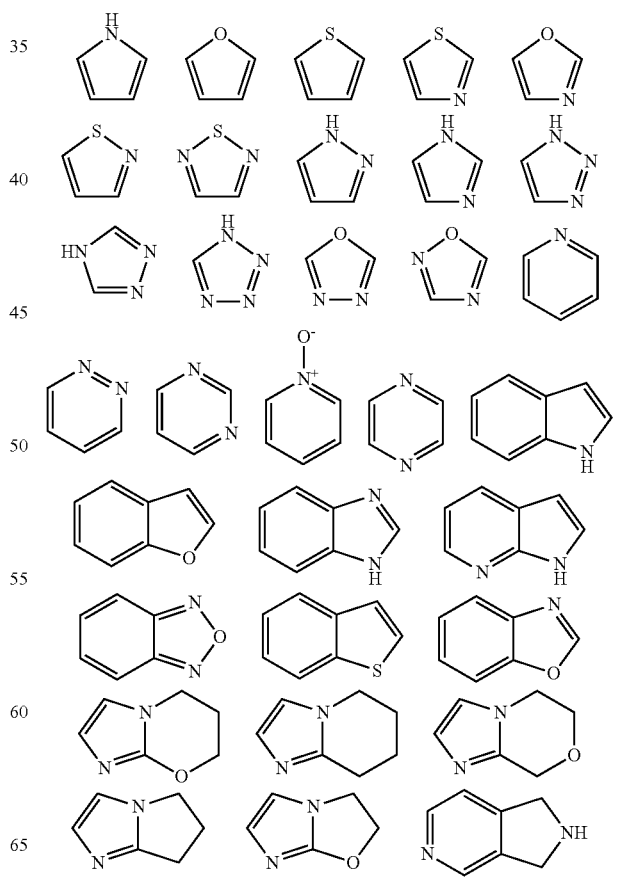

-continued

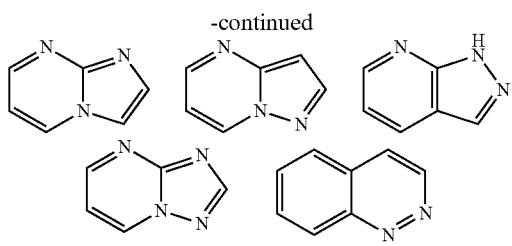

Many of the terms given above may be used repeatedly in the definition of a formula or group and in each case have one of the meanings given above, independently of one another.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesufonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

As used herein, the term "treatment" means the administration of a compound or composition according to the present invention to alleviate or eliminate symptoms of CMV disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Further Embodiments

In the following preferred embodiments, groups and substituents of the compounds of Formula (I) according to this invention are described in detail.

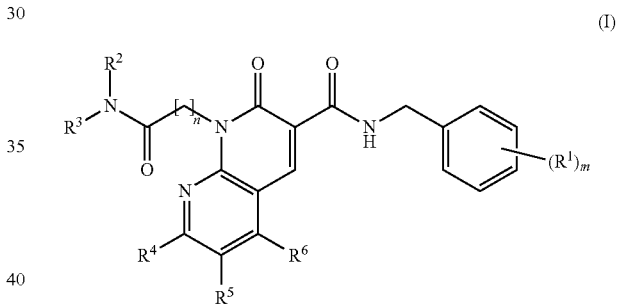

(I)

Any and each of the definitions below may be combined with each other.

n:
n-A: n is 1, 2 or 3.
n-B: n is 1 or 2.
n-C: n is 1.
$R^1$:
$R^1$-A: $R^1$ is halo, —CN, $(C_{1-6})$alkyl, OH, —O—$(C_{1-6})$alkyl, $(C_{1-6})$haloalkyl or nitro.
$R^1$-B: $R^1$ is F, Cl, Br, —CN, $(C_{1-3})$alkyl, OH, —O—$(C_{1-3})$alkyl, $(C_{1-3})$haloalkyl or nitro.
$R^1$-C: $R^1$ is F, Cl, Br, —CN, $CH_3$, OH or $CF_3$.
m:
m-A: m is 1, 2 or 3.
m-B: m is 1 or 2.
m-C: m is 1.
$R^2/R^3$:
$R^2/R^3$-A: $R^2$ is H or $(C_{1-6})$alkyl optionally substituted with halo, —CN, $(C_{1-6})$alkyl, $(C_{1-6})$haloalkyl, —$(C_{3-7})$cycloalkyl, —O—$(C_{1-6})$alkyl, OH—$NH_2$, —$NH(C_{1-6})$alkyl or —$N((C_{1-6})$alkyl$)_2$;

$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;

or $R^2$ and $R^3$, together with the N to which they are attached, are linked to form a heterocyclyl or heteroaryl; wherein each said heterocyclyl and heteroaryl are optionally mono-, di-, or tri-substituted with $R^{32}$;

$R^{32}$ is each independently selected from the group consisting of $R^{33}$, halo, oxo, —CN, OH, SH, —COOH, —O—$(C_{1-6})$alkyl, —S—$(C_{1-6})$alkyl, $(C_{3-7})$cycloalkyl, $(C_{1-6})$haloalkyl, —C(=O)—$(C_{1-6})$alkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, —NH$_2$, —NH$(C_{1-6})$alkyl, —N$((C_{1-6})$alkyl$)_2$, —NH$(C_{3-7})$cycloalkyl, —N$((C_{1-6})$alkyl$)(C_{3-7})$cycloalkyl, —NH—C(=O)$(C_{1-6})$alkyl, —NH—C(=O)—O$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

$R^2/R^3$-B: $R^2$ is H or $(C_{1-6})$alkyl;

$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;

or $R^2$ and $R^3$, together with the N to which they are attached, are linked to form a heterocyclyl; wherein said heterocyclyl is optionally mono-, di-, or tri-substituted with $R^{32}$;

$R^{32}$ is each independently selected from the group consisting of $R^{33}$, halo, oxo, —CN, OH, —COOH, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

$R^2/R^3$-C: $R^2$ and $R^3$, together with the N to which they are attached, are linked to form a heterocyclyl; wherein said heterocyclyl is optionally mono- or di-substituted with $R^{32}$;

$R^{32}$ is each independently selected from the group consisting of $R^{33}$, halo, oxo, —CN, OH, —COOH, —O—$(C_{1-6})$alkyl, $(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —C(=O)—NH—SO$_2(C_{1-6})$alkyl, —SO$_2$—NH—C(=O)—$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono- or di-substituted with OH, —O—$(C_{1-6})$alkyl, —NH$_2$, —NH$(C_{1-6})$alkyl or —N$((C_{1-6})$alkyl$)_2$.

$R^2/R^3$-D: $R^2$ and $R^3$, together with the N to which they are attached, are linked to form a heterocyclyl; wherein each said heterocyclyl is optionally mono- or di-substituted with $R^{32}$;

$R^{32}$ is each independently selected from the group consisting of $R^{33}$, halo, oxo, —CN, OH, $(C_{1-6})$haloalkyl, heterocyclyl optionally substituted with $(C_{1-6})$alkyl and heteroaryl optionally substituted with $(C_{1-6})$alkyl;

$R^{33}$ is $(C_{1-6})$alkyl optionally mono- or di-substituted with OH or —O—$(C_{1-6})$alkyl.

$R^4/R^5/R^6$:

$R^4/R^5/R^6$-A: $R^4$, $R^5$ and $R^6$ are each independently selected from the group consisting of halo, —CN, nitro, $R^{42}$, —C(=O)—$R^{42}$, —C(=O)O$R^{42}$, —O$R^{42}$, —S$R^{42}$, —SO$R^{42}$, —SO$_2R^{42}$, —N$(R^{43})R^{42}$, —$(C_{1-6})$alkyl-N$(R^{43})R^{42}$, —C(=O)—N$(R^{43})R^{42}$, —N$(R^{43})$—C(=O)$R^{42}$, —N$(R^{43})$—C(=O)—O$R^{42}$, O—C(=O)—N$(R^{43})R^{42}$, —C(=O)—N(H)—SO$_2R^{42}$, —SO$_2$—N(H)—C(=O)$R^{42}$, —N$(R^{43})$—SO$_2R^{42}$ and —SO$_2$—N$(R^{43})R^{42}$;

$R^{42}$ is each independently selected from the group consisting of H, $(C_{1-6})$alkyl, $(C_{2-6})$alkenyl, $(C_{2-6})$alkynyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, $(C_{3-7})$cycloalkyl, aryl, heterocyclyl and heteroaryl, wherein each said alkyl, alkenyl, alkynyl, cycloalkyl, aryl, heterocyclyl and heteroaryl, either alone or in combination with another radical, is optionally substituted with 1 to 3 substituents each independently selected from the group consisting of: oxo, halo, —CN, OH, —COOH, —O—$(C_{1-6})$alkyl, —S—$(C_{1-6})$alkyl, $(C_{3-7})$cycloalkyl, —O—$(C_{3-7})$cycloalkyl, $(C_{1-6})$haloalkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —C(=O)—NH$(C_{1-6})$alkyl, —C(=O)—N$((C_{1-6})$alkyl$)_2$, —NH$_2$, —NH$(C_{1-6})$alkyl, —N$((C_{1-6})$alkyl$)_2$, —NH—C(=O)$(C_{1-6})$alkyl, —NH—C(=O)—O$(C_{1-6})$alkyl, —C(=O)—N(H)—SO$_2(C_{1-6})$alkyl, —SO$_2$—N(H)—C(=O)$(C_{1-6})$alkyl, and $(C_{1-6})$alkyl optionally mono- or di-substituted with OH, —O—$(C_{1-6})$alkyl, —S—$(C_{1-6})$alkyl, —SO$(C_{1-6})$alkyl, —SO$_2(C_{1-6})$alkyl, —NH$_2$, —NH$(C_{1-6})$alkyl, —N$((C_{1-6})$alkyl$)_2$, —C(=O)-heterocyclyl, —C(=O)-heteroaryl, aryl, heterocyclyl or heteroaryl;

$R^{43}$ is H, $(C_{1-6})$haloalkyl or $(C_{1-6})$alkyl optionally mono- or di-substituted with OH, —O—$(C_{1-6})$alkyl or —O—$(C_{3-7})$cycloalkyl.

$R^4/R^5/R^6$-B: $R^4$, $R^5$ and $R^6$ are each independently selected from the group consisting of halo, —CN, nitro, $R^{42}$, —O$R^{42}$, —S$R^{42}$, —SO$R^{42}$, —SO$_2R^{42}$, —N$(R^{43})R^{42}$, —$(C_{1-3})$alkyl-N$(R^{43})R^{42}$, —C(=O)—N$(R^{43})R^{42}$, —N$(R^{43})$—C(=O)$R^{42}$ and —N$(R^{43})$—SO$_2R^{42}$;

$R^{42}$ is each independently selected from the group consisting of H, $(C_{1-6})$alkyl, $(C_{2-6})$alkenyl, —$(C_{1-3})$alkyl-$(C_{3-7})$cycloalkyl, —$(C_{1-3})$alkyl-aryl, —$(C_{1-3})$alkyl-heterocyclyl, —$(C_{1-3})$alkyl-heteroaryl, $(C_{3-7})$cycloalkyl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of: oxo, halo, —CN, OH, —COOH, —O—$(C_{1-3})$alkyl, $(C_{1-3})$haloalkyl, —SO$_2$NH$_2$, —SO$_2$—NH$(C_{1-3})$alkyl, —SO$_2$—N$((C_{1-3})$alkyl$)_2$, —NH$_2$, —NH$(C_{1-3})$alkyl, —N$((C_{1-3})$alkyl$)_2$, —NH—C(=O)$(C_{1-3})$alkyl and $(C_{1-6})$alkyl optionally mono- or di-substituted with OH, —O—$(C_{1-6})$alkyl, —S—$(C_{1-3})$alkyl, —SO$(C_{1-3})$alkyl, —SO$_2(C_{1-3})$alkyl, —C(=O)-heterocyclyl, —C(=O)-heteroaryl, aryl, heterocyclyl or heteroaryl;

$R^{43}$ is H, $(C_{1-3})$haloalkyl or $(C_{1-3})$alkyl optionally mono- or di-substituted with OH or —O—$(C_{1-3})$alkyl.

$R^4/R^5/R^6$-C: $R^4$, $R^5$ and $R^6$ are each independently selected from the group consisting of $R^{42}$ and —N$(R^{43})R^{42}$;

$R^{42}$ is each independently selected from the group consisting of H, $(C_{1-6})$alkyl, $—(C_{1-3})$alkyl-heterocyclyl, $—(C_{1-3})$alkyl-heteroaryl, heterocyclyl and heteroaryl, wherein each said alkyl, heterocyclyl and heteroaryl, either alone or in combination with another radical, is optionally substituted with 1 to 2 substituents each independently selected from the group consisting of: halo, oxo, —CN, OH, —COOH, —O—$(C_{1-3})$alkyl, $(C_{1-3})$haloalkyl, —SO$_2$NH$_2$, —SO$_2$—NH$(C_{1-3})$alkyl, —SO$_2$—N$((C_{1-3})$alkyl$)_2$, —NH$_2$, —NH$(C_{1-3})$alkyl, —N$((C_{1-3})$alkyl$)_2$, —NH—C(=O)$(C_{1-3})$alkyl and $(C_{1-6})$alkyl;

$R^{43}$ is H or $(C_{1-3})$alkyl optionally mono- or di-substituted with OH or —O—$(C_{1-3})$alkyl.

$R^4/R^5/R^6$-D: Two of $R^4$, $R^5$ and $R^6$ are H; while one of $R^4$, $R^5$ and $R^6$ are each independently selected from the group consisting of $R^{42}$ and —N$(R^{43})R^{42}$;

$R^{42}$ is each independently selected from the group consisting of H, $(C_{1-6})$alkyl, $—(C_{1-3})$alkyl-heterocyclyl, $—(C_{1-3})$alkyl-heteroaryl, heterocyclyl and heteroaryl, wherein each said alkyl, heterocyclyl and heteroaryl, either alone or in combination with another radical, is optionally substituted with 1 to 2 substituents each independently selected from the group consisting of: halo, oxo, —CN, OH, —COOH, —O—$(C_{1-3})$alkyl, $(C_{1-3})$haloalkyl, —SO$_2$NH$_2$, —SO$_2$—NH$(C_{1-3})$alkyl, —SO$_2$—N$((C_{1-3})$alkyl$)_2$, —NH$_2$, —NH$(C_{1-3})$alkyl, —N$((C_{1-3})$alkyl$)_2$, —NH—C(=O)$(C_{1-3})$alkyl and $(C_{1-6})$alkyl;

$R^{43}$ is H or $(C_{1-3})$alkyl optionally mono- or di-substituted with OH or —O—$(C_{1-3})$alkyl.

Representative embodiments of the compound aspects of the present invention are described above. Further subgeneric embodiments of the present invention are set forth in the following table, wherein each substituent group of each embodiment is defined according to the definitions set forth above:

| Embodiment | n | m | $R^1$ | $R^2/R^3$ | $R^4/R^5/R^6$ |
|---|---|---|---|---|---|
| E-1 | n-A | m-B | $R^1$-A | $R^2/R^3$-D | $R^4/R^5/R^6$-C |
| E-2 | n-A | m-A | $R^1$-A | $R^2/R^3$-C | $R^4/R^5/R^6$-C |
| E-3 | n-A | m-B | $R^1$-A | $R^2/R^3$-A | $R^4/R^5/R^6$-C |
| E-4 | n-A | m-A | $R^1$-A | $R^2/R^3$-C | $R^4/R^5/R^6$-A |
| E-5 | n-A | m-C | $R^1$-A | $R^2/R^3$-B | $R^4/R^5/R^6$-A |
| E-6 | n-A | m-B | $R^1$-A | $R^2/R^3$-D | $R^4/R^5/R^6$-D |
| E-7 | n-A | m-A | $R^1$-A | $R^2/R^3$-D | $R^4/R^5/R^6$-D |
| E-8 | n-A | m-B | $R^1$-A | $R^2/R^3$-A | $R^4/R^5/R^6$-D |
| E-9 | n-B | m-B | $R^1$-A | $R^2/R^3$-B | $R^4/R^5/R^6$-B |
| E-10 | n-B | m-C | $R^1$-B | $R^2/R^3$-C | $R^4/R^5/R^6$-C |
| E-11 | n-B | m-C | $R^1$-C | $R^2/R^3$-D | $R^4/R^5/R^6$-C |
| E-12 | n-B | m-B | $R^1$-B | $R^2/R^3$-C | $R^4/R^5/R^6$-B |
| E-13 | n-B | m-C | $R^1$-B | $R^2/R^3$-D | $R^4/R^5/R^6$-D |
| E-14 | n-B | m-C | $R^1$-C | $R^2/R^3$-D | $R^4/R^5/R^6$-D |
| E-15 | n-C | m-C | $R^1$-C | $R^2/R^3$-C | $R^4/R^5/R^6$-C |
| E-16 | n-C | m-C | $R^1$-C | $R^2/R^3$-D | $R^4/R^5/R^6$-D |

Examples of most preferred compounds according to this invention are each single compound, namely, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 2001, 2002, 2003, 2004, 2005, 2006, 2007, 2008, 2009, 2010, 2011, 2012, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 4001, 4002, 4003, 4004, 4005, 4006, 4007, 4008, 4009, 4010, 4011, 4012, 4013, 4014, 4015, 4016, 4017, 4018, 4019, 4020, 4021, 4022, 4023, 4024, 4025, 4026, 4027, 4028, 4029, 4030, 4031, 4032, 4033, 4034, 4035, 4036, 4037, 4038, 4039, 4040, 4041, 4042, 4043, 4044, 4045, 4046, 4047, 4048, 4049, 4050, 4051, 4052, 4053, 4054, 4055, 4056, 4057, 4058, 4059, 4060, 4061, 4062, 4063, 4064, 4065, 5001, 5002, 5003, 5004, 5005, 5006, 5007, 5008, 5009, 5010, 5011, 5012, 5013, 5014, 5015, 5016, 5017, 5018, 5019, 5020, 5021, 5022, 6001, 6002, 6003, 6004, 6005, 6006, 6007, 6008, 6009, 6010, 6011, 6012, 6013, 6014, 6015, 6016, 6017, 6018, 6019, 6020, 6021, 6022, 6023, 6024, 7001, 7002, 7003, 7004, 7005, 7006, 7007, 7008, 7009, 7010, 7011 and 7012.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders. The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds according to the invention with known excipients, for example inert diluents, carriers, disintegrants, adjuvants, surfactants, binders and/or lubricants. The tablets may also consist of several layers.

Suitable injectables may be obtained, for example, by mixing one or more compounds according to the invention with known excipients, for example inert diluents, carriers, co-solvent, adjuvants, surfactants and/or cyclodextrin complex. The injectable formulation may be an emulsion or suspension.

Combination Therapy

Combination therapy is contemplated wherein a compound of the invention, or a pharmaceutically acceptable salt thereof, is co-administered with at least one additional agent selected from: a CMV entry inhibitor, a CMV early transcription event inhibitor, a CMV helicase-primase inhibitor, another CMV DNA polymerase inhibitor, an inhibitor of UL97 kinase, a CMV protease inhibitor, a CMV terminase inhibitor, a CMV maturation inhibitor, an inhibitor of another target in the CMV life cycle, a CMV vaccine and a CMV biological agent.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being. Such agents can be selected from: a CMV entry inhibitor; a CMV early transcription event inhibitor; a CMV helicase-primase inhibitor; a CMV DNA polymerase inhibitor such as Ganciclovir (Cytovene), Valganciclovir (Valcyte; Cymeval), Cidofovir (Vistide), Foscarnet (Foscavir), CMX001, cyclopropavir (MBX-400) and Valaciclovir (Valtrex; Zelitrex); an inhibitor of UL97 kinase such as Maribavir; a CMV protease inhibitor; a CMV terminase inhibitor such as AIC246 (Letermovir); a CMV maturation inhibitor; other inhibitors such as Artesunate; a CMV vaccine such as TransVax and a CMV biological agent such as Cytogam (Cytotect).

EXAMPLES

Other features of the present invention will become apparent from the following non-limiting examples which illustrate the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. The reactants used in the examples below may be obtained either as described herein, or if not described herein, are themselves either commercially available or may be prepared from commercially available materials by methods known in the art. Flash chromatography is carried out on silica gel ($SiO_2$) according to the procedure of W. C. Still et al., J. Org. Chem., (1978), 43, 2923. Mass spectral analyses may be recorded using an electrospray mass spectrometer.

Compounds and intermediates can be purified by a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses may be recorded using flow injection analysis mass spectrometry or Waters Acquity Ultraperformance LC System consisting of a sample organizer, PDA detector, column manager, sample manager, binary solvent manager and SQ detector.

Reactions performed in microwave conditions are conducted in a Biotage Initiator 2.0 microwave synthesizer equipped with a Robot Sixty for vial manipulations. The temperature range is from 40-250° C. The pressure range is from 0-20 bar and the power range is from 0-400 Watts at 2.45 GHz. The vial size varies from 0.5 mL to 20 mL. The solvent absorption level is high by default. Specific reaction times and temperatures are given in the experimental section when applicable.

Preparative RP-HPLC is performed under standard conditions using one of the following specific measuring conditions:
A) Waters SunFire Prep OBD C18 column (5 µm, 19×50 mm) eluting firstly with a hold period of 1 min in initial gradient condition then eluting with a linear MeOH gradient containing 10 mM Ammonium Formate (pH 3.8) over 10 min at 30 mL/min. Fractions containing the desired product are pooled, concentrated and lyophilized.
B) Waters XBridge Prep OBD C18 column (5 µm, 19×50 mm) eluting firstly with a hold period of 1 min in initial gradient condition then eluting with a linear MeOH gradient containing 10 mM Ammonium Bicarbonate (pH 10.0) over 10 min at 30 mL/min. Fractions containing the desired product are pooled, concentrated and lyophilized.
C) Waters SunFire Prep OBD C18 column (5 µm, 19×50 mm) eluting firstly with a hold period of 1 min in initial gradient condition then eluting with a linear MeCN gradient containing 0.06% TFA (v/v) over 10 min at 30 mL/min. Fractions containing the desired product are pooled and lyophilized.
D) Waters XBridge Prep OBD C18 column (5 µm, 19×50 mm) eluting firstly with a hold period of 1 min in initial gradient condition then eluting with a linear MeCN gradient containing 10 mM Ammonium Bicarbonate (pH 10.0) over 10 min at 30 mL/min. Fractions containing the desired product are pooled and lyophilized.
E) Waters SunFire Prep OBD C18 column (5 µm, 19×50 mm) eluting firstly with a hold period of 0.5 min in initial gradient condition then eluting with a linear MeCN gradient containing 10 mM Ammonium Formate (pH 3.8) over 6.9 min at 45 mL/min. The eluents are warmed at 45° C. using a Timberline Instrument TL600 Mobile Phase Heater during the whole run. Fractions containing the desired product are pooled and lyophilized.
F) Waters XSelect Prep CSH OBD C18 column (5 µm, 30×75 mm) eluting firstly with a hold period of 0.5 min in initial gradient condition then eluting with a linear MeCN gradient containing 0.1% formic acid (v/v) over 6.4 min at 60 mL/min. The eluents are warmed at 45° C. using a Timberline Instrument TL600 Mobile Phase Heater during the whole run. Fractions containing the desired product are pooled and lyophilized.

Analytical UPLC is performed under standard conditions using one of the following specific measuring conditions:
A) Waters ACQUITY UPLC BEH C18 column (1.7 µm, 2.1×30 mm) eluting with a linear MeOH gradient containing 10 mM Ammonium Bicarbonate (pH 10) over 2.2 min at 0.75 mL/min.
B) Waters ACQUITY UPLC HSS C18 column (1.8 µm, 2.1×30 mm) eluting with a linear MeOH gradient containing 10 mM Ammonium Formate (pH 3.8) over 2.3 min at 0.8 mL/min.
C) Waters ACQUITY UPLC HSS C18 column (1.8 µm, 2.1×30 mm) eluting with a linear MeCN gradient containing 0.06% TFA (v/v) over 2.2 min at 0.9 mL/min.
D) Waters ACQUITY UPLC BEH C18 column (1.7 µm, 2.1×30 mm) eluting with a linear MeCN gradient containing 10 mM Ammonium Bicarbonate (pH 10) over 2.2 min at 0.75 mL/min.
E) Waters ACQUITY UPLC HSS C18 column (1.8 µm, 2.1×30 mm) eluting with a linear MeCN gradient containing 10 mM Ammonium Formate (pH 3.8) over 2.3 min at 0.8 mL/min. The eluents are warmed at 45° C. using a column preheater during the whole run.
F) Waters XSelect UPLC CSH C18 column (1.7 µm, 2.1×30 mm) eluting with a linear MeCN gradient containing 0.1% formic acid (v/v) over 2.0 min at 0.9 mL/min. The eluents are warmed at 45° C. using a column preheater during the whole run.

As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions. Retention time values are reported as minutes.

Abbreviations used in the examples include:

Ac: acetyl; AcOH: acetic acid; BEH: ethylene bridged hybrid; BOC or Boc: tert-butyloxycarbonyl; Bu: butyl; DCE: 1,2-dichloroethane; DCM: dichloromethane; DIAD: diisopropyl azodicarboxylate; DIPEA: diisopropylethylamine; DMAc: dimethylacetamide; DMAP: 4-dimethylaminopyridine; DMEM: Dulbecco's modified Eagle's medium; DMF: N,N-dimethylformamide; DMSO: dimethylsulfoxide; dppf: 1,1'-diphenylphosphinylferrocene; EDCI: 1-[3-(dimethylamino)propyl]-3-ethylcarbodiimide hydrochloride; EDTA: ethylenediaminetetraacetic acid; eq or equiv: equivalents; Et: ethyl; $Et_2O$: diethyl ether; EtOAc: ethyl acetate; EtOH: ethanol; HATU: [O-(7-azabenzotriazol-1-yl)-1,1,3,3-tetramethyluronium hexafluorophosphate]; HEPES: 4-(2-hydroxyethyl)-1-piperazineethanesulfonic acid; Hex: hexanes; HPLC: high performance liquid chromatography; HSS: high strength silica; $^i$Pr or i-Pr: 1-methylethyl (iso-propyl); $IC_{50}$: 50% inhibitory concentration; LiHMDS: lithium bis(trimethylsilyl) amide; Me: methyl; MeCN: acetonitrile; MeOH: methanol; MS: mass spectrometry; MTBE: methyl tert-butyl ether; $[M+H]^+$: protonated molecular ion; NBS: N-bromosuccinimide; NMP: N-methyl pyrrolidinone; NMR: nuclear magnetic resonance spectroscopy; OBD: optimum bed density; PDA: photodiode array; Ph: phenyl; Pr: propyl; RP: reverse phase; RT: room temperature (18 to 22° C.); RuPhos: 2-dicyclohexylphosphino-2',6'-diisopropoxybiphenyl; tert-butyl or t-butyl: 1,1-dimethylethyl; t-butyl XPhos: 2-di-tert-butylphosphino-2',4',6'-triisopropylbiphenyl; TBAF: tetrabutylammonium fluoride; TFA: trifluoroacetic acid; THF: tetrahydrofuran; TMS: trimethylsilyl; TPAP: tetra-n-propyl ammonium perruthenate; Tr: triphenylmethyl; $t_R$: retention time; UPLC: ultraperformance liquid chromatography; VSV: vesicular stomatitis virus; Xantphos: 4,5-Bis(diphenylphosphino)-9,9-dimethylxanthene.

Step 1: Methyl 3-chloro-3-oxopropanoate (Aldrich) (50.0 g, 366 mmol) is added dropwise to a cooled (ice bath) stirred solution of 4-chlorobenzylamine (Aldrich) (51.8 g, 366 mmol, 1.00 eq) and triethylamine (102 mL, 732 mmol, 2.00 eq) in dry DCM (1.25 L) over 30 min, keeping the temperature inside the flask below 10° C. The resulting mixture is stirred at RT for 16 h and washed with a saturated aqueous $NaHCO_3$ solution and brine. The organic layer is dried over $Na_2SO_4$, filtered and concentrated under reduced pressure. The residue is washed with 5% EtOAc in hexanes and dried to afford intermediate 1001A.

Step 2: 2-amino-3-formylpyridine (Apollo-Inter) (5.00 g, 40.9 mmol) and intermediate 1001A (11.8 g, 49.1 mmol, 1.20 eq) are charged in a microwave vial and EtOH (40 mL) is added. Piperidine (10.1 mL, 102 mmol, 2.50 eq) is added and the vial is sealed and warmed in a microwave oven at 120° C. for 20 min. The cooled solution is diluted with $Et_2O$ and sonicated. The residue is filtered and dried under vacuum to afford intermediate 1001B.

Step 3: Intermediate 1001B (5.00 g, 15.9 mmol) is charged in a round-bottom flask and suspended in DMF (30 mL). Potassium carbonate (6.22 g, 45.0 mmol, 2.82 eq) and methyl bromoacetate (1.50 mL, 16.3 mmol, 1.02 eq) are added and the solution is stirred at RT for 2 h. The solution is added to water and the residue is filtered and dried under vacuum. The solid is purified by trituration in EtOAc to afford intermediate 1001C.

Step 4: Intermediate 1001C (5.88 g, 15.2 mmol) is charged in a round-bottom flask and suspended in THF (70 mL). MeOH (20 mL) and NaOH 1.00 N (38.1 mL, 38.1 mmol, 2.50 eq) are added and the solution is stirred at 50° C. for 2 h. The reaction mixture is then partially concentrated and acidified with HCl 1 N. DCM is added to the mixture and the phases are Synthesis of Compound 1001

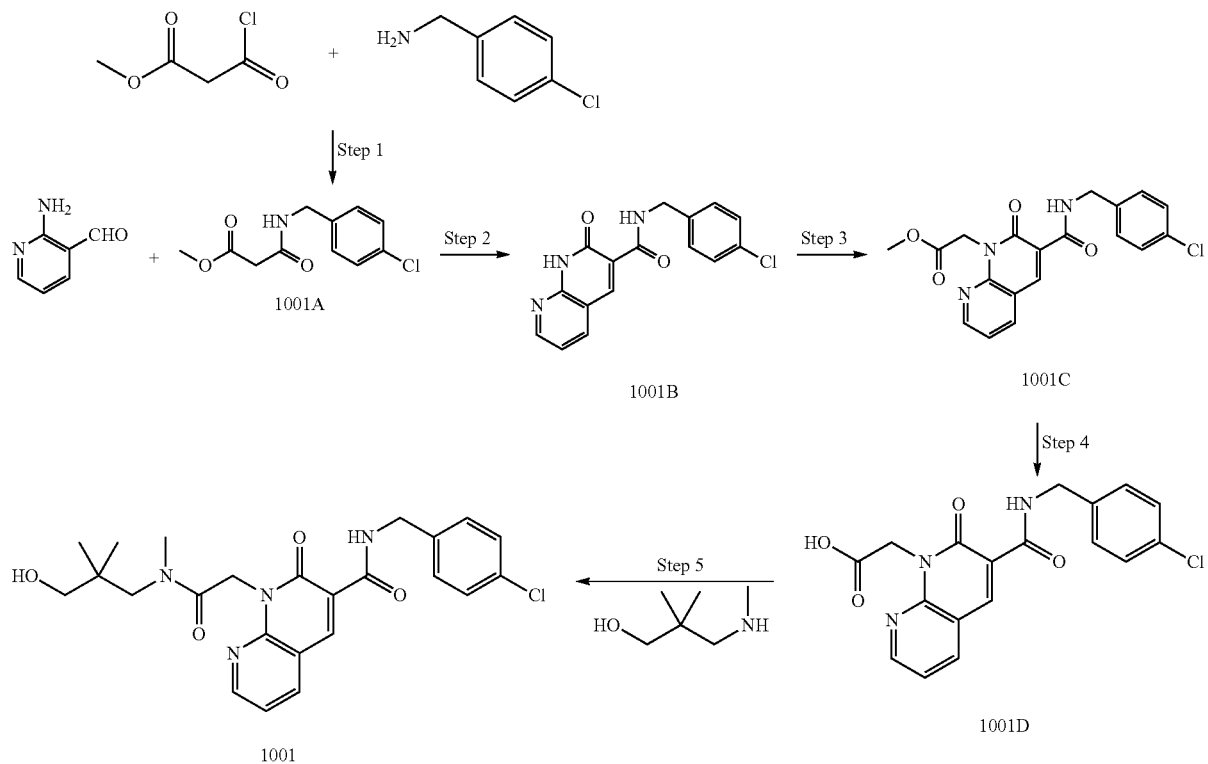

separated. The organic layer is dried over MgSO$_4$, filtered and concentrated to afford intermediate 1001D.

Step 5: Intermediate 1001D (50 mg, 0.14 mmol) is charged in a vial and dissolved in DMF (2 mL). Diisopropylethylamine (80 μL, 0.46 mmol, 3.4 eq) and 2,2-dimethyl-3-(methylamino)propan-1-ol (Chembrdg-bb) (31 mg, 0.27 mmol, 2.0 eq) are added followed by HATU (70 mg, 0.18 mmol, 1.4 eq) and the solution is stirred at RT for 1 h. Following completion of the reaction, the solution is filtered and purified by preparative HPLC to provide compound 1001 (t$_R$: 1.85, (M+H)$^+$: 471.3/473.3).

Synthesis of Compound 1002

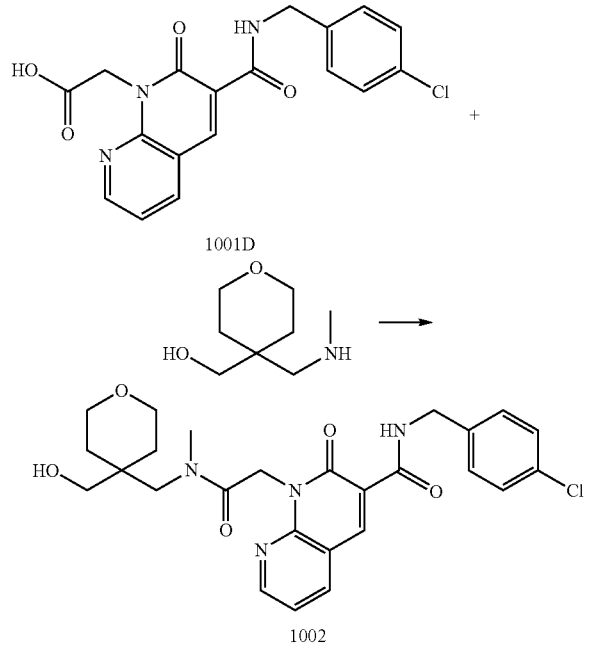

Compound 1002 (t$_R$: 1.74, (M+H)$^+$: 513.3/515.3) is prepared analogously to compound 1001, except that in step 5, intermediate 1001D is reacted with (4-[(methylamino)methyl]tetrahydro-2H-pyran-4-yl)methanol (Chembrdg-bb).

Synthesis of Compound 1003

Step 1: 1-benzyl-3-fluoro-3-methylazetidine (prepared analogously to the procedure described in J. Org. Chem. 2006, 71, 7100, herein incorporated by reference) (56.0 g, 313 mmol) is charged in a round-bottom flask and dissolved in EtOH (1.00 L). A 4.00 M HCl solution in dioxane (79.0 mL, 316 mmol, 1.01 eq) is added, followed by palladium hydroxide on carbon (28 g). The mixture is hydrogenated at 2 atm for 36 h at RT. The mixture is filtered through Celite and the Celite pad is washed with EtOH. The filtrate is concentrated under reduced pressure and the residue is purified by triturination in diethyl ether. The residue is purified by flash column chromatography (5% to 10% MeOH in DCM) to provide intermediate 1003A.

Step 2: Compound 1003 (t$_R$: 1.75, (M+H)$^+$: 443.1/445.3) is prepared analogously to compound 1001, except that in step 5, intermediate 1001D is reacted with intermediate 1003A.

Synthesis of Compound 1004

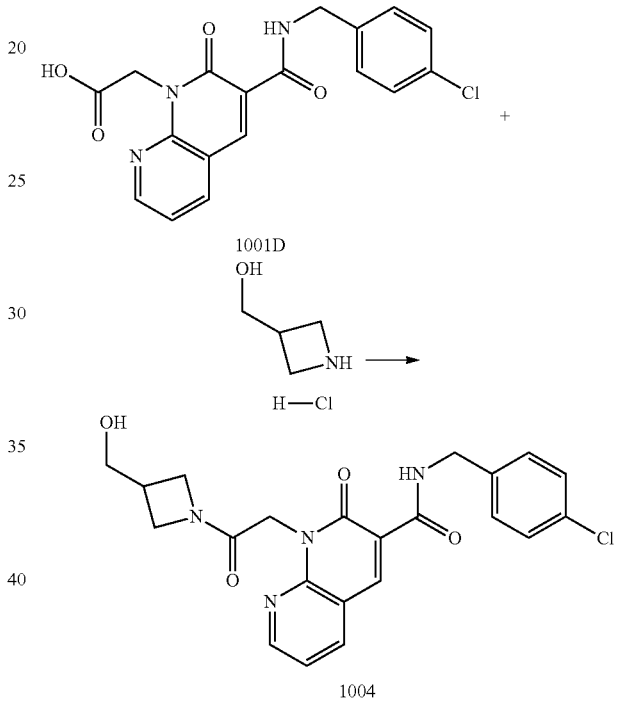

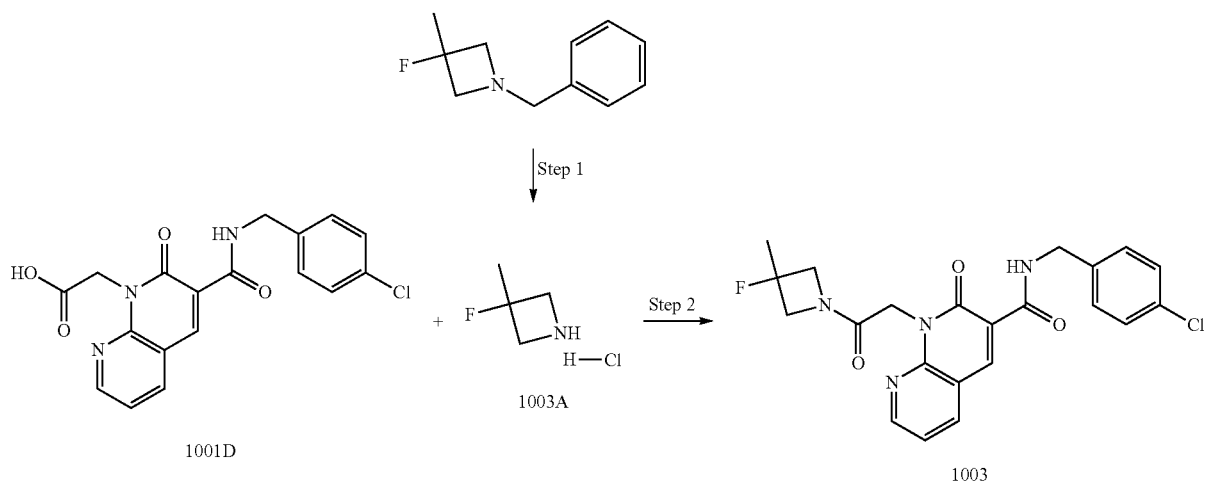

Compound 1004 ($t_R$: 1.58, (M+H)$^+$: 441.2/443.1) is prepared analogously to compound 1001, except that in step 5, intermediate 1001D is reacted with azetidin-3-ylmethanol hydrochloride (Parkway).

Synthesis of Compound 1005

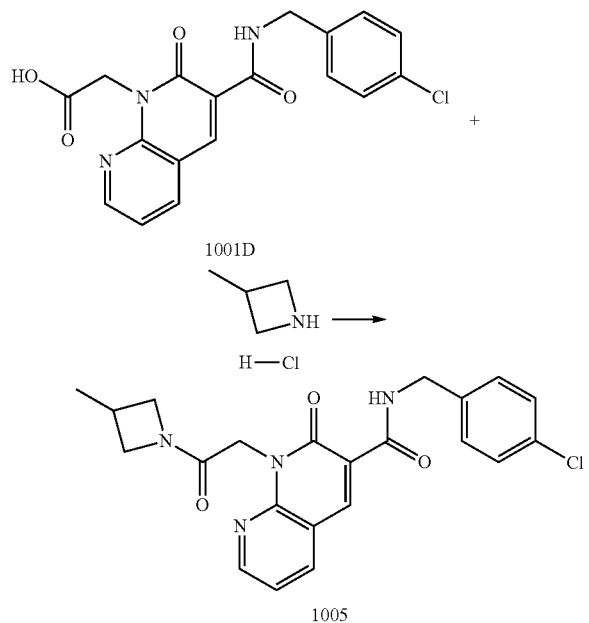

Compound 1005 ($t_R$: 1.89, (M+H)$^+$: 425.2) is prepared analogously to compound 1001, except that in step 5, intermediate 1001D is reacted with 3-methyl-azetidine hydrochloride (prepared analogously to the procedure described in J. Med. Chem. 2008, 51, 7380, herein incorporated by reference).

Step 1: A solution of sodium bis(trimethylsilyl)amide in THF (2M; 137 mL, 274 mmol, 2.36 eq) is added over 30 min to methyltriphenylphosphonium bromide (98.0 g, 274 mmol, 2.36 eq) in anhydrous THF (825 mL). The reaction mixture is stirred at RT for 1 h. A solution of tert-butyl 3-oxoazetidine-1-carboxylate (CNH-Tech) (20.0 g, 116 mmol) in anhydrous THF (115 mL) is added over 10 min, and the stirring is continued at RT for 1 h. The solution is diluted with hexanes (1.0 L), filtered through Celite, and the filtrate is concentrated under reduced pressure at 10° C. The crude material is purified by silica gel flash chromatography (20% diethyl ether in hexanes) to afford intermediate 1006A.

Step 2: In a plastic 2 L Erlenmeyer flask, solid 1-methyl-1-nitrosourea (30.9 g, 80 wt. %, 250 mmol) is added over 30 min to a cooled (−10° C.) mixture of diethyl ether (500 mL) and 5 M aqueous potassium hydroxide (250 mL, 1250 mmol). The mixture is stirred at 00° C. for 1 h. The layers are decanted, and the organic layer is transferred to a 1 L Erlenmeyer flask containing potassium hydroxide pellets (125 g, 2.22 mol). The flask containing diazomethane is placed in a cold bath (−10° C.) for 1 h while the next step is being set-up.

The above solution of diazomethane in ether (~500 mL, ~0.5 M, ~250 mmol, 5.0 eq) is transferred at 0° C. over 50 min to a mixture of 1006A (8.50 g, 50.2 mmol) in diethyl ether (300 mL) containing palladium (II) acetate (2.3 g, 10 mmol, 0.20 eq). The reaction mixture is stirred at RT for 16 h, then diluted with hexanes (500 mL). The crude mixture is filtered through Celite and the filtrate is concentrated under reduced pressure at 10° C. The crude material is purified by silica gel flash chromatography (5 to 10% diethyl ether in hexanes) to afford intermediate 1006B.

Step 3: TFA (50.0 mL, 65.2 mmol, 1.11 eq) is added over 20 min to a cold (0° C.) solution of intermediate 1006B (7.65 g, 58.5 mmol) in DCM (150 mL) and the mixture is stirred at RT for 1.5 h. The reaction mixture is concentrated under reduced pressure (without external heating). The crude material is dissolved in DCM, concentrated under reduced pressure (6×) and dried under high vacuum to provide intermediate 1006C.

Synthesis of Compound 1006

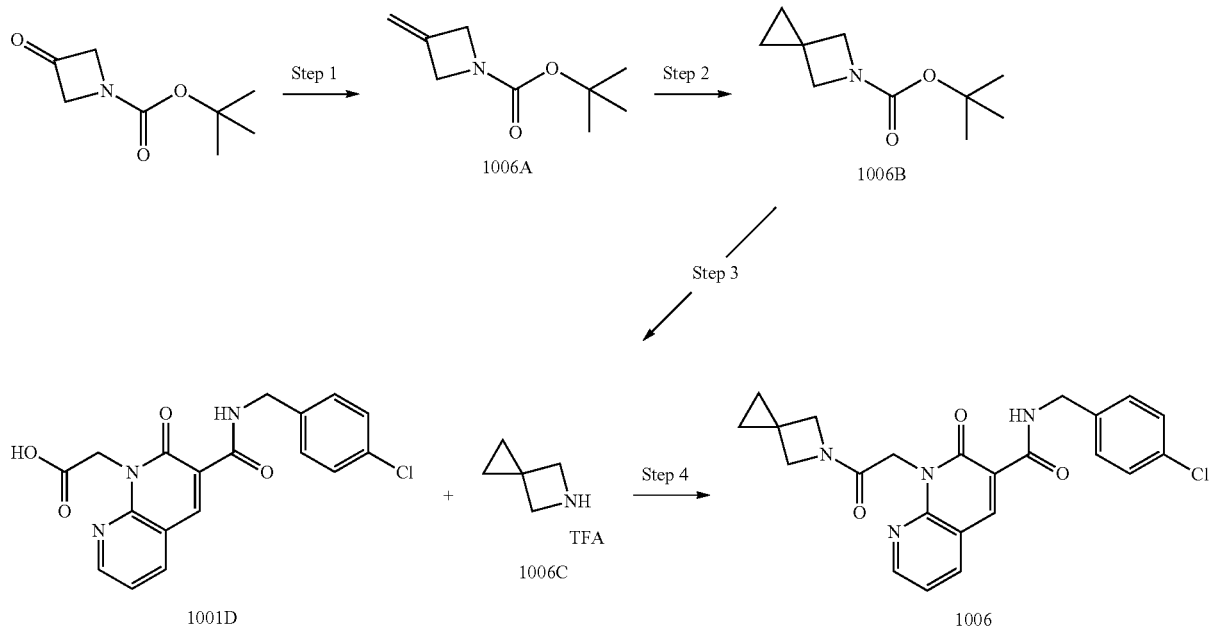

Step 4: Compound 1006 ($t_R$: 1.83, (M+H)$^+$: 437.3/439.2) is prepared analogously to compound 1001, except that in step 5, intermediate 1001D is reacted with intermediate 1006C.

Synthesis of Compound 1007

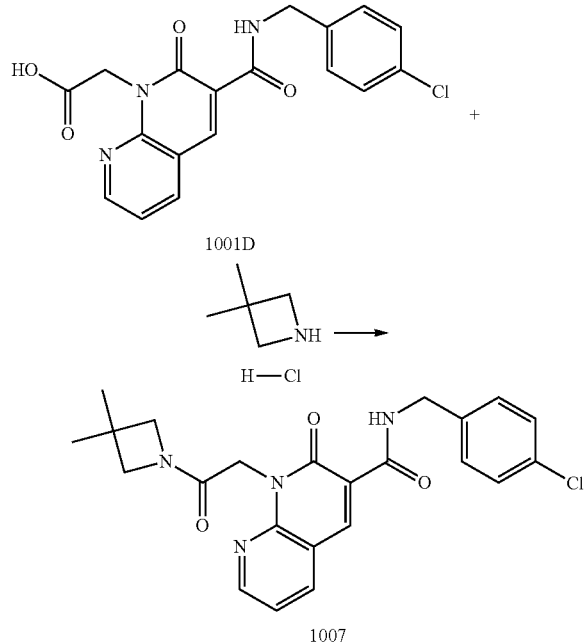

1007

Compound 1007 ($t_R$: 1.93, (M+H)$^+$: 439.2/441.1) is prepared analogously to compound 1001, except that in step 5, intermediate 1001D is reacted with 3,3-dimethyl-azetidine hydrochloride (prepared analogously to the procedure in J. Med. Chem. 2008, 51, 7380, herein incorporated by reference).

Synthesis of Compound 1008

Step 1: 3-(benzyloxy)cyclobutanone (Glsyntech) (300 mg, 1.70 mmol) and N-methylbenzylamine (Aldrich) (207 mg, 1.70 mol, 1.00 eq) are charged in a round-bottom flask and THF (4.0 mL) is added. AcOH (2 drops) is added and the reaction mixture is stirred for 10 min at RT. Sodium triacetoxyborohydride (1.08 g, 5.10 mmol, 3.00 eq) is added. The mixture is stirred for 2 h at RT and diluted with EtOAc. The organic phase is washed with water, saturated aqueous NaHCO$_3$ and brine, dried over Na$_2$SO$_4$, filtered and concentrated under reduced pressure to afford intermediate 1008A.

Step 2: Intermediate 1008A (479 mg, 1.70 mmol) is charged in a round-bottom flask and solubilized in EtOH (10 mL). A 4.00 M HCl solution in dioxane (0.500 mL, 2.00 mmol, 1.17 eq) is added, followed by palladium hydroxide 10% on carbon (100 mg). The mixture is hydrogenated at 1 atm for 48 h at RT. The mixture is filtered through celite and the celite pad is washed with EtOH. The filtrate is concentrated under reduced pressure to provide intermediate 1008B.

Step 3: Compound 1008 ($t_R$: 1.61, (M+H)$^+$: 455.2/457.2) is prepared analogously to compound 1001, except that in step 5, intermediate 1001D is reacted with intermediate 1008B.

Synthesis of Compound 1009

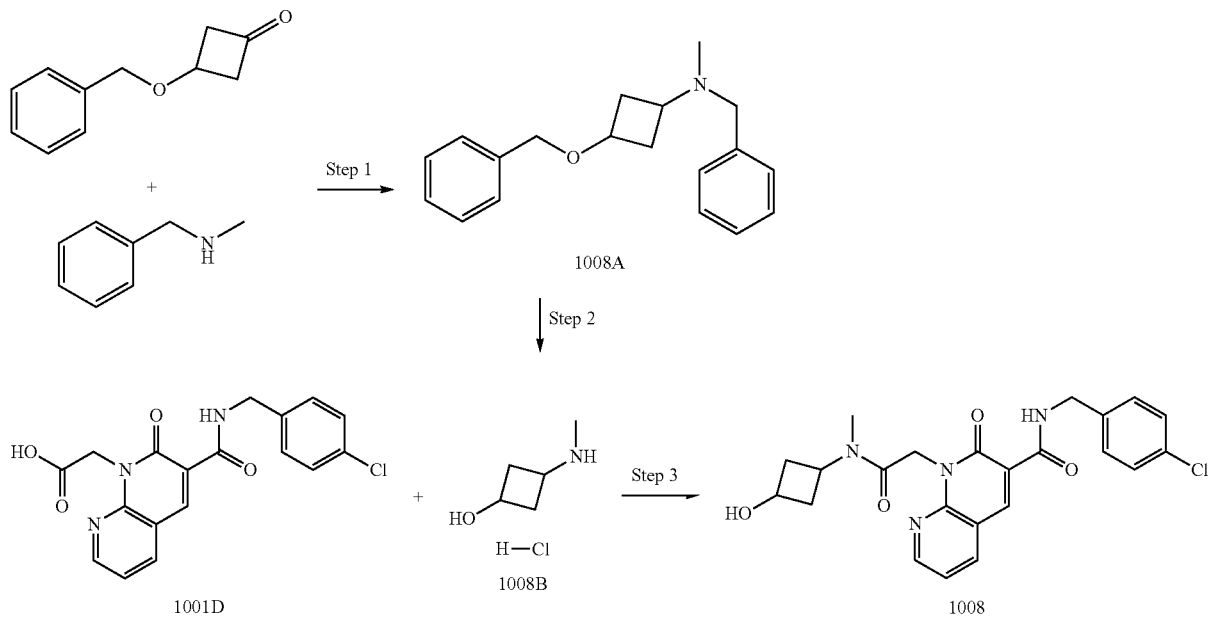

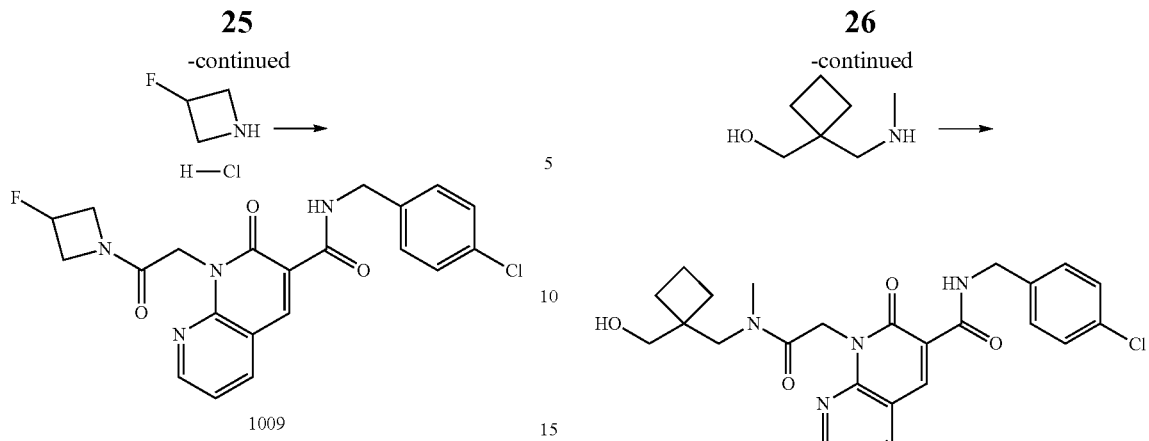

Compound 1009 ($t_R$: 1.65, (M+H)$^+$: 429.2/431.2) is prepared analogously to compound 1001, except that in step 5, intermediate 1001D is reacted with 3-fluoroazetidine hydrochloride (Apollo).

Synthesis of Compound 1010

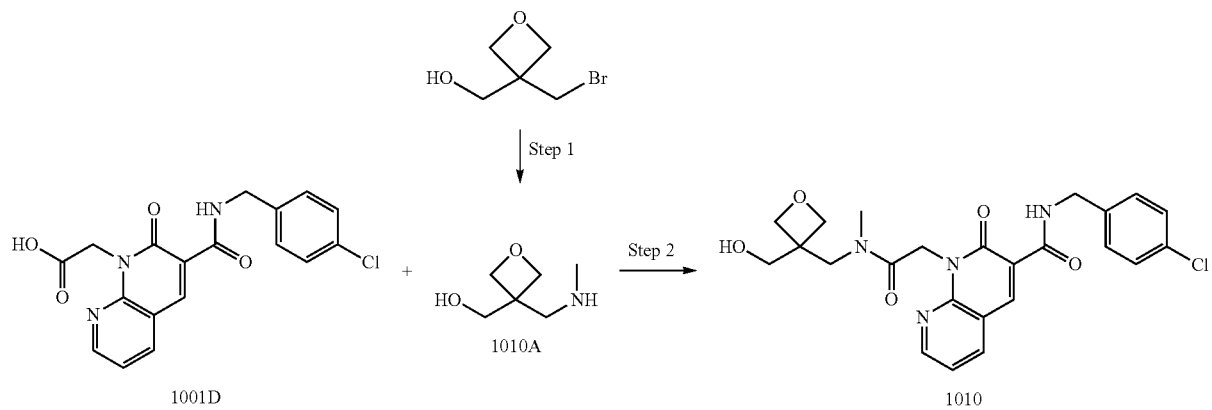

Step 1: 3-Bromomethyl-3-oxetanemethanol (Apollo-Inter) (400 mg, 2.21 mmol) is charged in a pressure vessel and 2.0 M methylamine in THF is added (7.7 mL, 15 mmol, 7.0 eq). The vessel is sealed and heated at 130° C. for 2 h. The mixture is cooled to RT and filtered. The filtrate is concentrated under reduced pressure to provide intermediate 1010A.

Step 2: Compound 1010 ($t_R$: 1.65, (M+H)$^+$: 485.2/487.2) is prepared analogously to compound 1001, except that in step 5, intermediate 1001D is reacted with intermediate 1010A.

Synthesis of Compound 1011

Compound 1011 ($t_R$: 1.8, (M+H)$^+$: 483.3/485.3) is prepared analogously to compound 1001, except that in step 5, intermediate 1001D is reacted with (1-[(methylamino)methyl]cyclobutyl) methanol (Chembrdg-bb).

Synthesis of Compound 1012

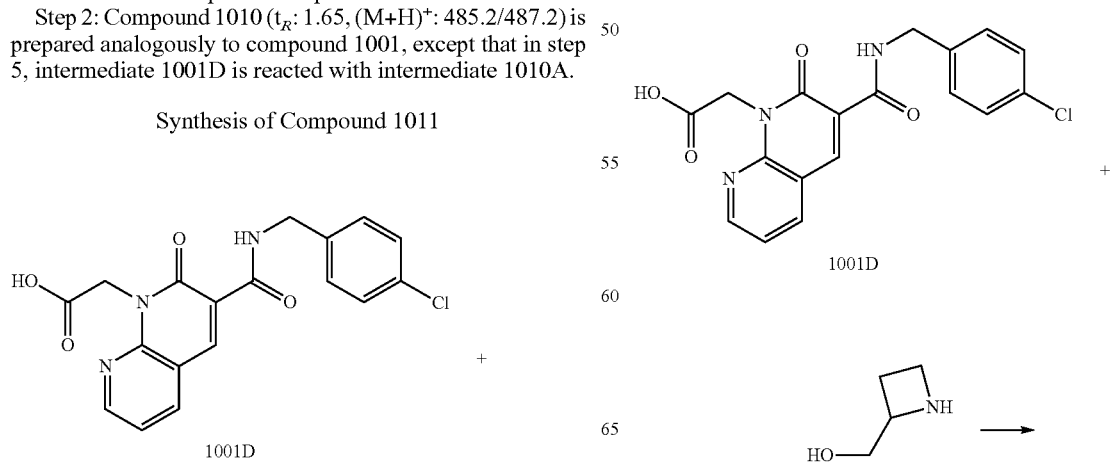

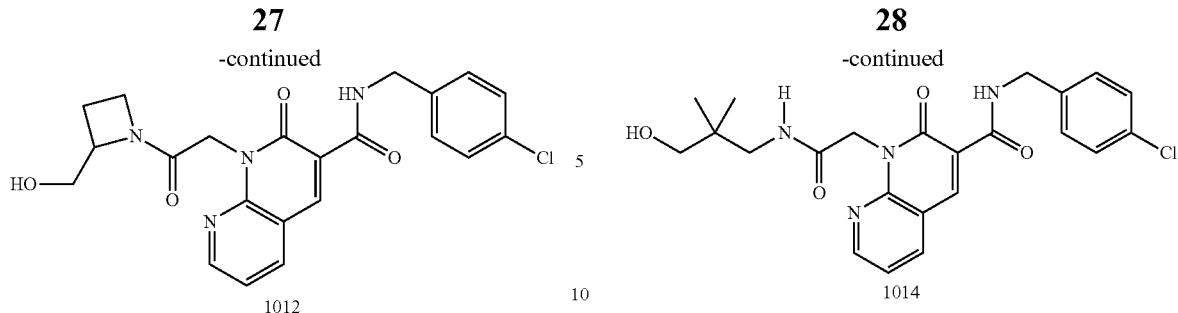

1012

Compound 1012 (t$_R$: 1.61, (M+H)$^+$: 441.2/443.2) is prepared analogously to compound 1001, except that in step 5, intermediate 1001D is reacted with azetidin-2-ylmethanol (Amatek).

Synthesis of Compound 1013

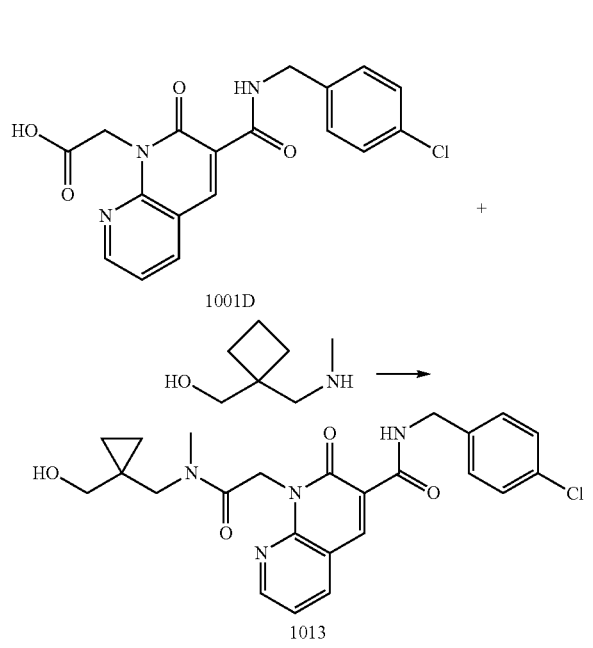

1013

Compound 1013 (t$_R$: 1.79, (M+H)$^+$: 469.3/471.3) is prepared analogously to compound 1001, except that in step 5, intermediate 1001D is reacted with (1-[(methylamino)methyl]cyclopropyl) methanol (Chembrdg-bb).

Synthesis of Compound 1014

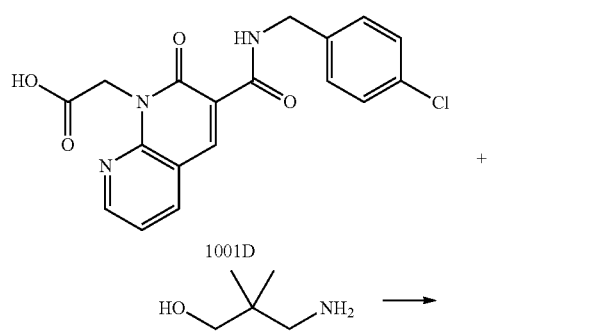

Compound 1014 (t$_R$: 1.8, (M+H)$^+$: 457.1) is prepared analogously to compound 1001, except that in step 5, intermediate 1001D is reacted with 3-amino-2,2-dimethyl-propan-1-ol (TCI-Europe).

Synthesis of Compound 1015

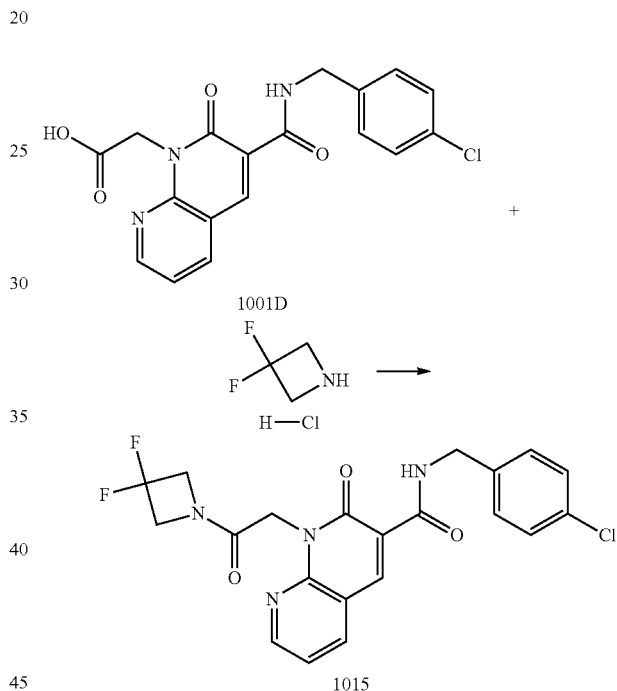

1015

Compound 1015 (t$_R$: 1.94, (M+H)$^+$: 447.2) is prepared analogously to compound 1001, except that in step 5, intermediate 1001D is reacted with 3,3-difluoroazetidine hydrochloride (Matrix).

Synthesis of Compound 1016

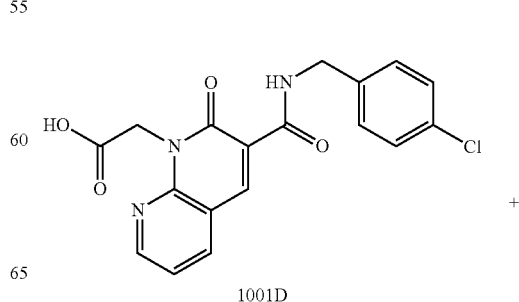

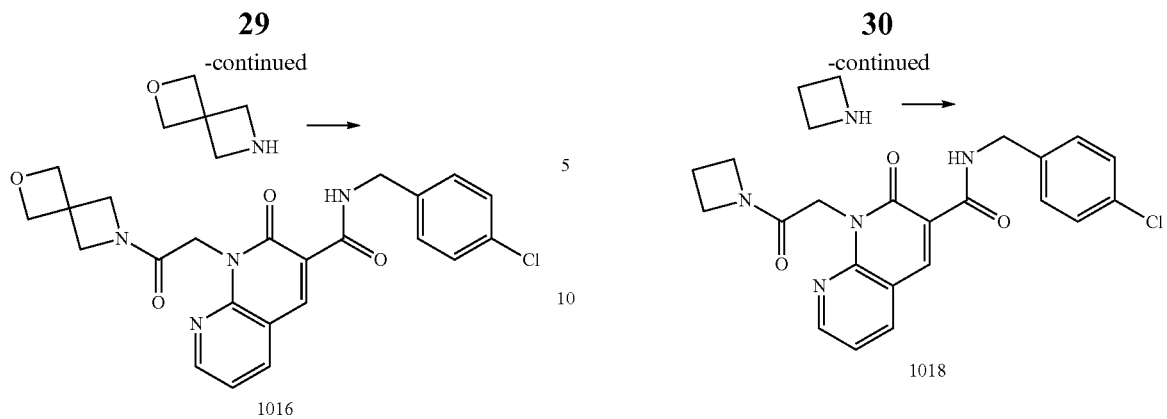

Compound 1016 ($t_R$: 1.6, (M+H)$^+$: 453.2/455.2) is prepared analogously to compound 1001, except that in step 5, intermediate 1001D is reacted with 2-oxa-6-azaspiro[3.3]heptane (Enamine-bb).

Compound 1018 ($t_R$: 1.68, (M+H)$^+$: 411.1/413.1) is prepared analogously to compound 1001, except that in step 5, intermediate 1001D is reacted with azetidine (Apollo-Inter).

Synthesis of Compound 1017

Synthesis of Compound 1019

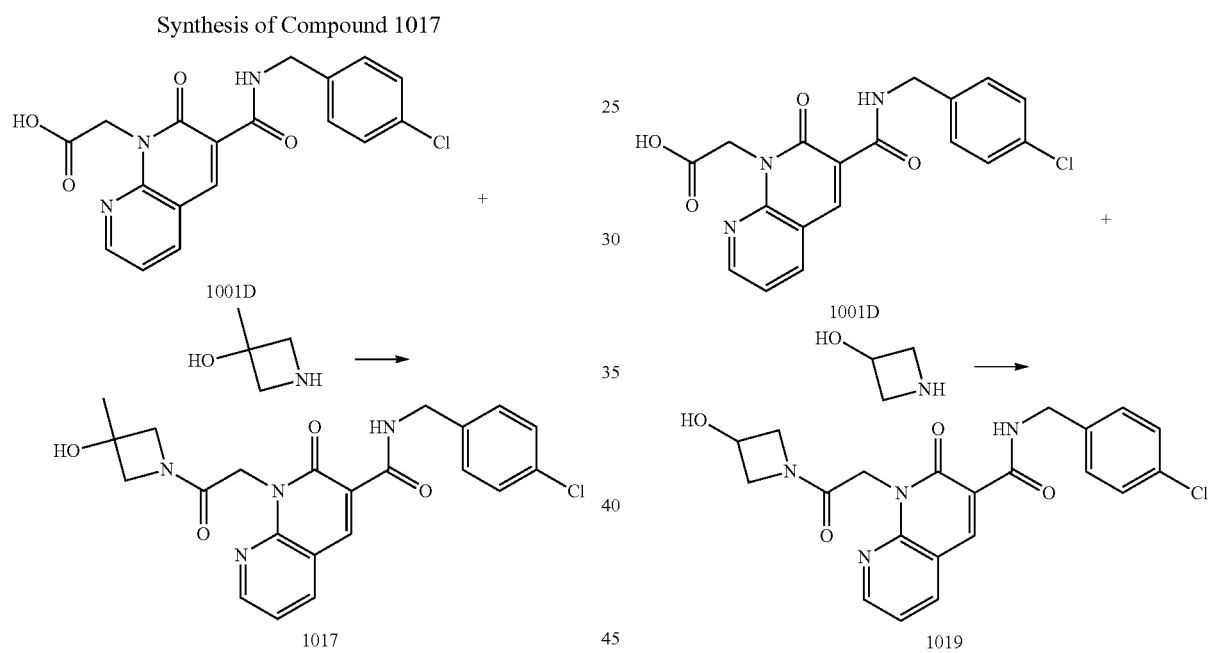

Compound 1017 ($t_R$: 1.68, (M+H)$^+$: 441.2/443.1) is prepared analogously to compound 1001, except that in step 5, intermediate 1001D is reacted with 3-methyl-azetidin-3-ol (Parkway).

Compound 1019 ($t_R$: 1.55, (M+H)$^+$: 427.2/429.1) is prepared analogously to compound 1001, except that in step 5, intermediate 1001D is reacted with 3-azetidinol (Chembrdg-bb).

Synthesis of Compound 1018

Synthesis of Compound 1020

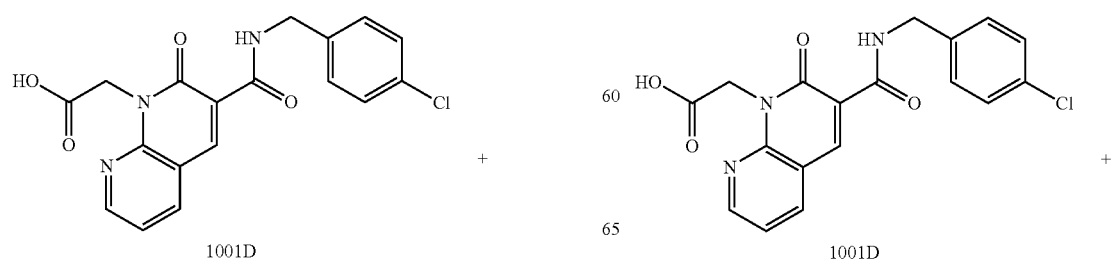

Compound 1020 ($t_R$: 1.66, (M+H)$^+$: 479.3/481.2) is prepared analogously to compound 1001, except that in step 5, intermediate 1001D is reacted with 2,2-difluoro-3-(methylamino)propan-1-ol (prepared analogously to the procedure described in US2009/137618, herein incorporated by reference).

Synthesis of Compound 1021

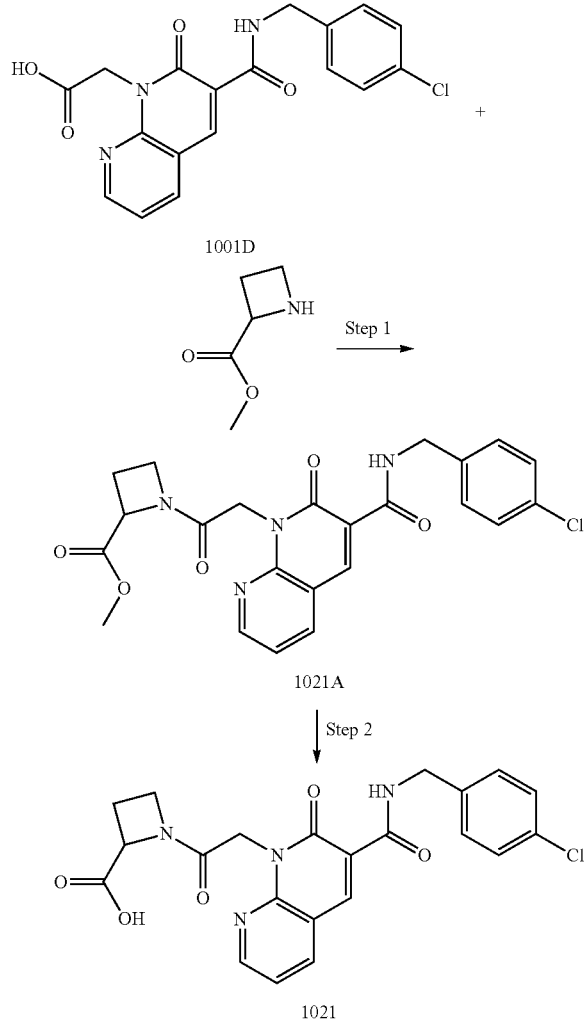

Step 1: Intermediate 1001D (1.50 g, 4.04 mmol) is charged in a round-bottom flask and dissolved in DMF (10.0 mL). Diisopropylethylamine (1.74 mL, 10.0 mmol, 2.48 eq) and azetidine-2-carboxylic acid methyl ester (Chem-Impex) (560 mg, 4.88 mmol, 1.21 eq) are added followed by HATU (1.79 g, 4.70 mmol, 1.16 eq) and the solution is stirred at RT for 20 h. The reaction mixture is diluted with EtOAc and washed with 0.5 N HCl solution. The organic layer is dried over MgSO$_4$, filtered and concentrated under reduced pressure to provide intermediate 1021A.

Step 2: Intermediate 1021A (1.89 g, 4.04 mmol) is charged in a round-bottom flask and suspended in THF (10 mL). MeOH (10 mL) and NaOH 2.5 N (3.20 mL, 8.00 mmol, 2.00 eq) are added and the solution is stirred at RT for 2 h. The reaction mixture is partially concentrated and acidified with a 1 N HCl solution. EtOAc is added to the mixture and the phases are separated. The organic layer is dried over MgSO$_4$, filtered and concentrated. The residue is purified by preparative HPLC to provide compound 1021 ($t_R$: 1.35, (M+H)$^+$: 455.1/457.0).

Synthesis of Compound 1022

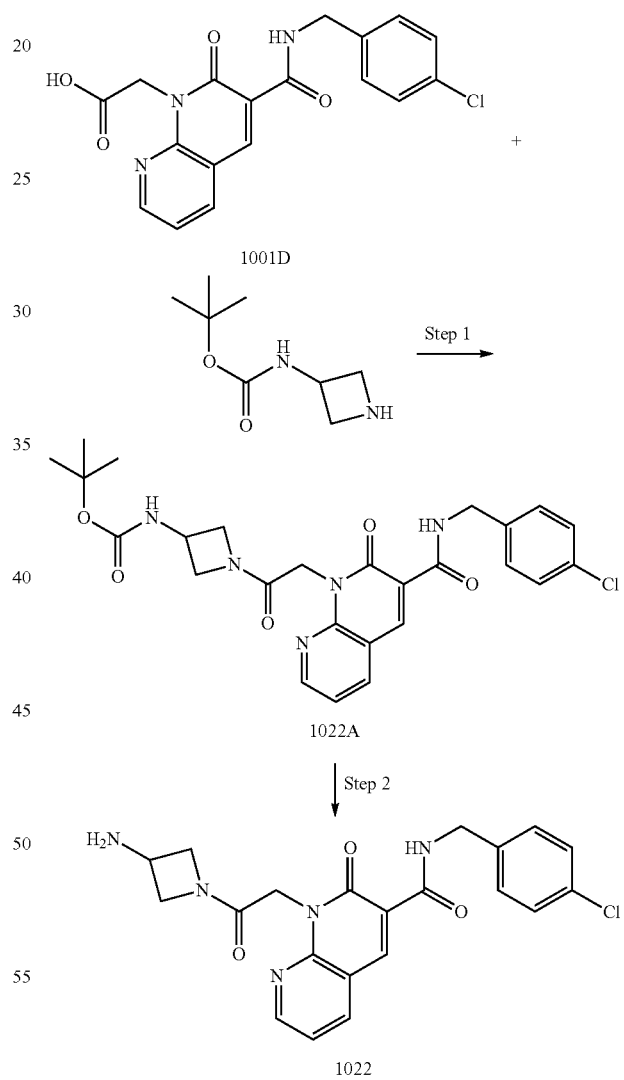

Step 1: Intermediate 1022A is prepared analogously to compound 1001, except that in step 5, intermediate 1001D is reacted with 3-N-boc-amino-azetidine (Betapharma).

Step 2: Intermediate 1022A (75 mg, 0.14 mmol) is charged in a round-bottom flask and a 4 M HCl solution in dioxane (3.0 mL) is added. The solution is stirred at RT for 1 h and concentrated. The residue is purified by preparative HPLC to provide compound 1022 ($t_R$: 1.52, (M+H)$^+$: 426.1/428.1).

Synthesis of Compound 1023

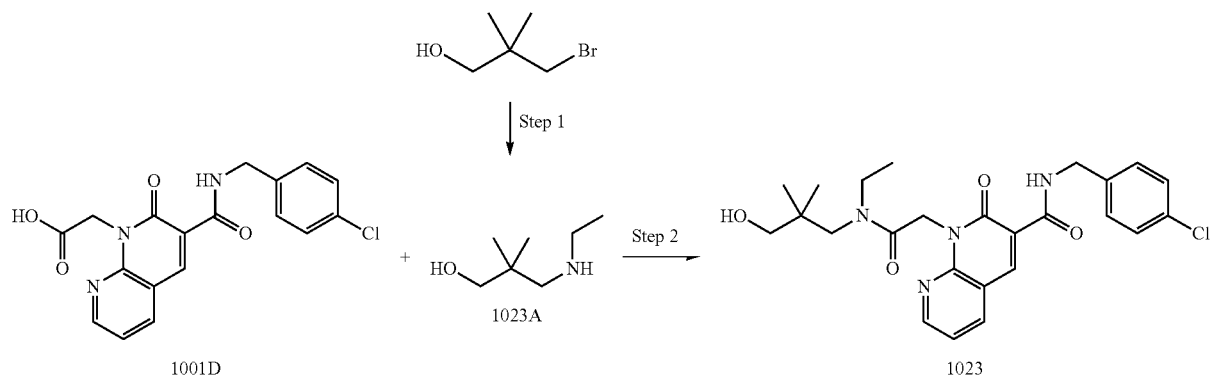

Step 1: 3-Bromo-2,2-dimethyl-1-propanol (Aldrich) (167 mg, 1.00 mmol) is charged in a pressure vessel and 2.0 M ethylamine in THF is added (3.5 mL, 7.0 mmol, 7.0 eq). The vessel is sealed and heated at 180° C. for 3 h. The mixture is cooled to RT and concentrated under reduced pressure. The residue is suspended in MeCN and concentrated under reduced pressure to provide intermediate 1023A.

Step 2: Compound 1023 ($t_R$: 1.9, (M+H)$^+$: 485.3/487.3) is prepared analogously to compound 1001, except that in step 5, intermediate 1001D is reacted with intermediate 1023A.

Synthesis of Compound 1024

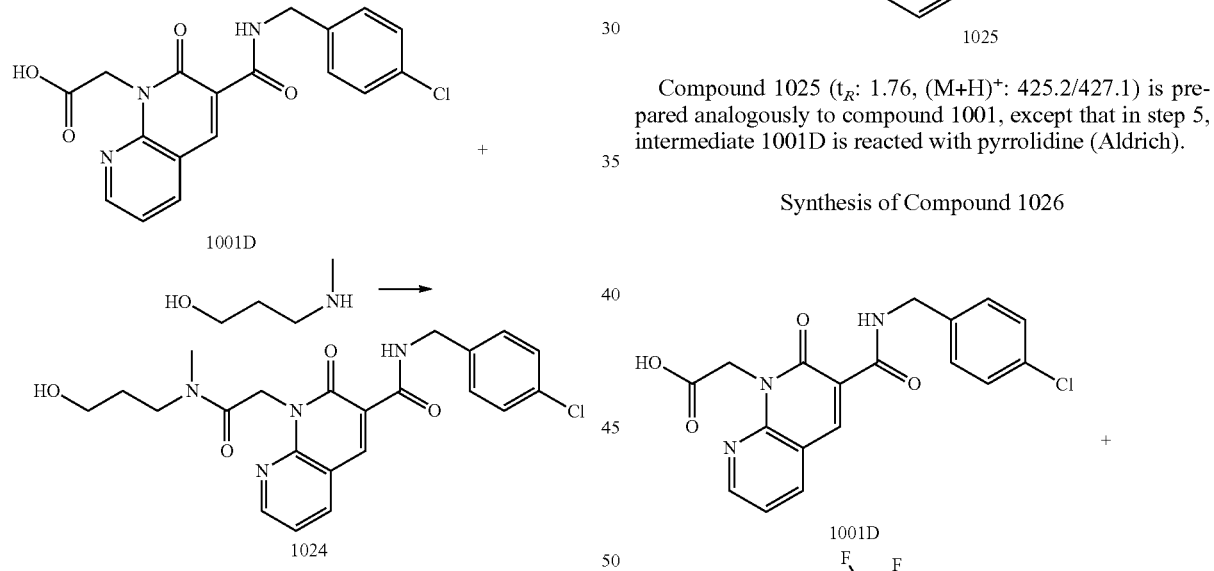

Compound 1024 ($t_R$: 1.62, (M+H)$^+$: 443.2/445.1) is prepared analogously to compound 1001, except that in step 5, intermediate 1001D is reacted with 3-(methylamino)-1-propanol (TCI-US).

Synthesis of Compound 1025

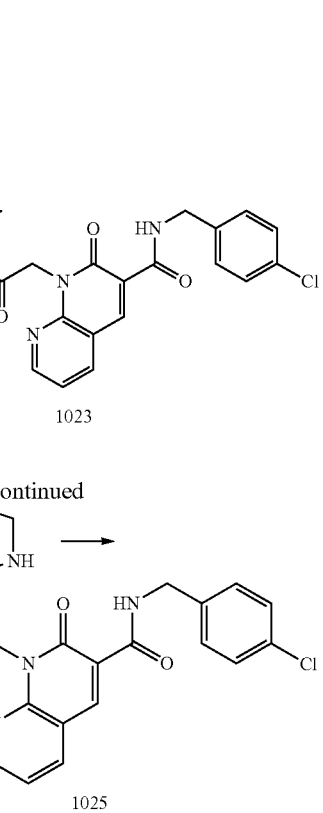

Compound 1025 ($t_R$: 1.76, (M+H)$^+$: 425.2/427.1) is prepared analogously to compound 1001, except that in step 5, intermediate 1001D is reacted with pyrrolidine (Aldrich).

Synthesis of Compound 1026

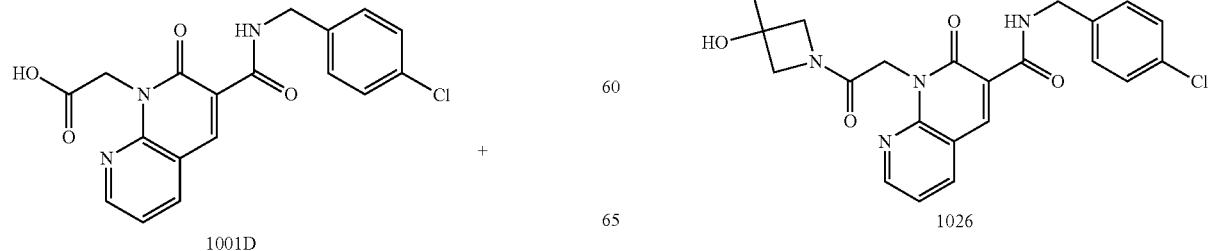

Compound 1026 ($t_R$: 1.74, (M+H)+: 495/497) is prepared analogously to compound 1001, except that in step 5, intermediate 1001D is reacted with 3-(trifluoromethyl)azetidin-3-ol (Enamine-bb).
Synthesis of Compound 1027
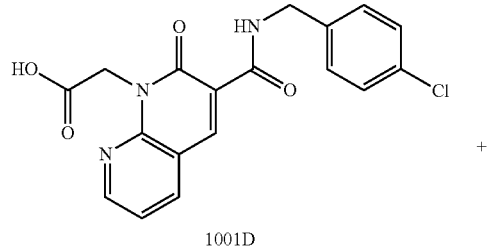
1001D
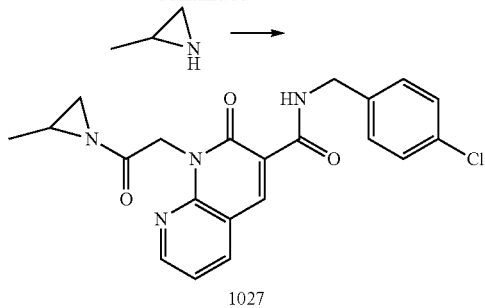
1027
Compound 1027 ($t_R$: 1.83, (M+H)+: 411.1/413.1) is prepared analogously to compound 1001, except that in step 5, intermediate 1001D is reacted with 2-methylaziridine (Aldrich).
Synthesis of Compound 1028
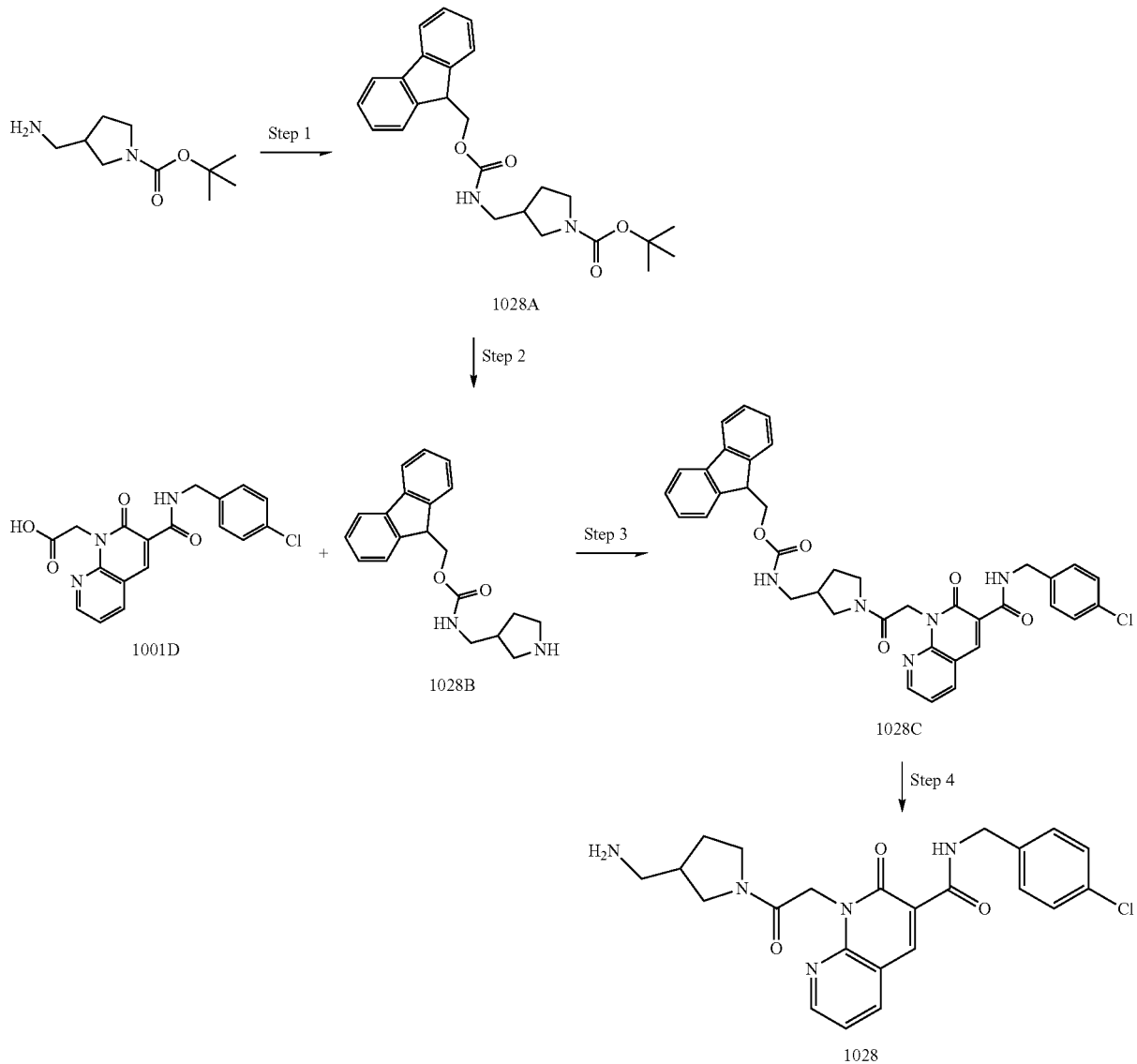

Step 1: 3-(Aminomethyl)-1-N-boc-pyrrolidine (Astatech) (500 mg, 2.50 mmol) and pyridine (494 mg, 6.24 mmol, 2.50 eq) are charged in a round-bottom flask and dissolved in THF (70 mL). 9-Fluorenylmethyloxycarbonyl chloride (1.29 g, 5.00 mmol, 2 eq) is added and the solution is stirred at RT for 16 h. The reaction mixture is diluted with EtOAc and washed with water. The organic layer is dried over Na$_2$SO$_4$, filtered and concentrated under reduced pressure. The residue is purified by flash column chromatography (100% hexanes to 100% EtOAc) to provide intermediate 1028A.

Step 2: Intermediate 1028A (468 mg, 1.11 mmol) is charged in a round-bottom flask and dissolved in TFA (5.00 mL). The solution is stirred at RT for 1 h and concentrated to afford intermediate 1028B.

Step 3: Intermediate 1028C is prepared analogously to compound 1001, except that in step 5, intermediate 1001D is reacted with intermediate 1028B.

Step 4: Intermediate 1028C (349 mg, 0.516 mmol) is charged in a round-bottom flask and dissolved in DCM (5.00 mL). Piperidine (77 µL, 0.77 mmol, 1.5 eq) is added and the solution is stirred at RT for 16 h. The reaction mixture is concentrated under reduced pressure and the residue is purified by preparative HPLC to provide compound 1028 (t$_R$: 0.85, 0.89, (M+H)$^+$: 454.1/456.1).

Synthesis of Compound 1029

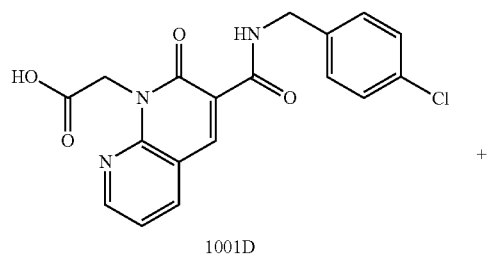

Compound 1029 (t$_R$: 1.67, (M+H)$^+$: 469.1/471.2) is prepared analogously to compound 1021, except that in step 1, intermediate 1001D is reacted with methyl-prolinate (ABCR).

Synthesis of Compound 1030

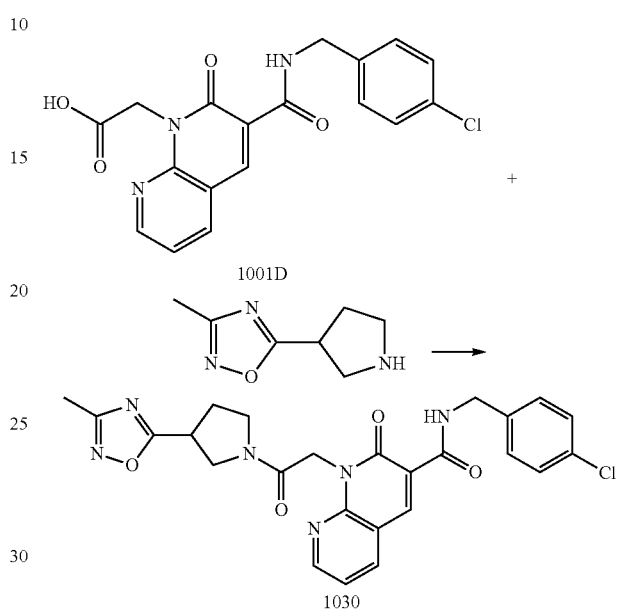

Compound 1030 (t$_R$: 1.72, (M+H)$^+$: 507.2/509.2) is prepared analogously to compound 1001, except that in step 5, intermediate 1001D is reacted with 1,2,4-oxadiazole-3-methyl-5-(3-pyrrolidinyl) (Princeton).

Synthesis of Compound 1031

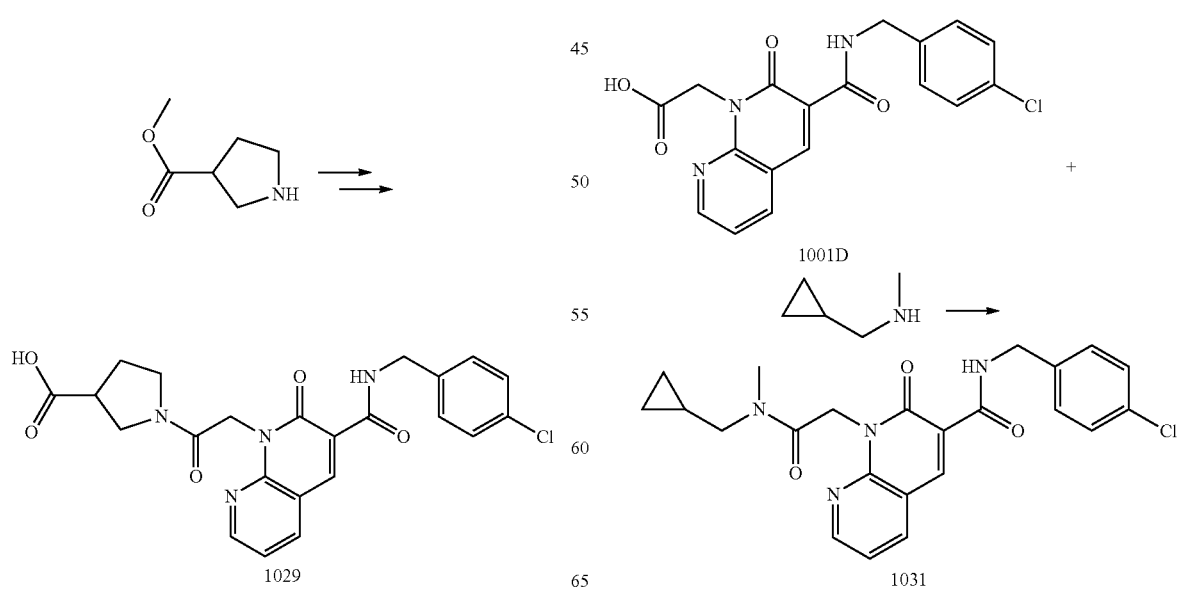

Compound 1031 (t$_R$: 1.94, (M+H)$^+$: 439.2/441.2) is prepared analogously to compound 1001, except that in step 5, intermediate 1001D is reacted with (cyclopropylmethyl)(methyl)amine (Enamine-bb).

Synthesis of Compound 1032

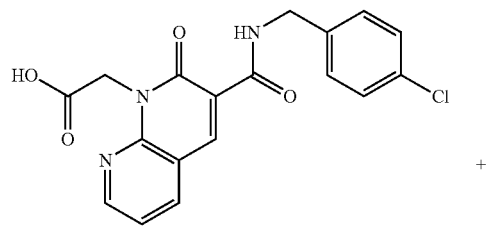

1001D

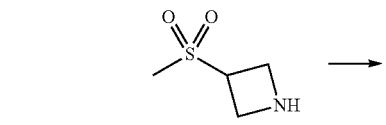

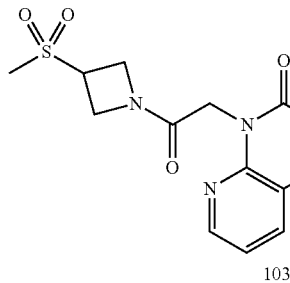

1032

Compound 1032 (t$_R$: 1.52, (M+H)$^+$: 489.0/491.0) is prepared analogously to compound 1001, except that in step 5, intermediate 1001D is reacted with 3-methylsulfonyl-azetidine (Paradigm).

Synthesis of Compound 1033

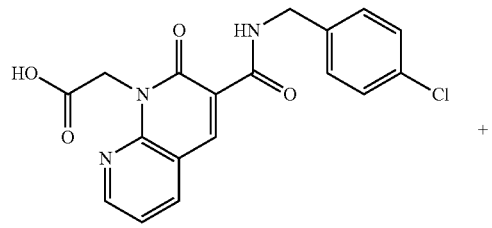

1001D

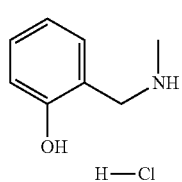

H—Cl

-continued

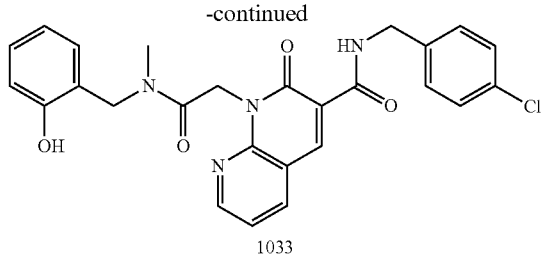

1033

Compound 1033 (t$_R$: 1.86, (M+H)$^+$: 491.2/493.1) is prepared analogously to compound 1001, except that in step 5, intermediate 1001D is reacted with 2-hydroxy-N-methylbenzylamine hydrochloride (TCI-US).

Synthesis of Compound 1034

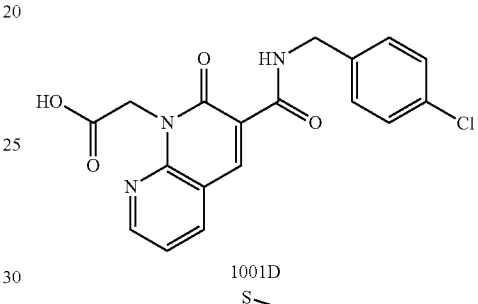

1001D

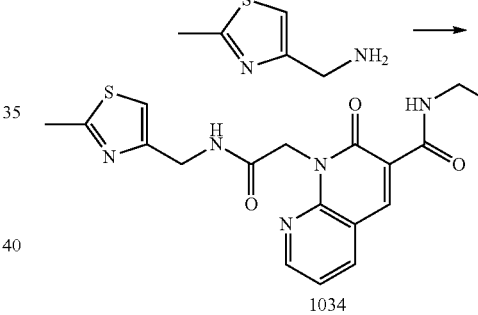

1034

Compound 1034 (t$_R$: 1.81, (M+H)$^+$: 482) is prepared analogously to compound 1001, except that in step 5, intermediate 1001D is reacted with (2-methyl-1,3-thiazol-4-yl)methylamine (Apollo-Inter).

Synthesis of Compound 1035

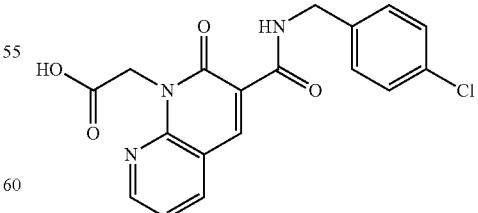

1001D

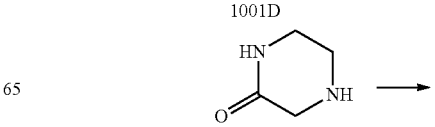

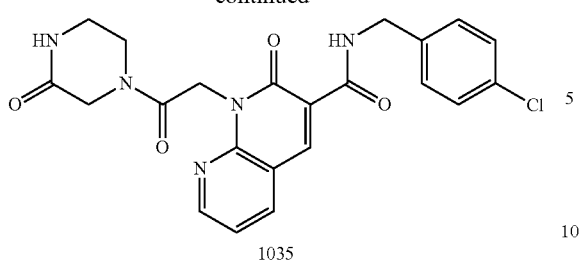
1035

Compound 1035 (t$_R$: 1.54, (M+H)$^+$: 454.2) is prepared analogously to compound 1001, except that in step 5, intermediate 1001D is reacted with 2-oxopiperzaine (Aldrich).

Synthesis of Compound 1036

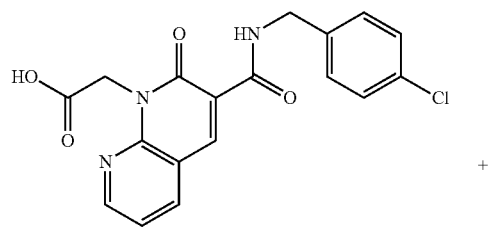
1001D

+

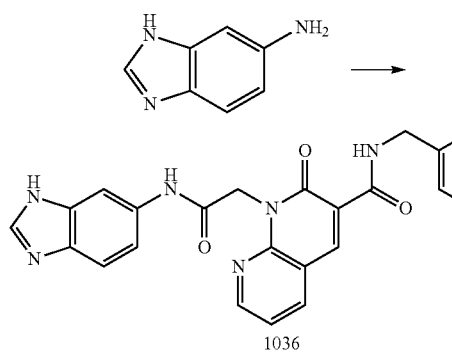
1036

Compound 1036 (t$_R$: 1.65, (M+H)$^+$: 487.2) is prepared analogously to compound 1001, except that in step 5, intermediate 1001D is reacted with 5-aminobenzimidazole (Oakwood).

Synthesis of Compound 1037

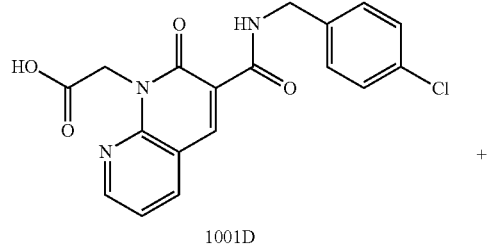
1001D

+

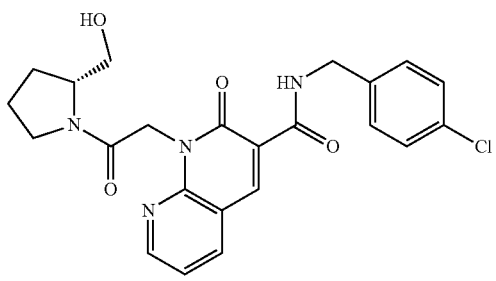
1037

Compound 1037 (t$_R$: 1.68, (M+H)$^+$: 455.2/457.1) is prepared analogously to compound 1001, except that in step 5, intermediate 1001D is reacted with (R)-(−)-2-pyrrolidinemethanol (Aldrich).

Synthesis of Compound 1038

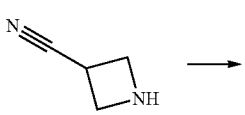

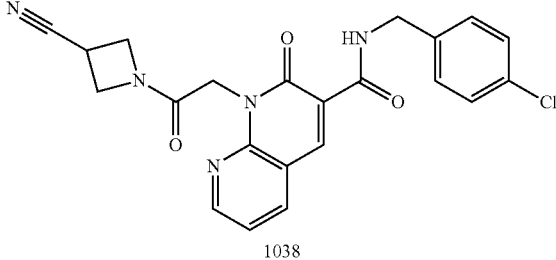
1038

Compound 1038 ($t_R$: 1.66, (M+H)$^+$: 436.1) is prepared analogously to compound 1001, except that in step 5, intermediate 1001D is reacted with azetidine-3-carbonitrile hydrochloride (Fluorochem).

Synthesis of Compound 1039

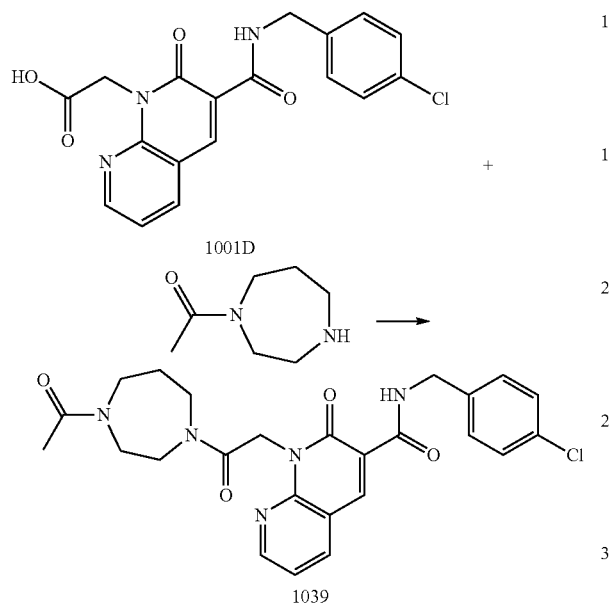

Compound 1039 ($t_R$: 1.68, (M+H)$^+$: 496.1) is prepared analogously to compound 1001, except that in step 5, intermediate 1001D is reacted with N-acetylhomopiperazine (Fluka).

Synthesis of Compound 1040

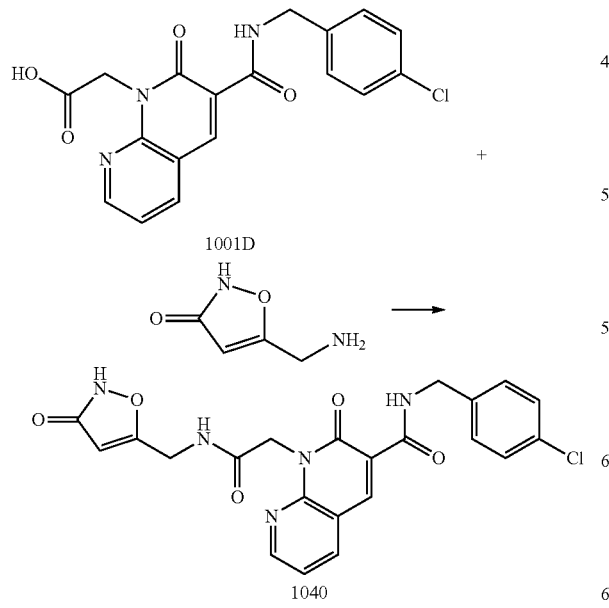

Compound 1040 ($t_R$: 1.44, (M+H)$^+$: 468.1/470.1) is prepared analogously to compound 1001, except that in step 5, intermediate 1001D is reacted with muscimol (Chem-Impex).

Synthesis of Compound 1041

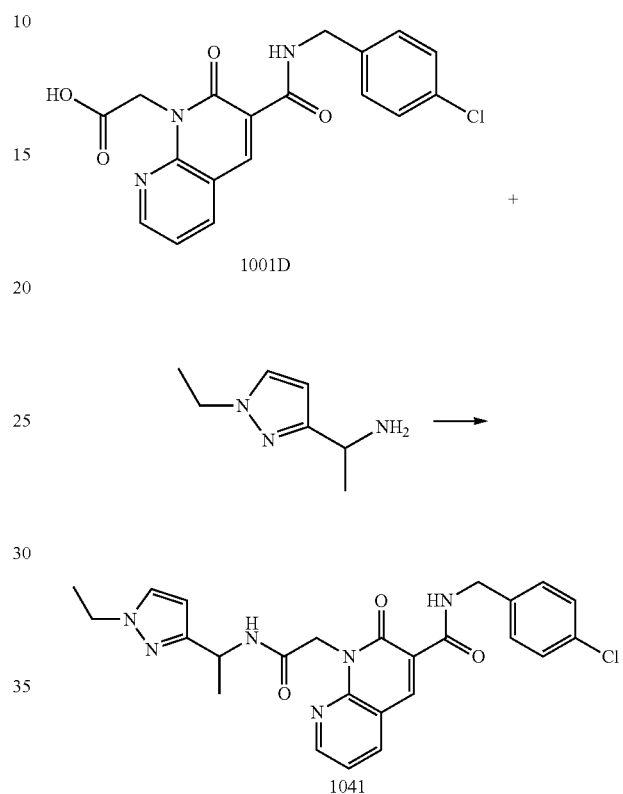

Compound 1041 ($t_R$: 1.81, (M+H)$^+$: 493.1) is prepared analogously to compound 1001, except that in step 5, intermediate 1001D is reacted with 1-(1-ethyl-1H-pyrazol-3-yl)-ethylamine (Akos).

Synthesis of Compound 1042

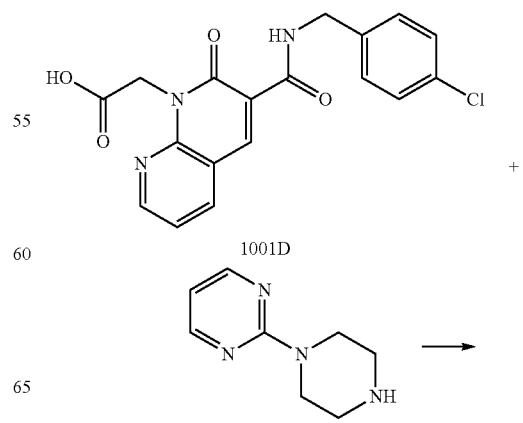

-continued

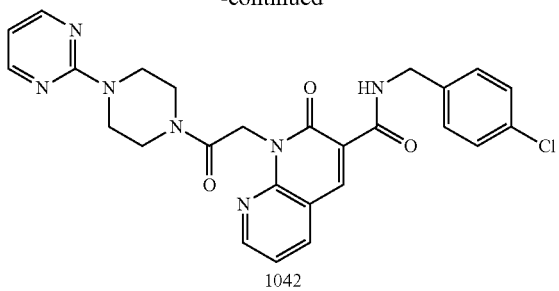

1042

Compound 1042 ($t_R$: 1.93, (M+H)$^+$: 518.1) is prepared analogously to compound 1001, except that in step 5, intermediate 1001D is reacted with 2-(1-piperazinyl)pyrimidine (Acros).

Synthesis of Compound 1043

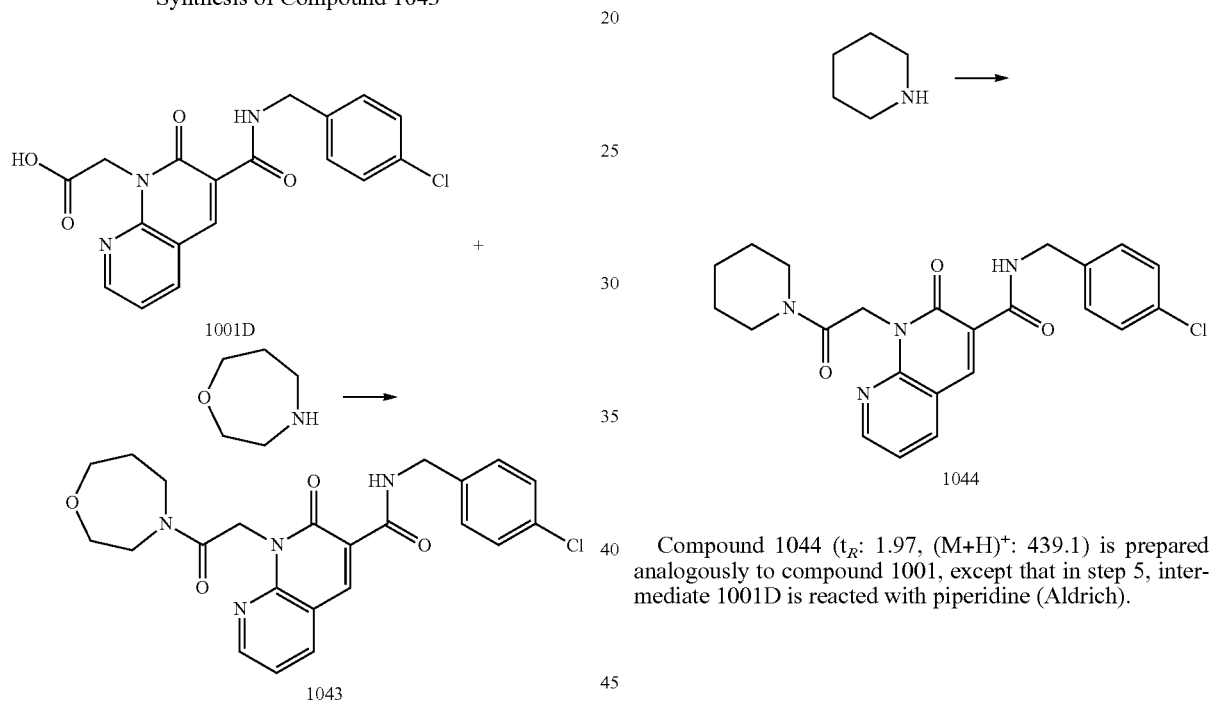

1043

Compound 1043 ($t_R$: 1.8, (M+H)$^+$: 455.1) is prepared analogously to compound 1001, except that in step 5, intermediate 1001D is reacted with 1,4-oxazepane (Oakwood).

Synthesis of Compound 1044

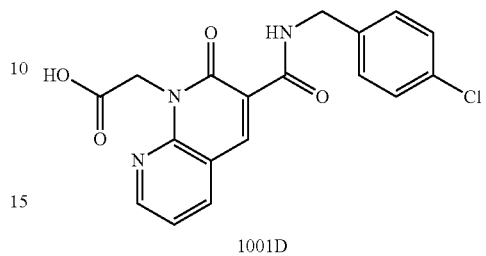

1044

Compound 1044 ($t_R$: 1.97, (M+H)$^+$: 439.1) is prepared analogously to compound 1001, except that in step 5, intermediate 1001D is reacted with piperidine (Aldrich).

Synthesis of Compound 2001

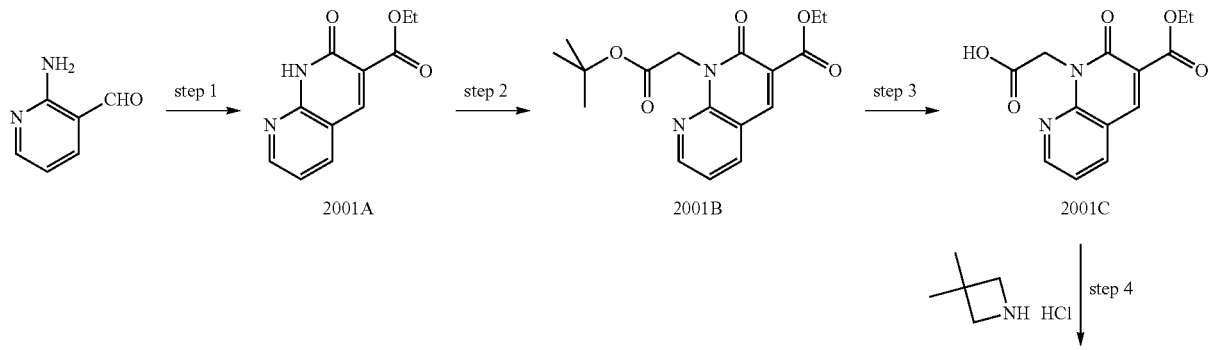

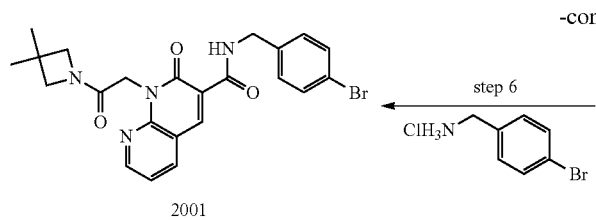

2001

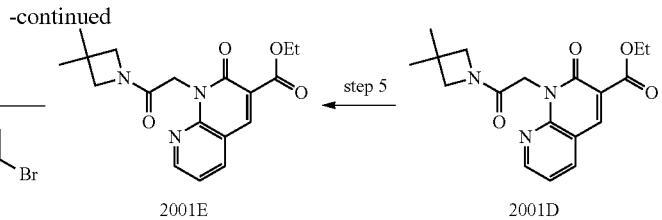

2001E  2001D

Step 1: 2-aminopyridine-3-carboxaldehyde (Aldrich) (6.00 g, 49.1 mmol) and diethylmalonate (9.44 g, 58.9 mmol, 1.20 eq) are charged in a microwave vial and EtOH (60 mL) is added. Piperidine (12.2 mL, 122 mmol, 2.50 eq) is added and vial is sealed and warmed in a microwave oven at 120° C. for 20 min. The cooled solution is diluted with $Et_2O$ and sonicated. The resulting solid is filtered and dried under vacuum to afford intermediate 2001A.

Step 2: Intermediate 2001A (3.00 g, 13.7 mmol) is charged in a round-bottom flask and suspended in DMF (20 mL). Potassium carbonate (5.76 g, 41.7 mmol, 3.03 eq) and tert-butyl bromoacetate (TCI) (2.34 mL, 15.8 mmol, 1.15 eq) are added and the solution is stirred at RT for 3 h. The solution is added to water and the resulting solid is filtered and dried under vacuum. The solid is purified by trituration in EtOAc to afford intermediate 2001B.

Step 3: TFA (8.0 mL) is added to a solution of intermediate 2001B (3.00 g, 9.03 mmol) dissolved in DCM (20 mL) in a round-bottom flask and the reaction mixture is stirred at RT for 5 h. The solution is concentrated under reduced pressure to provide intermediate 2001C.

Step 4: Intermediate 2001C (1.00 g, 3.62 mmol) is dissolved in DMF (18.0 mL) in a round-bottom flask, then diisopropylethylamine (3.15 mL, 18.1 mmol, 5.00 eq) and 3,3-dimethyl-azetidine hydrochloride (prepared analogously to the procedure in J. Med. Chem. 2008, 51, 7380, herein incorporated by reference) (385 mg, 4.52 mmol, 1.25 eq) are added followed by HATU (2.06 g, 5.43 mmol, 1.50 eq). The mixture is stirred at RT for 1 h, diluted with EtOAc and washed with brine (3×). The organic layer is dried over $MgSO_4$, filtered and concentrated under reduced pressure to provide intermediate 2001D.

Step 5: Intermediate 2001D (417 mg, 1.21 mmol) is dissolved in THF (8.0 mL) and MeOH (2.0 mL) in a round-bottom flask, then a 2.5 M aqueous solution of lithium hydroxide (0.93 mL, 2.32 mmol, 1.50 eq) is added and the reaction mixture is stirred at RT for 3 h. The reaction mixture is acidified to approximately pH 2 using a 1 M aqueous HCl solution. The solution is extracted with EtOAc. The organic layer is dried over $MgSO_4$, filtered and concentrated under reduced pressure to provide intermediate 2001E.

Step 6: Intermediate 2001E (57 mg, 0.18 mmol) is dissolved in DMF (2.0 mL), then diisopropylethylamine (160 µL, 0.90 mmol, 5.0 eq) and 4-bromobenzylamine hydrochloride (Aldrich) (60 mg, 0.27 mmol, 1.5 eq) are added followed by HATU (100 mg, 0.27 mmol, 1.5 eq) and the reaction mixture is stirred at RT for 2 h. The solution is filtered and purified by preparative HPLC to provide compound 2001 ($t_R$: 1.97, $(M+H)^+$: 483.0/485.0).

Synthesis of Compound 2002

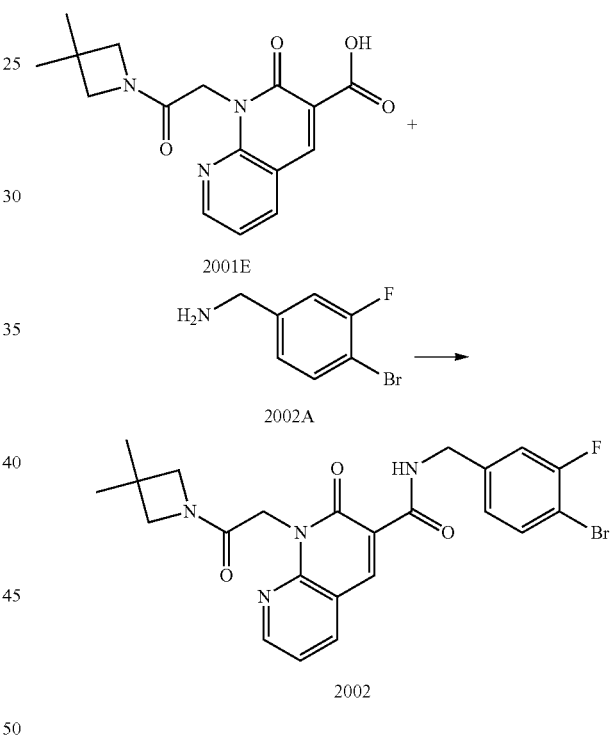

Compound 2002 ($t_R$: 1.97, $(M+H)^+$: 501.2/503.1) is prepared analogously to compound 2001, except that in step 6, intermediate 2001E is reacted with intermediate 2002A.

Synthesis of Intermediate 2002A 4-bromo-3-fluorobenzonitrile (Combi-Blocks) (1.00 g, 5.00 mmol) is charged in a round-bottom flask and dissolved in THF (25 mL). The solution is cooled in an ice bath (0° C.). A 10 M solution of borane-dimethylsulfide complex (2.00 mL, 20.0 mmol, 4.00 eq) is added over 5 min. The ice bath is removed after the addition and the solution is heated at reflux for 1.5 h. Following completion of the reaction, the solution is cooled in an ice bath (0° C.) and MeOH (5 mL) is added. The solution is concentrated under reduced pressure, dissolved in EtOAc and filtered. The filtrate is concentrated under reduced pressure to provide intermediate 2002A.

Synthesis of Compound 2003

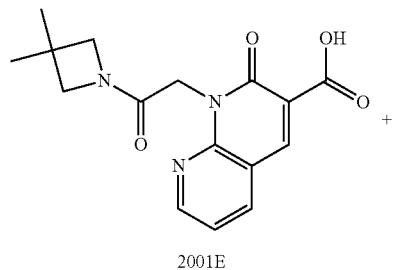

2001E

+

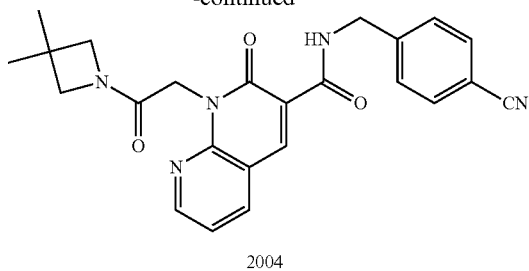

2004

Compound 2004 ($t_R$: 1.66, (M+H)$^+$: 430.2) is prepared analogously to compound 2001, except that in step 6, intermediate 2001E is reacted with 4-cyanobenzylamine (Matrix).

Synthesis of Compound 2005

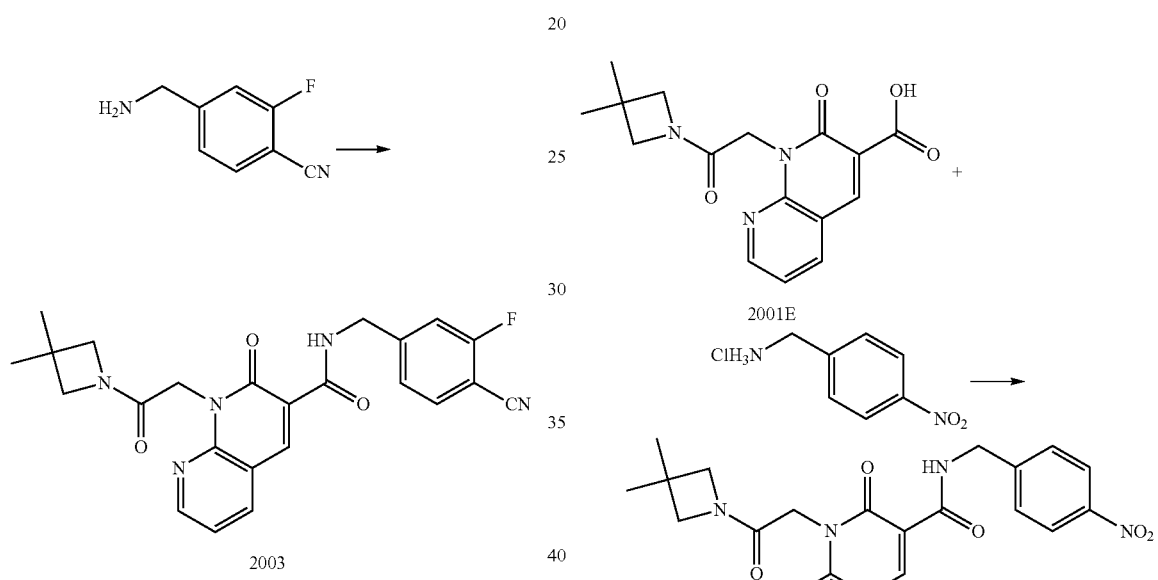

2003

Compound 2003 ($t_R$: 1.73, (M+H)$^+$: 446.3) is prepared analogously to compound 2001, except that in step 6, intermediate 2001E is reacted with 4-(aminomethyl)-2-fluorobenzonitrile (JW Pharlab).

Synthesis of Compound 2004

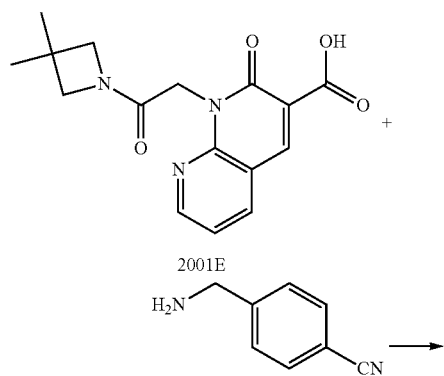

Compound 2005 ($t_R$: 1.79, (M+H)$^+$: 450.2) is prepared analogously to compound 2001, except that in step 6, intermediate 2001E is reacted with 4-nitrobenzylamine hydrochloride (Aldrich).

Synthesis of Compound 2006

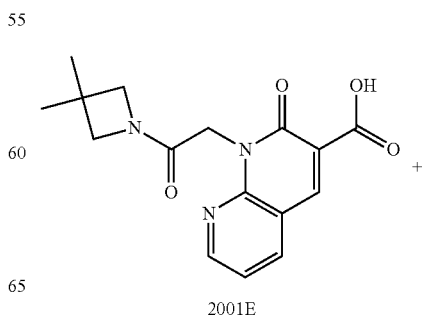

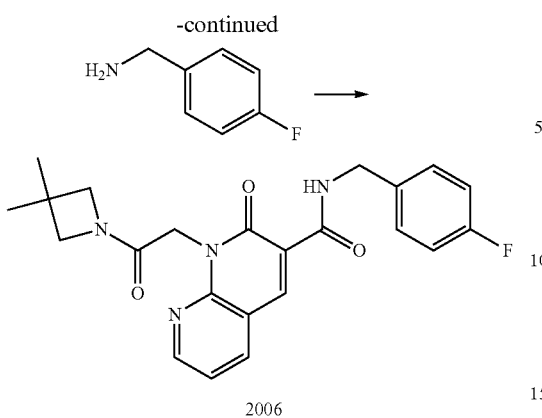

2006

Compound 2006 ($t_R$: 1.78, (M+H)⁺: 423.3) is prepared analogously to compound 2001, except that in step 6, intermediate 2001E is reacted with 4-fluorobenzylamine (Aldrich).

Synthesis of Compound 2007

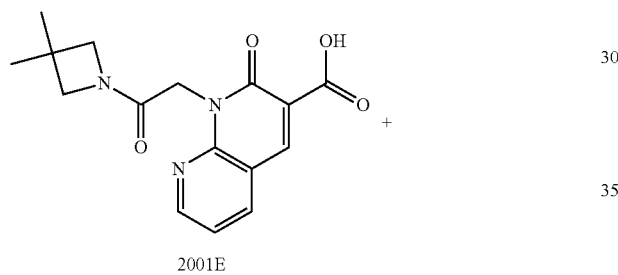

2001E

2007

Compound 2007 ($t_R$: 2.07, (M+H)⁺: 473.1/475.1/477.1) is prepared analogously to compound 2001, except that in step 6, intermediate 2001E is reacted with 2,4-dichlorobenzylamine (Aldrich).

Synthesis of Compound 2008

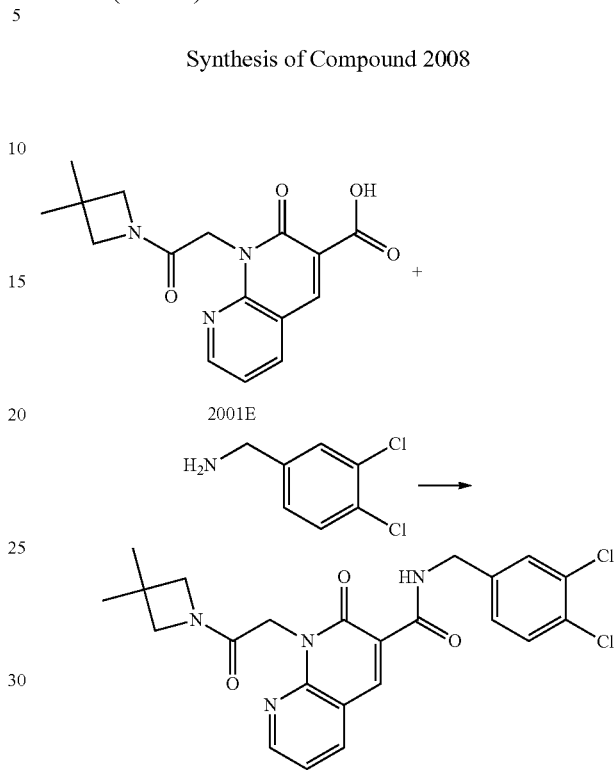

2001E

2008

Compound 2008 ($t_R$: 2.03, (M+H)⁺: 473.1/475.1/477.0) is prepared analogously to compound 2001, except that in step 6, intermediate 2001E is reacted with 3,4-dichlorobenzylamine (Aldrich).

Synthesis of Compound 2009

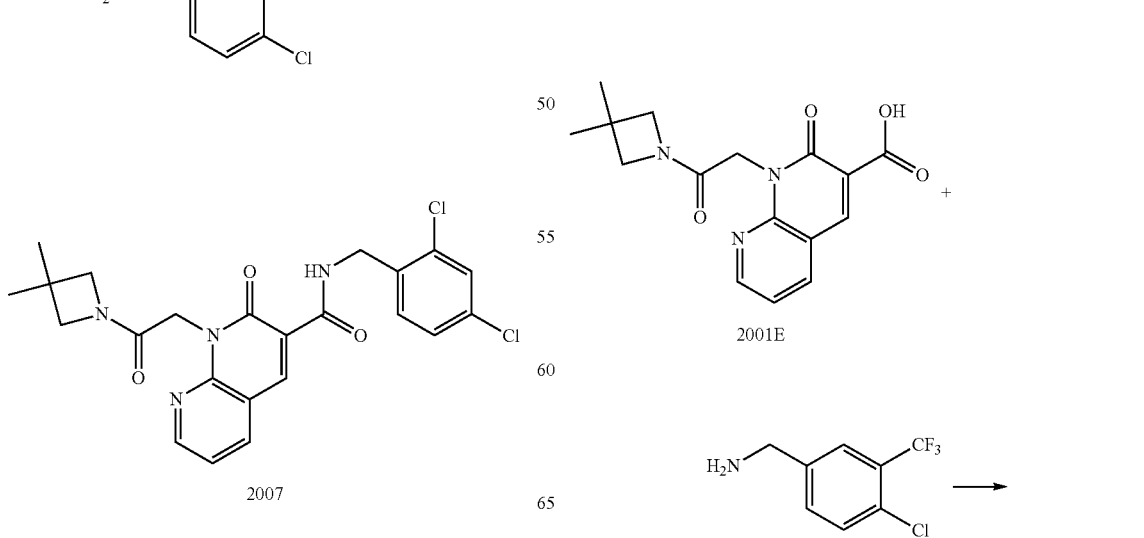

2001E

-continued

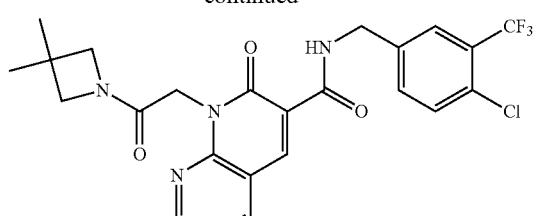

2009

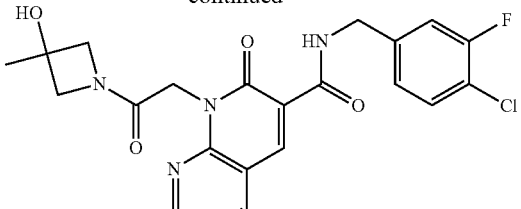

2010

Compound 2009 (t$_R$: 2.03, (M+H)$^+$: 507.1/509.1) is prepared analogously to compound 2001, except that in step 6, intermediate 2001E is reacted with 4-chloro-3-(trifluoromethyl)benzylamine (Matrix).

Synthesis of Compound 2010

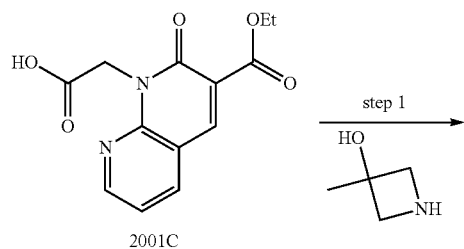

2001C

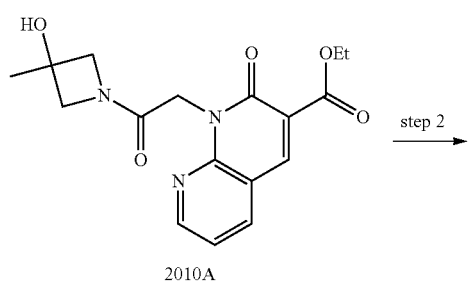

2010A

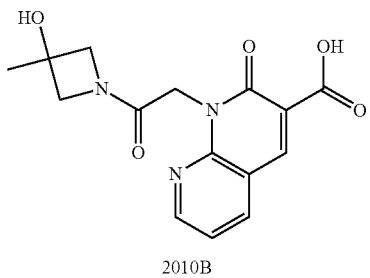

2010B

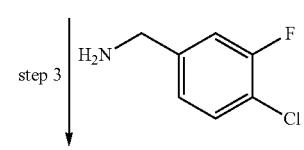

step 3

Step 1: Intermediate 2010A is prepared analogously to intermediate 2001D, except that in step 4, intermediate 2001C is reacted with 3-methyl-azetidin-3-ol (Parkway).

Step 2: Intermediate 2010B is prepared analogously to intermediate 2001E.

Step 3: Intermediate 2010B (50 mg, 0.16 mmol) is dissolved in DMF (2.0 mL), then diisopropylethylamine (110 μL, 0.63 mmol, 4.0 eq) and 4-chloro-3-fluorobenzylamine (Oakwood) (30 mg, 0.19 mmol, 1.2 eq) are added followed by HATU (78 mg, 0.21 mmol, 1.2 eq) and the reaction mixture is stirred at RT. Following completion of the reaction, the solution is filtered and purified by preparative HPLC to provide compound 2010 (t$_R$: 1.71, (M+H)$^+$: 459.2/461.2).

Synthesis of Compound 2011

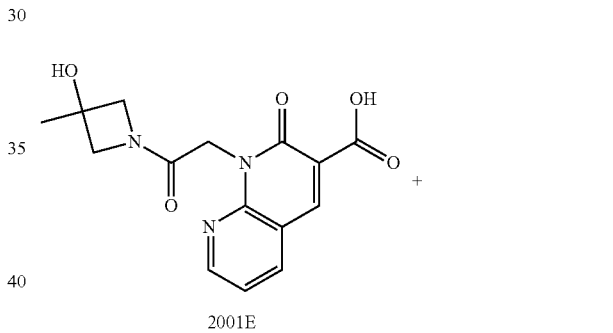

2001E

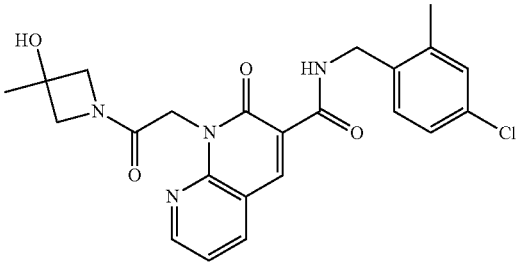

2011

Compound 2011 (t$_R$: 1.82, (M+H)$^+$: 455.2/457.2) is prepared analogously to compound 2010, except that in step 3, intermediate 2010B is reacted with 4-chloro-2-methylbenzylamine (Oakwood).

Synthesis of Compound 2012

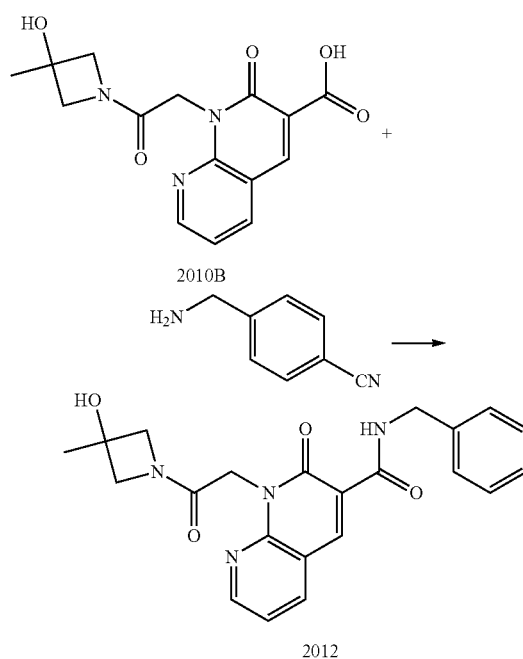

Compound 2012 ($t_R$: 1.38, (M+H)$^+$: 432.1) is prepared analogously to compound 2010, except that in step 3, intermediate 2010C is reacted with 4-cyanobenzylamine (Matrix).

Step 1: 2-Amino-4-chloropyridine (Oakwood) (51.0 g, 400 mmol) is dissolved in THF (1.00 L) in a round-bottom flask and cooled to −10° C. A 2.0 M solution of sodium bis(trimethylsilyl)amide in THF (400 mL, 800 mmol, 2.00 eq) is added dropwise, followed by a solution of di-tert-butyl dicarbonate (90.0 g, 400 mmol, 1.00 eq) in THF (500 mL) and the reaction mixture is stirred at RT for 16 h. The solution is diluted with EtOAc and washed successively with a saturated aqueous solution of ammonium chloride and brine. The solution is concentrated under reduced pressure and the remaining solid is washed with hexanes to afford intermediate 3001A.

Step 2: In a 2-neck round-bottom flask fitted with an addition funnel, a 2.5 M solution of n-BuLi in hexanes (125 mL, 313 mmol, 2.50 eq) is added over 30 min to a cooled (−78° C.) solution of intermediate 3001A (28.4 g, 125 mmol) in THF (500 mL). The resulting solution is stirred at −78° C. for 1 h. DMF (48.4 mL, 625 mmol, 5.00 eq) is added dropwise and the reaction mixture is stirred at −78° C. for 2 h. A saturated aqueous solution of ammonium chloride (500 mL) is added and the solution is warmed to RT. The layers are separated and the organic layer is washed successively with a saturated aqueous ammonium chloride solution (5×300 mL) and brine (2×250 mL). The organic layer is dried over anhydrous sodium sulfate, filtered and concentrated under reduced pressure. The crude residue is purified by flash chromatography (EtOAc/hexanes) to provide intermediate 3001B.

Step 3: TFA (102 mL, 1.32 mol) is added over 30 min to a cooled solution (0° C.) of intermediate 3001B (68.0 g, 265 mmol) dissolved in DCM (800 mL) and the solution is stirred at RT for 21 h. The solution is concentrated under reduced pressure and then water (500 mL) is added. The solution is cooled to 0° C. and neutralized with a saturated aqueous

Synthesis of Compound 3001

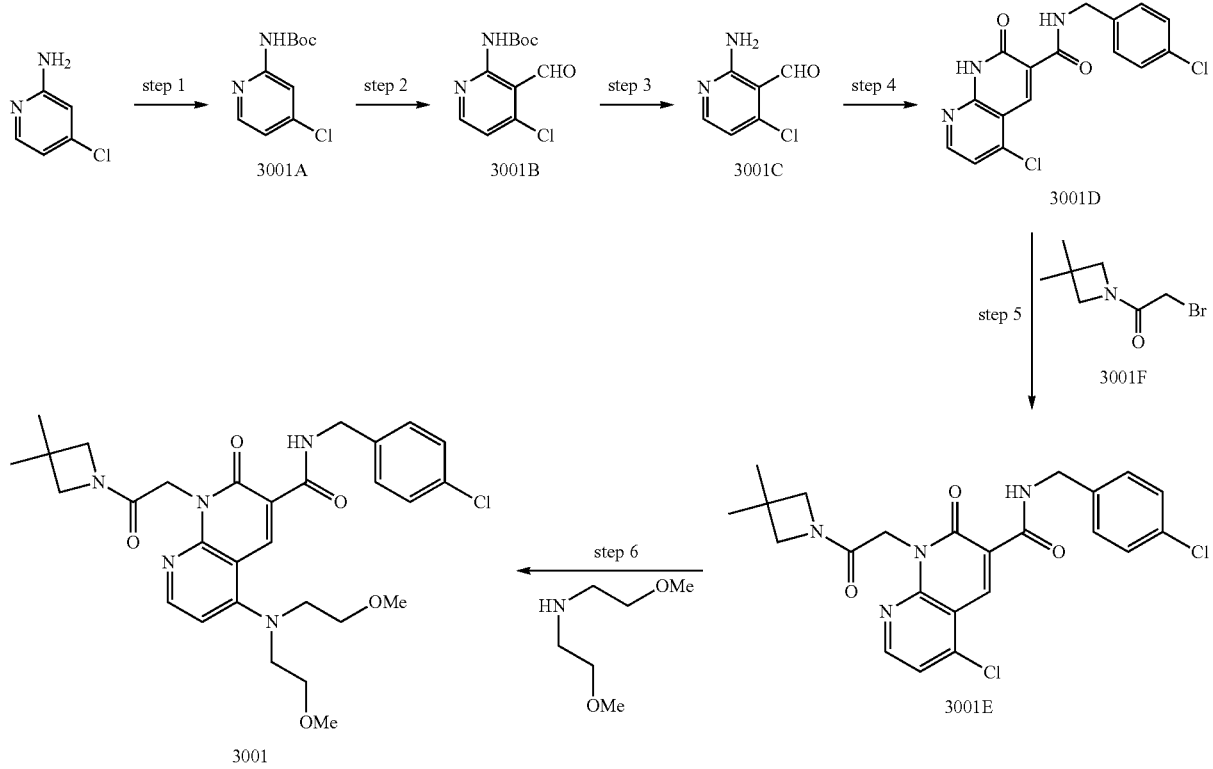

solution of sodium bicarbonate. The resulting suspension is filtered, washed with water and dried under vacuum to provide intermediate 3001C.

Step 4: Intermediate 3001C (5.90 g, 37.7 mmol) and intermediate 1001A (9.11 g, 37.7 mmol, 1.00 eq) are charged in a round-bottom flask and dissolved in THF (120 mL). A 1.0 M solution of titanium(IV) chloride in DCM (11.3 mL, 11.3 mmol, 0.300 eq) is added and the solution is stirred at RT for 18 h. MeOH is added. The reaction mixture is stirred for 15 min and then concentrated under reduced pressure. The residue is suspended in EtOAc and a saturated aqueous solution of sodium bicarbonate is added. After stirring the solution for 15 min, the solid is filtered and dried under vacuum to afford intermediate 3001D.

Step 5: Intermediate 3001D (2.10 g, 6.03 mmol) is charged in a round-bottom flask and suspended in DMF (30 mL). Potassium carbonate (2.50 g, 18.1 mmol, 3.00 eq) and intermediate 3001F (1.62 g, 7.84 mmol, 1.30 eq) are added and the solution is stirred at RT for 18 h. The solution is diluted with EtOAc and washed with brine (3×). The organic layer is dried over MgSO$_4$, filtered and concentrated under reduced pressure to provide intermediate 3001E.

Synthesis of Intermediate 3001F 3,3-dimethyl-azetidine hydrochloride (prepared analogously to the procedure in J. Med. Chem. 2008, 51, 7380, herein incorporated by reference) (1.00 g, 11.7 mmol) is dissolved in DCM (40 mL) and NaOH (1.00 M aqueous solution) (11.7 mL, 11.7 mmol, 1.00 eq) is added. The solution is filtered on a phase separator. Bromoacetyl bromide (1.02 mL, 11.7 mmol, 1.00 eq) is added followed by triethylamine (2.46 mL, 17.6 mmol, 1.50 eq). The solution is stirred at −10° C. for 2 h, diluted with DCM and washed with water (3×). The organic layer is dried over MgSO$_4$, filtered and concentrated under reduced pressure to provide intermediate 3001F.

Step 6: Intermediate 3001E (40 mg, 0.085 mmol) is charged in a vial and dissolved in DMF (1 mL). Diisopropylethylamine (40 μL, 0.25 mmol, 3.0 eq) is added followed by bis(2-methoxyethyl)amine (TCI) (22 mg, 0.17 mmol, 2.0 eq) and the solution is stirred at 50° C. for 16 h. Following completion of the reaction, the solution is filtered and purified by preparative HPLC to provide compound 3001 (t$_R$: 1.97, (M+H)$^+$: 570.3).

Synthesis of Compound 3002

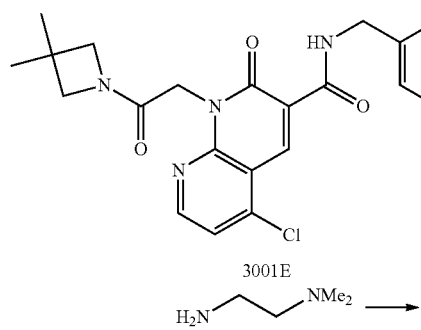

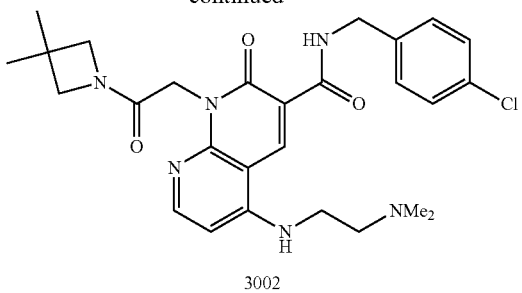

Compound 3002 (t$_R$: 1.8, (M+H)$^+$: 525.3) is prepared analogously to compound 3001, except that in step 6, intermediate 3001E is reacted with N,N-dimethylethylene diamine (Aldrich).

Synthesis of Compound 3003

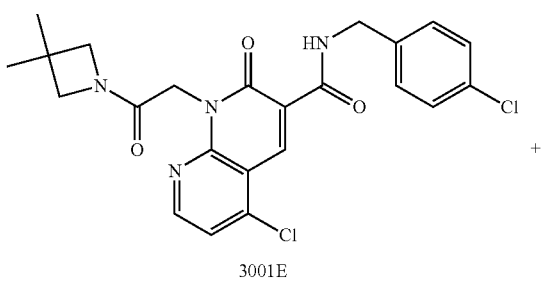

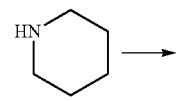

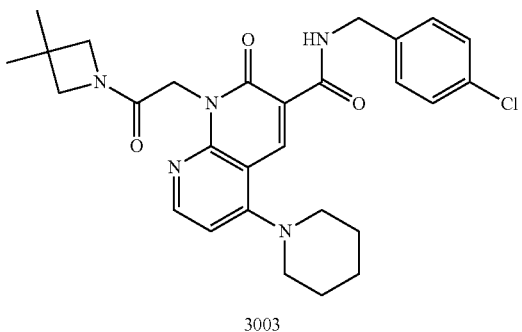

Compound 3003 (t$_R$: 1.75, (M+H)$^+$: 522.1/524.0) is prepared analogously to compound 3001, except that in step 6, intermediate 3001E is reacted with piperidine.

Synthesis of Compound 3004

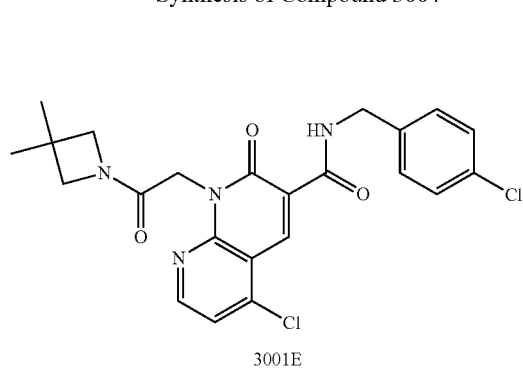

3001E

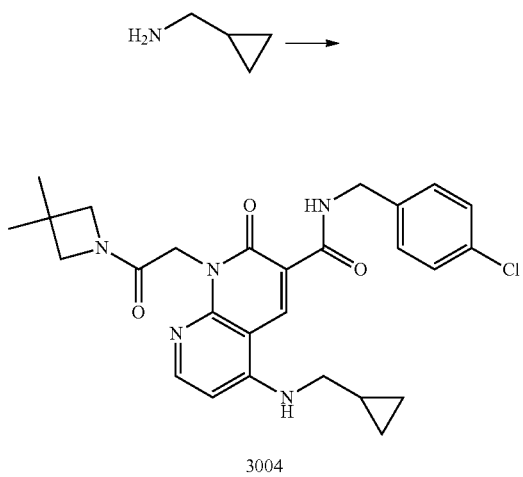

3004

Compound 3004 (t$_R$: 2.09, (M+H)$^+$: 508.3/510.3) is prepared analogously to compound 3001, except that in step 6, intermediate 3001E is reacted with cyclopropane methylamine (TCI).

Synthesis of Compound 3005

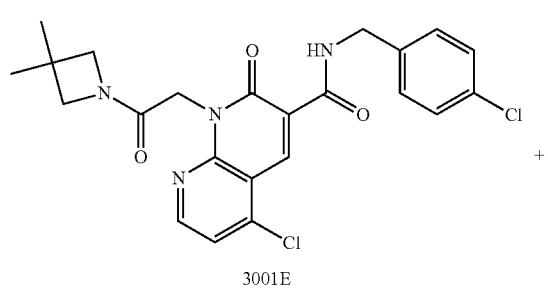

3001E

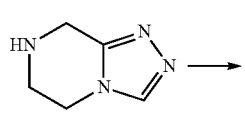

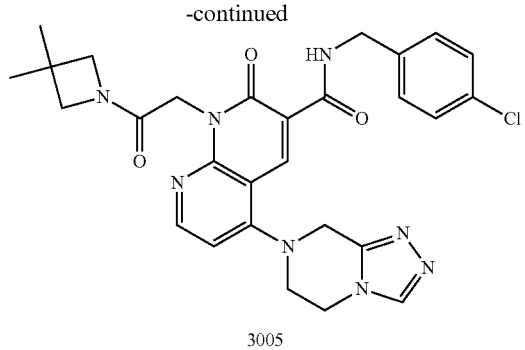

3005

Compound 3005 (t$_R$: 1.82, (M+H)$^+$: 561.1) is prepared analogously to compound 3001, except that in step 6, intermediate 3001E is reacted with 5,6,7,8-tetrahydro-[1,2,4]-triazolo-[4,3,A]-pyrazine (ChemgenX).

Synthesis of Compound 3006

3001E

3006

Compound 3006 (t$_R$: 1.95, (M+H)$^+$: 526.1) is prepared analogously to compound 3001, except that in step 6, intermediate 3001E is reacted with 1-amino-2-methyl propan-2-ol (Tyger).

Synthesis of Compound 3007

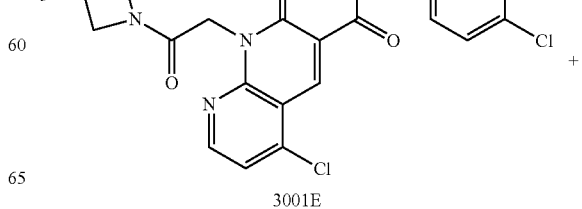

3001E

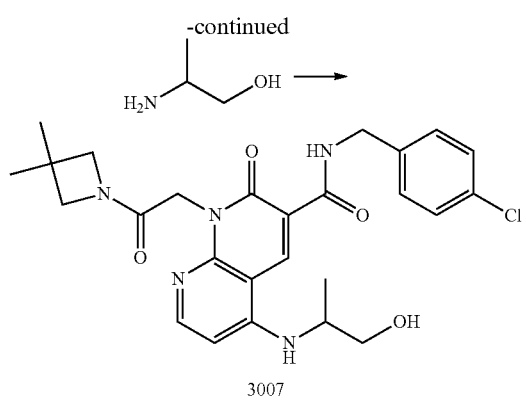
3007
Compound 3007 ($t_R$: 1.93, (M+H)$^+$: 512) is prepared analogously to compound 3001, except that in step 6, intermediate 3001E is reacted with 2-amino-1-propanol (Aldrich).
Synthesis of Compound 3008
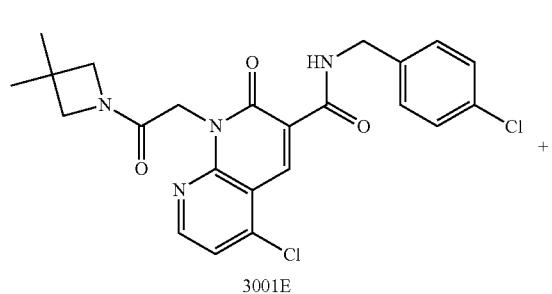
3001E
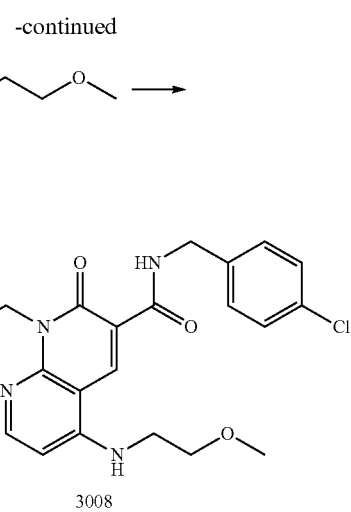
3008
Compound 3008 ($t_R$: 1.96, (M+H)$^+$: 512) is prepared analogously to compound 3001, except that in step 6, intermediate 3001E is reacted with 2-methoxyethylamine (Aldrich).
Synthesis of Compound 3009
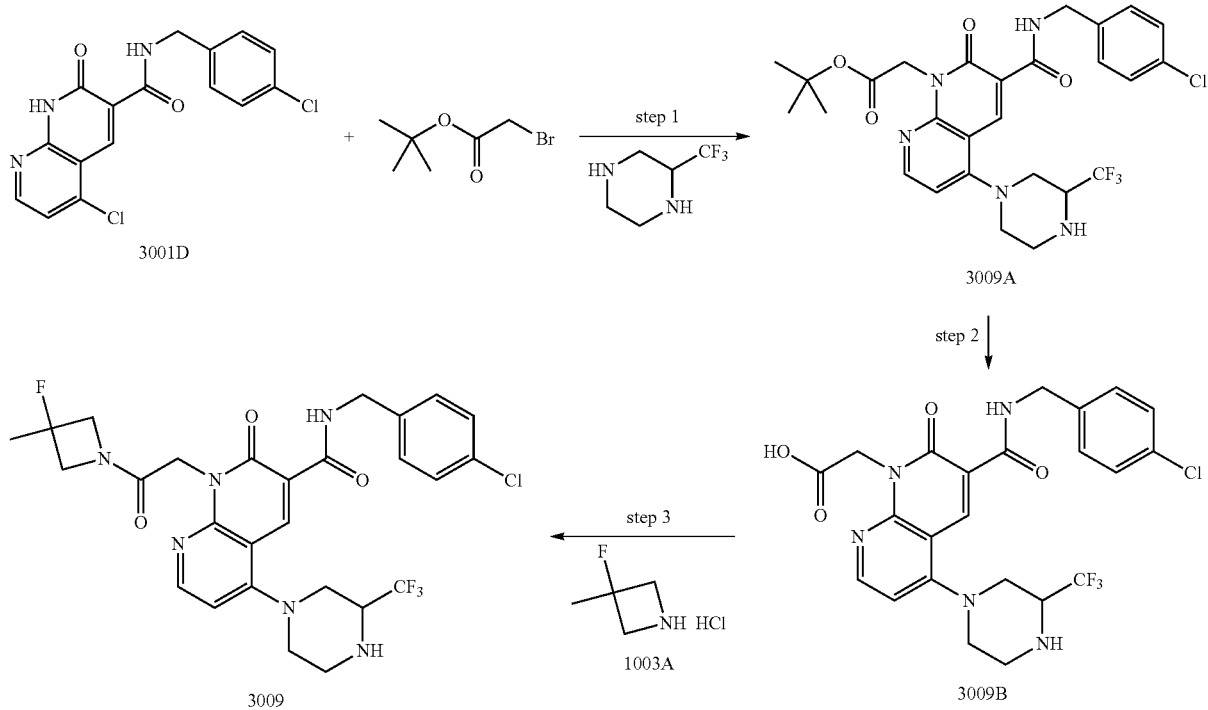

Step 1: Intermediate 3001D (200 mg, 0.574 mmol) is charged in a vial and dissolved in DMF (5 mL). Potassium carbonate (158 mg, 1.15 mmol, 2.00 eq) and tert-butyl bromoacetate (TCI) (168 mg, 0.862 mmol, 1.50 eq) are added and solution is stirred at RT for 72 h. Diisopropylethylamine (200 μL, 1.15 mmol, 2.00 eq) is added followed by 2-(trifluoromethyl)piperazine (Matrix) (133 mg, 0.862 mmol, 1.50 eq) and the solution is stirred at 75° C. for 24 h. The cooled solution is then diluted with EtOAc and washed with water. The organic layer is dried over MgSO$_4$, filtered and concentrated under reduced pressure to provide intermediate 3009A.

Step 2: Intermediate 3009A (333 mg, 0.574 mmol) is dissolved in TFA (5.0 mL) and the reaction mixture is stirred at RT for 2 h. The solution is concentrated under reduced pressure to provide intermediate 3009B.

Step 3: Intermediate 3009B (300 mg, 0.574 mmol) is dissolved in DMF (3.0 mL). Diisopropylethylamine (500 μL, 2.87 mmol, 5.0 eq) and intermediate 1003A (216 mg, 1.72 mmol, 3.00 eq) are added followed by HATU (436 mg, 1.15 mmol, 2.00 eq) and the reaction mixture is stirred at RT for 3 h. Following completion of the reaction, the solution is filtered and purified by preparative HPLC to provide compound 3009 ($t_R$: 1.97, (M+H)$^+$: 595.4).

Synthesis of Compound 3010

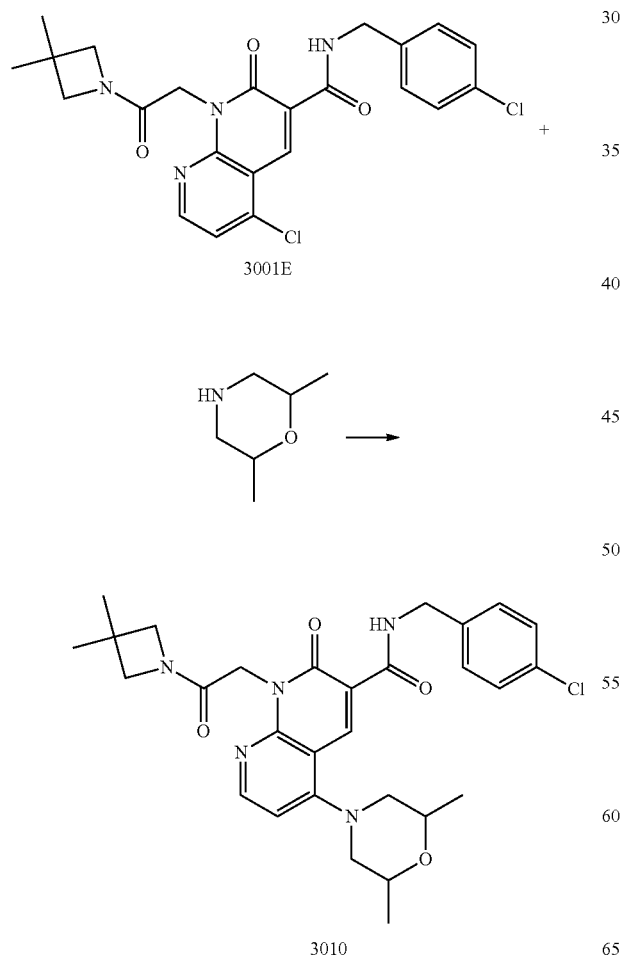

3010

Compound 3010 ($t_R$: 2.05, (M+H)$^+$: 552.3/554.3) is prepared analogously to compound 3001, except that in step 6, intermediate 3001E is reacted with 2,6-dimethylmorpholine (Aldrich).

Synthesis of Compound 3011

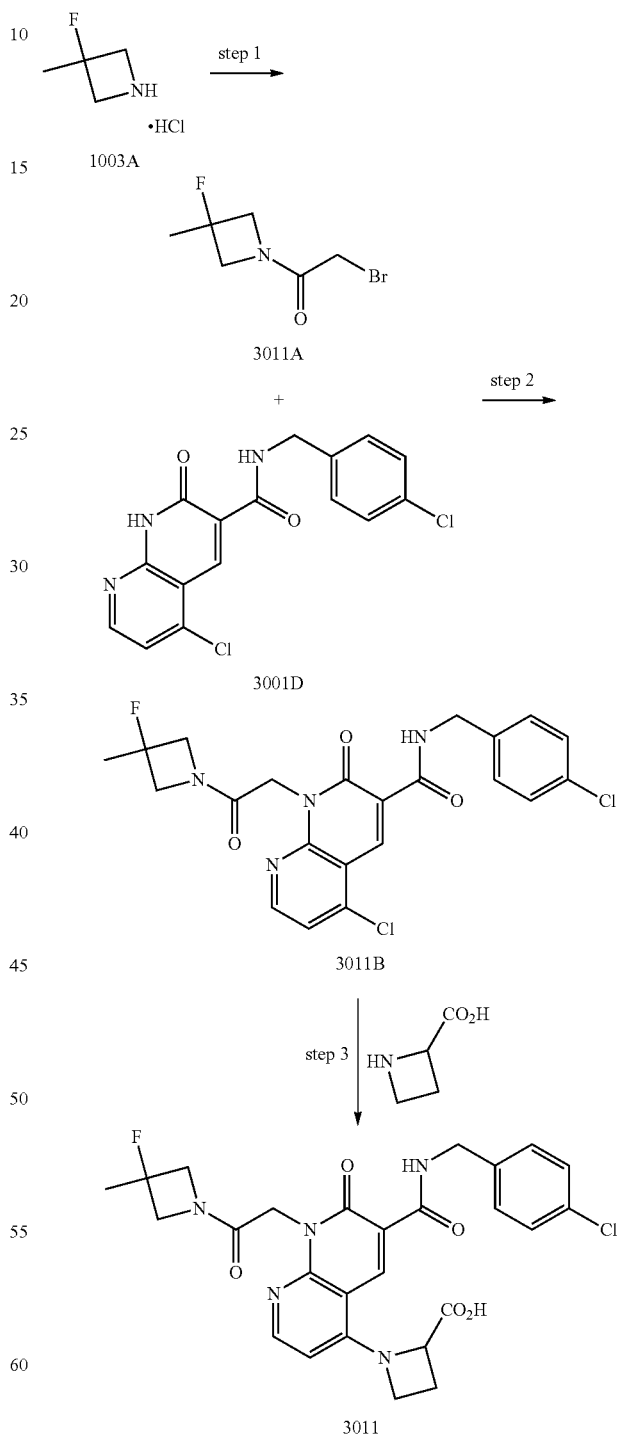

Step 1: Intermediate 1003A (5.22 g, 41.6 mmol) is dissolved in DCM (75 mL) and NaOH (1.00 M aqueous solution) (41.6 mL, 41.6 mmol, 1.00 eq) is added. The solution is filtered on a phase separator. Bromoacetyl bromide (3.62 mL, 41.6 mmol, 1.00 eq) is added followed by triethylamine (8.69 mL, 62.4 mmol, 1.50 eq). The solution is stirred at −10° C. for 2 h, diluted with DCM and washed with water (3×). The organic layer is dried over MgSO$_4$, filtered and concentrated under reduced pressure to provide intermediate 3011A.

Step 2: Intermediate 3001D (300 mg, 0.862 mmol) is charged in a round-bottom flask and suspended in DMF (7.0 mL). Potassium carbonate (357 g, 2.59 mmol, 3.00 eq) and intermediate 3011A (217 mg, 1.03 mmol, 1.20 eq) are added. The solution is stirred at RT for 18 h, diluted with EtOAc and washed with brine (3×). The organic layer is dried over MgSO$_4$, filtered and concentrated under reduced pressure to provide intermediate 3011B.

Step 3: Intermediate 3011B (50 mg, 0.11 mmol) is charged in a vial and dissolved in NMP (0.5 mL). Diisopropylethylamine (55 µL, 0.31 mmol, 3.0 eq) is added followed by azetidine-2-carboxylic acid (Toronto) (21 mg, 0.21 mmol, 2.0 eq) and the solution is stirred at 120° C. for 4 h. Following completion of the reaction, the solution is filtered and purified by preparative HPLC to provide compound 3011 (t$_R$: 1.71, (M+H)$^+$: 542.3/544.3).

Synthesis of Compound 3012

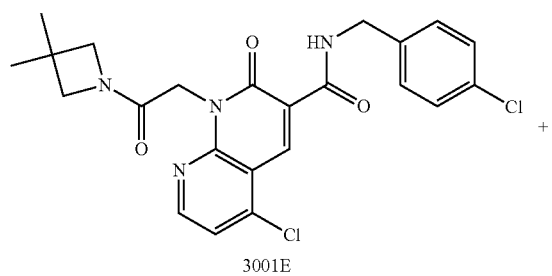

Compound 3012 (t$_R$: 1.83, (M+H)$^+$: 572) is prepared analogously to compound 3001, except that in step 6, intermediate 3001E is reacted with thiomorpholine 1,1-dioxide (TCI).

Synthesis of Compound 3013

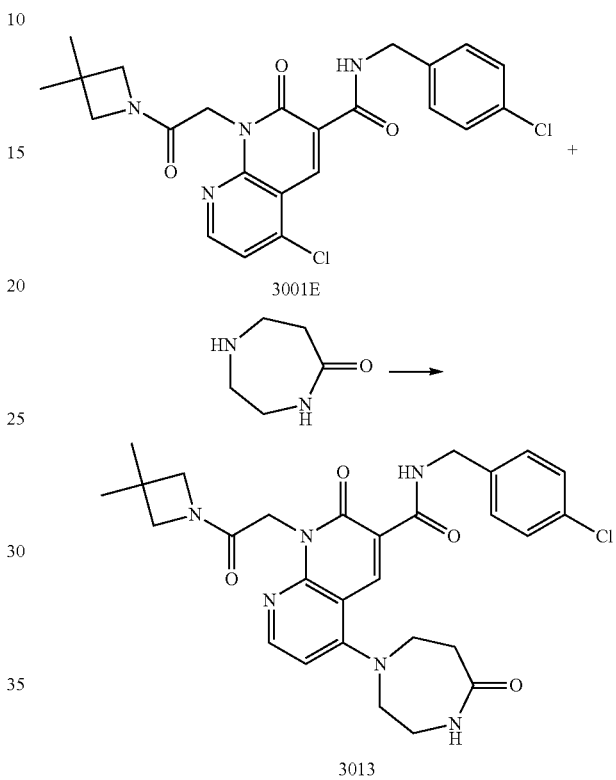

Compound 3013 (t$_R$: 1.85, (M+H)$^+$: 551.1) is prepared analogously to compound 3001, except that in step 6, intermediate 3001E is reacted with 2,3,6,7-tetrahydro-(1H)-1,4-diazepin-5-(4H)-one (Matrix).

Synthesis of Compound 3014

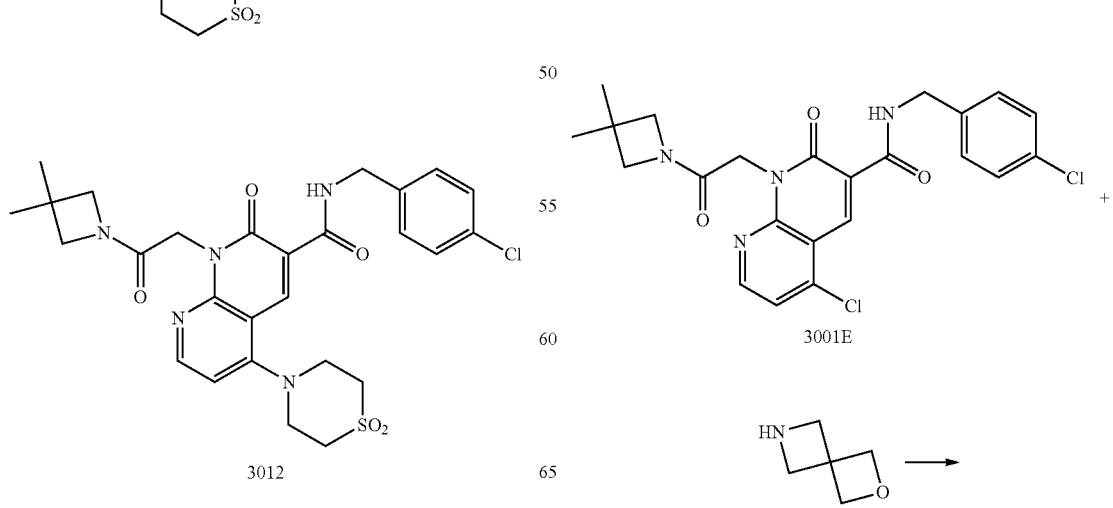

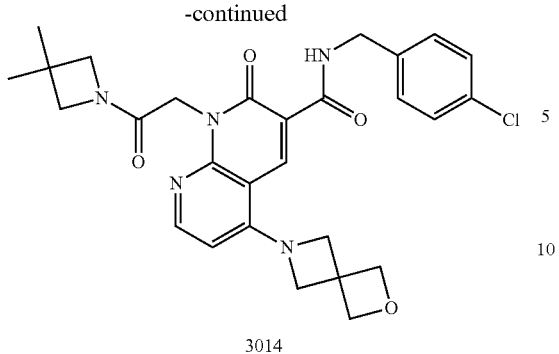

3014

Compound 3014 (t_R: 1.91, (M+H)+: 536.3) is prepared analogously to compound 3001, except that in step 6, intermediate 3001E is reacted with 2-oxa-6-aza-spiro-[3.3]-heptane (Enamine-BB).

Synthesis of Compound 3015

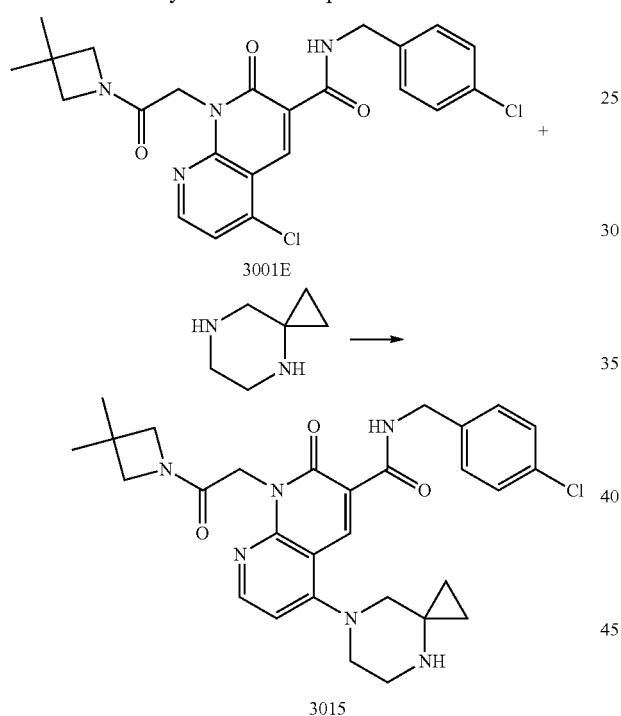

3015

Compound 3015 (t_R: 1.97, (M+H)+: 549.4/551.3) is prepared analogously to compound 3001, except that in step 6, intermediate 3001E is reacted with 4,7-diaza-spiro[2.5]octane (JW Pharmlab).

Synthesis of Compound 3016

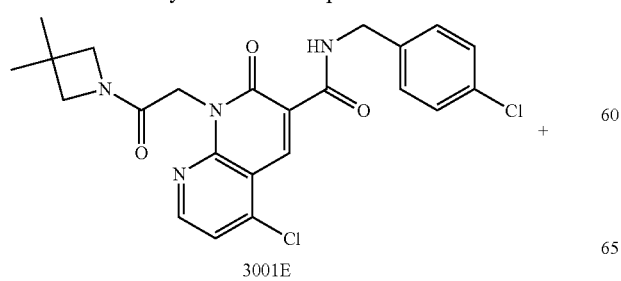

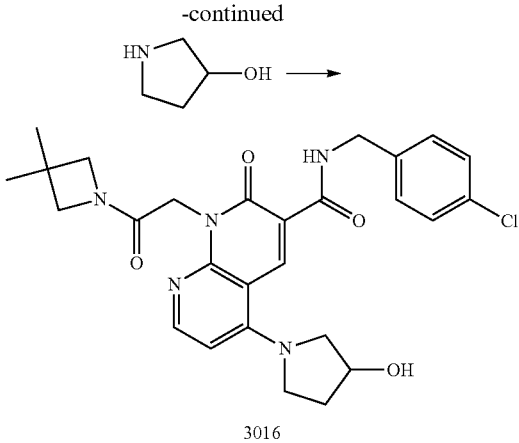

3016

Compound 3016 (t_R: 1.91, (M+H)+: 524) is prepared analogously to compound 3001, except that in step 6, intermediate 3001E is reacted with 3-pyrrolidinol (TCI).

Synthesis of Compound 3017

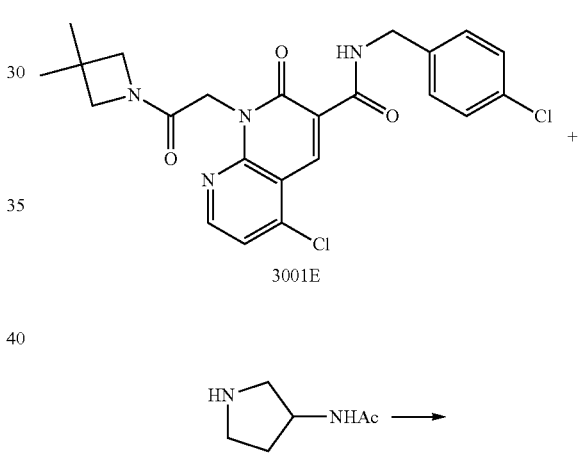

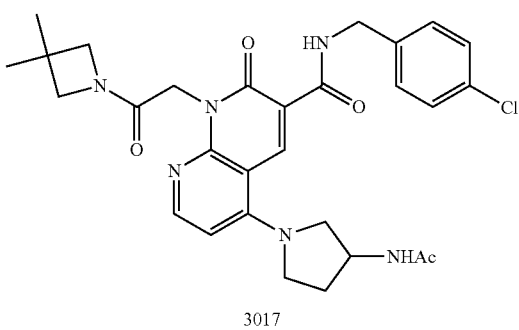

3017

Compound 3017 (t_R: 1.93, (M+H)+: 565.1) is prepared analogously to compound 3001, except that in step 6, intermediate 3001E is reacted with 3-acetamidopyrrolidine (TCI).

Synthesis of Compound 3018

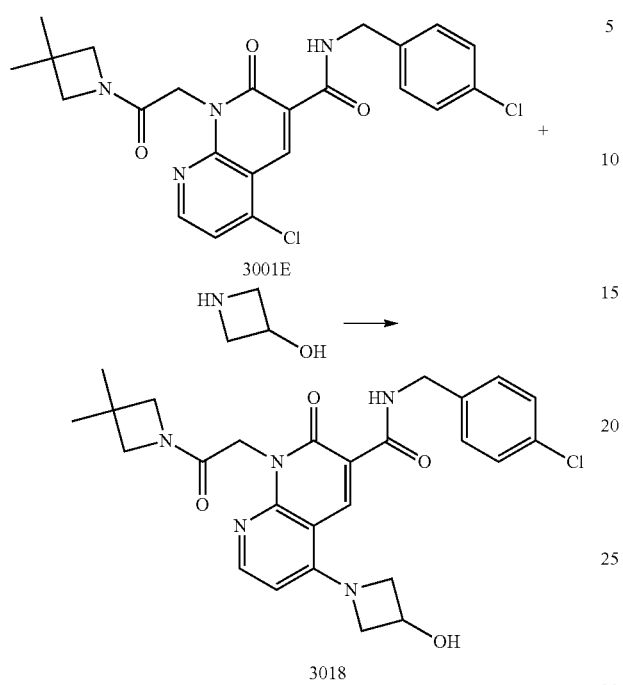

Compound 3018 ($t_R$: 1.9, (M+H)$^+$: 510) is prepared analogously to compound 3001, except that in step 6, intermediate 3001E is reacted with 3-azetidinol (Chembrdg-bb).

Synthesis of Compound 3019

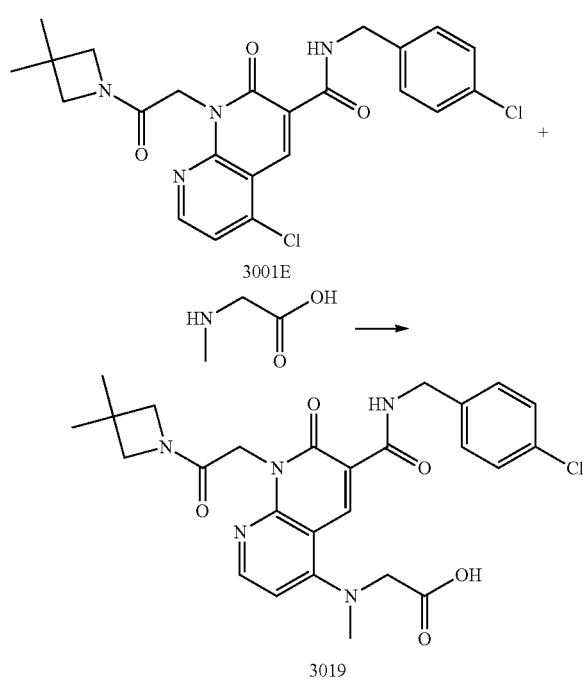

Compound 3019 ($t_R$: 1.71, (M+H)$^+$: 526.3) is prepared analogously to compound 3001, except that in step 6, intermediate 3001E is reacted with sarcosine (Aldrich).

Synthesis of Compound 3020

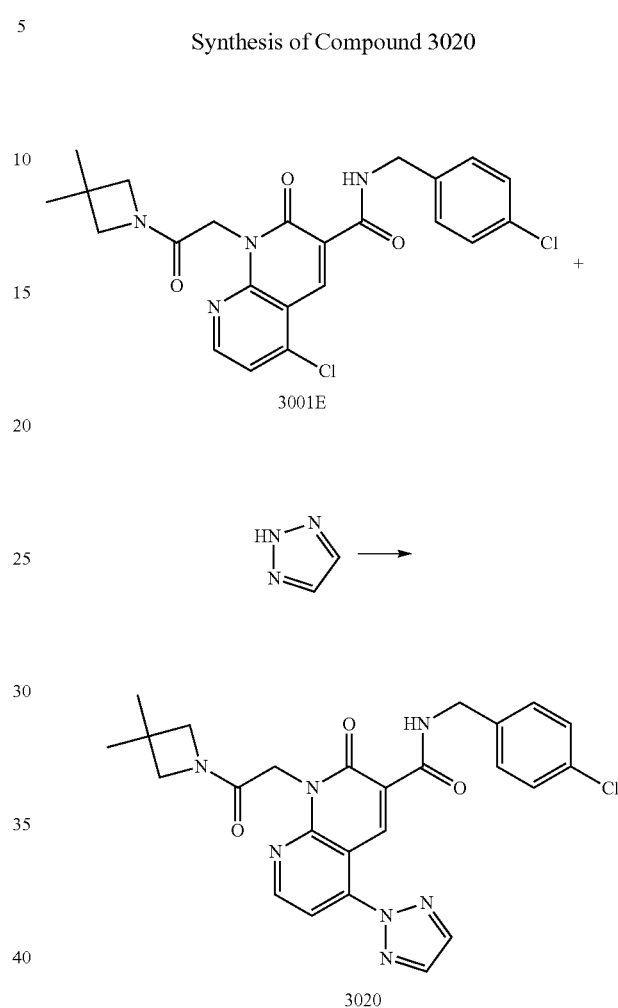

Compound 3020 ($t_R$: 1.94, (M+H)$^+$: 506) is prepared analogously to compound 3001, except that in step 6, intermediate 3001E is reacted with 1,2,3-triazole (Aldrich).

Synthesis of Compound 3021

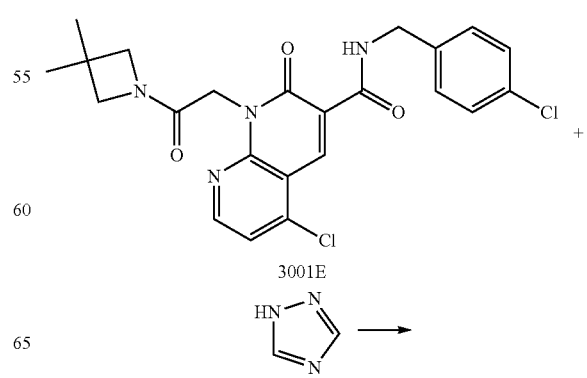

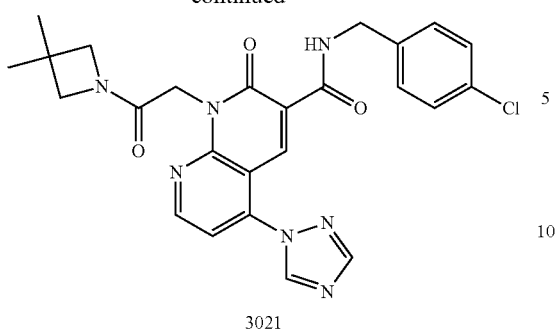

3021

Compound 3021 (t$_R$: 1.82, (M+H)$^+$: 506/508) is prepared analogously to compound 3001, except that in step 6, intermediate 3001E is reacted with 1,2,4-triazole (Aldrich).

Synthesis of Compound 3022

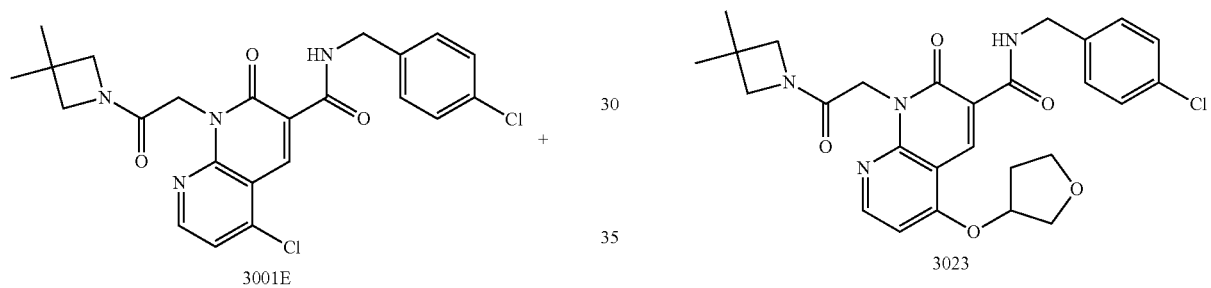

3022

Compound 3022 (t$_R$: 1.9, (M+H)$^+$: 525.2) is prepared analogously to compound 3001, except that in step 6, intermediate 3001E is reacted with 2-hydroxymethyloxetane (VWR).

Synthesis of Compound 3023

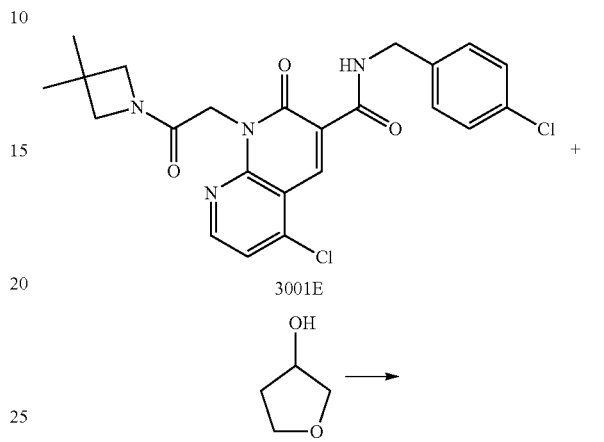

3023

Compound 3023 (t$_R$: 1.91, (M+H)$^+$: 525.2) is prepared analogously to compound 3001, except that in step 6, intermediate 3001E is reacted with 3-hydroxytetrahydrofuran (Aldrich).

Synthesis of Compound 3024

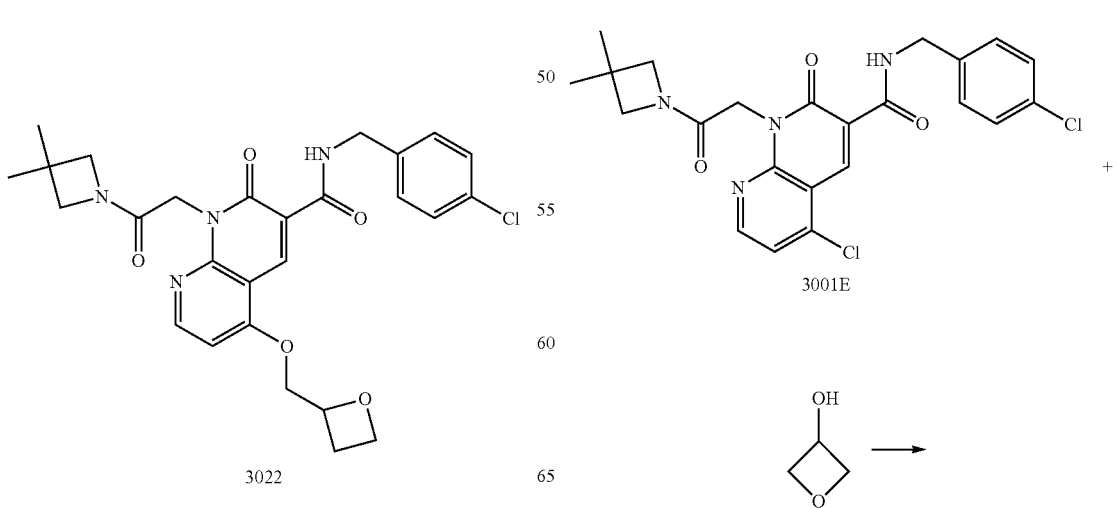

-continued

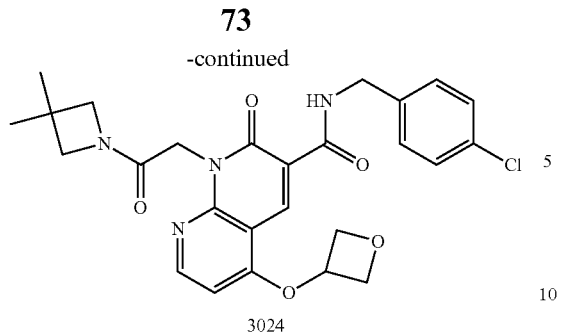

Compound 3024 ($t_R$: 1.89, (M+H)$^+$: 511.3) is prepared analogously to compound 3001, except that in step 6, intermediate 3001E is reacted with oxetan-3-ol (Accelachem).

Synthesis of Compound 3025

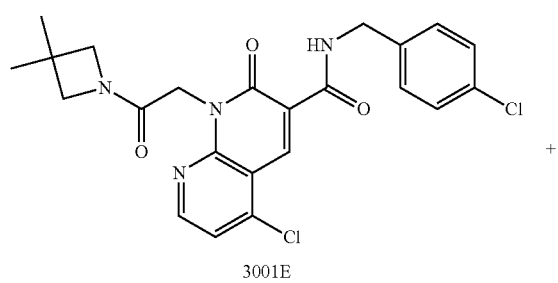

Compound 3025 ($t_R$: 2.01, (M+H)$^+$: 532) is prepared analogously to compound 3001, except that in step 6, intermediate 3001E is reacted with 3-hydroxypyridine (Aldrich).

Synthesis of Compound 3026

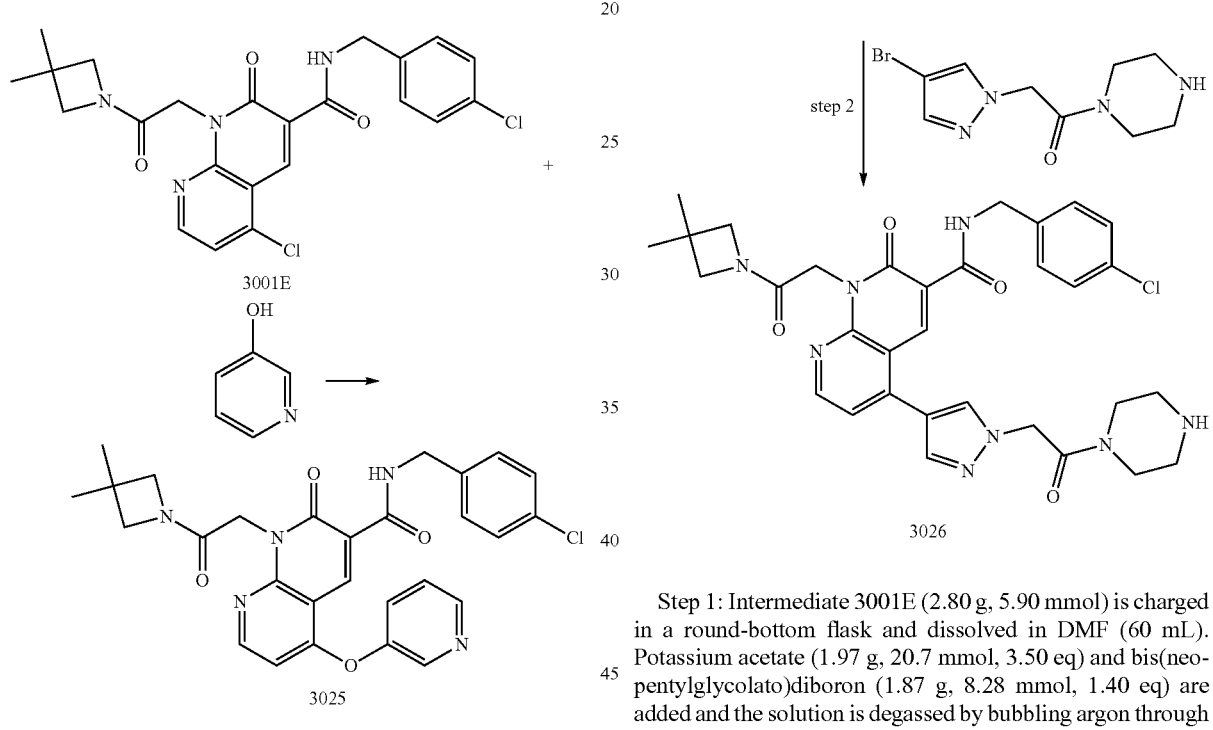

Step 1: Intermediate 3001E (2.80 g, 5.90 mmol) is charged in a round-bottom flask and dissolved in DMF (60 mL). Potassium acetate (1.97 g, 20.7 mmol, 3.50 eq) and bis(neopentylglycolato)diboron (1.87 g, 8.28 mmol, 1.40 eq) are added and the solution is degassed by bubbling argon through solution for 30 min. [1,1'-Bis(diphenylphosphino)ferrocene]dichloropalladium(II) (430 mg, 0.59 mmol, 0.10 eq) is added and the solution is stirred at 95° C. for 5 h. The cooled solution is diluted with EtOAc (200 mL) and washed with water (2×100 mL) and brine (2×100 mL). The organic layer is dried over MgSO$_4$. The solution is filtered and activated charcoal (3 g) is added to the solution which is stirred for 1 h. The crude mixture is filtered and then concentrated under reduced pressure. The residue is dissolved in Et$_2$O (30 mL), and the solution is filtered. The filtrate is concentrated under reduced pressure to afford 3026A.

Step 2: 2-(4-bromo-pyrazol-1-yl)-1-piperazin-1-yl-ethanone (Art-Chem-BB) (45 mg, 0.16 mmol, 1.5 eq) is charged in a microwave vial, then a solution of potassium carbonate (45 mg, 0.33 mmol, 3.0 eq) in water (100 µL) degassed by bubbling argon through solution for 5 min is added. Intermediate 3026A (60 mg, 0.11 mmol) is added as a solution in DMF (1 mL). The solution is purged under argon for 5 min, then bis(tricyclohexylphosphine) palladium(0) (7.3 mg, 0.010 mmol, 0.10 eq) is added. The vial is sealed and warmed in a microwave oven at 120° C. for 15 min. The cooled solution is diluted with THF (0.8 mL), filtered and purified by preparative HPLC to provide compound 3026 ($t_R$: 1.83, $(M+H)^+$: 631.3/633.3).

Synthesis of Compound 3027

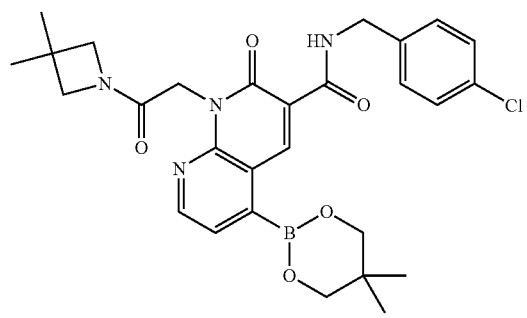

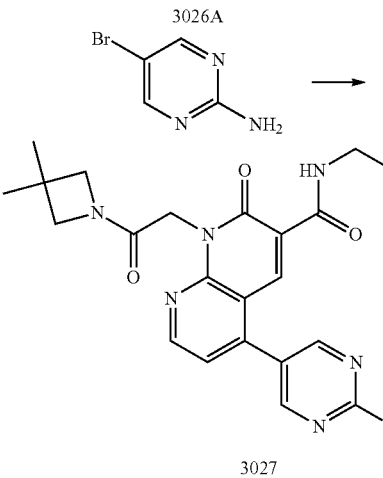

Compound 3027 ($t_R$: 1.83, $(M+H)^+$: 532.2/534.2) is prepared analogously to compound 3026, except that in step 2, intermediate 3026A is reacted with 5-bromo-2-aminopyrimidine (Aldrich).

Synthesis of Compound 3028

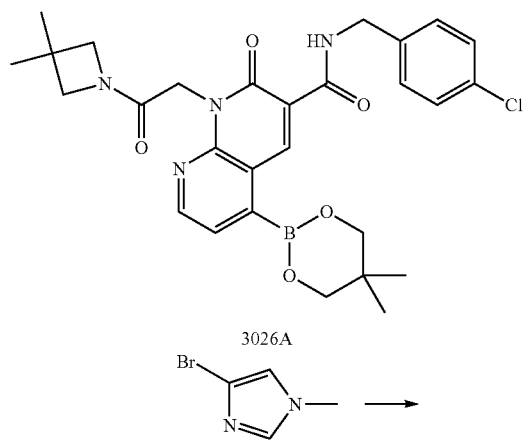

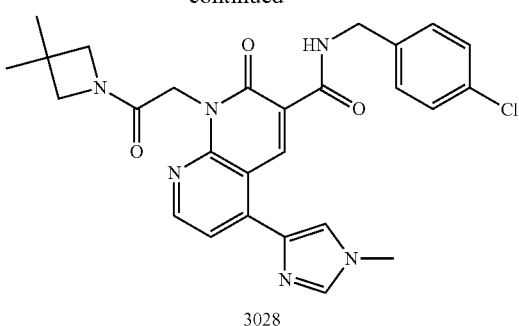

Compound 3028 ($t_R$: 1.87, $(M+H)^+$: 519.2/521.2) is prepared analogously to compound 3026, except that in step 2, intermediate 3026A is reacted with 4-bromo-1-methyl-1H-imidazole (CombiBlocks).

Synthesis of Compound 3029

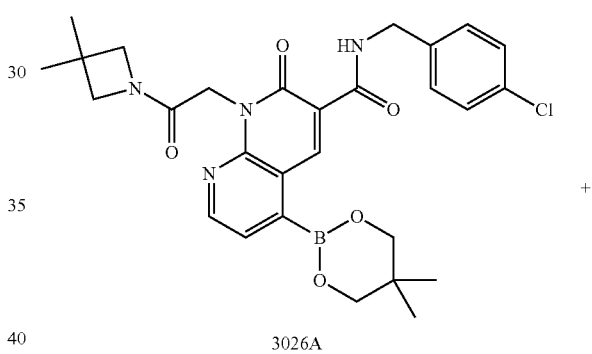

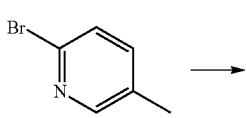

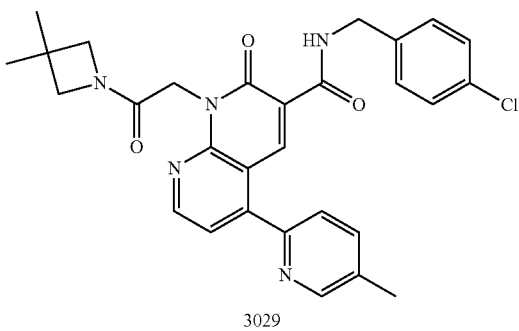

Compound 3029 (t$_R$: 1.93, (M+H)$^+$: 530.2/532.2) is prepared analogously to compound 3026, except that in step 2, intermediate 3026A is reacted with 2-bromo-5-methylpyridine (Aldrich).

Synthesis of Compound 3030

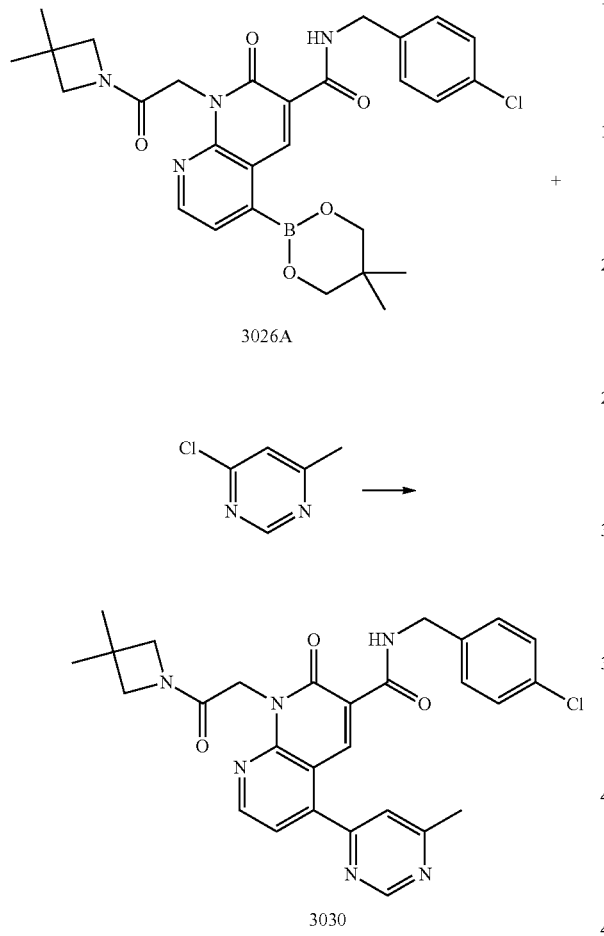

Compound 3030 (t$_R$: 1.87, (M+H)$^+$: 531.2/533.2) is prepared analogously to compound 3026, except that in step 2, intermediate 3026A is reacted with 4-chloro-6-methylpyrimidine (Medinoah).

Synthesis of Compound 3031

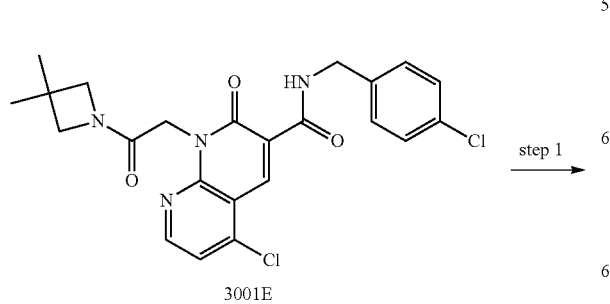

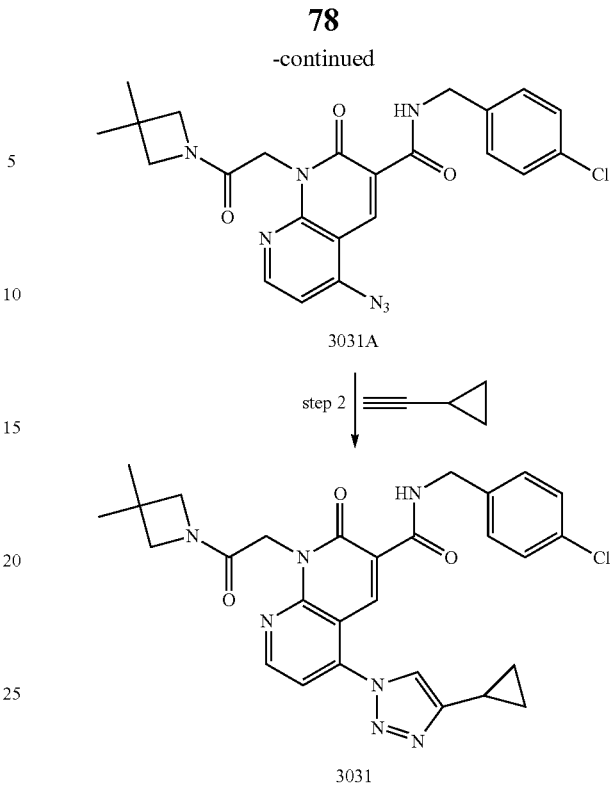

Step 1: Intermediate 3001E (600 mg, 1.27 mmol) is charged in a vial and dissolved in DMF (13 mL). Sodium azide (107 mg, 1.65 mmol, 1.30 eq) is then added and the solution is stirred at RT. Following completion of the reaction, the solution is diluted with EtOAc and washed with water (3×) and brine (3×). The organic layer is dried over MgSO$_4$, filtered and then concentrated under reduced pressure. The residue is triturated with Et$_2$O and hexanes to afford intermediate 3031A.

Step 2: Intermediate 3031A (50 mg, 0.10 mmol) is charged in a round-bottom flask and dissolved in DMSO (5 mL). Cyclopropylacetylene (ABChem-Tech) (14 mg, 0.21 mmol, 2.0 eq) is added followed by a 2:1 tert-butanol/water solution (0.5 mL), a 1 M aqueous sodium ascorbate solution (0.11 mL) and a 0.3 M aqueous copper(II) sulfate solution (70 µL). The mixture is stirred at 50° C. for 16 h. The solution is filtered and purified by preparative HPLC to provide compound 3031 (t$_R$: 1.83, (M+H)$^+$: 546.2).

Synthesis of Compound 3032

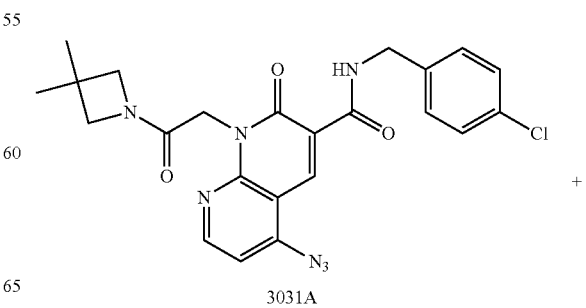

Synthesis of Compound 3033

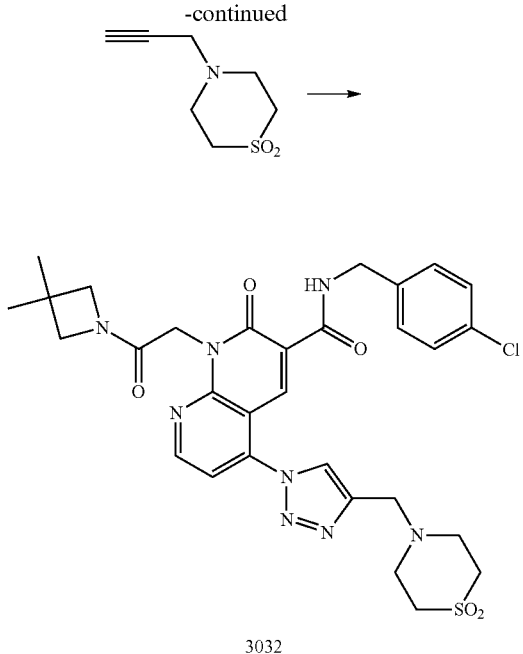

3032

Compound 3032 ($t_R$: 1.77, (M+H)$^+$: 653.2) is prepared analogously to compound 3031, except that in step 2, intermediate 3031A is reacted with 4-propargylthiomorpholine 1,1-dioxide (Apollo).

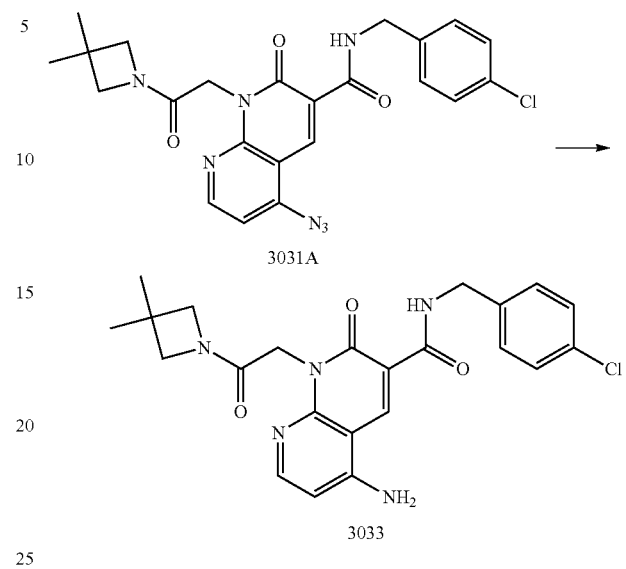

Intermediate 3031A (73 mg, 0.15 mmol) is charged in a round-bottom flask then THF (0.5 mL) and water (0.5 mL) are added. Triphenylphosphine (40 mg, 0.15 mmol, 1.0 eq) is added and the reaction mixture is stirred at RT. Following completion of the reaction, the solution is concentrated under reduced pressure and purified by preparative HPLC to provide compound 3033 ($t_R$: 1.36, (M+H)$^+$: 454.0/456.0).

Synthesis of Compound 3034

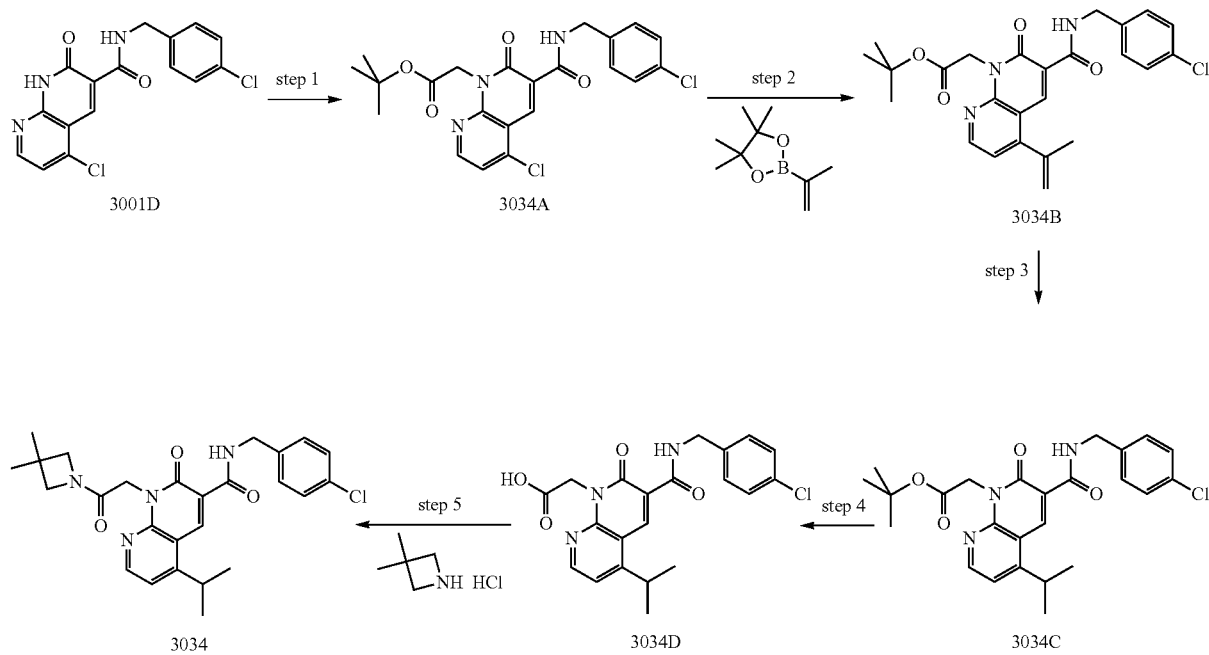

Step 1: Intermediate 3001D (200 mg, 0.574 mmol) is charged in a vial and dissolved in DMF (5 mL). Potassium carbonate (158 mg, 1.15 mmol, 2.00 eq) and tert-butyl bromoacetate (TCI) (168 mg, 0.862 mmol, 1.50 eq) are added. The solution is stirred at RT for 72 h, diluted with EtOAc and washed with water. The organic layer is dried over MgSO₄, filtered and concentrated under reduced pressure to provide intermediate 3034A.

Step 2: Intermediate 3034A (500 mg, 1.08 mmol) is charged in a round-bottom flask with 2-isoprenyl-4,4,5,5-tetramethyl-1,3,2-dioxaborolane (Aldrich) (218 mg, 1.30 mmol, 1.20 eq) and potassium carbonate (179 mg, 1.30 mmol, 1.20 eq) then water (2 mL) and 1,2-dimethoxyethane (12 mL) are added. The solution is degassed by bubbling argon through solution for 5 min, then tetrakis(triphenylphosphine) palladium(0) (125 mg, 0.108 mmol, 0.100 eq) is added. The reaction mixture is heated at 100° C. for 1 h. The cooled solution is diluted with EtOAc and washed with water (2×). The organic layer is dried over MgSO₄, filtered and concentrated under reduced pressure. The residue is purified by flash chromatography (EtOAc/hexanes) to afford intermediate 3034B.

Step 3: Intermediate 3034B (90 mg, 0.19 mmol) is charged in a round-bottom flask and dissolved in EtOAc (4 mL). MeOH (1 mL) and palladium on charcoal (5% w/w) (41 mg, 0.019 mmol, 0.1 eq) are added. The flask is submitted to vacuum/hydrogen refill cycles (3×) and the solution is stirred at RT under a hydrogen atmosphere (balloon) for 1 h. The solution is filtered and concentrated under reduced pressure to afford intermediate 3034C.

Step 4: TFA (1.0 mL) is added to a solution of intermediate 3034C (88 mg, 0.19 mmol) dissolved in DCM (5.0 mL) and the reaction mixture is stirred at RT for 2 h. The solution is concentrated under reduced pressure to provide intermediate 3034D.

Step 5: Intermediate 3034D (33 mg, 0.063 mmol) is dissolved in DMF (1.0 mL), then diisopropylethylamine (50 μL, 0.31 mmol, 5.0 eq) and 3,3-dimethyl-azetidine hydrochloride (prepared analogously to the procedure in J. Med. Chem. 2008, 51, 7380, herein incorporated by reference) (13 mg, 0.094 mmol, 1.5 eq) are added followed by HATU (35 mg, 0.094 mmol, 1.5 eq) and the reaction mixture is stirred at RT for 3 h. Following completion of the reaction, the solution is filtered and purified by preparative HPLC to provide compound 3034 (t_R: 1.93, (M+H)⁺: 481.2/483.1).

Synthesis of Compound 3035

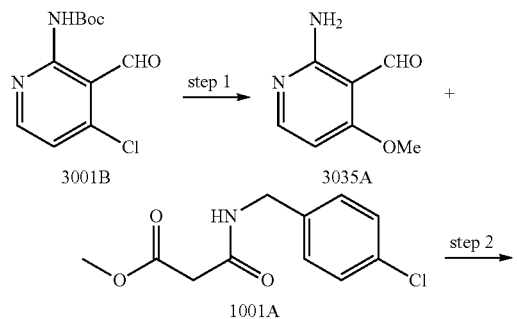

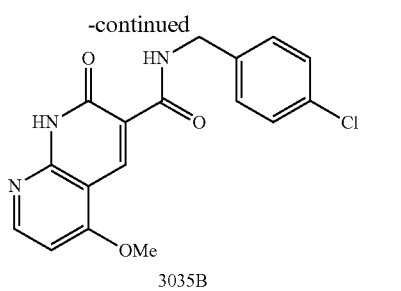

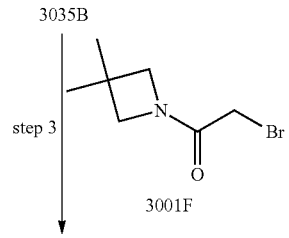

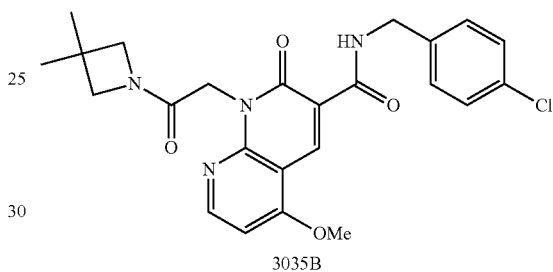

Step 1: Intermediate 3001A (13.5 g, 52.6 mmol) is charged in a round-bottom flask, dissolved in THF (300 mL) and the solution is cooled in an ice bath (0° C.). A 0.500 M solution of sodium methoxide in MeOH (315 mL, 158 mmol, 3.00 eq) is added. The ice bath is removed and the solution is stirred at RT for 3 h. Following completion of the reaction, the reaction mixture is acidified to approximately pH 2 using a 1 M aqueous HCl solution. The solution is then warmed to 55° C. for 6 h. The cooled solution is neutralized to approximately pH 7 with solid potassium carbonate. The resulting precipitate is filtered and the aqueous layer is extracted with EtOAc. The organic layer is washed with brine, dried over MgSO₄, filtered and concentrated under reduced pressure. The combined solids are washed with Et₂O to afford intermediate 3035A.

Step 2: Intermediate 3035A (8.00 g, 52.6 mmol) and intermediate 1001A (15.3 g, 63.1 mmol, 1.20 eq) are charged in a microwave vial and EtOH (40 mL) is added. Piperidine (12.4 mL, 131 mmol, 2.50 eq) is added and the vial is sealed and warmed in a microwave oven at 120° C. for 20 min. The cooled solution is diluted with Et₂O and sonicated. The resulting solid is filtered and dried under vacuum to afford intermediate 3035B.

Step 3: Intermediate 3035B (565 mg, 1.64 mmol) is charged in a round-bottom flask and suspended in DMF (10 mL). Potassium carbonate (681 mg, 4.93 mmol, 3.00 eq) and intermediate 3001F (592 mg, 2.88 mmol, 1.75 eq) are added and the solution is stirred at RT for 18 h. The solution is diluted with EtOAc and washed with brine (3×). The organic layer is dried over MgSO₄, filtered and concentrated under reduced pressure. The crude mixture is purified by flash chromatography (EtOAc/hexanes) to provide intermediate 3035 (t$_R$: 1.95, (M+H)$^+$: 469.2).

Synthesis of Compound 3036

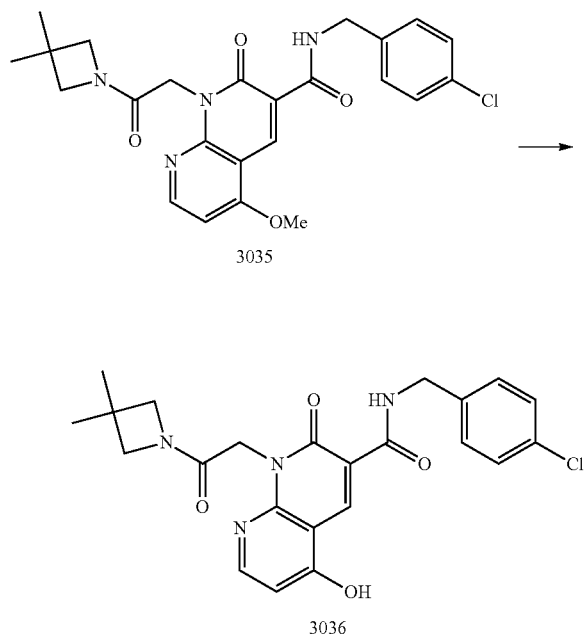

3035

3036

A hydrogen bromide solution (33% w/w in AcOH) (15.0 mL, 82.8 mmol, 105 eq) is added to compound 3035 (369 mg, 0.787 mmol) in a round-bottom flask and the reaction mixture is stirred at 75° C. for 18 h. The cooled reaction mixture is diluted with EtOAc and washed successively with water, a saturated aqueous solution of sodium thiosulfate, water and brine. The organic layer is dried over MgSO$_4$; filtered and then concentrated under reduced pressure to afford compound 3036 (t$_R$: 1.98, (M+H)$^+$: 455.2).

Synthesis of Compound 3037

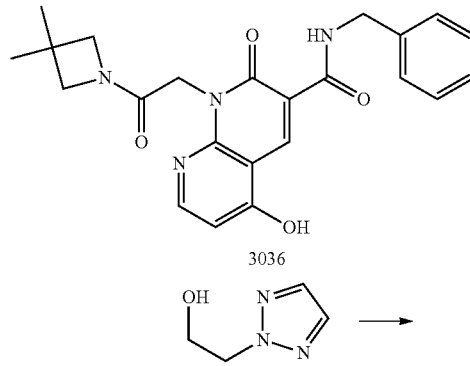

3036

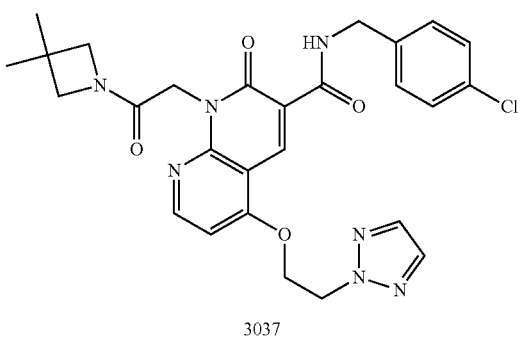

3037

Compound 3036 (50 mg, 0.11 mmol) is dissolved in THF (1.5 mL) in a round-bottom flask, then 2H-1,2,3-triazole-2-ethanol (Aldrich) (15 mg, 0.13 mmol, 1.2 eq) and triphenylphosphine (32 mg, 0.12 mmol, 1.1 eq) are added followed by DIAD (24 µL, 0.12 mmol, 1.1 eq) and the reaction mixture is stirred at RT for 2 h. Following completion of the reaction, the solution is concentrated under reduced pressure and purified by preparative HPLC to provide compound 3037 (t$_R$: 1.89, (M+H)$^+$: 550.3/552.3).

Synthesis of Compound 3038

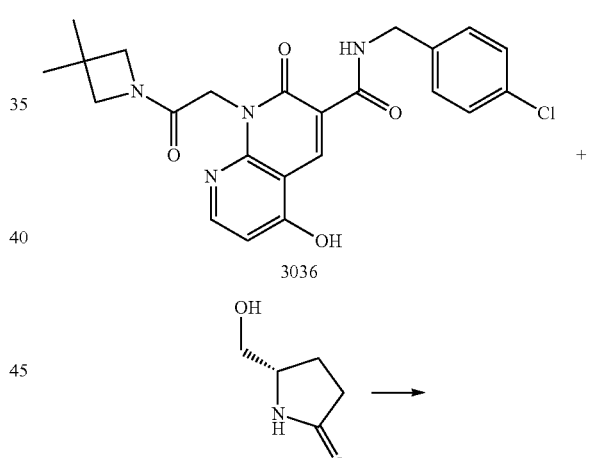

3036

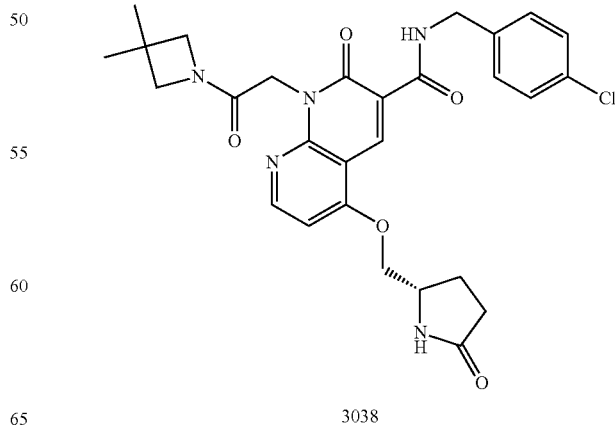

3038

Compound 3038 ($t_R$: 1.93, (M+H)$^+$: 552.2) is prepared analogously to compound 3037, except that compound 3036 is reacted with (S)-(+)-5-(hydroxymethyl)-2-pyrrolidinone (Aldrich).

Synthesis of Compound 3039

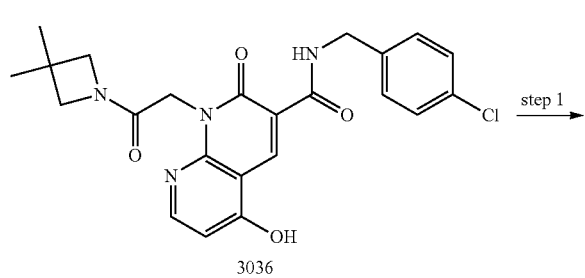
3036

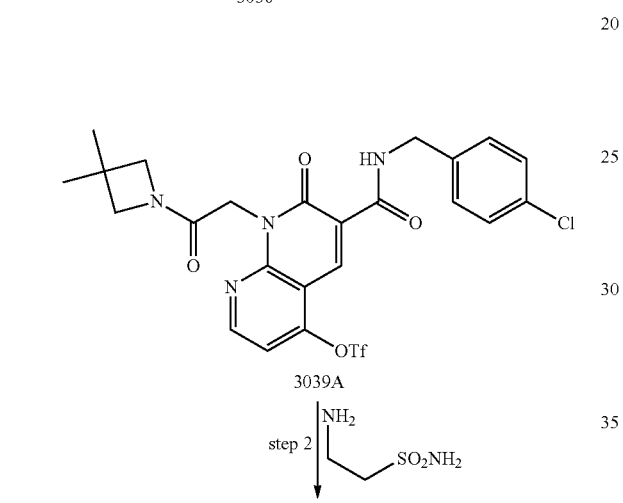
3039A

3039

Step 1: Compound 3036 (2.30 g, 5.05 mmol) is dissolved in MeCN (100 mL) in a round-bottom flask, then potassium carbonate (1.40 g, 10.1 mmol, 2.00 eq) and N-phenyl trifluoromethanesulfonimide (2.71 g, 7.58 mmol, 1.50 eq) are added and the reaction mixture is stirred at RT for 3 h. Following completion of the reaction, the solution is concentrated under reduced pressure and purified by flash chromatography (EtOAc/hexanes) to afford intermediate 3039A.

Step 2: Intermediate 3039A (60 mg, 0.10 mmol) is dissolved in dioxane (1.0 mL), then 2-aminoethane sulfonamide (Alinda) (38 mg, 0.31 mmol, 3.0 eq) is added and the reaction mixture is stirred at RT for 5 h. Following completion of the reaction, AcOH is added (100 μL) and the crude mixture is purified by preparative HPLC to provide compound 3039 ($t_R$: 1.87, (M+H)$^+$: 561.3/563.2).

Synthesis of Compound 3040

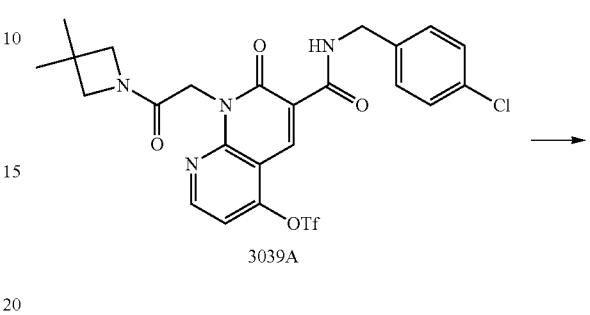
3039A

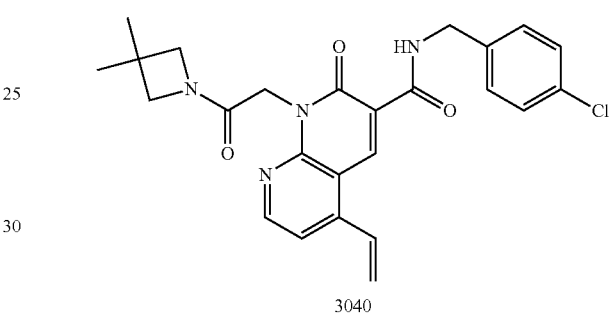
3040

Intermediate 3039A (2.70 g, 5.70 mmol) is charged in a round-bottom flask along with 2,4,6-trivinylcyclotriboroxane pyridine complex (Aldrich) (2.06 g, 8.56 mmol, 1.50 eq) and potassium carbonate (866 mg, 6.27 mmol, 1.10 eq) then water (10 mL) and 1,2-dimethoxyethane (70 mL) are added. The solution is degassed by bubbling argon through solution for 5 min, then tetrakis(triphenylphosphine) palladium(0) (660 mg, 0.570 mmol, 0.100 eq) is added. The reaction mixture is heated at 100° C. for 2.5 h. The cooled solution is diluted with DCM and washed with water (2×). The organic layer is dried over MgSO$_4$, filtered and concentrated under reduced pressure. The residue is purified by flash chromatography (MeOH/DCM) to afford compound 3040 ($t_R$: 1.94, (M+H)$^+$: 465/467).

Synthesis of Compound 3041

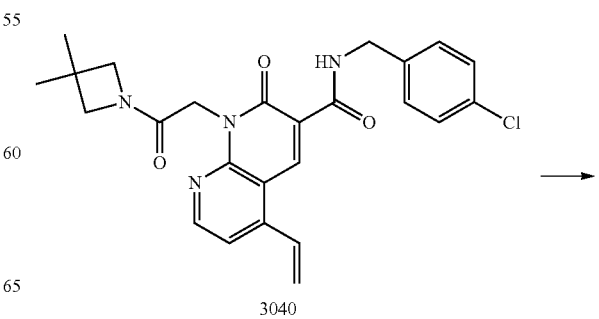
3040

-continued

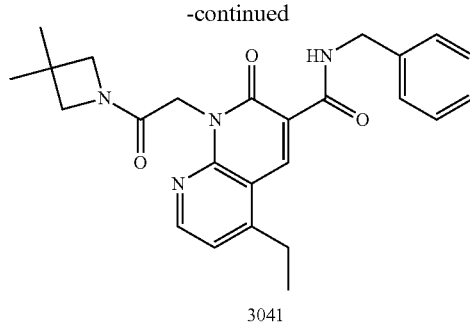

3041

Compound 3040 (20 mg, 0.043 mmol) is charged in a round-bottom flask and dissolved in a 4:1 EtOAc/MeOH mixture then palladium on charcoal (5% w/w) (9 mg, 0.004 mmol, 0.1 eq) is added. The flask is submitted to vacuum/hydrogen refill cycles (3×) then the solution is stirred at RT under a hydrogen atmosphere (balloon) for 1 h. The solution is filtered and concentrated under reduced pressure and the crude mixture is purified by preparative HPLC to provide compound 3041 ($t_R$: 1.97, (M+H)$^+$: 467/469).

Synthesis of Compound 3042

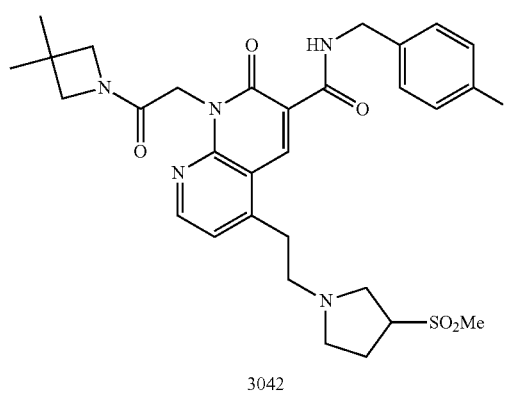

3042

Compound 3040 (40 mg, 0.086 mmol) is dissolved in EtOH (1.0 mL), then diisopropylethylamine (20 µL, 0.13 mmol, 1.5 eq) and 3-(methanesulfonyl)pyrrolidine (Chem Impex) (19 mg, 0.13 mmol, 1.5 eq) are added and the reaction mixture is stirred at RT for 5 h. Following completion of the reaction, AcOH is added (100 µL) and the crude mixture is purified by preparative HPLC to provide compound 3042 ($t_R$: 1.85, (M+H)$^+$: 614/616).

Synthesis of Compound 3043

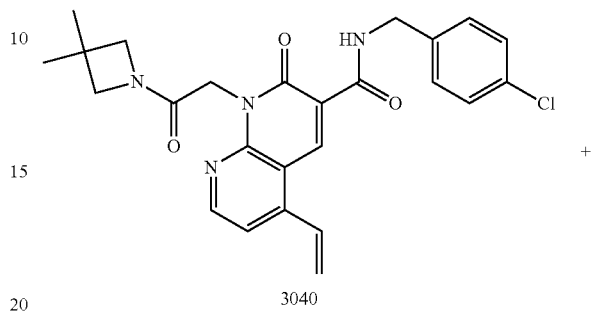

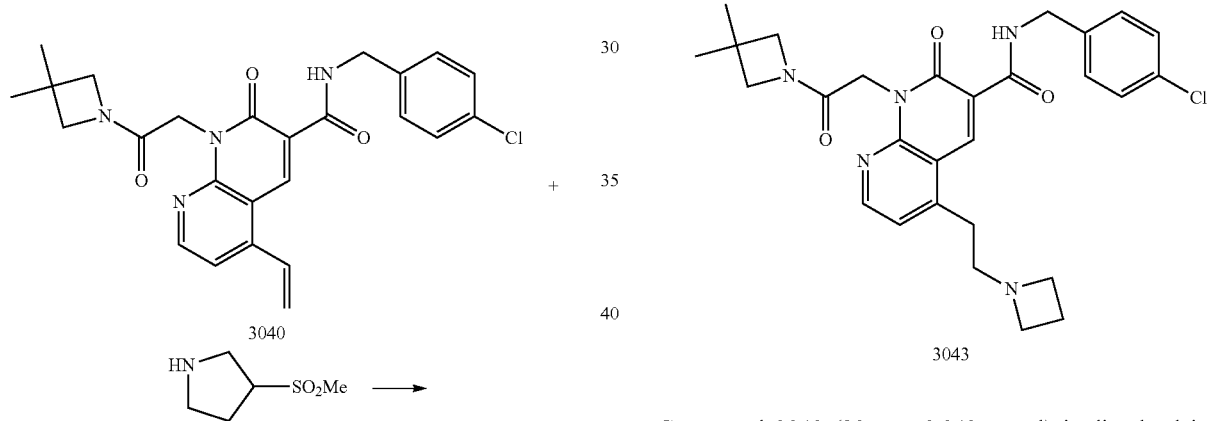

3043

Compound 3040 (20 mg, 0.043 mmol) is dissolved in EtOH (1.0 mL), then azetidine (Apollo) (8.7 µL, 0.13 mmol, 3.0 eq) is added and the reaction mixture is stirred at RT. Following completion of the reaction, AcOH is added (100 µL) and the crude mixture is purified by preparative HPLC to provide compound 3043 ($t_R$: 1.99, (M+H)$^+$: 522).

Synthesis of Compound 3044

3040 step 1 →

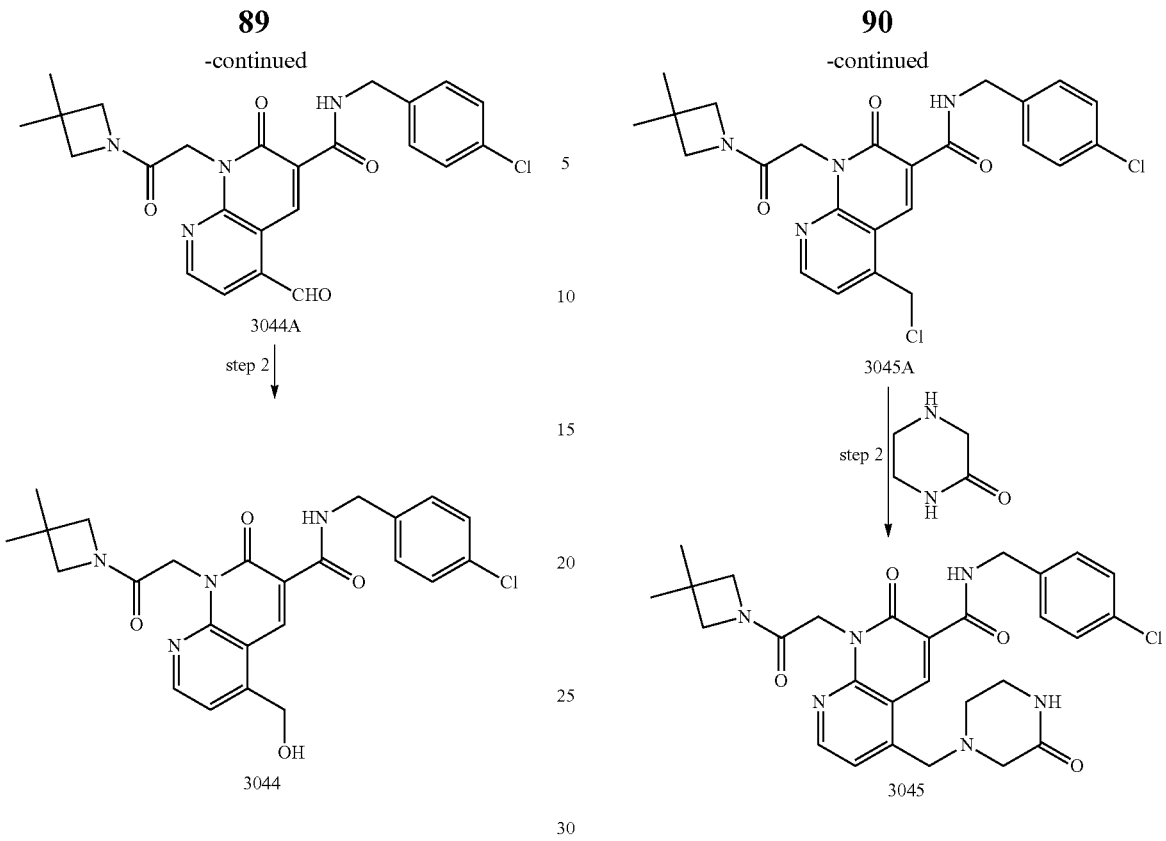

Step 1: Compound 3040 (100 mg, 0.215 mmol) is dissolved in DCM (2.5 mL) and MeOH (1 mL) in a round-bottom flask, then water (0.5 mL), a 2.5% solution of osmium tetraoxide in tert-butanol (0.08 mL, 0.007 mmol, 0.03 eq) and sodium periodate (140 mg, 0.645 mmol, 3.00 eq) are added and the reaction mixture is stirred at RT for 2 h. Following completion of the reaction, the solution is concentrated under reduced pressure and purified by flash chromatography (MeOH/DCM) to afford intermediate 3044A.

Step 2: Intermediate 3044A (20 mg, 0.043 mmol) is dissolved in MeOH (1 mL), then sodium borohydride (1.6 mg, 0.043 mmol, 1.0 eq) is added and the reaction mixture is stirred at RT for 30 min. The reaction mixture is diluted with EtOAc and washed with water. The organic layer is dried over $MgSO_4$; filtered and concentrated under reduced pressure. The crude mixture is purified by preparative HPLC to provide compound 3044 ($t_R$: 1.82, $(M+H)^+$: 467/469).

Synthesis of Compound 3045

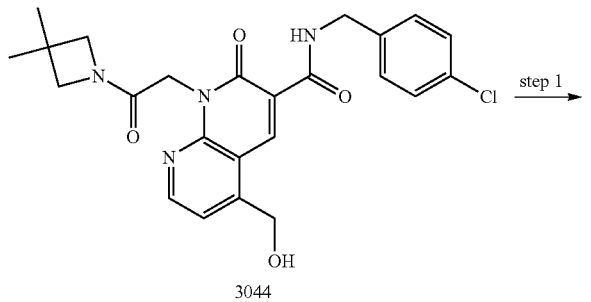

Step 1: Compound 3044 (60 mg, 0.13 mmol) is charged in a vial and suspended in DCM (1.5 mL). DMF (one drop) is added followed by thionyl chloride (19 µL, 0.26 mmol, 2.0 eq) and the solution is stirred at RT for 1 h. The reaction mixture is concentrated under reduced pressure to provide intermediate 3045A.

Step 2: Intermediate 3045A (20 mg, 0.041 mmol) is dissolved in DMF (1.0 mL), then 2-oxopiperazine (Aldrich) (12 mg, 0.12 mmol, 3.0 eq) is added and the reaction mixture is stirred at RT for 2 h. The crude mixture is filtered and purified by preparative HPLC to provide compound 3045 ($t_R$: 1.81, $(M+H)^+$: 551/553).

Synthesis of Compound 3046

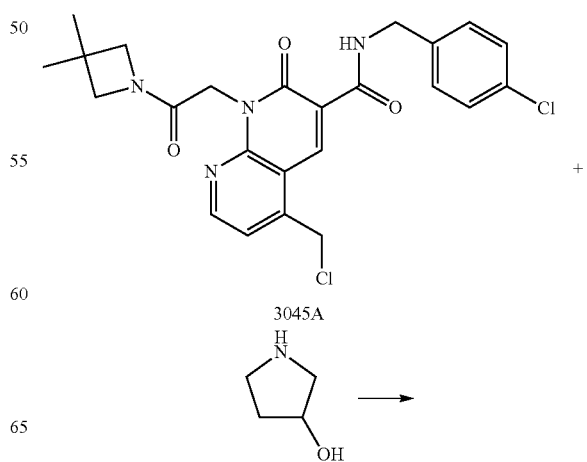

-continued

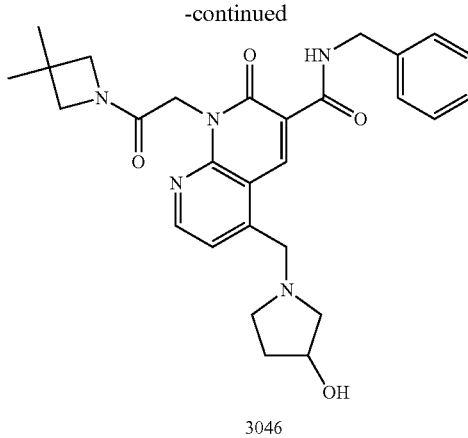

3046

Intermediate 3045A (20 mg, 0.041 mmol) is dissolved in DMF (1.0 mL), then 3-pyrrolidinol (TCI) (11 mg, 0.12 mmol, 3.0 eq) is added and the reaction mixture is stirred at RT for 2 h. The crude mixture is filtered and purified by preparative HPLC to provide compound 3046 ($t_R$: 1.87, (M+H)$^+$: 538/540).

Synthesis of Compound 3047

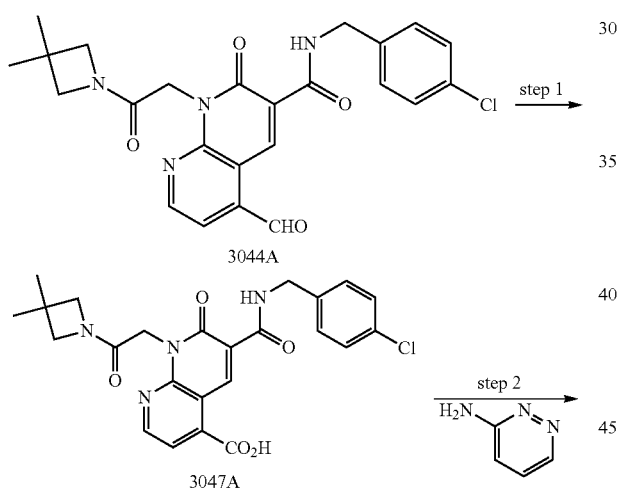

Step 1: Intermediate 3044A (1.38 g, 2.96 mmol) is charged in a round-bottom flask, dissolved in tert-butanol (31.0 mL) in a round-bottom flask, then a solution of sodium phosphate monobasic (6.12 g, 44.3 mmol, 15.0 eq) in water (24.0 mL) is added followed by a 2.0 M solution of 2-methyl-2-butene in THF (9.16 mL, 18.3 mmol, 6.20 eq) and sodium chlorite (1.34 g, 11.8 mmol, 4.00 eq). The reaction mixture is stirred at RT for 2 h, diluted with DCM and washed with brine. The organic layer is dried over MgSO$_4$; filtered and concentrated under reduced pressure. The crude residue is triturated in Et$_2$O to provide intermediate 3047A.

Step 2: Intermediate 3047A (50 mg, 0.10 mmol) is dissolved in DMF (1.0 mL), then triethylamine (38 μL, 0.26 mmol, 2.5 eq) and 3-aminopyridazine (TCI) (15 mg, 0.15 mmol, 1.5 eq) are added followed by HATU (63 mg, 0.17 mmol, 1.6 eq) and the reaction mixture is stirred at RT for 12 h. The solution is filtered and purified by preparative HPLC to provide compound 3047 ($t_R$: 1.79, (M+H)$^+$: 558.2).

Synthesis of Compound 3048

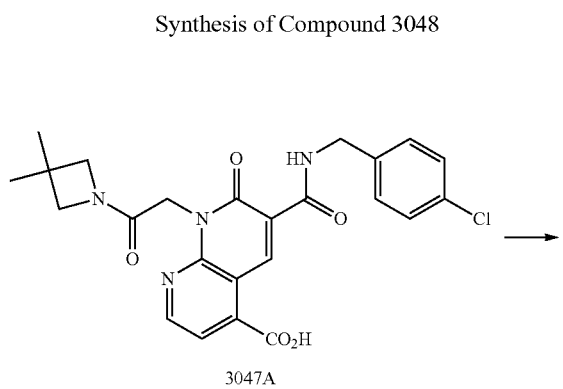

3047A

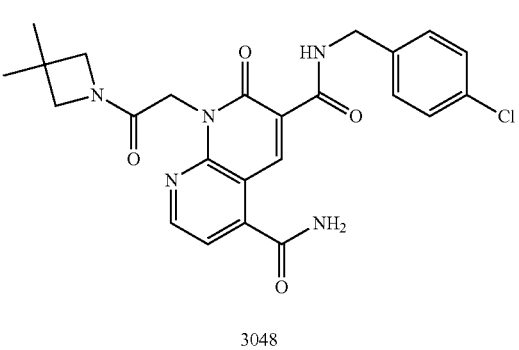

3048

Compound 3048 ($t_R$: 1.74, (M+H)$^+$: 482.2) is prepared analogously to compound 3047, except that in step 2, intermediate 3047A is reacted with ammonium chloride.

Synthesis of Compound 3049

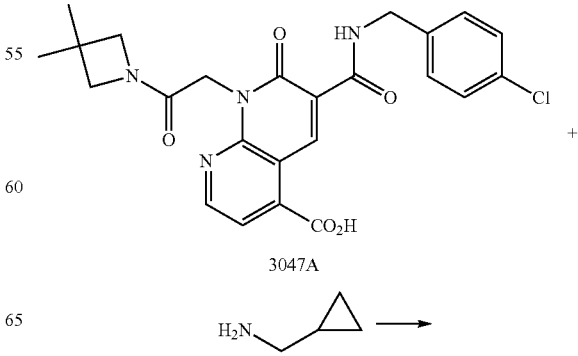

3047A

-continued

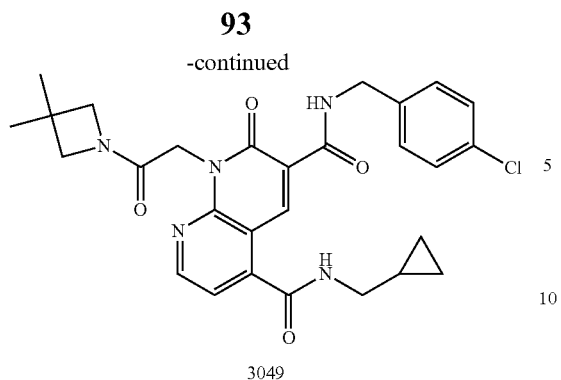

3049

Compound 3049 (t$_R$: 1.86, (M+H)$^+$: 536.3) is prepared analogously to compound 3047, except that in step 2, intermediate 3047A is reacted with cyclopropane methylamine (TCI).

Synthesis of Compound 3050

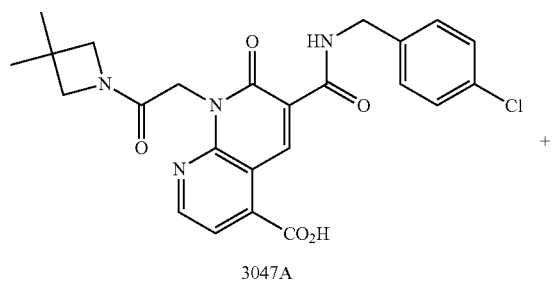

3047A

+

-continued

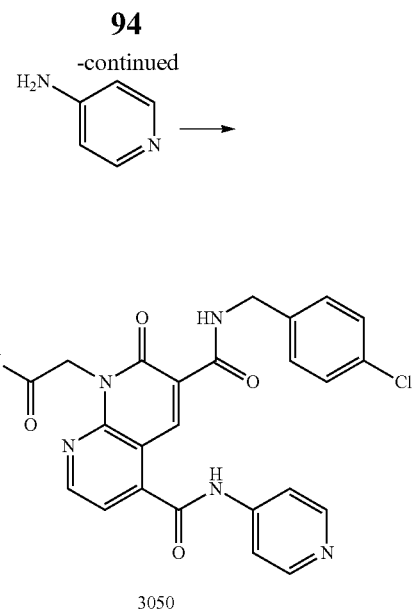

3050

Compound 3050 (t$_R$: 1.85, (M+H)$^+$: 559.3) is prepared analogously to compound 3047, except that in step 2, intermediate 3047A is reacted with 4-aminopyridine (Aldrich).

Synthesis of Compound 3051

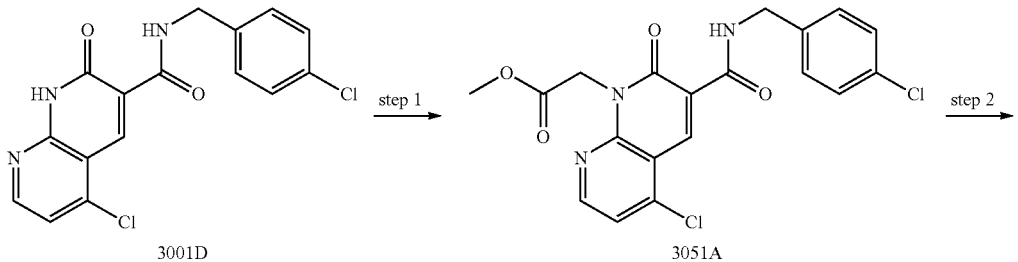

3001D     step 1     3051A     step 2

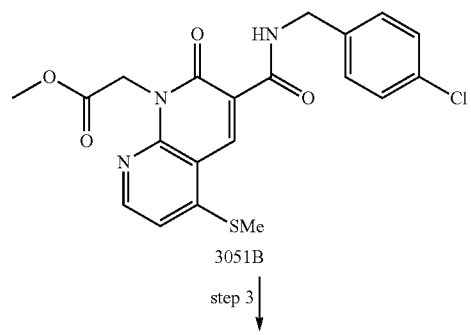

3051B step 3

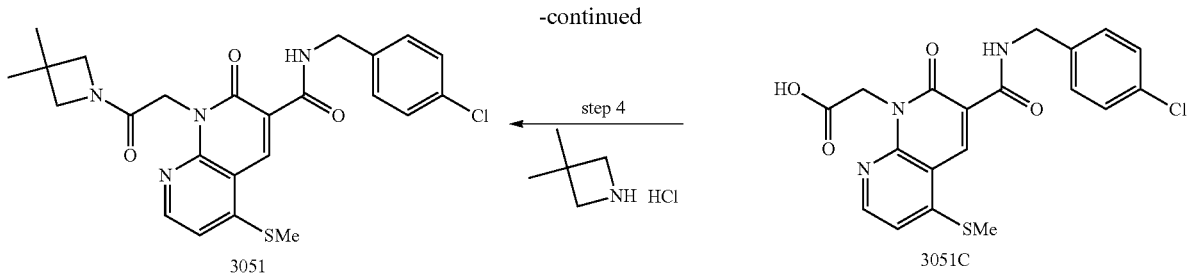

Step 1: Intermediate 3001D (200 mg, 0.574 mmol) is charged in a round-bottom flask and suspended in DMF (5 mL). Potassium carbonate (158 mg, 1.15 mmol, 2.00 eq) and methyl bromoacetate (TCI) (132 mg, 0.862 mmol, 1.50 eq) are added and the solution is stirred at RT for 3 h. The solution is added to water and the resulting solid is filtered and dried under vacuum. The crude mixture is purified by flash chromatography (MeOH/DCM) to afford intermediate 3051A.

Step 2: Sodium thiomethoxide (27.6 mg, 0.394 mmol, 1.20 eq) is added to intermediate 3051A (138 mg, 0.328 mmol) in DMF (1 mL) in a round-bottom flask and the solution is stirred at RT for 2 h. The reaction mixture is diluted with EtOAc and washed with brine. The organic layer is dried over MgSO$_4$; filtered and concentrated under reduced pressure to afford intermediate 3051B.

Step 3: Intermediate 3051B (146 mg, 0.328 mmol) is dissolved in THF (5.0 mL) and MeOH (2.5 mL) in a round-bottom flask, then a 1.0 M aqueous solution of NaOH (2.00 mL, 2.00 mmol, 6.10 eq) is added. The reaction mixture is warmed to 50° C. and stirred for 3 h. The reaction mixture is concentrated under reduced pressure and acidified to approximately pH 2 using a 1 M aqueous HCl solution. The resulting solid is filtered and washed with hexanes to provide intermediate 3051C.

Step 4: Intermediate 3051C (137 mg, 0.328 mmol) is dissolved in DMF (5.0 mL) in a round-bottom flask, then diisopropylethylamine (285 μL, 1.64 mmol, 5.0 eq) and 3,3-dimethyl-azetidine hydrochloride (prepared analogously to the procedure in J. Med. Chem. 2008, 51, 7380, herein incorporated by reference) (41.6 mg, 0.489 mmol, 1.50 eq) are added followed by TBTU (126 mg, 0.394 mmol, 1.20 eq). The reaction mixture is stirred at RT for 18 h. The crude mixture is purified by preparative HPLC to provide compound 3051 (t$_R$: 1.96, (M+H)$^+$: 485.2).

Synthesis of Compound 3052

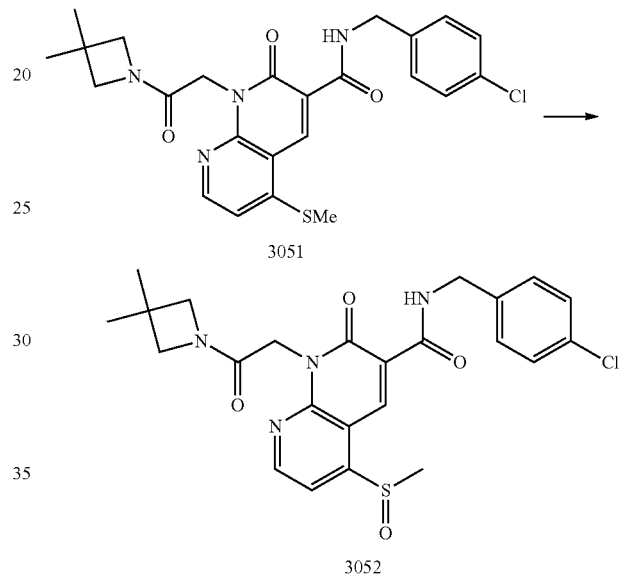

Compound 3051 (277 mg, 0.571 mmol) is dissolved in DCM (5.0 mL) and MeOH (4.0 mL) in a round-bottom flask, then a saturated aqueous solution of sodium bicarbonate (1.0 mL) is added followed by a solution of oxone (702 mg, 1.14 mmol, 2.00 eq) in water (2.0 mL) and the reaction mixture is stirred at RT for 1 h. The reaction mixture is extracted with DCM and washed with brine. The organic layer is dried over MgSO$_4$; filtered and concentrated under reduced pressure. The crude mixture is purified by preparative HPLC to provide compound 3052 (t$_R$: 1.76, (M+H)$^+$: 501.3).

Synthesis of Compound 4001

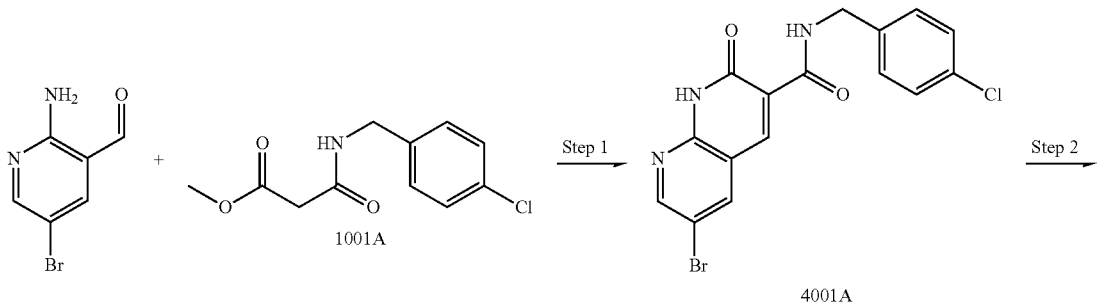

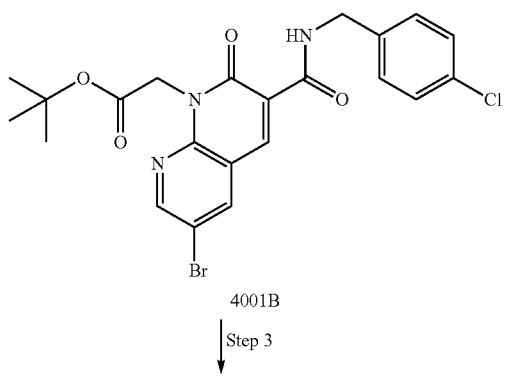

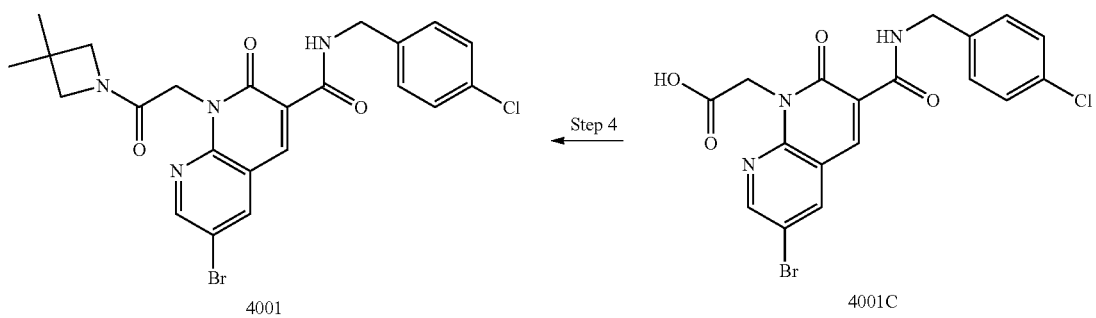

Step 1: 2-Amino-5-bromonicotinaldehyde (Apollo-Inter) (7.00 g, 34.8 mmol) and intermediate 1001A (10.1 g, 41.8 mmol, 1.20 eq) are charged in a microwave vial and EtOH (35 mL) is added. Piperidine (8.62 mL, 87.1 mmol, 2.50 eq) is added and the vial is sealed and warmed in a microwave oven at 120° C. for 20 min. The resulting solid is collected by filtration, washed with methyl t-butyl ether and dried under vacuum to afford intermediate 4001B.

Step 2: Intermediate 4001A (10.5 g, 26.8 mmol) is charged in a round-bottom flask and suspended in DMF (130 mL). Potassium carbonate (11.2 g, 81.1 mmol, 3.03 eq) and t-butyl bromoacetate (4.55 mL, 30.8 mmol, 1.15 eq) are added and the solution is stirred at RT for 16 h. The solution is added to water and the resulting solid is filtered and dried under vacuum. The solid is washed with acetone and methyl t-butyl ether to afford intermediate 4001B.

Step 3: Intermediate 4001B (11.6 g, 22.9 mmol) is charged in a round-bottom flask, dissolved in DCM (90.0 mL) and TFA (90.0 mL) is added. The solution is stirred at RT for 4 h and concentrated. The residue is suspended in toluene and concentrated under reduced pressure to provide intermediate 4001C.

Step 4: Intermediate 4001C (5.00 g, 11.0 mmol) is charged in a round-bottom flask and dissolved in DMF (100 mL). Diisopropylethylamine (9.66 mL, 55.5 mmol, 5.00 eq) and 3,3-dimethyl-azetidine hydrochloride (prepared analogously to the procedure in J. Med. Chem. 2008, 51, 7380, herein incorporated by reference) (1.51 g, 17.8 mmol, 1.60 eq) are added followed by HATU (6.75 g, 17.8 mmol, 1.60 eq) and the solution is stirred at RT for 16 h. Following completion of the reaction, the reaction mixture is diluted with water and the resulting solid is collected by filtration and washed with methyl t-butyl ether. The product is purified by preparative HPLC to provide compound 4001 ($t_R$: 1.57, (M+H)$^+$: 517.0/518.9/520.9).

Synthesis of Compound 4002

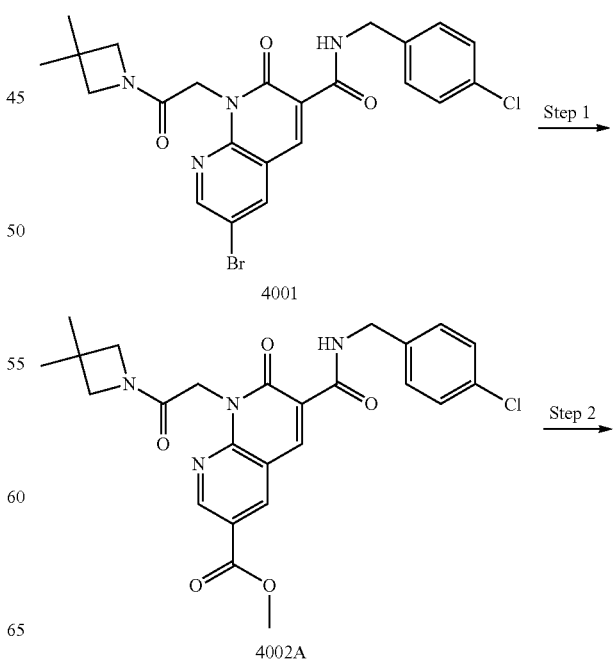

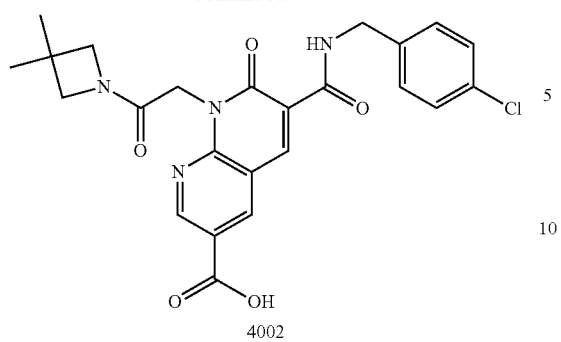
4002

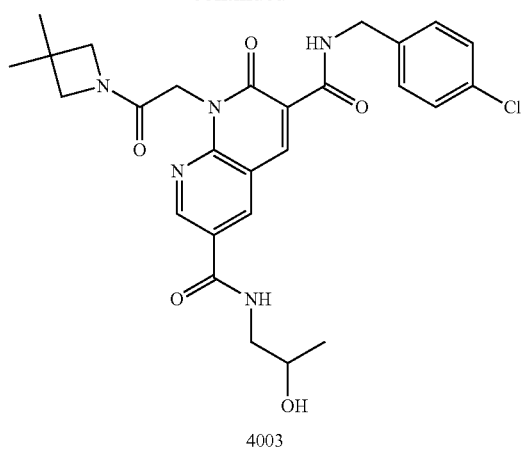
4003

Step 1: Compound 4001 (500 mg, 0.966 mmol), palladium (II) acetate (22 mg, 0.097 mmol, 0.10 eq) and Xantphos (112 mg, 0.193 mmol, 0.200 eq) are charged in a vial. MeOH (2.50 mL) and triethylamine (12.5 mL) are added. The reaction mixture is degassed with CO and stirred for 36 h at 70° C. under 1 atm of CO. The reaction mixture is diluted with methyl t-butyl ether and the resulting solid is collected by filtration. The solid is washed with methyl t-butyl ether to provide intermediate 4002A.

Step 2: Intermediate 4002A (100 mg, 0.201 mmol) is charged in a round-bottom flask and suspended in THF (5.0 mL). MeOH (2.5 mL) and NaOH 5 N (0.201 mL, 1.01 mmol, 5.00 eq) are added and the solution is stirred at 60° C. for 2 h. The reaction mixture is acidified with HCl 2 N and concentrated. The residue is purified by preparative HPLC to provide compound 4002 ($t_R$: 1.03, (M+H)$^+$: 483.0/484.9).

Compound 4002 (40 mg, 0.052 mmol) is charged in a vial and dissolved in NMP (1.0 mL). Diisopropylethylamine (73 μL, 0.42 mmol, 8.0 eq) and 1-amino-2-propanol (Aldrich) (12 mg, 0.16 mmol, 3.0 eq) are added followed by HATU (49 mg, 0.13 mmol, 2.5 eq) and the solution is stirred at RT for 3 h. Following completion of the reaction, the solution is filtered and purified by preparative HPLC to provide compound 4003 ($t_R$: 1.81, (M+H)$^+$: 540.1).

Synthesis of Compound 4003

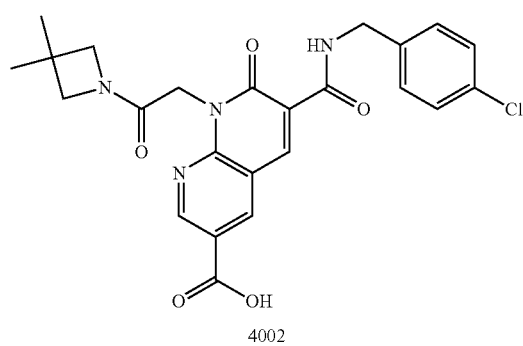

Synthesis of Compound 4004

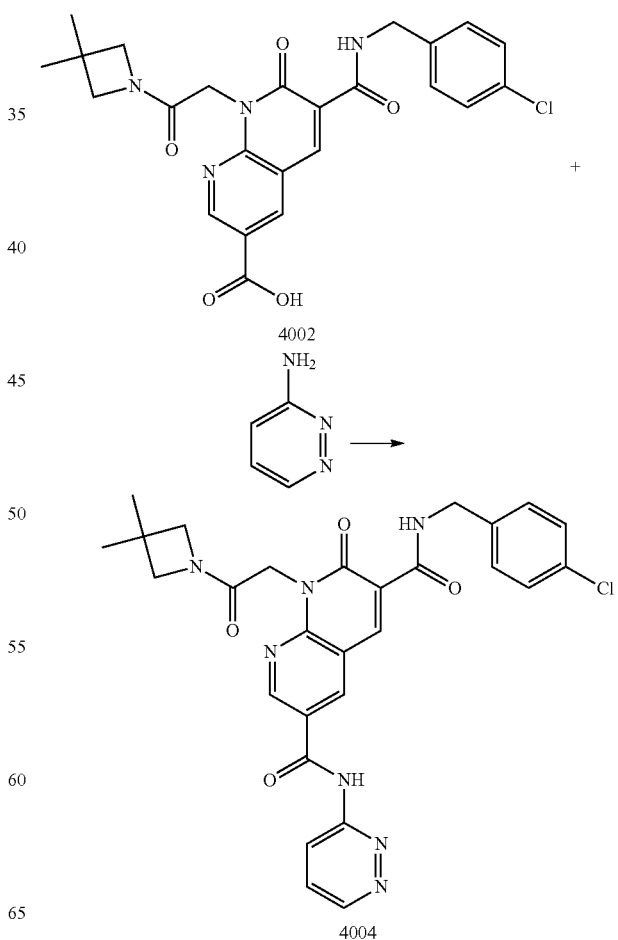
4004

Compound 4004 ($t_R$: 1.94, (M+H)$^+$: 560.1) is prepared analogously to compound 4003, except that compound 4002 is reacted with 3-aminopyridazine (TCI-US).

Synthesis of Compound 4005

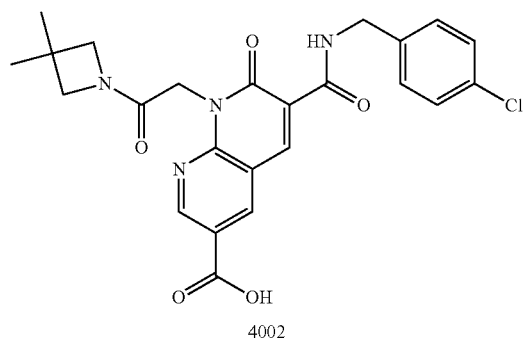
4002

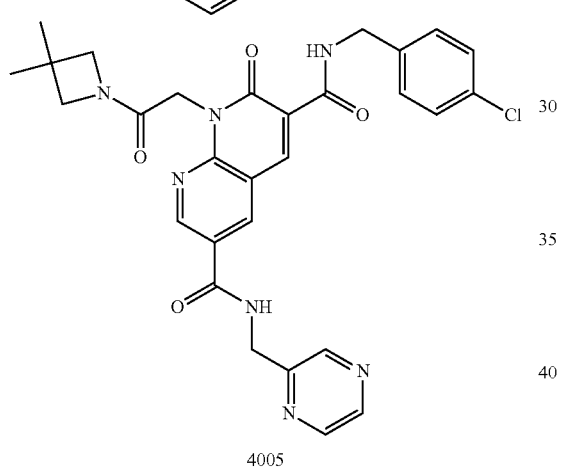
4005

Compound 4005 ($t_R$: 1.89, (M+H)$^+$: 574.1) is prepared analogously to compound 4003, except that compound 4002 is reacted with 1-pyrazin-2-ylmethanamine (Oakwood).

Synthesis of Compound 4006

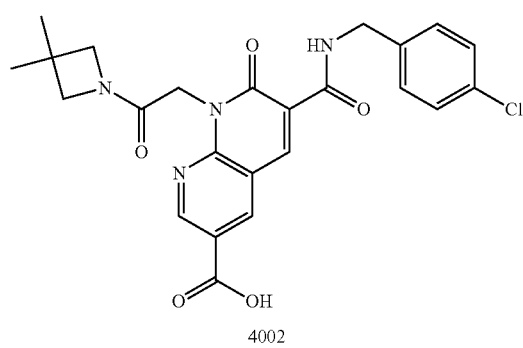
4002

-continued

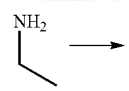

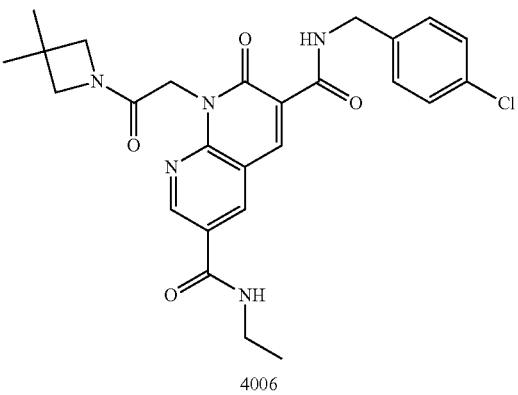
4006

Compound 4006 ($t_R$: 1.95, (M+H)$^+$: 510.1) is prepared analogously to compound 4003, except that compound 4002 is reacted with ethylamine (Aldrich).

Synthesis of Compound 4007

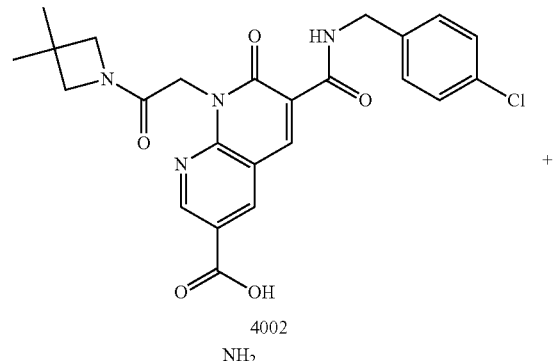
4002

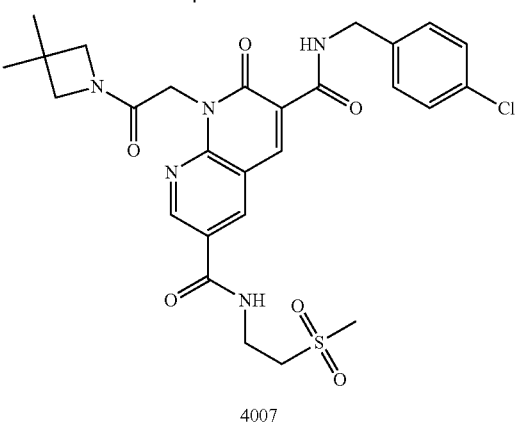
4007

Compound 4007 ($t_R$: 1.27, (M+H)$^+$: 588.0/590.0) is prepared analogously to compound 4003, except that compound 4002 is reacted with 2-(methylsulfonyl)ethanamine (Princeton).

Synthesis of Compound 4008

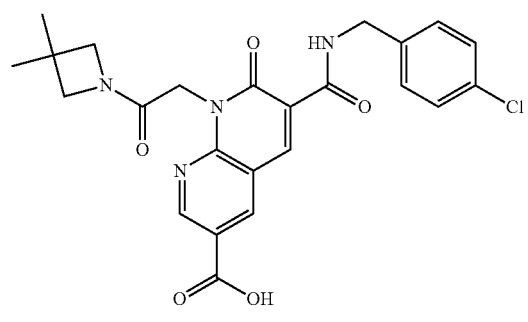
4002

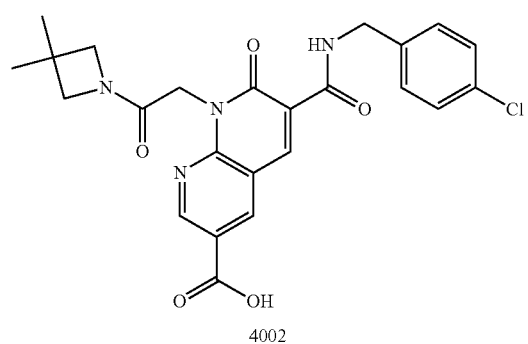
4008

Compound 4008 ($t_R$: 1.93, (M+H)$^+$: 536.1) is prepared analogously to compound 4003, except that compound 4002 is reacted with cyclopropanemethylamine (Alfa).

Synthesis of Compound 4009

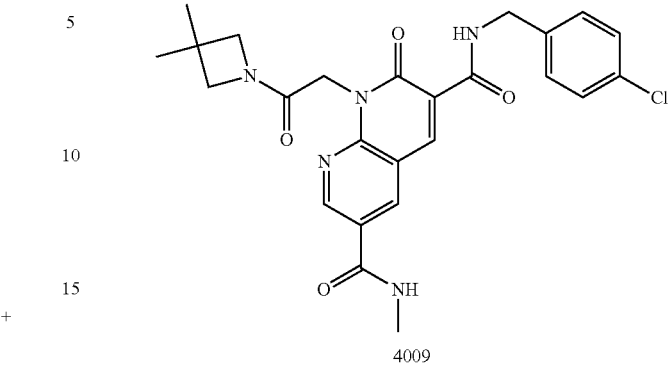
4009

Compound 4009 ($t_R$: 1.25, (M+H)$^+$: 496.0/498.0) is prepared analogously to compound 4003, except that compound 4002 is reacted with methylamine (Aldrich).

Synthesis of Compound 4010

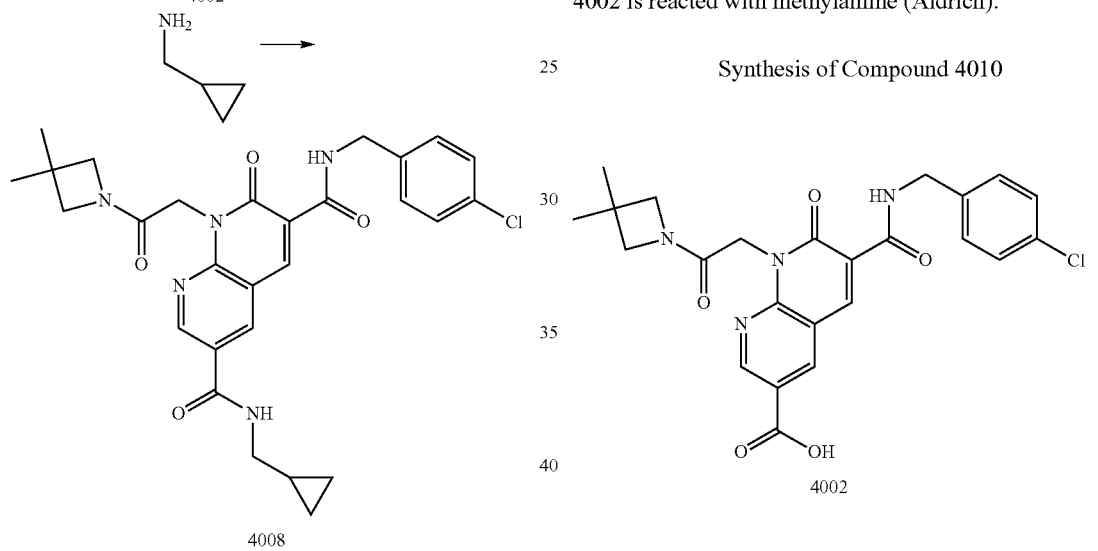
4002

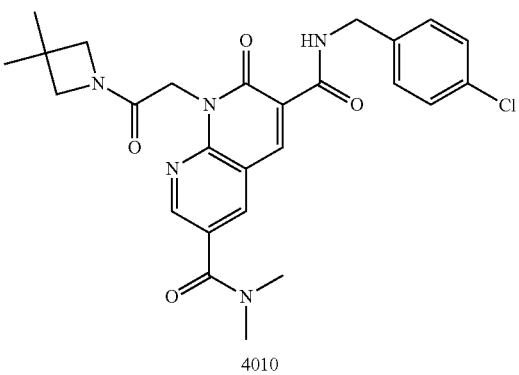
4010

Compound 4010 ($t_R$: 1.27, (M+H)$^+$: 510.0/511.9) is prepared analogously to compound 4003, except that compound 4002 is reacted with dimethylamine (Aldrich).

Synthesis of Compound 4011

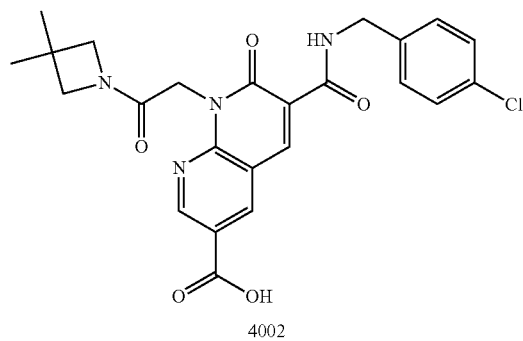
4002

+

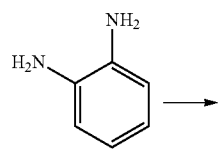

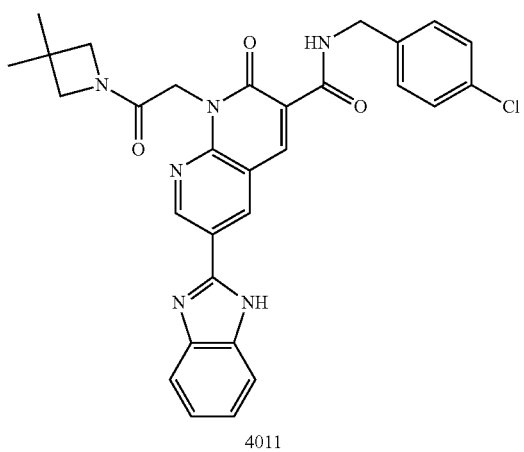
4011

Compound 4002 (74 mg, 0.15 mmol) is charged in a round-bottom flask and suspended in DMF (3.0 mL). Triethylamine (63 µL, 0.46 mmol, 3.0 eq) and o-phenylenediamine (ABCR) (3.0 eq) are added, followed by HATU (70 mg, 0.19 mmol, 1.2 eq) and the solution is stirred at RT for 1 h. Methyl t-butyl ether is added and the resulting solid is collected by filtration. The solid is suspended in AcOH (3.0 mL) and the reaction mixture is stirred for 1 h at 80° C. Following completion of the reaction, the mixture is concentrated under reduced pressure. The residue is purified by preparative HPLC to provide compound 4011 ($t_R$: 1.25, (M+H)$^+$: 555.0/557.1).

Synthesis of Compound 4012

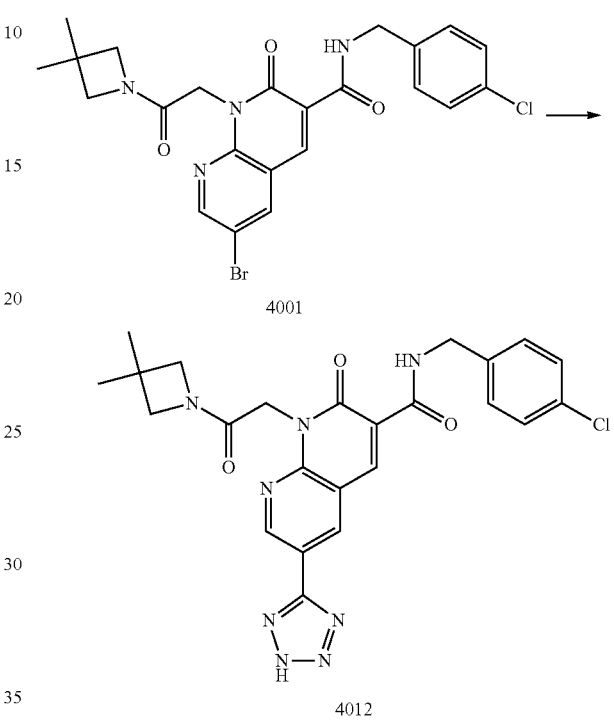

Compound 4001 (100 mg, 0.193 mmol) is charged in a vial and suspended in N,N-dimethylacetamide (3.0 mL). Zinc cyanide (45 mg, 0.39 mmol, 2.0 eq) and bis(tri-t-butylphosphine)palladium (0) (10 mg, 0.019 mmol, 0.10 eq) are added. The vial is sealed and the mixture is heated at 100° C. for 5 h. The reaction mixture is cooled to RT and filtered. Ammonium chloride (21 mg, 0.39 mmol, 2 eq) and sodium azide (25 mg, 0.39 mmol, 2.0 eq) are added to the solution and the vial is sealed and heated at 120° C. for 7 h. The mixture is filtered and purified by preparative HPLC to provide compound 4012 ($t_R$: 1.3, (M+H)$^+$: 506.9/509.0).

Synthesis of Compound 4013

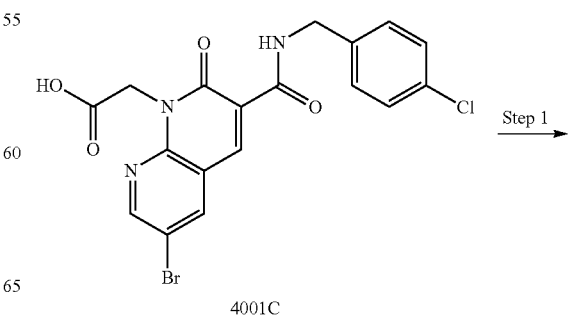
4001C

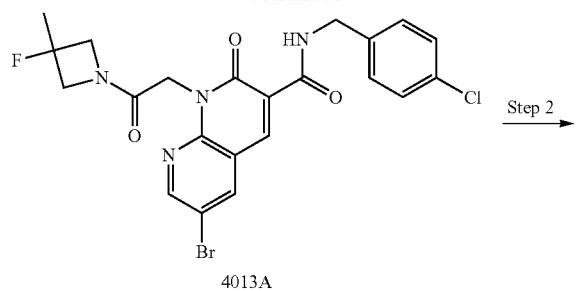

4013A

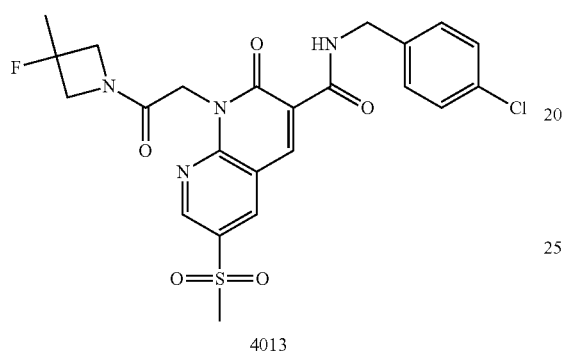

4013

Step 1: Intermediate 4013A is prepared analogously to compound 4001, except that in step 4, intermediate 4001C is reacted with intermediate 1003A.

Step 2: Intermediate 4013A (200 mg, 0.383 mmol) is charged in a pressure vessel and dissolved in DMSO (0.65 mL). Copper(I) iodide (7.3 mg, 0.038 mmol, 0.10 eq), L-proline (8.8 mg, 0.076 mmol, 0.20 eq), NaOH (3.1 mg, 0.076 mmol, 0.20 eq) and sodium methanesulfinate (47 mg, 0.46 mmol, 1.2 eq) are added. The vessel is sealed and the mixture is heated under argon at 95° C. for 24 h. The reaction mixture is cooled to RT and added to water. The resulting solid is collected by filtration and purified by preparative HPLC to provide compound 4013 ($t_R$: 1.66, (M+H)$^+$: 521.3/523.3).

Synthesis of Compound 4014

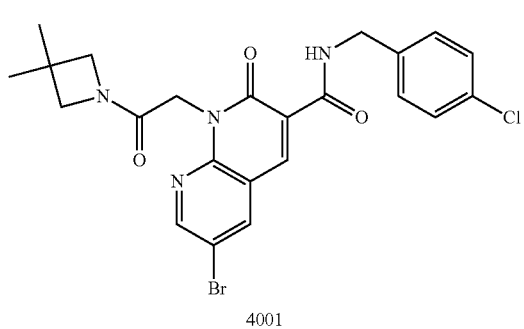

4001

+

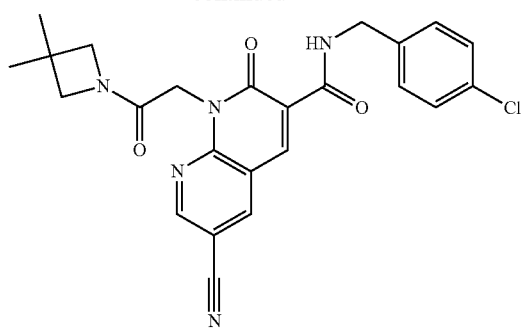

4014

Compound 4001 (100 mg, 0.193 mmol) is charged in a vial and suspended in N,N-dimethylacetamide (3.0 mL). Zinc cyanide (45 mg, 0.39 mmol, 2 eq) and bis(tri-t-butylphosphine)palladium (0) (10 mg, 0.019 mmol, 0.10 eq) are added. The vial is sealed and the mixture is heated at 100° C. for 5 h. The reaction mixture is filtered and purified by preparative HPLC to provide compound 4014 ($t_R$: 1.4, (M+H)$^+$: 464.0/466.0).

Synthesis of Compound 4015

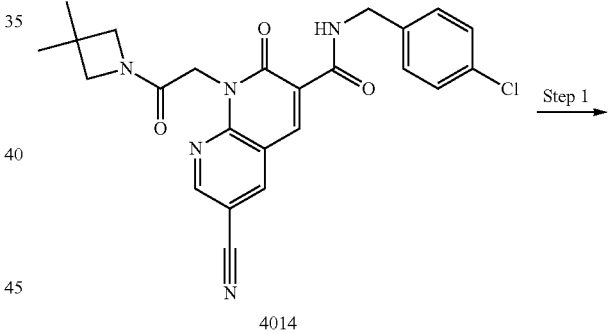

4014

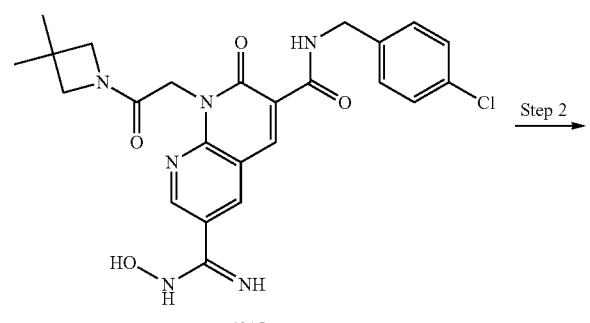

4015A

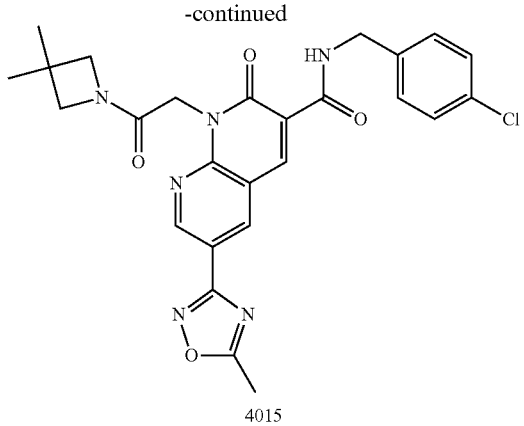

4015

Step 1: Compound 4014 (200 mg, 0.431 mmol) is charged in a vial and suspended in EtOH (3.0 mL). Hydroxylamine 50% in water (0.13 mL, 0.47 mmol, 1.1 eq) is added. The reaction mixture is stirred at 60° C. for 1 h and concentrated under reduced pressure to provide intermediate 4015A.

Step 2: Intermediate 4015A (30 mg, 0.060 mmol) is charged in a vial and dissolved in DMF (1.0 mL). Acetyl chloride (4.3 μL, 0.063 mmol, 1.1 eq) is added and the reaction mixture is stirred for 45 min at RT. Diisopropylethylamine (21 μL, 0.12 mmol, 2.0 eq) is added. The reaction mixture is stirred for 5 h at 100° C., filtered and purified by preparative HPLC to provide compound 4015 (t$_R$: 2.07, (M+H)$^+$: 521).

Synthesis of Compound 4016

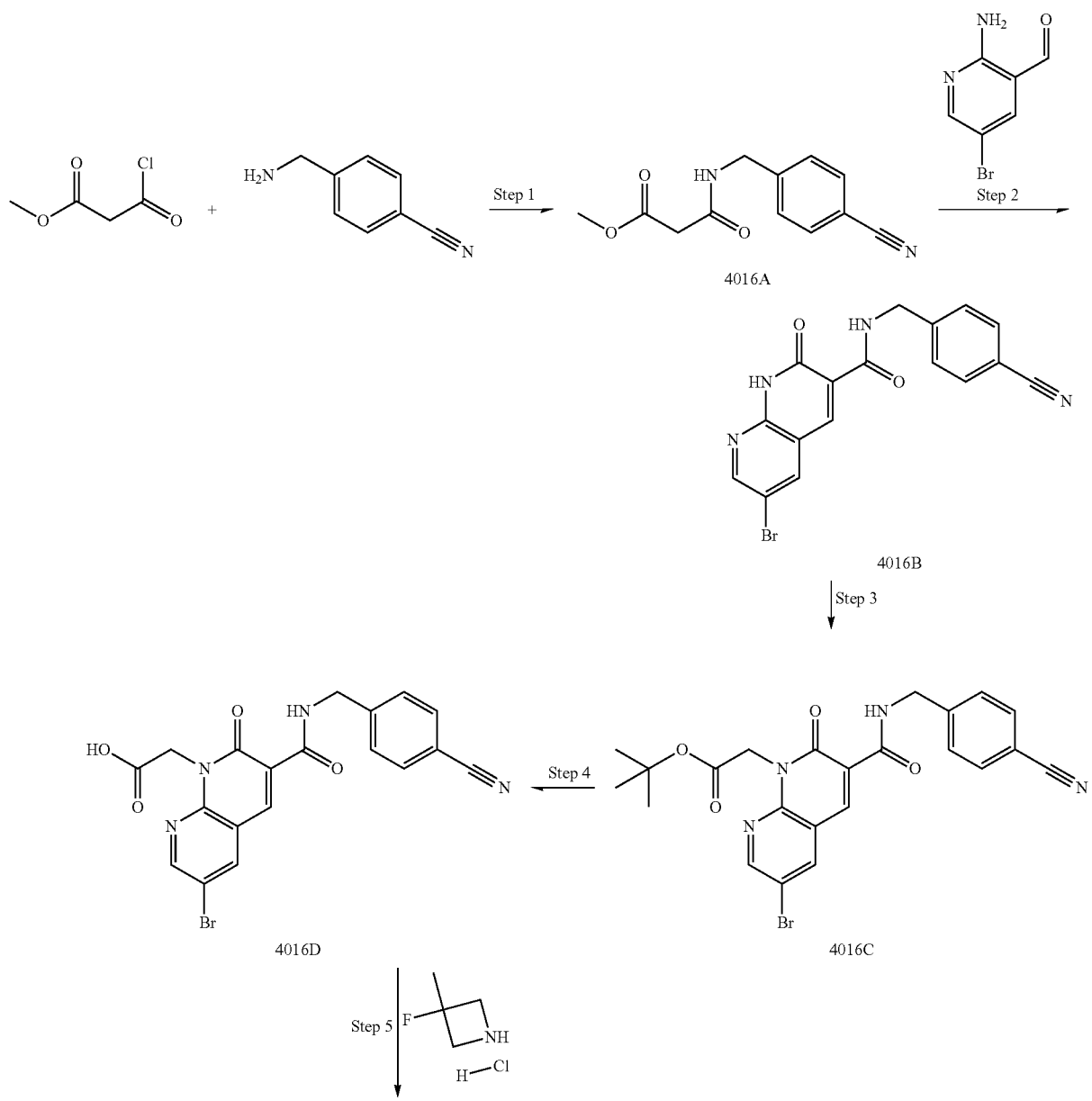

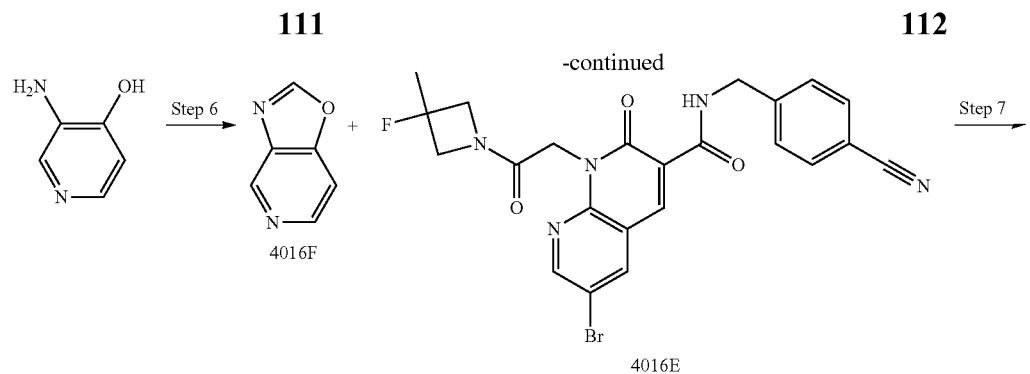

Step 1: Intermediate 4016A is prepared analogously to compound 1001A, except that methyl 3-chloro-3-oxopropanoate is reacted with 4-cyanobenzylamine (Matrix).

Step 2: Intermediate 4016B is prepared analogously to intermediate 4001A.

Step 3: Intermediate 4016C is prepared analogously to intermediate 4001B.

Step 4: Intermediate 4016D is prepared analogously to intermediate 4001C.

Step 5: Intermediate 4016E is prepared analogously to compound 4001, except that intermediate 4016D is reacted with intermediate 1003A.

Step 6: 3-Amino-4-hydroxypyridine (Fluorochem) (500 mg, 4.54 mmol) is charged in a microwave vial and suspended in trimethylorthoformate (5.0 mL). AcOH (0.400 mL) is added and vial is sealed and warmed in a microwave oven at 160° C. for 30 min. The reaction mixture is concentrated and the residue is purified by flash chromatography (50% EtOAc in hexanes to 100% EtOAc) to provide intermediate 4016F.

Step 7: Intermediate 4016E (100 mg, 0.195 mmol) is charged in a microwave vial and dissolved in DMF (4.0 mL). Intermediate 4016F (28 mg, 0.23 mmol, 1.2 eq), potassium acetate (38 mg, 0.39 mmol, 2.0 eq), tetra-butylammonium bromide (63 mg, 0.20 mmol, 1.0 eq) and copper (I) iodide (74 mg, 0.39 mmol, 2 eq) are added and the reaction mixture is degassed with argon. Bis(tri-t-butylphosphine)palladium (0) (10 mg, 0.020 mmol, 0.10 eq) is added and the vial is sealed and warmed in a microwave oven at 160° C. for 15 min. The reaction mixture is concentrated and the residue is purified by flash chromatography (10% MeOH in DCM) and by preparative HPLC to provide compound 4016 ($t_R$: 1.67, (M+H)$^+$: 552.4).

Synthesis of Compound 4017

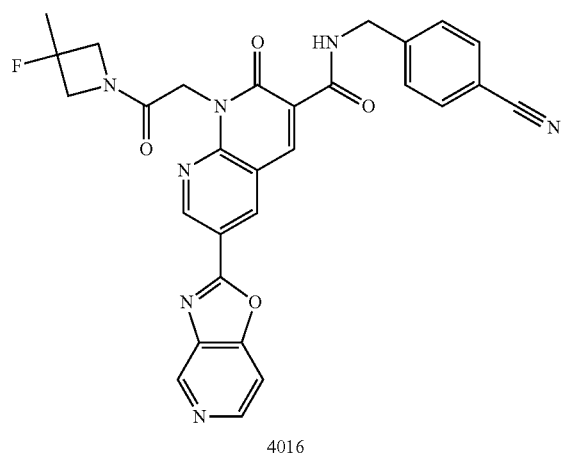 [SMILES: CC1(F)CN(C(=O)Cn2c(=O)c(C(=O)NCc3ccc(C#N)cc3)cc3cc(-c4nc5cnccc5o4)cnc32)C1]

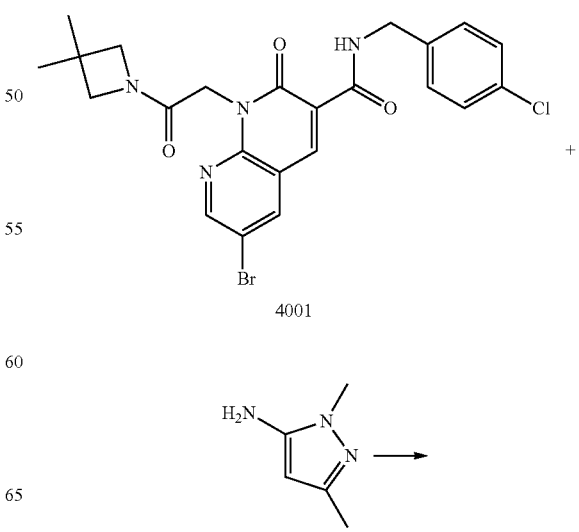

113
-continued

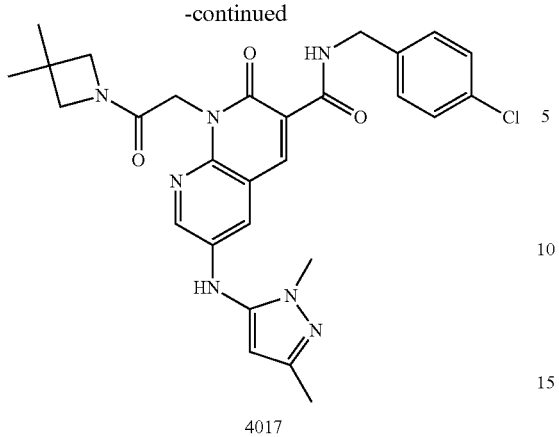
4017

114
-continued

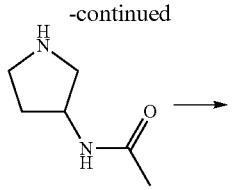

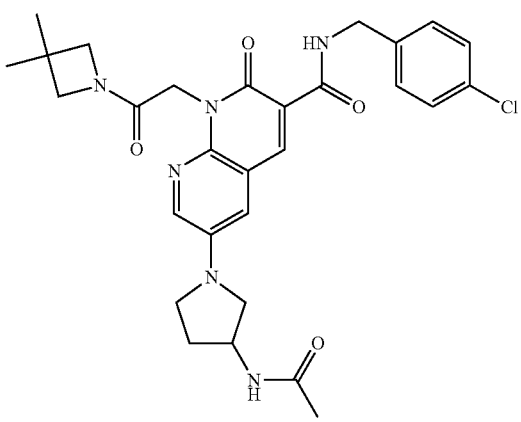
4018

Compound 4001 (50 mg, 0.097 mmol), 5-amino-1,3-dimethylpyrazole (Lancaster) (22 mg, 0.19 mmol, 2 eq), palladium (II) acetate (2.2 mg, 0.0097 mmol, 0.10 eq), RuPhos (9.1 mg, 0.019 mmol, 0.20 eq) and cesium carbonate (63 mg, 0.19 mmol, 2.0 eq) are charged in a vial and toluene (1.0 mL) is added. The vial is sealed and the reaction mixture is stirred under argon at 110° C. for 16 h. The reaction mixture is concentrated and the residue is purified by preparative HPLC to provide compound 4017 ($t_R$: 1.97, (M+H)$^+$: 548.2).

Synthesis of Compound 4018

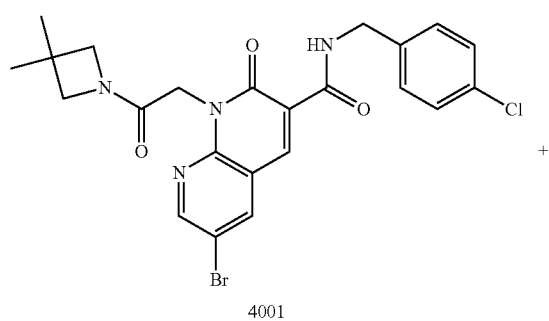
4001
+

Compound 4018 ($t_R$: 1.89, (M+H)$^+$: 565.3) is prepared analogously to compound 4017, except that compound 4001 is reacted with 3-acetamidopyrrolidine (TCI-US).

Synthesis of Compound 4019

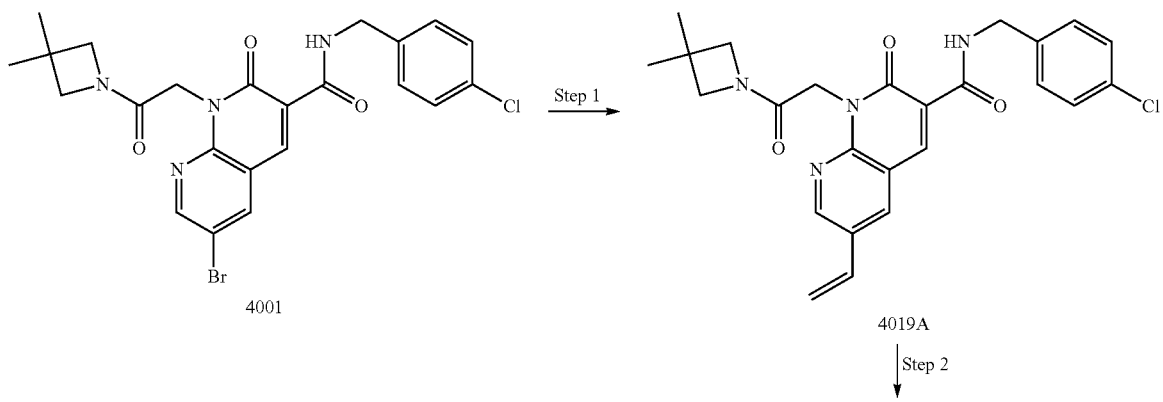

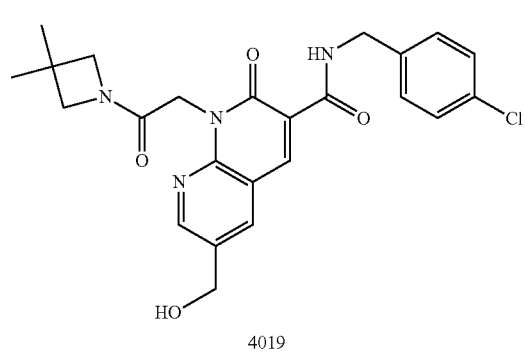

4019

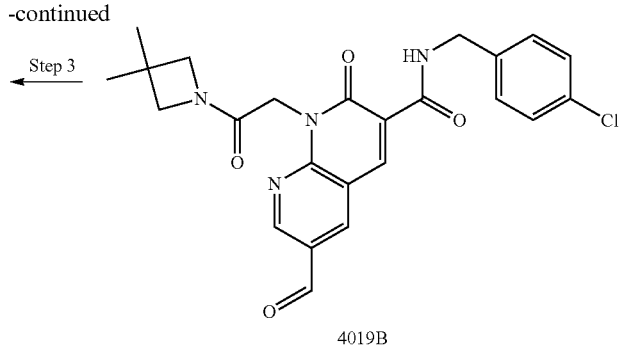

4019B

Step 1: Compound 4001 (5.70 g, 11.0 mmol) is charged in a round-bottom flask and dissolved in DMF (70 mL). Dichlorobis(triphenylphosphine)palladium (0) (772 mg, 1.10 mmol, 0.100 eq) and tributyl(vinyl)tin (3.70 ml, 12.1 mmol, 1.10 eq) are added and the solution is degassed with argon. The reaction mixture is heated at 80° C. for 2 h. Methyl t-butyl ether is added and the resulting solid is collected by filtration. The solid is washed with hexanes and methyl t-butyl ether to provide intermediate 4019A.

Step 3: Intermediate 4019B (750 mg, 1.61 mmol) is charged in a round-bottom flask and MeOH (25 mL) is added. At 0° C., sodium borohydride (61 mg, 1.6 mmol, 1.0 eq) is added and the reaction mixture is stirred for 1 h at RT. Water is added and the resulting solid is collected by filtration. The solid is purified by preparative HPLC to provide compound 4019 ($t_R$: 1.26, (M+H)$^+$: 469.0/471.0).

Synthesis of Compound 4020

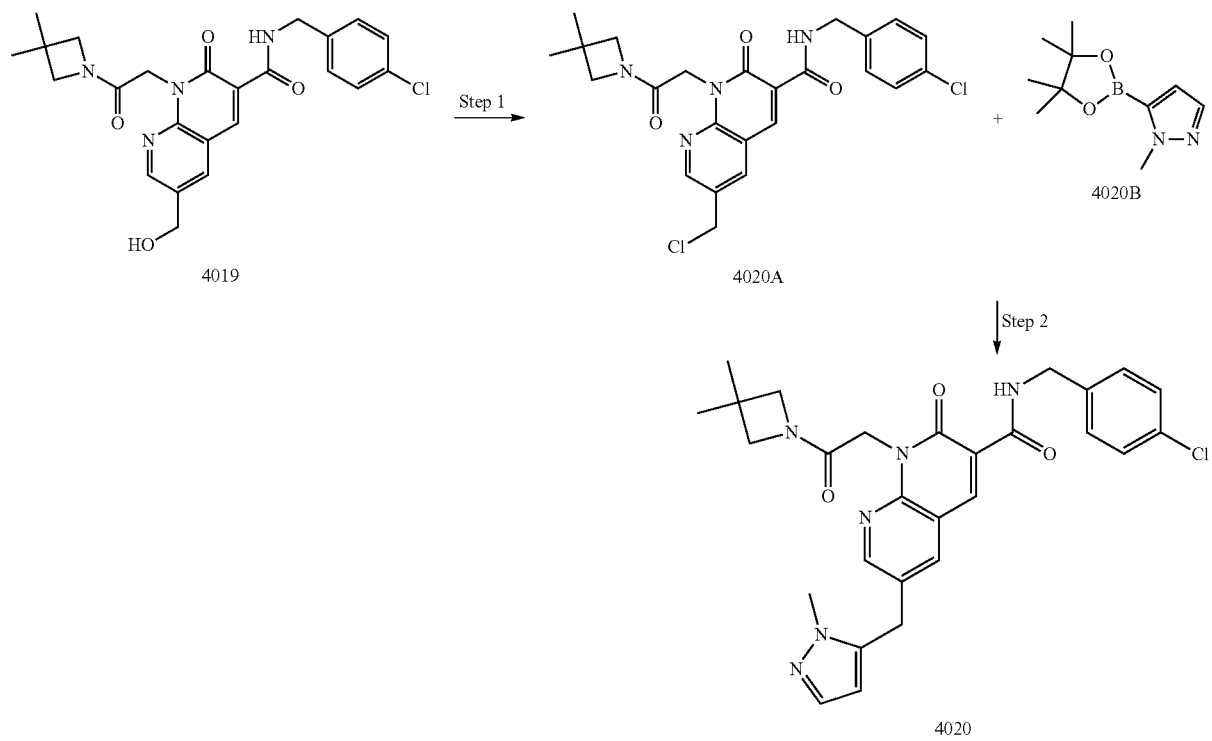

Step 2: Intermediate 4019A (4.07 g, 8.75 mmol) is charged in a round-bottom flask and suspended in DCM (100 mL) and MeOH (42.0 mL). Water (21.0 mL), osmium tetroxide 2.5% in t-butanol (3.17 mL, 0.262 mmol, 0.0300 eq) and sodium periodate (5.61 g, 26.2 mmol, 3.00 eq) are added and the reaction mixture is stirred for 3 h at RT. Methyl t-butyl ether is added and the resulting solid is collected by filtration. The solid is washed with water and methyl t-butyl ether to provide intermediate 4019B.

Step 1: Compound 4019 (753 mg, 1.56 mmol) is charged in a round-bottom flask and dissolved in DCM (20 mL). DMF (3 drops) and thionyl chloride (227 µL, 3.13 mmol, 2.00 eq) are added and the reaction mixture is stirred for 1 h at RT. The reaction mixture is concentrated under reduced pressure to provide intermediate 4020A.

Step 2: Intermediate 4020A (75 mg, 0.15 mmol) is charged in a microwave vial and dissolved in DMF (1.7 mL). Water (0.17 mL), intermediate 4020B (Frontier) (42 mg, 0.20 mmol, 1.3 eq), potassium carbonate (64 mg, 0.46 mmol, 3.0 eq) and bis(tri-t-butylphosphine)palladium (0) (12 mg, 0.023 mmol, 0.15 eq) are added and the vial is sealed and warmed in a microwave oven at 125° C. for 10 min. The reaction mixture is filtered and purified by preparative HPLC to provide compound 4020 ($t_R$: 1.4, (M+H)$^+$: 533.0/535.0).

Synthesis of Compound 4021

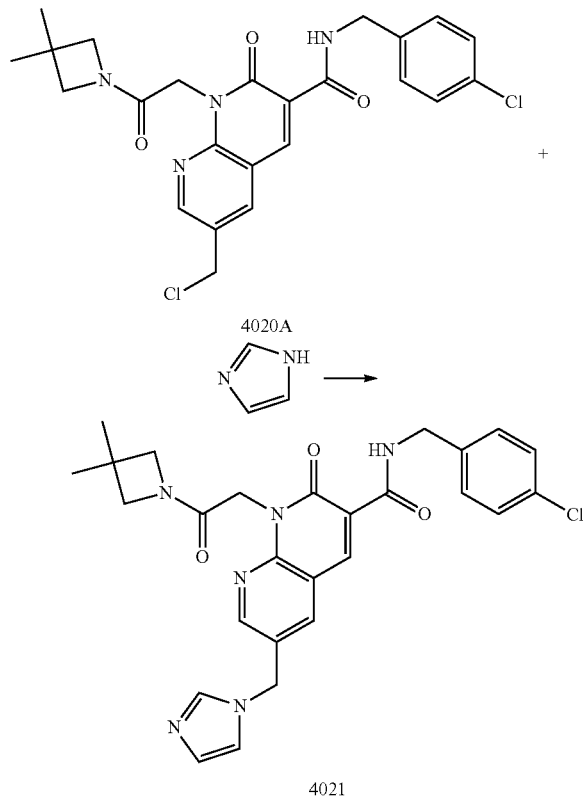

Intermediate 4020A (75 mg, 0.15 mmol) is charged in a vial and dissolved in DMF (1.0 mL). Imidazole (19 mg, 0.28 mmol, 1.8 eq), potassium carbonate (74 mg, 0.54 mmol, 3.5 eq) and potassium iodide (77 mg, 0.46 mmol, 3.0 eq) are added and the vial is sealed and warmed at 70° C. for 3 h. The reaction mixture is diluted with MeCN and water, filtered and purified by preparative HPLC to provide compound 4021 ($t_R$: 1.87, (M+H)$^+$: 519.2/521.2).

Synthesis of Compound 4022

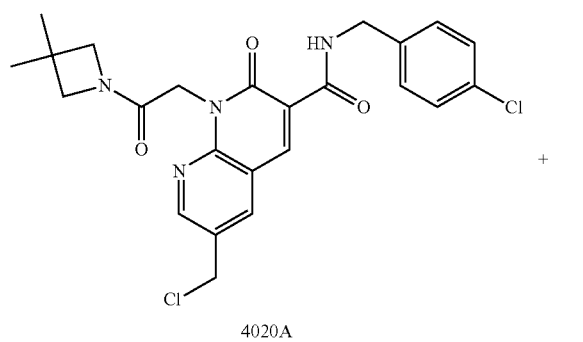

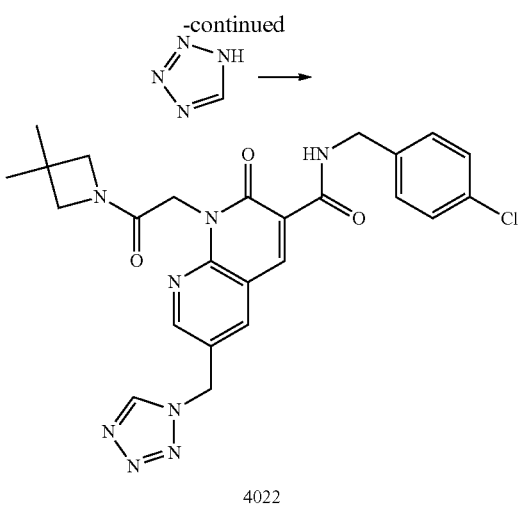

Compound 4022 ($t_R$: 1.33, (M+H)$^+$: 521.0/523.0) is prepared analogously to compound 4021, except that intermediate 4020A is reacted with tetrazole (Aldrich) and triethylamine instead of imidazole and potassium carbonate.

Synthesis of Compound 4023

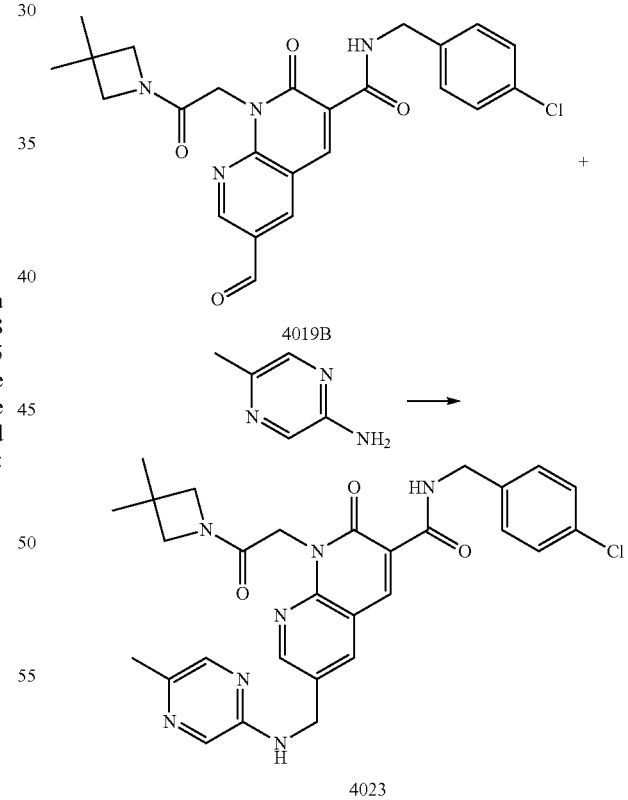

Intermediate 4019B (41 mg, 0.054 mmol) and 5-methylpyrazin-2-amine (Chem-Impex) (12 mg, 0.11 mmol, 2.0 eq) are charged in a vial and NMP (1.0 mL) is added. 4.0 M HCl in dioxane (0.50 mL, 0.20 mmol, 3.7 eq) is added and the vial is stirred at RT for 1 h. Sodium cyanoborohydride (15 mg, 0.24 mmol, 4.4 eq) is added and stirring is continued for 5 h at RT. The reaction mixture is filtered and purified by preparative HPLC to provide compound 4023 ($t_R$: 1.94, (M+H)$^+$: 560.1).

Synthesis of Compound 4024

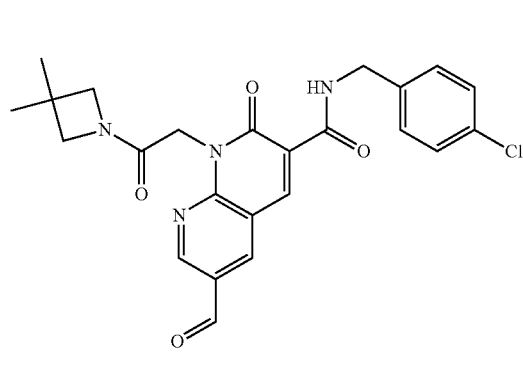

4019B

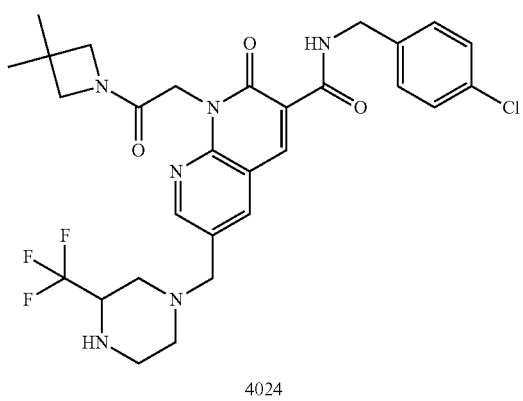

4024

Compound 4024 ($t_R$: 2, (M+H)$^+$: 605.1) is prepared analogously to compound 4023, except that intermediate 4019B is reacted with (±)-2-(trifluoromethyl)piperazine (Matrix).

Synthesis of Compound 4025

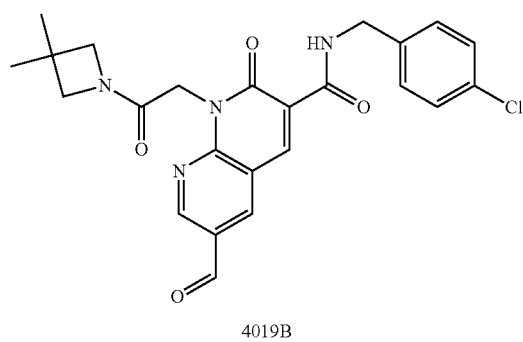

4019B

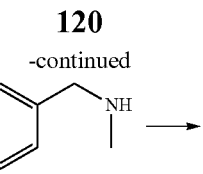

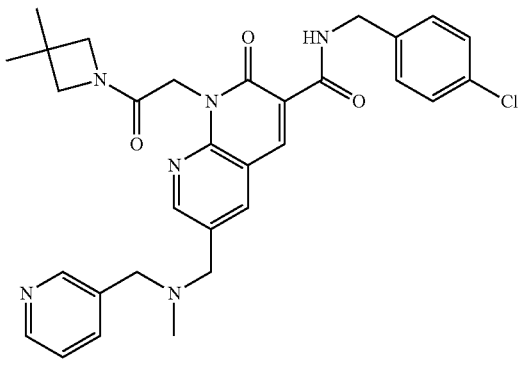

4025

Compound 4025 ($t_R$: 1.04, (M+H)$^+$: 573.1/575.0) is prepared analogously to compound 4023, except that intermediate 4019B is reacted with N-methyl-N-(3-pyridylmethyl)amine (Alfa).

Synthesis of Compound 4026

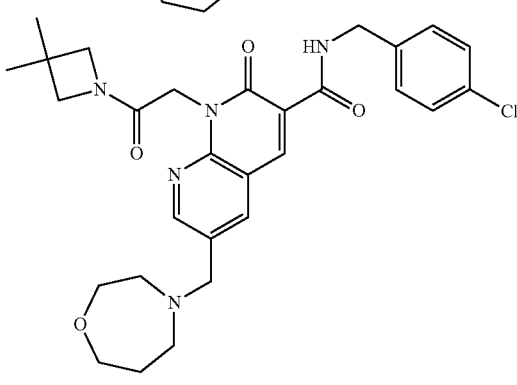

4026

Compound 4026 (t$_R$: 1.73, (M+H)$^+$: 552.3) is prepared analogously to compound 4023, except that intermediate 4019B is reacted with 1,4-oxazepane (Oakwood).

Synthesis of Compound 4027

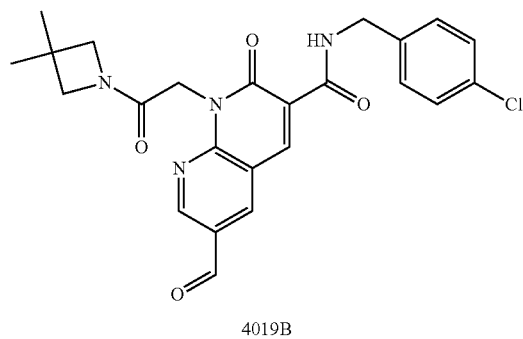

4019B

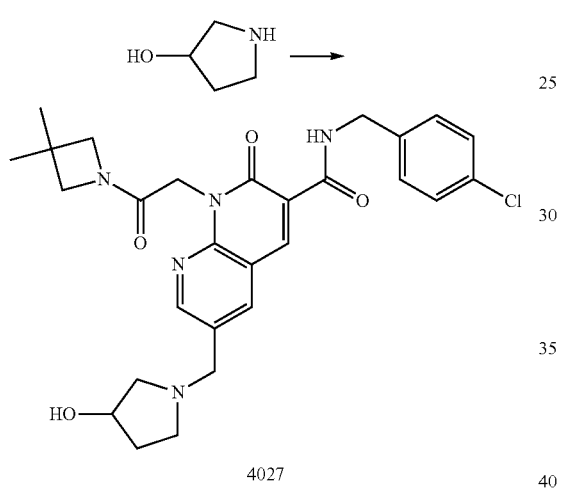

4027

Compound 4027 (t$_R$: 1.08, (M+H)$^+$: 538.1/540.0) is prepared analogously to compound 4023, except that intermediate 4019B is reacted with (±)-3-pyrrolidinol (TCI-Europe).

Synthesis of Compound 4028

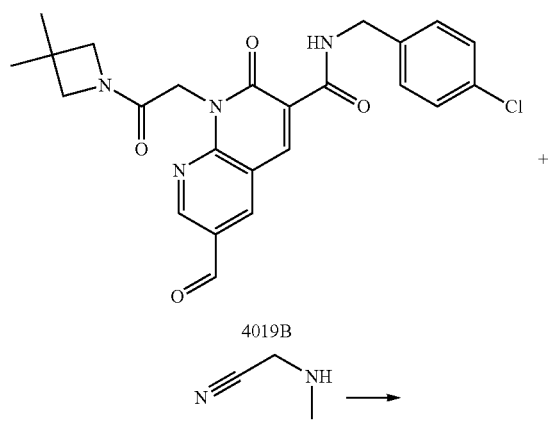

4019B

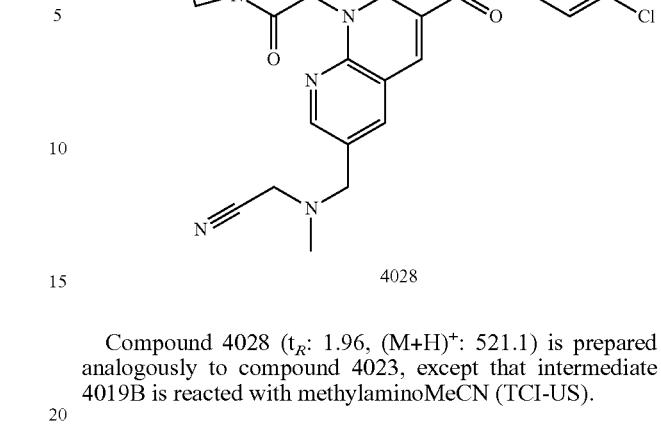

4028

Compound 4028 (t$_R$: 1.96, (M+H)$^+$: 521.1) is prepared analogously to compound 4023, except that intermediate 4019B is reacted with methylaminoMeCN (TCI-US).

Synthesis of Compound 4029

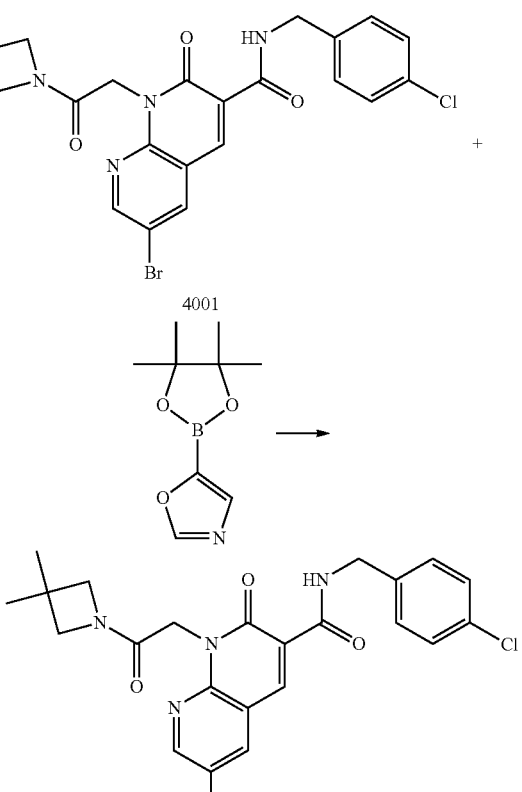

4029

Compound 4001 (30 mg, 0.054 mmol), 5-(4,4,5,5-tetramethyl-1,3,2-dioxaborolan-2-yl)oxazole (Boropharm) (21 mg, 0.11 mmol, 2 eq), sodium carbonate (17 mg, 0.16 mmol, 3.0 eq) and palladium (0) tetrakis(triphenylphosphine) (6.2 mg, 0.0054 mmol, 0.10 eq) are charged in a microwave vial and 2-Me-THF (1.0 mL) and water (0.30 mL) are added. The vial is purged with argon, sealed and warmed in a microwave oven at 100° C. for 30 min. The reaction mixture is filtered and purified by preparative HPLC to provide compound 4029 (t$_R$: 2, (M+H)$^+$: 506).

Synthesis of Compound 4030

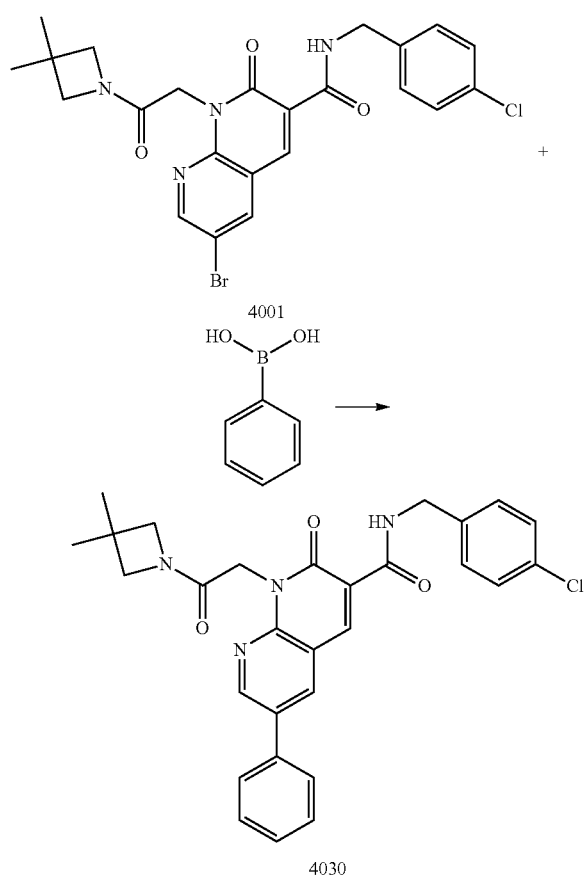

Compound 4030 ($t_R$: 1.7, (M+H)$^+$: 515.0/517.0) is prepared analogously to compound 4029, except that compound 4001 is reacted with phenylboronic acid (Aldrich).

Synthesis of Compound 4031

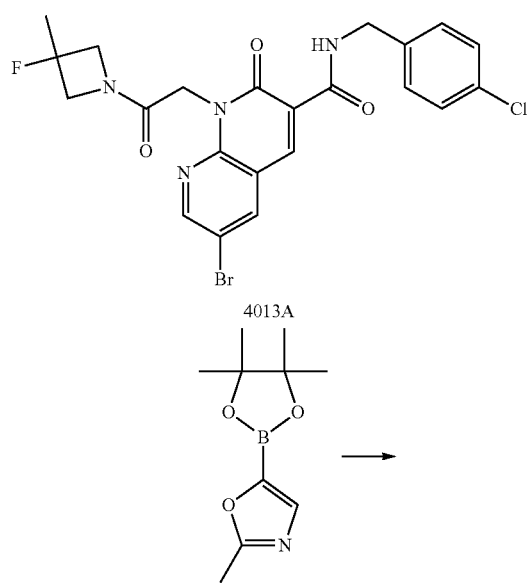

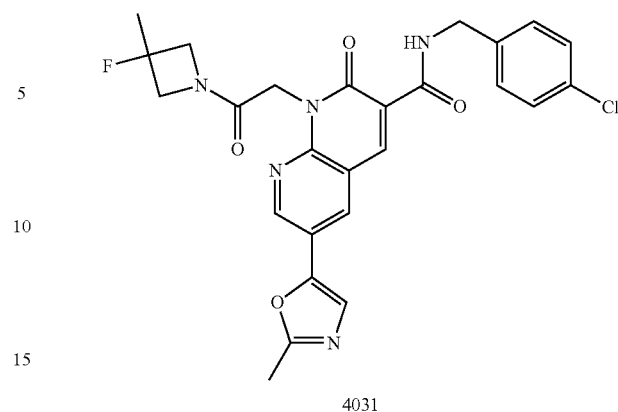

Compound 4031 ($t_R$: 1.93, (M+H)$^+$: 524.4/526.3) is prepared analogously to compound 4029 using intermediate 4013A and 2-methyl-5-(4,4,5,5-tetramethyl-1,3,2-dioxaborolan-2-yl)-1,3-oxazole (Boropharm).

Synthesis of Compound 4032

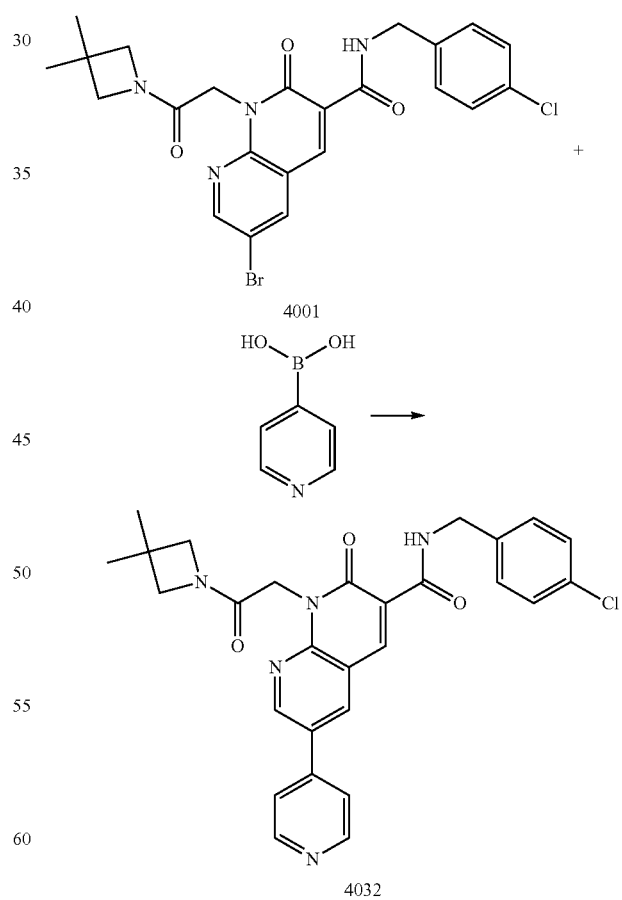

Compound 4032 ($t_R$: 1.1, (M+H)$^+$: 516.0/518.1) is prepared analogously to compound 4029, except that compound 4001 is reacted with pyridine-4-boronic acid (Aldrich).

Synthesis of Compound 4033

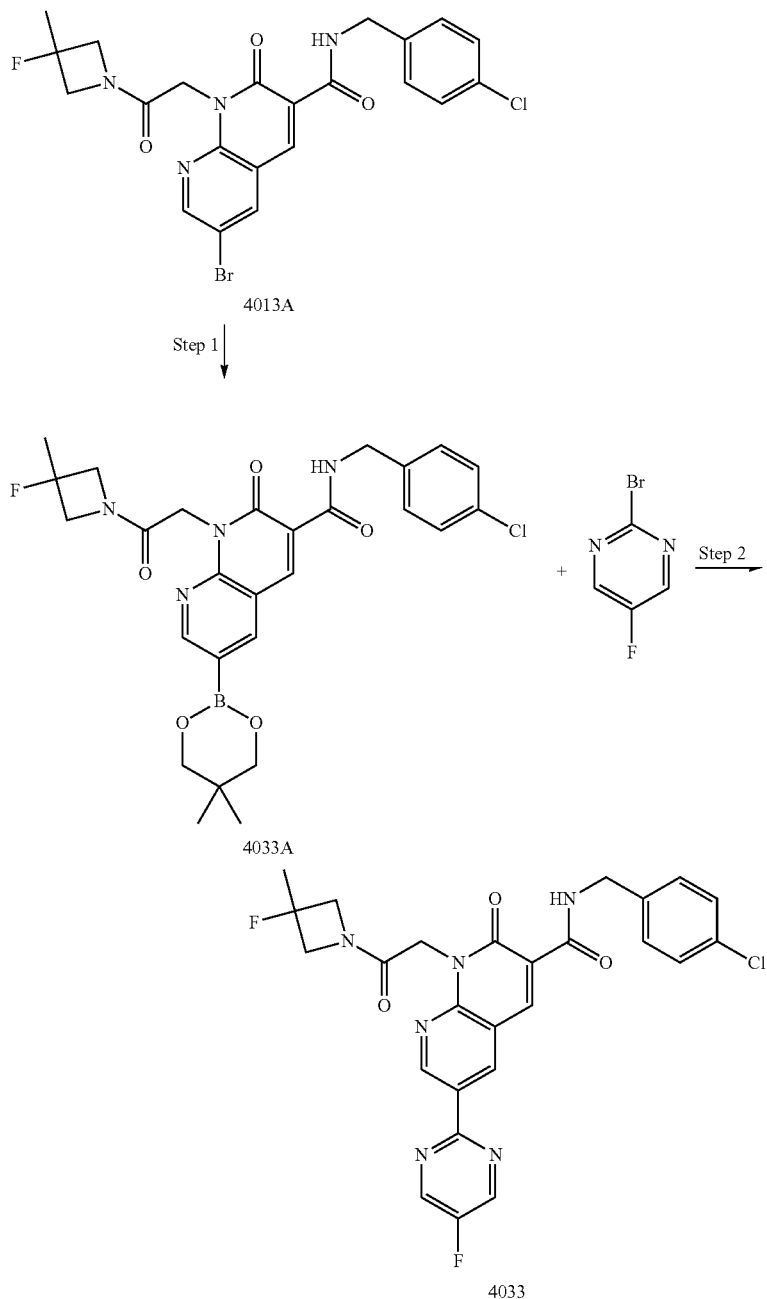

Step 1: Intermediate 4013A (8.00 g, 15.3 mmol), bis(neopentylglycolato)diboron (4.85 g, 21.5 mmol, 1.40 eq) and potassium acetate (5.10 g, 53.7 mmol, 3.50 eq) are charged in a round-bottom flask and DMF (120 mL) is added. The reaction mixture is degassed for 30 min with argon and [1,1'-bis(diphenylphosphino)ferrocene]dichloropalladium (II) (732 mg, 1.53 mmol, 0.100 eq) is added. The reaction mixture is stirred for 3 h at 95° C., cooled to RT and Et$_2$O is added. The resulting solid is collected by filtration and purified by trituration in water. The solid is filtered and dried under vacuum to provide intermediate 4033A.

Step 2: Intermediate 4033A (100 mg, 0.180 mmol), 2-bromo-5-fluoropyrimidine (Frontier) (48 mg, 0.27 mmol, 1.5 eq), potassium carbonate (87 mg, 0.63 mmol, 3.5 eq) and bis(tri-t-butylphosphine)palladium (0) (18 mg, 0.036 mmol, 0.20 eq) are charged in a microwave vial and DMF (1.5 mL) and water (0.50 mL) are added. The vial is purged with argon, sealed and warmed in a microwave oven at 125° C. for 10 min. The reaction mixture is filtered and purified by preparative HPLC to provide compound 4033 (t$_R$: 1.92, (M+H)$^+$: 539.3/541.3).

Synthesis of Compound 4034

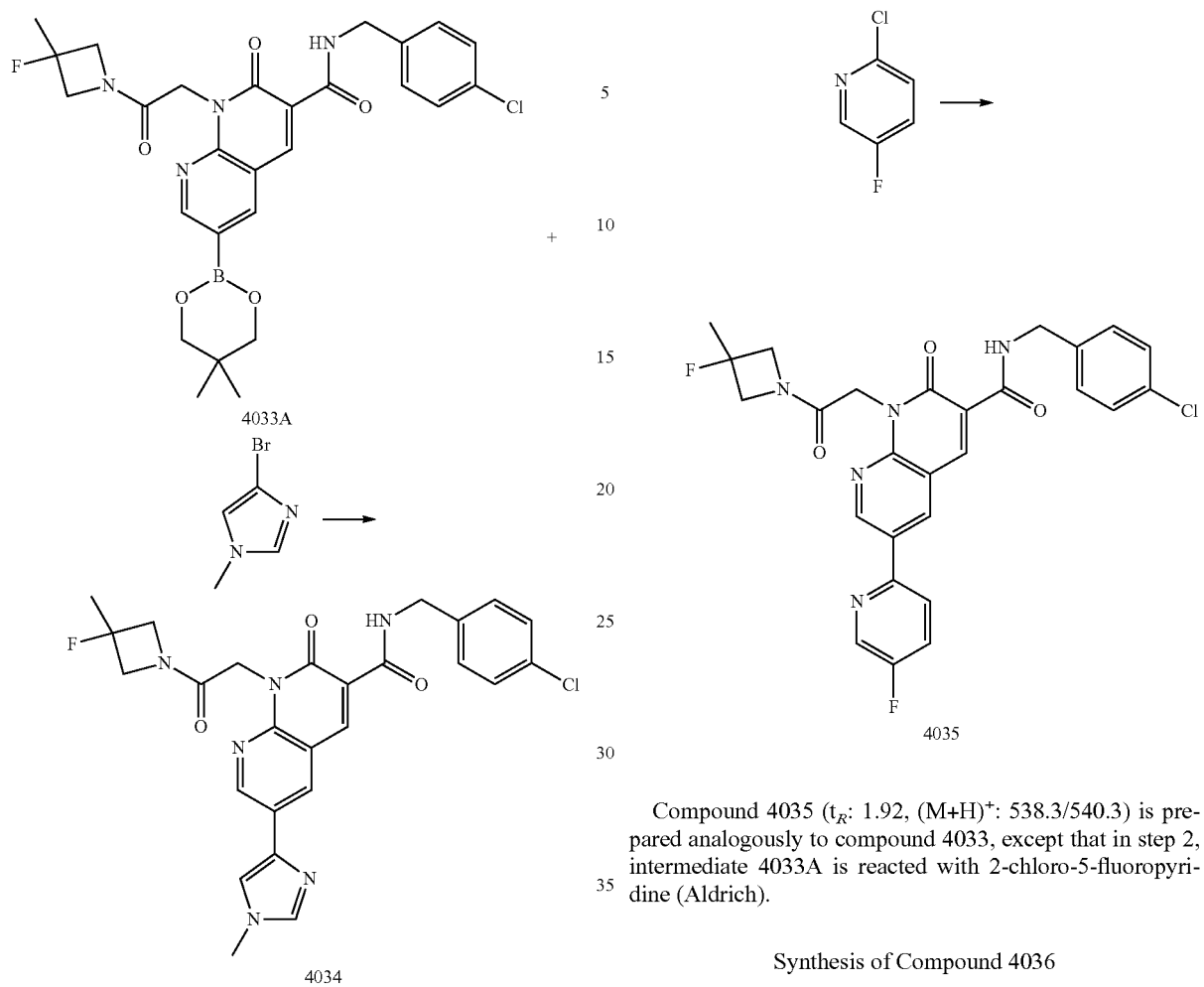

Compound 4034 (t$_R$: 1.77, (M+H)$^+$: 523.2/525.2) is prepared analogously to compound 4033, except that in step 2, intermediate 4033A is reacted with 4-bromo-1-methyl-1H-imidazole (Combi-Blocks).

Synthesis of Compound 4035

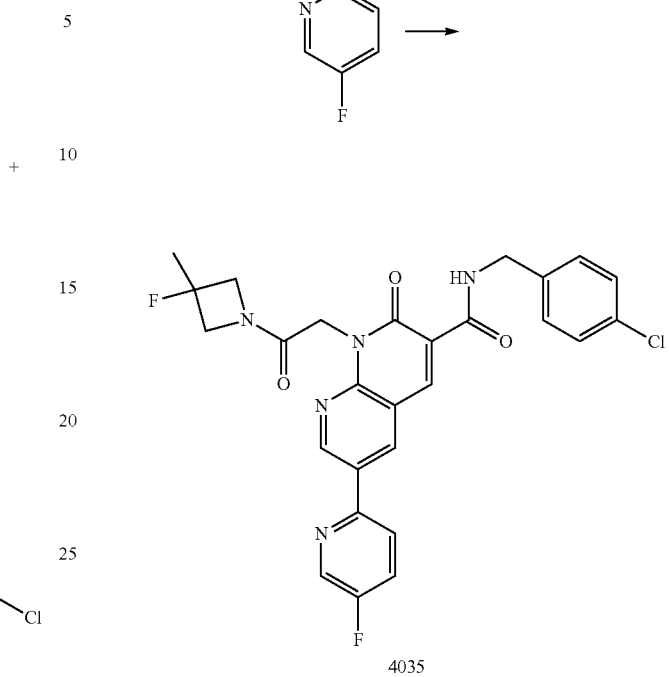

Compound 4035 (t$_R$: 1.92, (M+H)$^+$: 538.3/540.3) is prepared analogously to compound 4033, except that in step 2, intermediate 4033A is reacted with 2-chloro-5-fluoropyridine (Aldrich).

Synthesis of Compound 4036

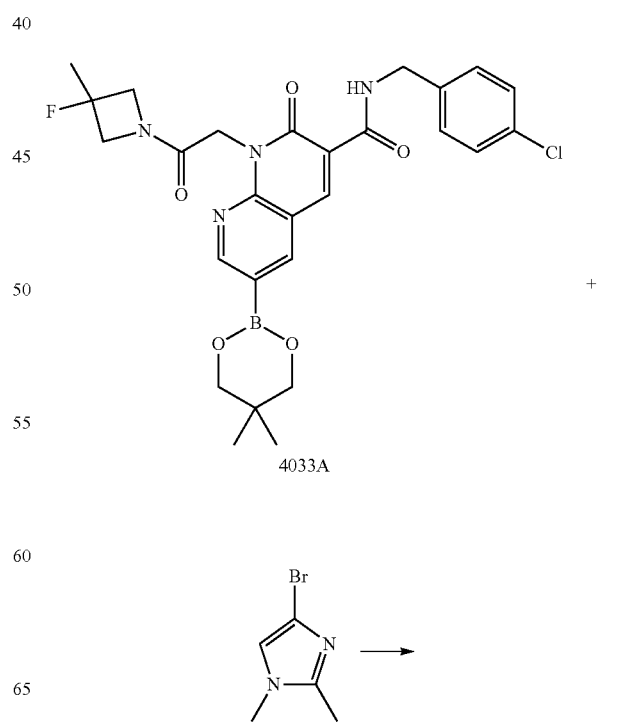

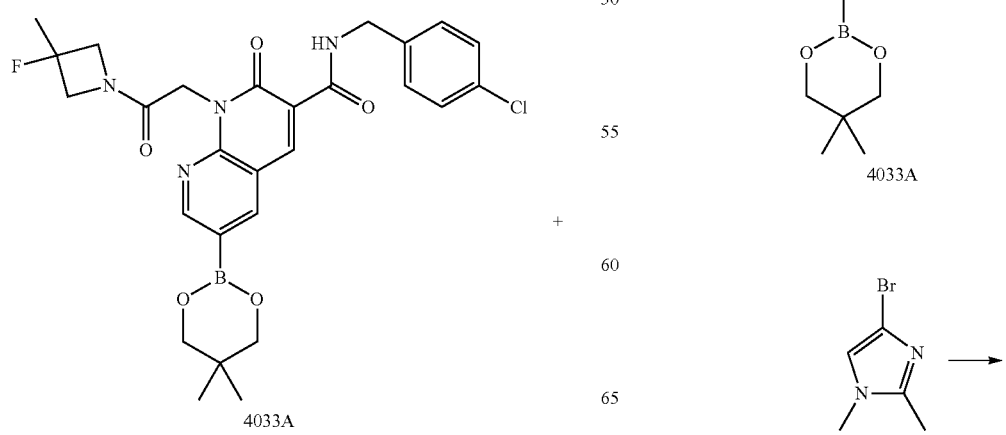

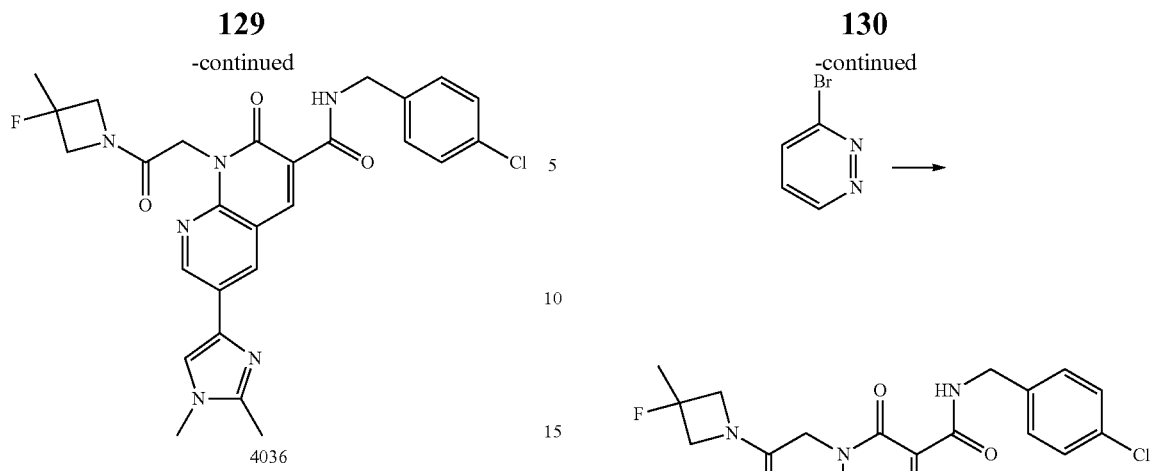
Compound 4036 ($t_R$: 1.21, (M+H)$^+$: 521.0/523.2) is prepared analogously to compound 4033, except that in step 2, intermediate 4033A is reacted with 4-bromo-1,2-dimethyl-1H-imidazole (Combi-Blocks).
Synthesis of Compound 4037
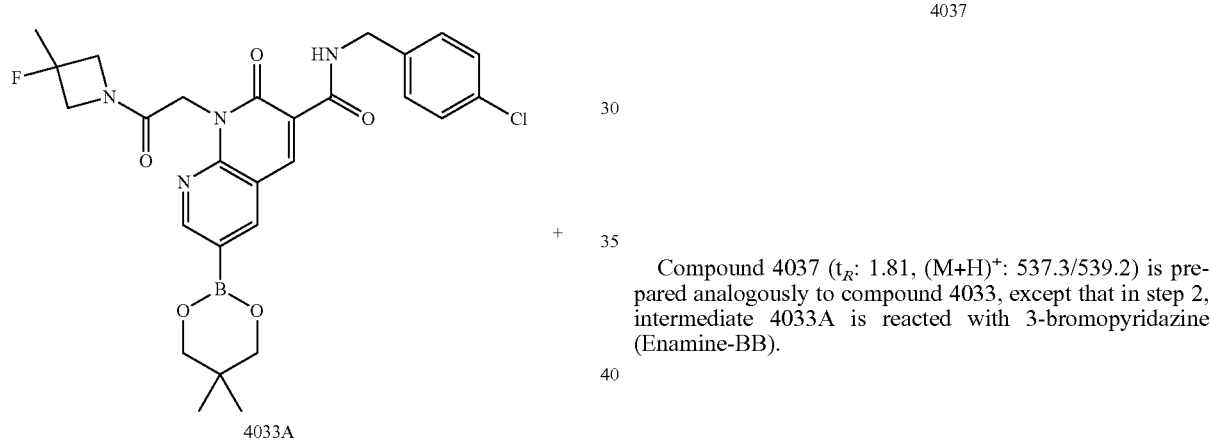
Compound 4037 ($t_R$: 1.81, (M+H)$^+$: 537.3/539.2) is prepared analogously to compound 4033, except that in step 2, intermediate 4033A is reacted with 3-bromopyridazine (Enamine-BB).
Synthesis of Compound 4038
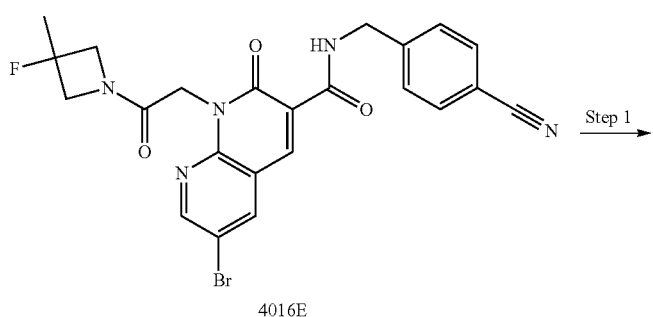

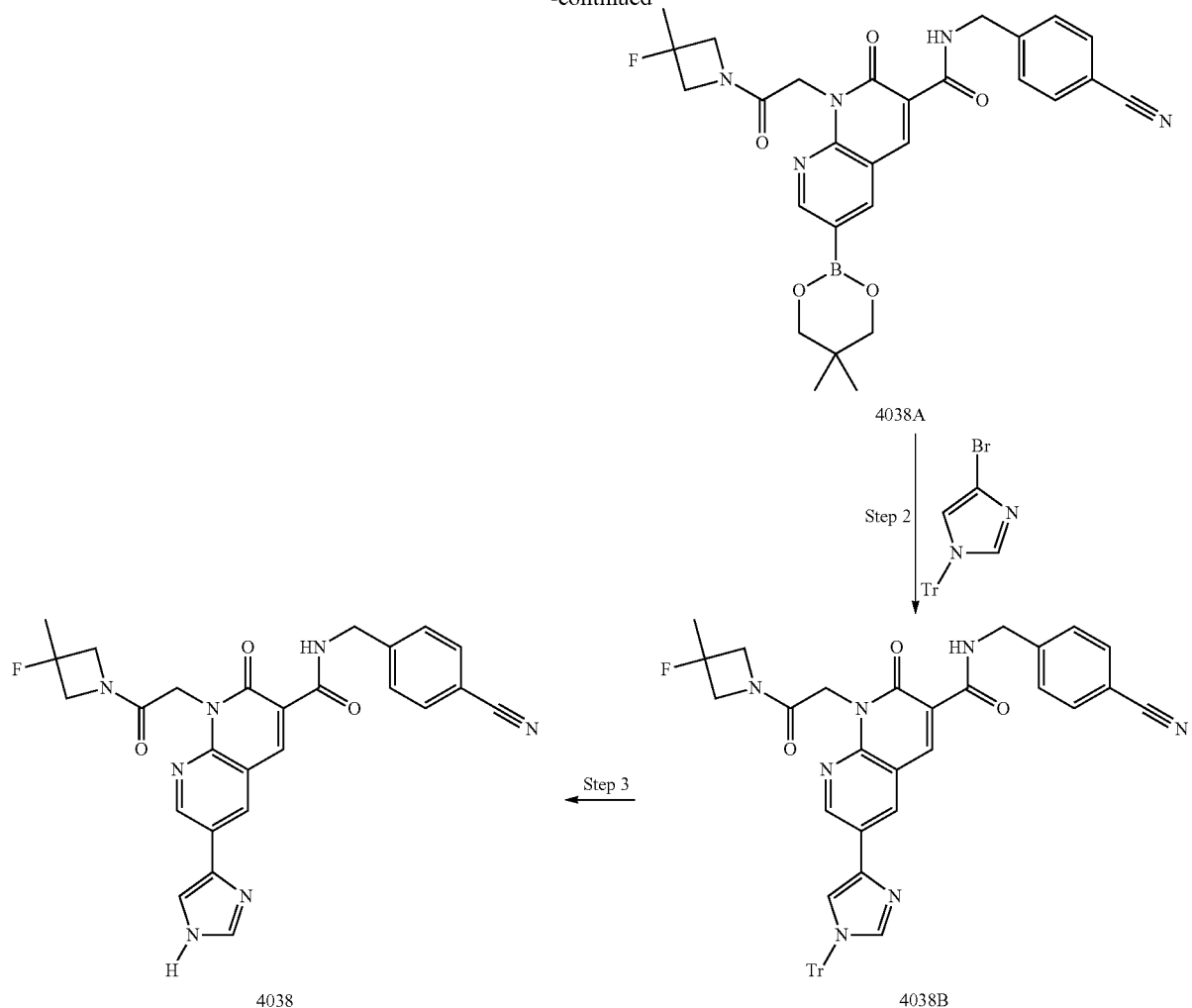

4038A

4038B

4038

Step 1: Intermediate 4038A is prepared analogously to intermediate 4033A.

Step 2: Intermediate 4038B is prepared analogously to compound 4033, except that intermediate 4038A is reacted with 4-bromo-1-trityl-1H-imidazole (Combi-Blocks).

Step 3: Intermediate 4038B (827 mg, 1.12 mmol) is charged in a round-bottom flask and dissolved in DCM (10.0 mL). TFA (10.0 mL) is added and the reaction mixture is stirred for 1 h at RT. The reaction mixture is concentrated and the residue is purified by preparative HPLC to provide compound 4038 ($t_R$: 1.51, (M+H)$^+$: 498.3).

Synthesis of Compound 4039

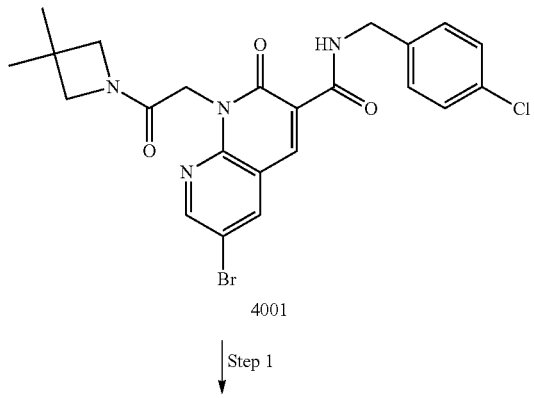

4001

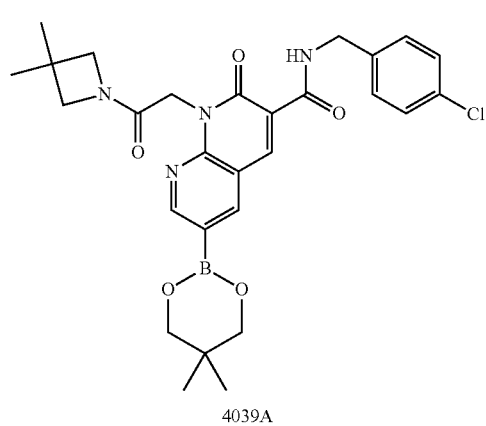

4039A

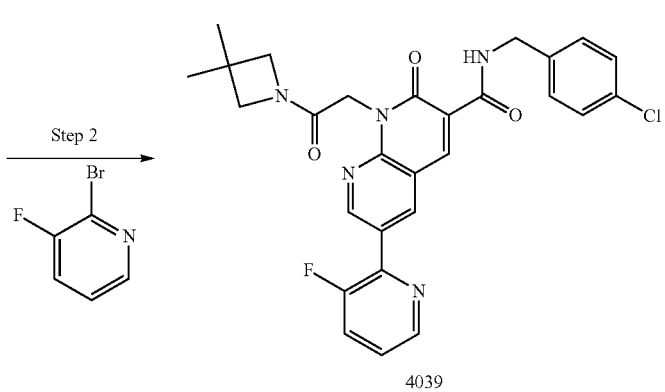

Step 2

4039

Step 1: Intermediate 4039A is prepared analogously to intermediate 4033A.

Step 2: Intermediate 4039A (30 mg, 0.054 mmol), 2-bromo-3-fluoropyridine (Oakwood) (19 mg, 0.11 mmol, 2.0 eq), sodium carbonate (17 mg, 0.16 mmol, 3.0 eq) and bis(tri-t-butylphosphine)palladium (0) (6 mg, 0.005 mmol, 0.1 eq) are charged in a microwave vial and 2-methyltetrahydrofuran (1.0 mL) and water (0.30 mL) are added. The vial is purged with argon, sealed and warmed in a microwave oven at 100° C. for 30 min. The reaction mixture is filtered and purified by preparative HPLC to provide compound 4039 ($t_R$: 2.11, (M+H)$^+$: 534).

Synthesis of Compound 4040

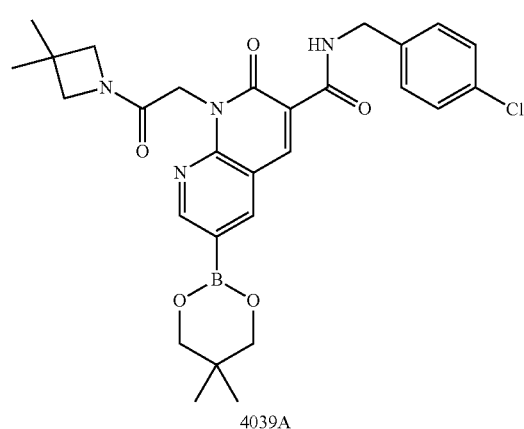

4039A

+

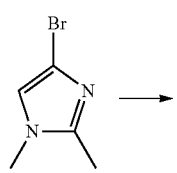

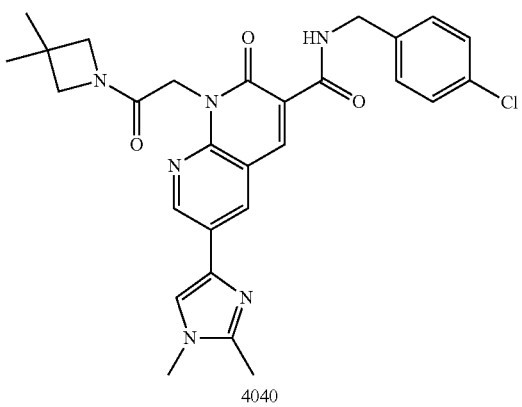

4040

Compound 4040 ($t_R$: 1.9, (M+H)$^+$: 533.4/535.4) is prepared analogously to compound 4039, except that in step 2, intermediate 4039A is reacted with 4-bromo-1,2-dimethyl-1H-imidazole (Combi-Blocks).

Synthesis of Compound 4041

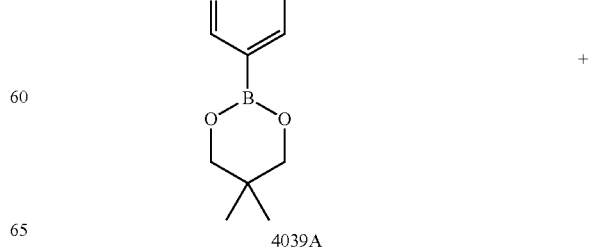

4039A

+

-continued

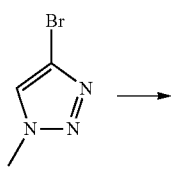

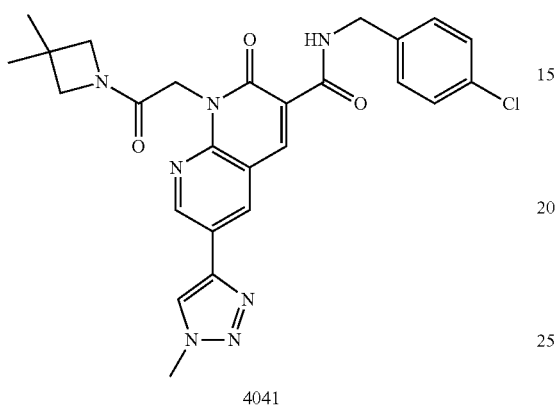

4041

Compound 4041 (t$_R$: 1.97, (M+H)$^+$: 520.1) is prepared analogously to compound 4039, except that in step 2, intermediate 4039A is reacted with 4-bromo-1-methyl-1H-1,2,3-triazole (Anichem).

Synthesis of Compound 4042

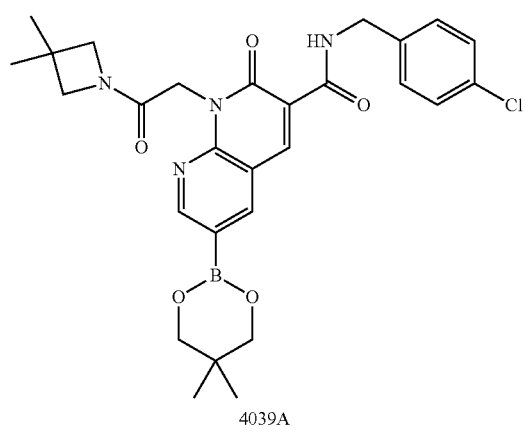

4039A

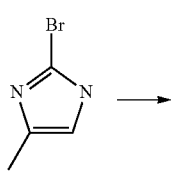

-continued

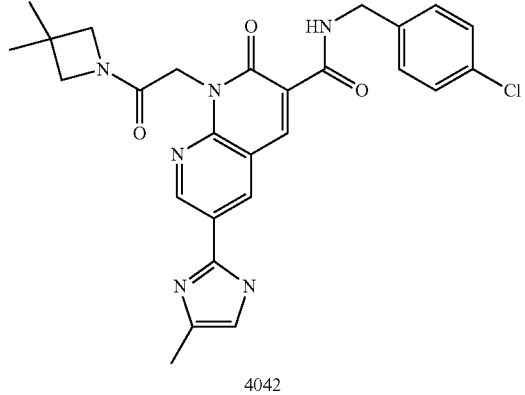

4042

Compound 4042 (t$_R$: 1.96, (M+H)$^+$: 519.1) is prepared analogously to compound 4039, except that in step 2, intermediate 4039A is reacted with 2-bromo-4-methyl-1H-imidazole (Combi-Blocks).

Synthesis of Compound 4043

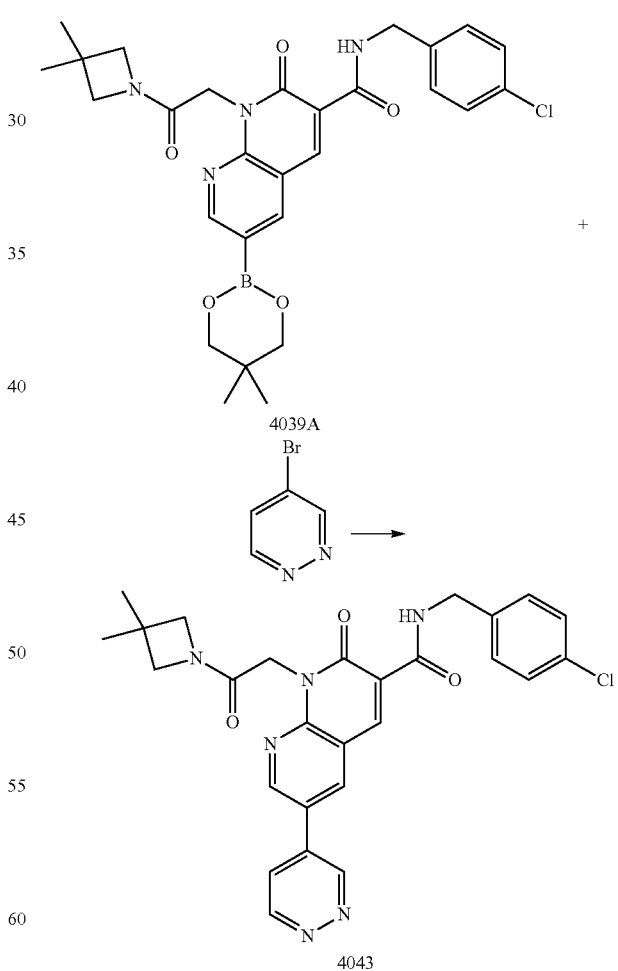

4043

Compound 4043 (t$_R$: 1.92, (M+H)$^+$: 517) is prepared analogously to compound 4039, except that in step 2, intermediate 4039A is reacted with 4-bromo-pyridazine (Princeton).

Synthesis of Compound 4044

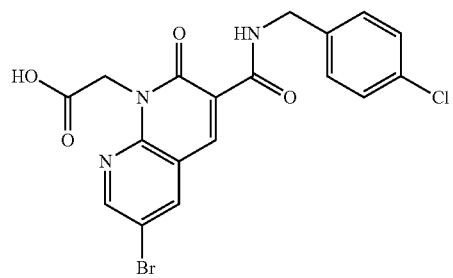

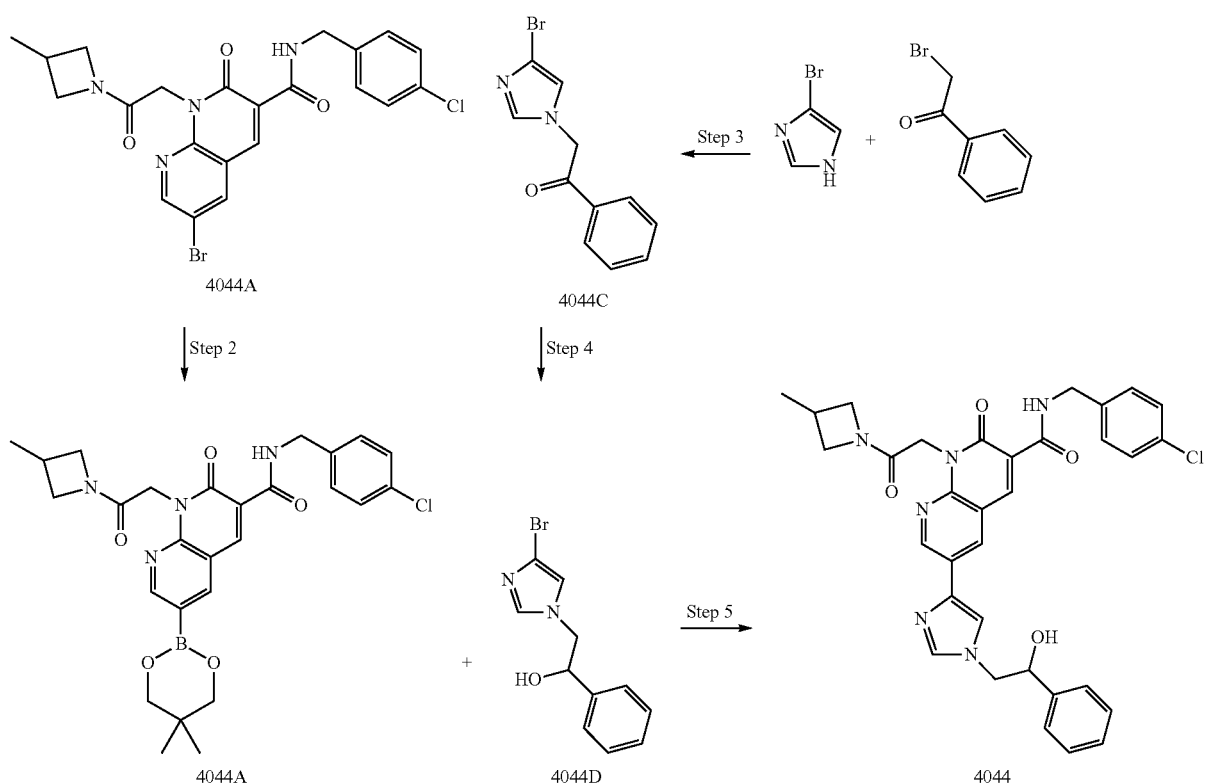

Step 1: Intermediate 4044A is prepared analogously to compound 4001, except that in step 4, intermediate 4001C is reacted with 3-methyl-azetidine hydrochloride (prepared analogously to the procedure in J. Med. Chem. 2008, 51, 7380, herein incorporated by reference).

Step 2: Intermediate 4044B is prepared analogously to intermediate 4033A.

Step 3: 4-Bromo-1H-imidazole (Aldrich) (500 mg, 3.40 mmol) is charged in a round-bottom flask and dissolved in THF (10 mL). 2-Bromoacetophenone (Aldrich) (1.35 g, 6.80 mmol, 2.00 eq) and potassium carbonate (940 mg, 6.80 mmol, 2.00 eq) are added. The reaction mixture is stirred for 16 h at RT, diluted with EtOAc and washed with water. The organic layer is dried over MgSO$_4$, filtered and concentrated under reduced pressure. The residue is purified by flash chromatography (100% hexanes to 50% EtOAc in hexanes) to provide intermediate 4044C.

Step 4: Intermediate 4044C (77 mg, 0.29 mmol) is charged in a round-bottom flask and dissolved in DMF (1.0 mL). Sodium borohydride (16 mg, 0.44 mmol, 1.5 eq) is added. The reaction mixture is stirred for 1 h at RT, diluted with EtOAc and washed with water and brine. The organic layer is dried over MgSO$_4$, filtered and concentrated under reduced pressure to provide intermediate 4044D.

Step 5: Compound 4044 (t$_R$: 1.41, (M+H)$^+$: 609.2/611.3) is prepared analogously to compound 4033, except that intermediate 4044B is reacted with intermediate 4044D.

139

Synthesis of Compound 4045

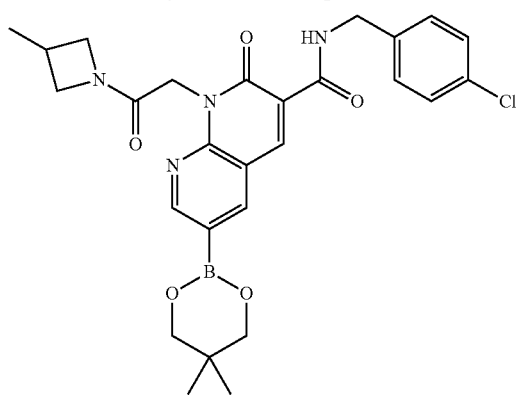

4044B

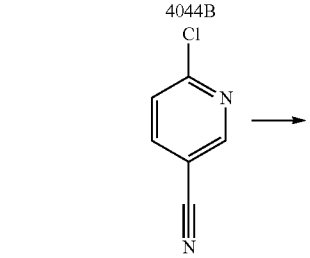

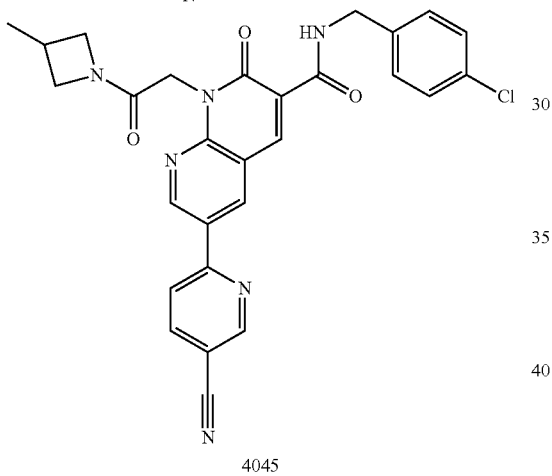

4045

Compound 4045 (t$_R$: 1.48, (M+H)$^+$: 527.1/529.0) is prepared analogously to compound 4033, except that intermediate 4044B is reacted with 2-chloro-5-cyanopyridine (Matrix).

Synthesis of Compound 4046

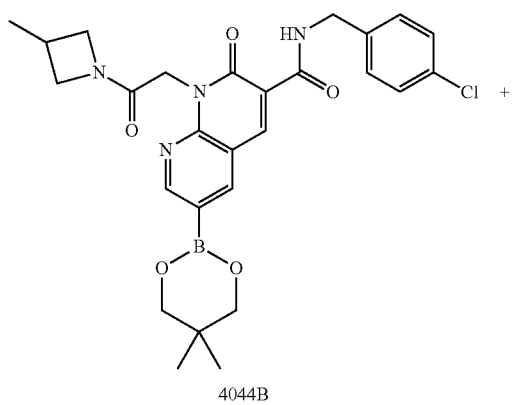

4044B

140

-continued

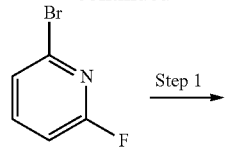

Step 1

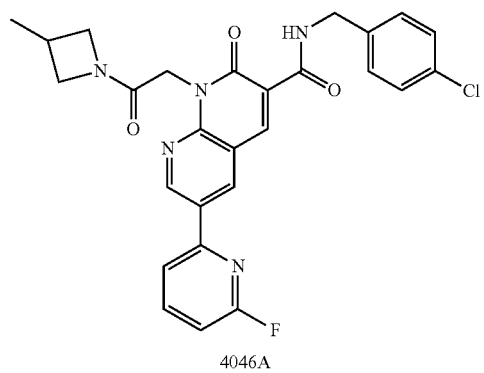

4046A

Step 2

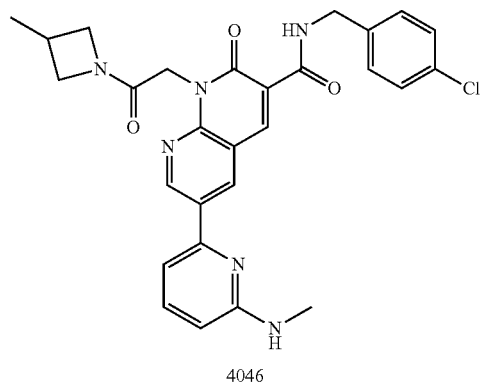

4046

Step 1: Intermediate 4046A is prepared analogously to compound 4033, except that intermediate 4044B is reacted with 2-bromo-6-fluoropyridine (Matrix).

Step 2: Intermediate 4046A (73 mg, 0.086 mmol) is charged in a pressure vessel and suspended in DMSO (0.70 mL). 2 M methylamine in THF (0.50 mL, 1.0 mmol, 12 eq) and diisopropylethylamine (0.060 mL, 0.35 mmol, 4.0 eq) are added. The vessel is sealed and heated at 140° C. for 20 h. The mixture is cooled to RT, diluted with MeCN and water, filtered and purified by preparative HPLC to provide compound 4046 (t$_R$: 1.55, (M+H)$^+$: 531.1/533.0).

Synthesis of Compound 4047
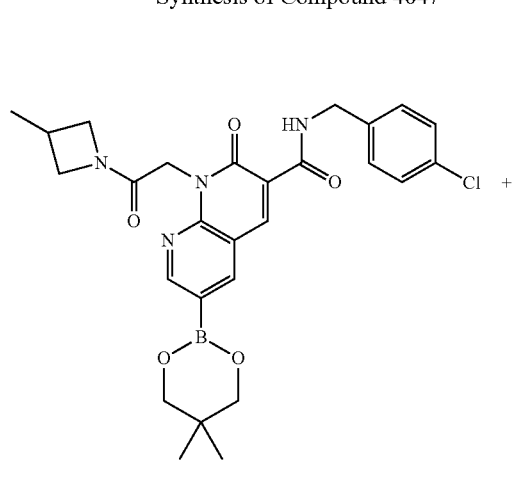
4044B
+
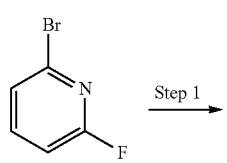
Step 1 →
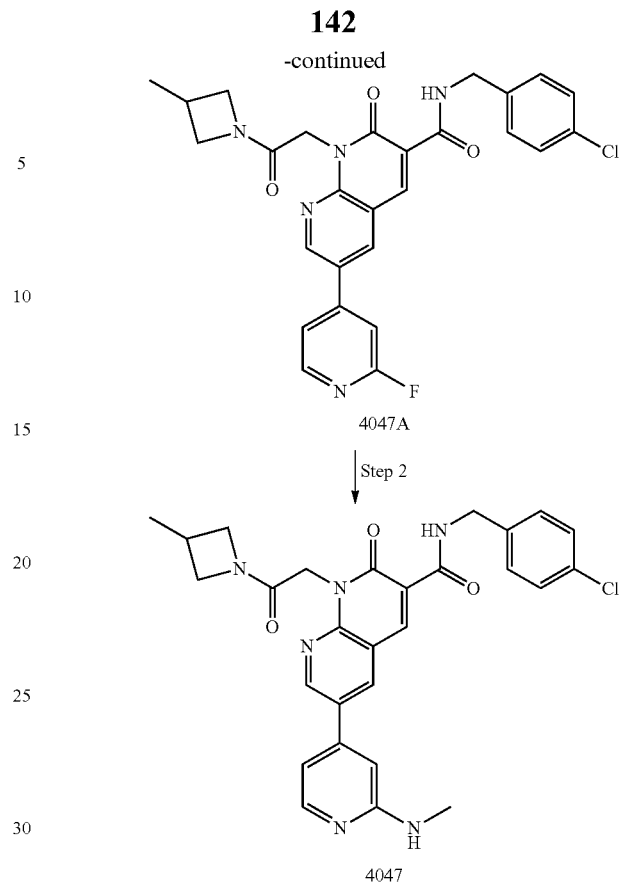
Step 1: Intermediate 4047A is prepared analogously to compound 4033, except that intermediate 4044B is reacted with 4-bromo-2-fluoropyridine (Matrix).
Step 2: Compound 4047 ($t_R$: 1.77, (M+H)$^+$: 531.3/533.2) is prepared analogously to compound 4046.
Synthesis of Compound 4048
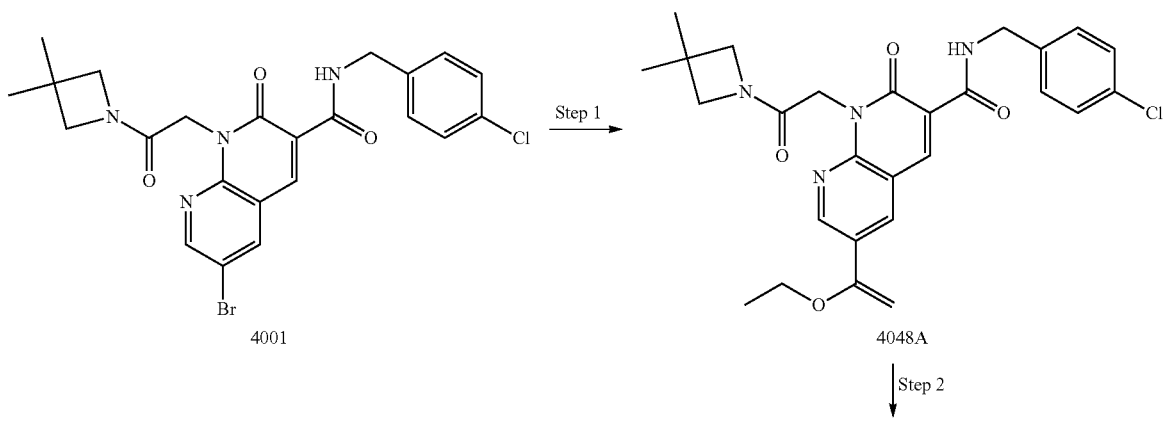

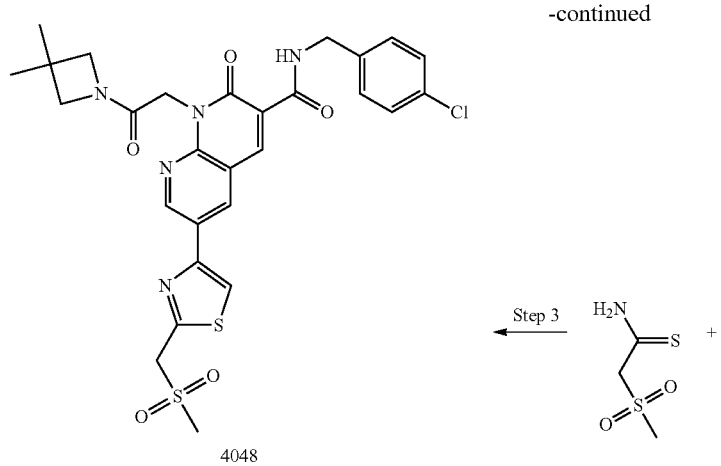

Step 1: Tributyl(1-ethoxyvinyl)tin (2.96 mL, 8.50 mmol, 1.10 eq) is charged in a microwave vial and a degassed solution of compound 4001 (4.00 g, 7.73 mmol) in DMF is added. (Tri-t-butylphosphine)palladium (0) (980 mg, 0.85 mmol, 0.10 eq) is added and the vial is sealed and warmed in a microwave oven at 125° C. for 25 min. The reaction mixture is diluted with EtOAc and washed with water and brine. The organic layer is dried over $MgSO_4$, filtered and concentrated under reduced pressure. The residue is purified by trituration in $Et_2O$ to provide intermediate 4048A.

Step 2: Intermediate 4048A (3.39 g, 6.65 mmol) is charged in a round-bottom flask and dissolved in THF (40 mL). Water (3.0 mL) and N-bromosuccinimide (1.20 g, 6.72 mmol, 1.01 eq) are added. The reaction mixture is stirred for 30 min at RT, diluted with EtOAc and washed with water and brine. The organic layer is dried over $MgSO_4$, filtered and concentrated under reduced pressure. The residue is purified by trituration in DCM to provide intermediate 4048B.

Step 3: Intermediate 4048B (75 mg, 0.13 mmol) and 2-(methylsulfonyl)ethanethioamide (Maybr-Int) (25 mg, 0.16 mmol) are charged in a round-bottom flask and suspended in 1,4-dioxane (4.0 mL). The reaction mixture is stirred for 2 h at 80° C. and concentrated under reduced pressure. The residue is purified by preparative HPLC to provide compound 4048 ($t_R$: 1.86, $(M+H)^+$: 614.2/616.2).

Synthesis of Compound 4049

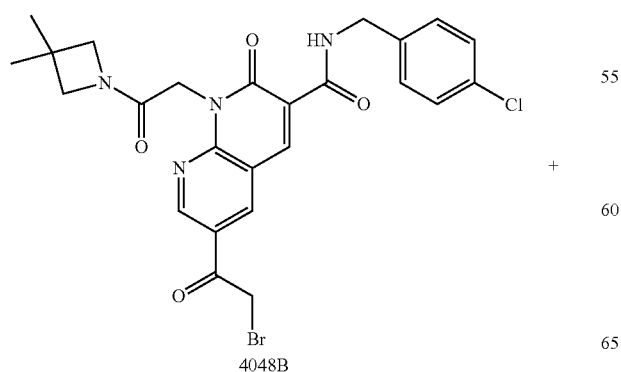

Compound 4049 ($t_R$: 1.95, $(M+H)^+$: 559.4/561.3) is prepared analogously to compound 4048, except that in step 3, intermediate 4048B is reacted with 2-iminopiperidine hydrochloride (Aldrich).

Synthesis of Compound 4050

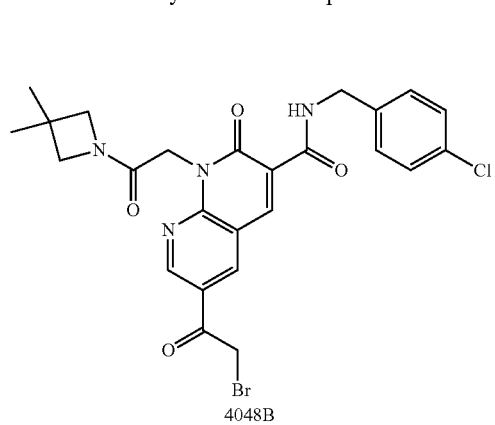
4048B

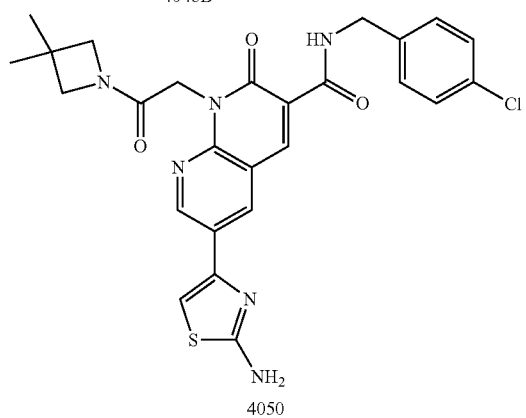
4050

Compound 4050 (t$_R$: 1.89, (M+H)$^+$: 537.1/539.1) is prepared analogously to compound 4048, except that in step 3, intermediate 4048B is reacted with thiourea (Aldrich).

Synthesis of Compound 4051

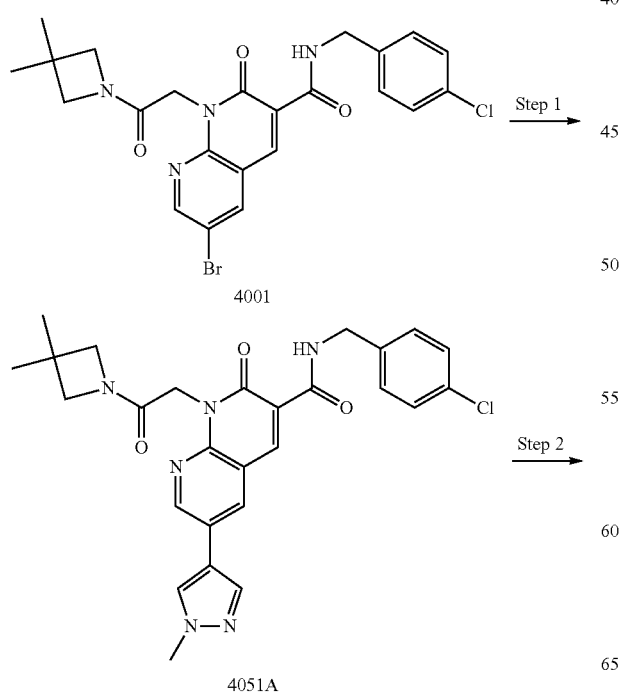
4001

4051A

-continued

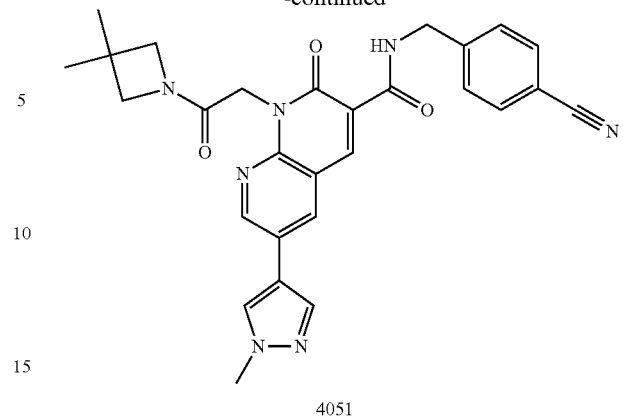
4051

Step 1: Intermediate 4051A is prepared analogously to compound 4029, except that compound 4001 is reacted with 1-methyl-4-(4,4,5,5-tetramethyl-1,3,2-dioxaborolan-2-yl)-1H pyrazole (Frontier).

Step 2: Intermediate 4051A (92 mg, 0.18 mmol) is charged in a vial and suspended in N,N-dimethylacetamide (3.0 mL). Zinc cyanide (42 mg, 0.36 mmol, 2.0 eq) and bis(tri-t-butylphosphine)palladium (0) (9 mg, 0.018 mmol, 0.10 eq) are added. The vial is sealed and the mixture is heated at 140° C. for 16 h. The reaction mixture is filtered and purified by preparative HPLC to provide compound 4051 (t$_R$: 1.2, (M+H)$^+$: 510).

Synthesis of Compound 4052

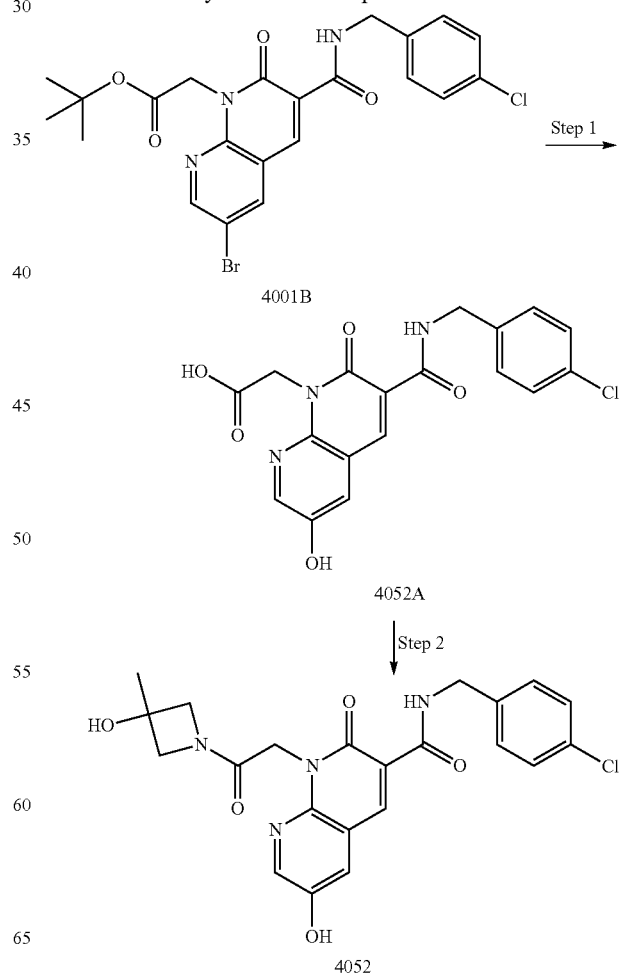
4001B

4052A

4052

Step 1: Intermediate 4001B (2.59 g, 5.11 mmol), t-butyl Xphos (868 mg, 2.04 mmol, 0.400 eq), bis(dibenzylideneacetone)palladium(0) (468 mg, 0.511 mmol, 0.100 eq) and potassium hydroxide (1.72 g, 30.7 mmol, 6.00 eq) are charged in a round-bottom flask and suspended in 1,4-dioxane (20.0 mL) and water (20.0 mL). The reaction mixture is heated for 1 h at 100° C., then acidified using 4 N HCl in 1,4-dioxane and concentrated under reduced pressure. The residue is suspended in toluene and re-concentrated under reduced pressure to provide intermediate 4052A.

Step 2: Intermediate 4052A (2.58 g, 6.66 mmol) is charged in a round-bottom flask and dissolved in DMF (40 mL). Diisopropylethylamine (4.60 mm, 26.4 mmol, 3.97 eq) and 3-methyl-azetidin-3-ol (Parkway) (870 mg, 10.0 mmol, 1.50 eq) are added followed by HATU (4.00 g, 10.5 mmol, 1.58 eq). The solution is stirred at RT for 30 min. Following completion of the reaction, the mixture is filtered and purified by preparative HPLC to provide compound 4052 ($t_R$: 1.00, (M+H)$^+$: 457.0/459.0).

Step 1: Intermediate 4052A (2.00 g, 5.16 mmol) is charged in a round-bottom flask and dissolved in DMF (50 mL). Diisopropylethylamine (4.49 mL, 25.8 mmol, 5.00 eq) and 3,3-dimethyl-azetidine hydrochloride (prepared analogously to the procedure in J. Med. Chem. 2008, 51, 7380, herein incorporated by reference) (1.00 g, 8.25 mmol, 1.60 eq) are added followed by HATU (3.14 g, 8.25 mmol, 1.60 eq) and the solution is stirred at RT for 3 days. The solution is added to water and the mixture is acidified with 1 N HCl. The solid is collected by filtration and washed with acetone and methyl t-butyl ether. The solid is purified by trituration in EtOAc to afford intermediate 4053A.

Step 2: Intermediate 4053A (50 mg, 0.11 mmol), 1-bromo-2-chloroethane (12 μL, 0.14 mmol, 1.3 eq) and potassium carbonate (76 mg, 0.55 mmol, 5.0 eq) are charged in a vial and suspended in acetone (4.0 mL). The vial is sealed and stirred at 75° C. for 4 h. The reaction mixture is concentrated to provide intermediate 4053B which is used without purification.

Step 3: Intermediate 4053B (20 mg, 0.039 mmol) is charged in a vial and dissolved in DMF (2.0 mL). 2-oxopiperazine (Aldrich) (12 mg, 0.12 mmol, 3.0 eq), diisopropyl- Synthesis of Compound 4053

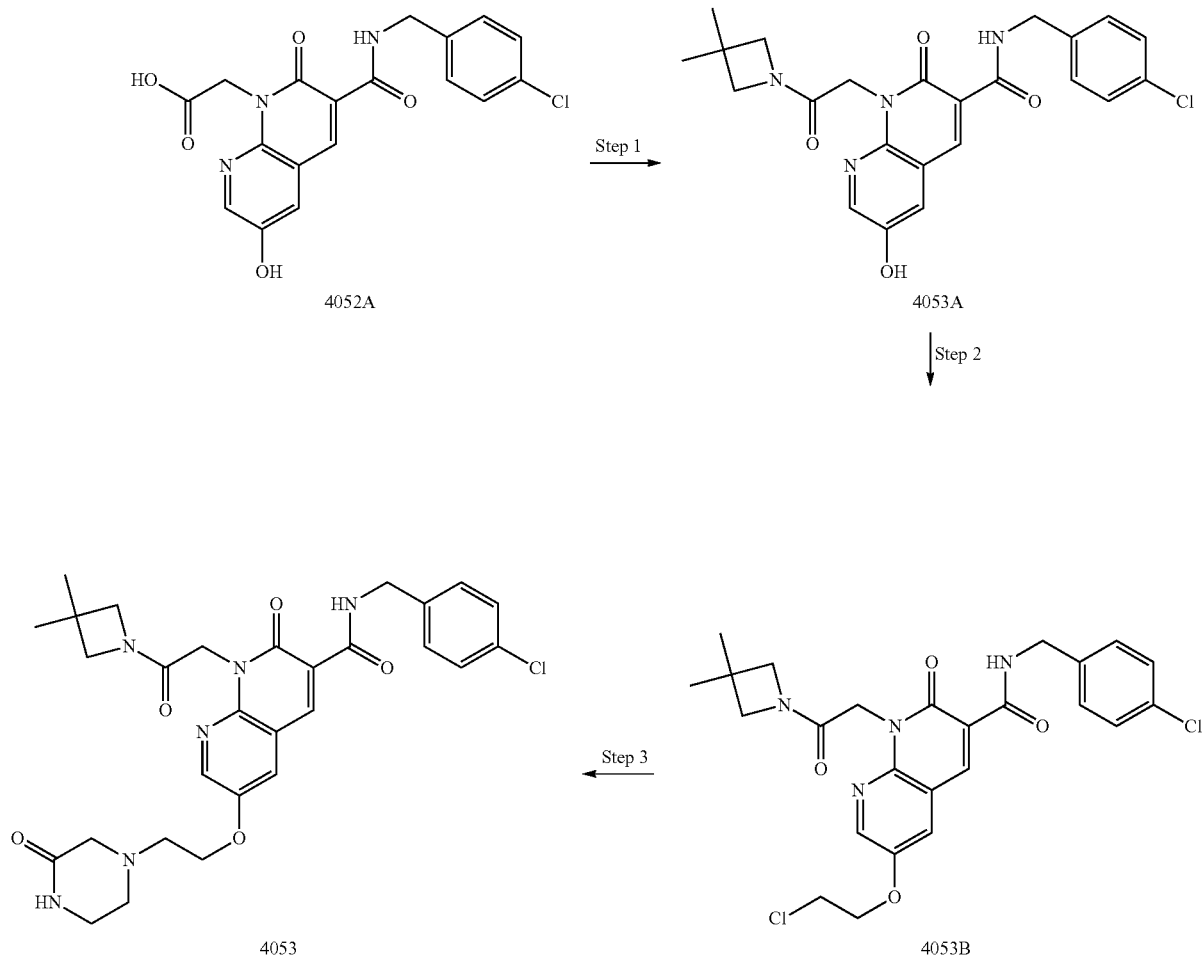

ethylamine (17 μL, 0.10 mmol, 2.5 eq) and potassium iodide (2.0 mg, 0.012 mmol, 0.30 eq) are added and the vial is sealed. The reaction mixture is stirred for 16 h at 120° C., filtered and purified by preparative HPLC to provide compound 4053 ($t_R$: 1.1, (M+H)$^+$: 581.1/583.1).

Synthesis of Compound 4054

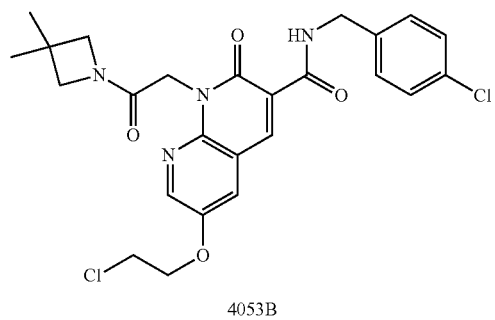

4053B

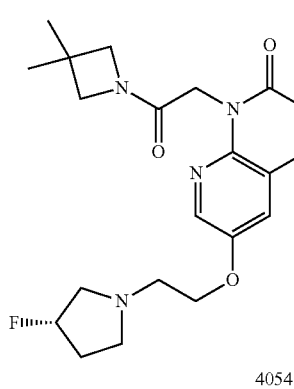

4054

Compound 4054 ($t_R$: 1.2, (M+H)$^+$: 570.0/572.0) is prepared analogously to compound 4053, except that in step 3, intermediate 4053B is reacted with (S)-(+)-3-fluoropyrrolidine hydrochloride (Aldrich).

Synthesis of Compound 4055

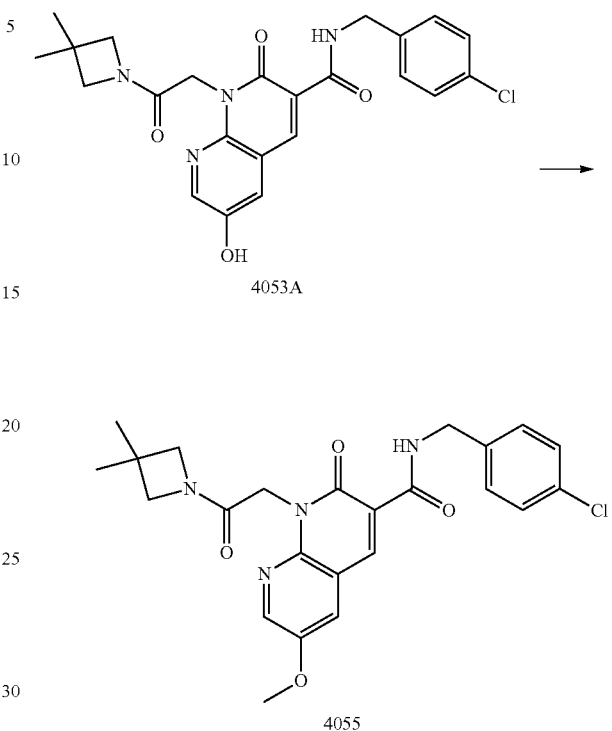

4053A

4055

Intermediate 4053A (100 mg, 0.220 mmol) and cesium carbonate (179 mg, 550 mmol, 2.5 eq) are charged in a vial and suspended in DMF (1.0 mL). Iodomethane (27 μL, 0.44 mmol, 2.0 eq) is added and the vial is sealed. The reaction mixture is stirred for 16 h at 70° C., filtered, acidified with AcOH and purified by preparative HPLC to provide compound 4055 ($t_R$: 1.5, (M+H)$^+$: 469.0/471.1).

Synthesis of Compound 4056

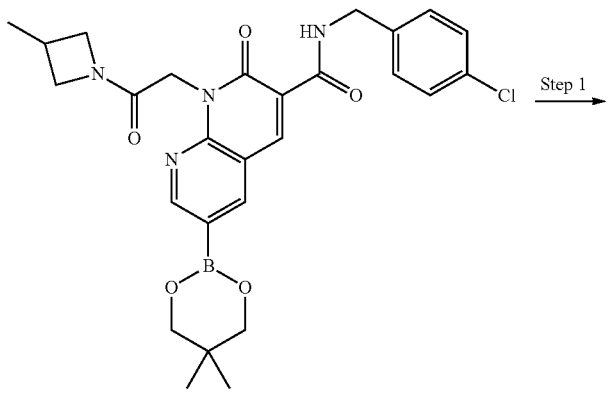

4044B

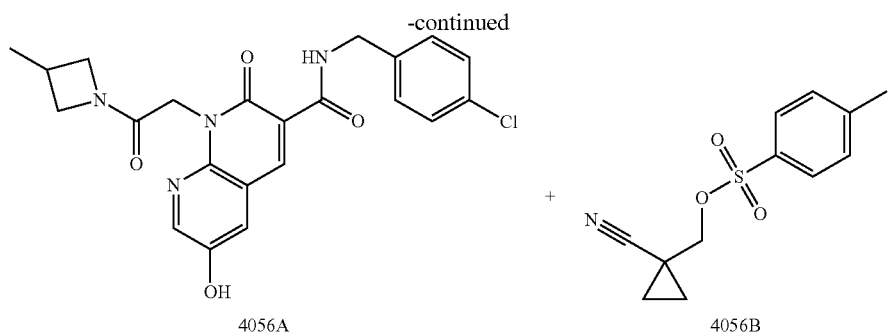

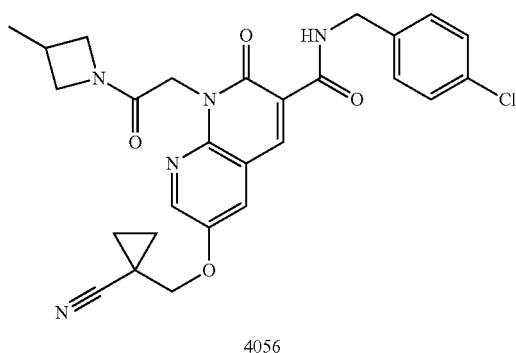

Step 1: Intermediate 4044B (50 mg, 0.093 mmol) is charged in a vial and dissolved in THF (1.0 mL). 5.0 N NaOH (82 µL, 0.41 mmol, 4.4 eq) is added and the reaction mixture is cooled to 0° C. Hydrogen peroxide 30% (205 µL, 1.81 mmol, 19.4 eq) is added dropwise. The vial is sealed and warmed at 50° C. for 90 min. The reaction mixture is diluted with EtOAc and washed with 1 N NaOH. The aqueous phase is acidified using 6 N HCl and washed with EtOAc. The organic layer is dried over MgSO$_4$, filtered and concentrated under reduced pressure to provide intermediate 4056A.

Step 2: Intermediate 4056A (46 mg, 0.10 mmol), intermediate 4056B (prepared analogously to the procedure in Bioorg. Med. Chem. 2008, 16, 8922, herein incorporated by reference) (39 mg, 0.16 mmol, 1.5 eq), cesium carbonate (102 mg, 0.312 mmol, 3.0 eq) and potassium iodide (9.5 mg, 0.057 mmol, 0.55 eq) are charged in a vial and suspended in DMF (1.5 mL). The vial is sealed and heated at 70° C. for 16 h. The reaction mixture is then diluted with MeOH, filtered and purified by preparative HPLC to provide compound 4056 (t$_R$: 1.9, (M+H)$^+$: 520.2/522.2).

Synthesis of Compound 4057

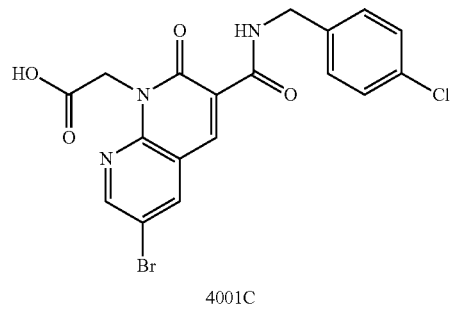

4001C

Step 1

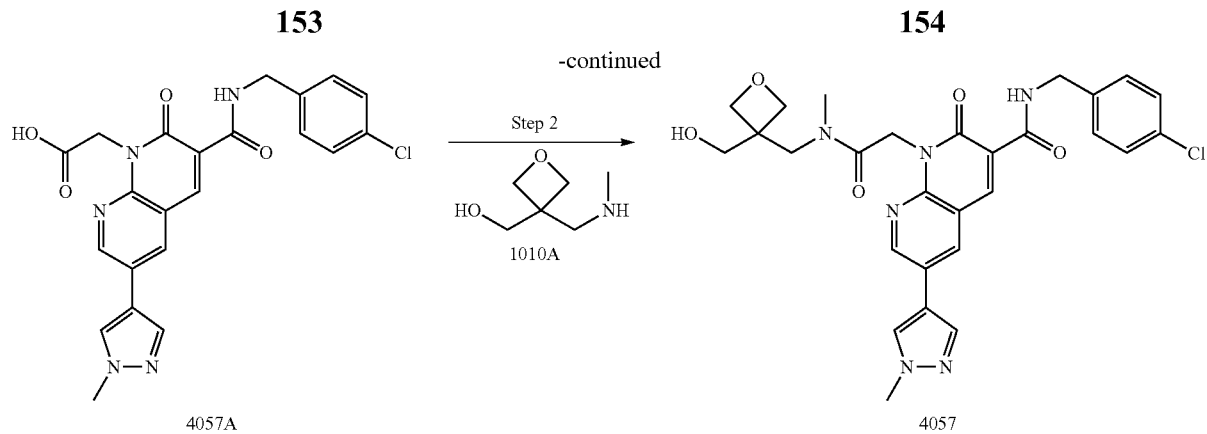

4057A · 4057

Step 1: Compound 4001C (200 mg, 0.444 mmol), 1-methyl-4-(4,4,5,5-tetramethyl-1,3,2-dioxaborolan-2-yl)-1H pyrazole (Frontier) (120 mg, 0.577 mmol, 1.30 eq), potassium carbonate (184 mg, 1.33 mmol, 3.00 eq) and bis(tri-t-butylphosphine)palladium (0) (45 mg, 0.089 mmol, 0.20 eq) are charged in a microwave vial and DMF (8.0 mL) and water (0.80 mL) are added. The vial is purged with argon, sealed and warmed in a microwave oven at 125° C. for 10 min. The reaction mixture is diluted with 1 N HCl and stirred for 10 min at RT. The resulting solid is collected by filtration, washed with water and dried under vacuum to provide intermediate 4057A.

Step 2: Intermediate 4057A (40 mg, 0.089 mmol) is charged in a vial and dissolved in DMF (1.5 mL). Diisopropylethylamine (63 μL, 0.36 mmol, 4.0 eq) and intermediate 1010A (15 mg, 0.12 mmol, 1.3 eq) are added followed by HATU (48 mg, 0.13 mmol, 1.4 eq). The solution is stirred at RT for 1 h. Following completion of the reaction, the solution is filtered and purified by preparative HPLC to provide compound 4057 ($t_R$: 1.1, (M+H)$^+$: 565.1/567.1).

Synthesis of Compound 4058

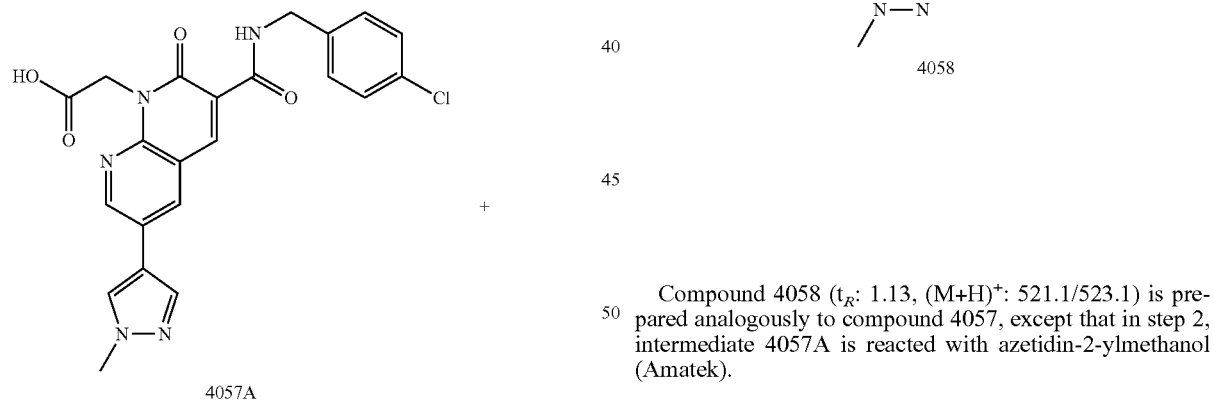

Compound 4058 ($t_R$: 1.13, (M+H)$^+$: 521.1/523.1) is prepared analogously to compound 4057, except that in step 2, intermediate 4057A is reacted with azetidin-2-ylmethanol (Amatek).

Synthesis of Compound 4059

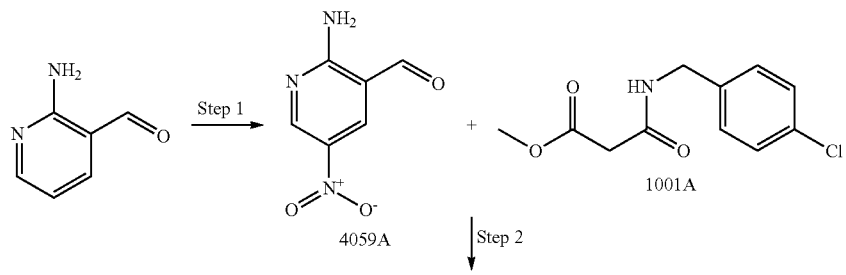

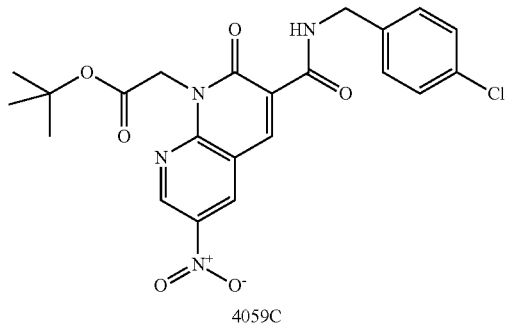
4059C

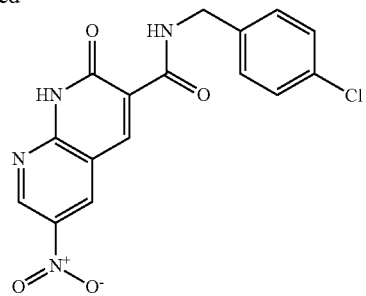
4059B

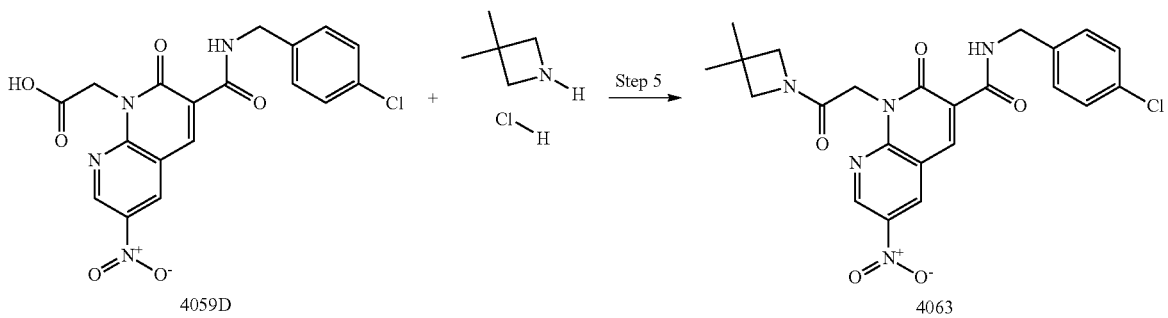

4059D        4063

Step 1: 2-amino-3-formylpyridine (Apollo-Inter) (750 mg, 6.14 mmol) is charged in a round-bottom flask and dissolved in concentrated sulfuric acid (5.00 mL). At 0° C., fuming nitric acid (0.400 mL) is added and the reaction mixture is stirred for 18 h at RT. The reaction is added to ice water (75 mL). The resulting solid is collected by filtration and washed with water and methyl t-butyl ether to provide intermediate 4059A.

Step 2: Intermediate 4059A (677 mg, 4.05 mmol) and intermediate 1001A (1.18 g, 4.87 mmol, 1.20 eq) are charged in a microwave vial and EtOH (12 mL) is added. Piperidine (1.00 mL, 10.1 mmol, 2.50 eq) is added and vial is sealed and warmed in a microwave oven at 120° C. for 20 min. The resulting solid is collected by filtration, washed with methyl t-butyl ether and dried under vacuum to afford intermediate 4059B.

Step 3: Intermediate 4059B (530 mg, 1.48 mmol) is charged in a round-bottom flask and suspended in DMF (10 mL). Potassium carbonate (613 mg, 4.44 mmol, 3.00 eq) and t-butyl bromoacetate (0.262 mL, 1.77 mmol, 1.20 eq) are added and the solution is stirred at RT for 18 h. The solution is added to water and the resulting solid is filtered and dried under vacuum. The solid is washed with methyl t-butyl ether to afford intermediate 4059C.

Step 4: Intermediate 4059C (699 mg, 1.48 mmol) is charged in a round-bottom flask and suspended in DCM (7.0 mL). TFA (7.0 mL) is added. The solution is stirred at RT for 4 h and concentrated. The residue is suspended in toluene and concentrated under reduced pressure to provide intermediate 4059D.

Step 5: Intermediate 4059D (40 mg, 0.096 mmol) is charged in a round-bottom flask and suspended in DMF (1.0 mL). Diisopropylethylamine (84 µL, 0.48 mmol, 5.0 eq) and 3,3-dimethyl-azetidine hydrochloride (prepared analogously to the procedure in J. Med. Chem. 2008, 51, 7380, herein incorporated by reference) (19 mg, 0.15 mmol, 1.60 eq) are added followed by HATU (58 mg, 0.15 mmol, 1.6 eq) and the solution is stirred at RT for 1 h. Following completion of the reaction, the reaction mixture is diluted with water and the resulting solid is collected by filtration and washed with methyl t-butyl ether. The product is purified by preparative HPLC to provide compound 4059 ($t_R$: 1.48, (M+H)$^+$: 484.0/486.0).

Synthesis of Compound 4060

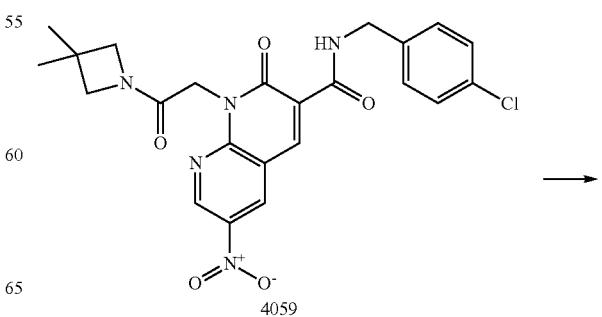
4059

-continued

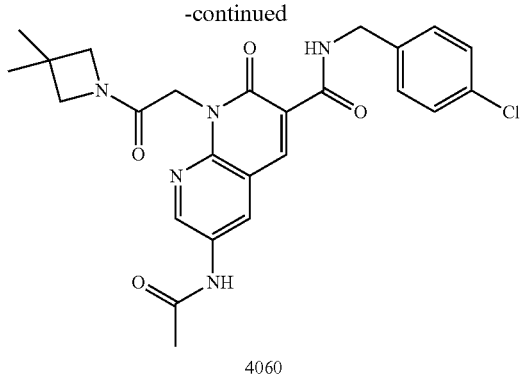

4060

Compound 4059 (109 mg, 0.104 mmol) is charged in a round-bottom flask and suspended in AcOH (5.0 mL). Iron dust (115 mg, 2.06 mmol, 19.8 eq) is added and the reaction mixture is stirred for 18 h at 90° C. The reaction mixture is cooled to RT and filtered through celite. The celite pad is washed with MeCN and the filtrate is concentrated under reduced pressure. The residue is purified by preparative HPLC to provide compound 4060 ($t_R$: 1.27, (M+H)$^+$: 496.0/498.1).

Synthesis of Compound 4061

Step 1: A solution of tert-butyl 3-(hydroxymethyl)azetidine-1-carboxylate (Milestone) (500 mg, 2.67 mmol) in DCM (15 mL) is treated with triethylamine (595 µL, 4.27 mmol, 1.60 eq) and cooled to 0° C. Methanesulfonyl chloride (310 uL, 4.01 mmol, 1.50 eq) is added and the reaction mixture is warmed to RT and stirred for 16 h at RT. At 0° C., triethylamine (200 µL) and methanesulfonyl chloride (100 µL) are added and the reaction mixture is stirred for 1 h at RT. The reaction mixture is treated with an aqueous sodium bicarbonate solution and diluted with DCM. The phases are separated and the aqueous layer is extracted with DCM (3×). The combined organic layers are dried over MgSO$_4$, filtered over a small plug of silica gel and concentrated to provide intermediate 4061A, which is used without further purification.

Step 2: Intermediate 4061A (708 mg, 2.67 mmol) is treated with a solution of TBAF 1 M in THF (24.0 mL, 24.0 mmol, 9.00 eq) and heated under argon at 65° C. for 1 h. The reaction mixture is concentrated to approximately half the volume and diluted with water. The aqueous layer is extracted with EtOAc (3×) and the combined organic layers are washed with 0.25 M aqueous HCl and a saturated sodium bicarbonate solution. The organic layer is dried over MgSO$_4$ and filtered over a small plug of silica gel and concentrated to provide intermediate 4061B.

Step 3: Intermediate 4061B (25 mg, 0.13 mmol) is charged in a round-bottom flask and dissolved in TFA (1.0 mL). The solution is stirred at RT for 1 h and concentrated to afford intermediate 4061C.

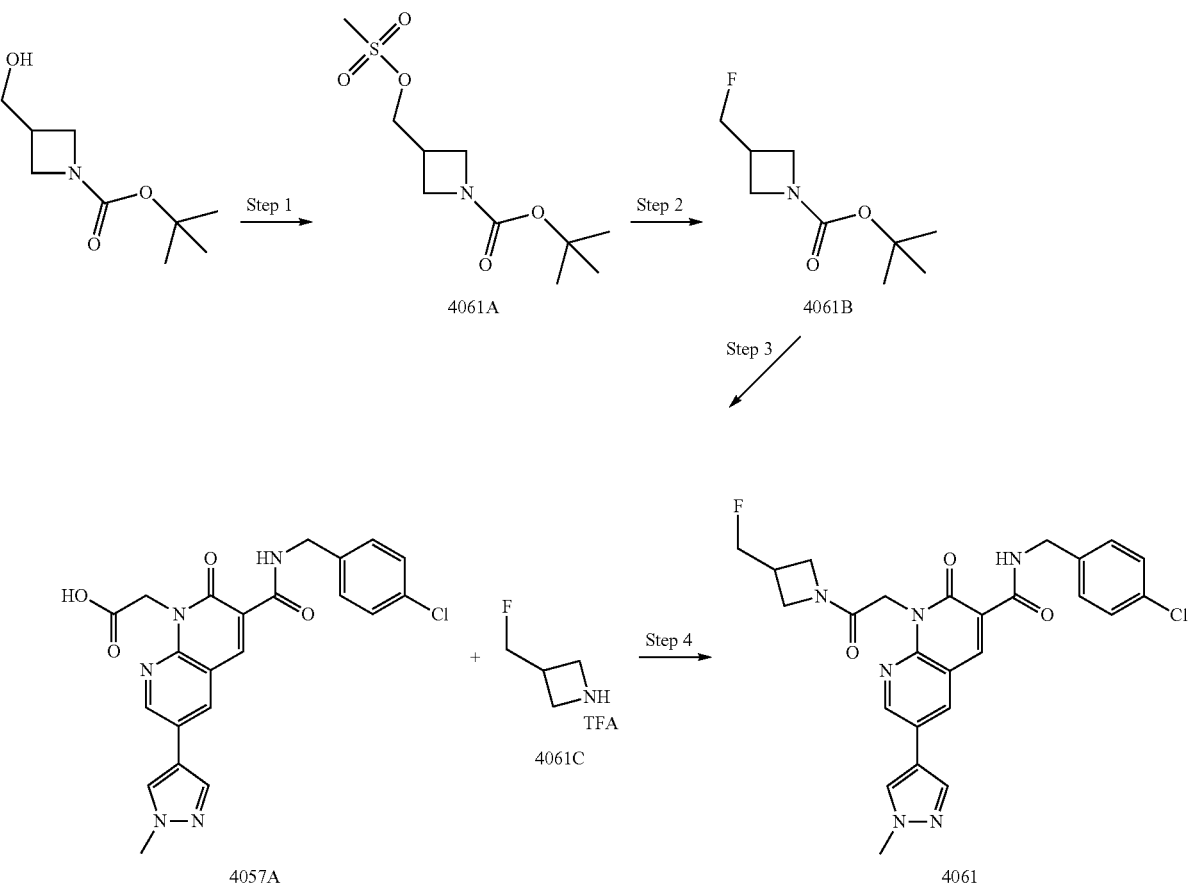 [SMILES: CC(C)(C)OC(=O)N1CC(CO)C1 ; CC(C)(C)OC(=O)N1CC(COS(C)(=O)=O)C1 ; CC(C)(C)OC(=O)N1CC(CF)C1 ; Cn1cc(-c2cnc3c(c2)cc(C(=O)NCc2ccc(Cl)cc2)c(=O)n3CC(=O)O)cn1 ; FCC1CNC1 ; Cn1cc(-c2cnc3c(c2)cc(C(=O)NCc2ccc(Cl)cc2)c(=O)n3CC(=O)N2CC(CF)C2)cn1]

Step 4: Compound 4061 is prepared analogously to compound 4057, except that intermediate 4057A is reacted with intermediate 4061C.

Synthesis of Compound 4062

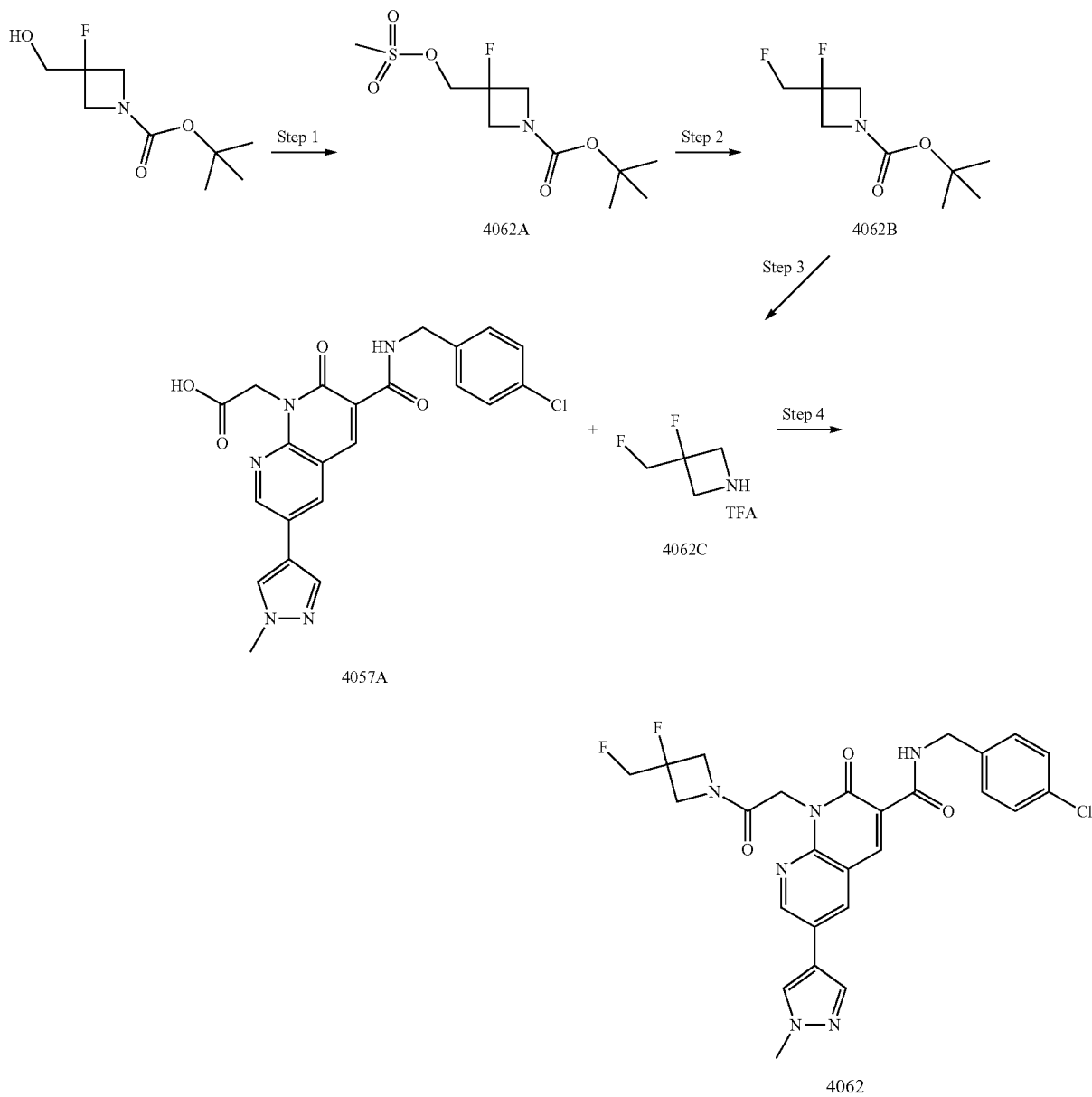

Step 1: A solution of 3-fluoro-3-hydroxymethyl-azetidine-1-carboxylic acid tert-butyl ester (prepared analogously to the procedure in J. Org. Chem., 74, 2009, 2250, herein incorporated by reference) (350 mg, 1.71 mmol) in DCM (10 mL) is treated with triethylamine (380 µL, 2.73 mmol, 1.60 eq) and cooled to 0° C. Methanesulfonyl chloride (198 uL, 2.56 mmol, 1.50 eq) is added and the reaction mixture is warmed to RT and stirred for 16 h at RT. At 0° C., triethylamine (200 µL) and methanesulfonyl chloride (200 µL) are added and the reaction mixture is stirred for 1 h at RT. The reaction mixture is treated with an aqueous sodium bicarbonate solution and diluted with DCM. The phases are separated and the aqueous layer is extracted with DCM (3×). The combined organic layers are dried over $MgSO_4$, filtered over a small plug of silica gel and concentrated to provide intermediate 4062A, which is used without further purification.

Step 2: Intermediate 4062A (434 mg, 1.52 mmol) is treated with a solution of TBAF 1 M in THF (13.8 mL, 13.8 mmol, 9.00 eq) and heated under argon at 65° C. for 1 h. The reaction mixture is concentrated to approximately half the volume and diluted with water. The aqueous layer is extracted with EtOAc (3×) and the combined organic layers are washed with 0.25 M aqueous HCl and a saturated sodium bicarbonate solution. The organic layer is dried over $MgSO_4$, filtered and concentrated. The residue is purified by flash chromatography (10% to 25% EtOAc in hexanes) to provide intermediate 4062B.

Step 3: Intermediate 4062B (28 mg, 0.14 mmol) is charged in a round-bottom flask and dissolved in TFA (1.0 mL). The solution is stirred at RT for 1 h and concentrated to afford intermediate 4062C.

Step 4: Compound 4062 is prepared analogously to compound 4057, except that intermediate 4062C is reacted with intermediate 4057A.

Synthesis of Compound 4063

C. for 20 min. The reaction mixture is diluted with water and acidified to pH ~7 with 1 N HCl. The mixture is washed with DCM (3×). The organic layer is dried over MgSO$_4$, filtered and concentrated under reduced pressure to provide intermediate 4063A.

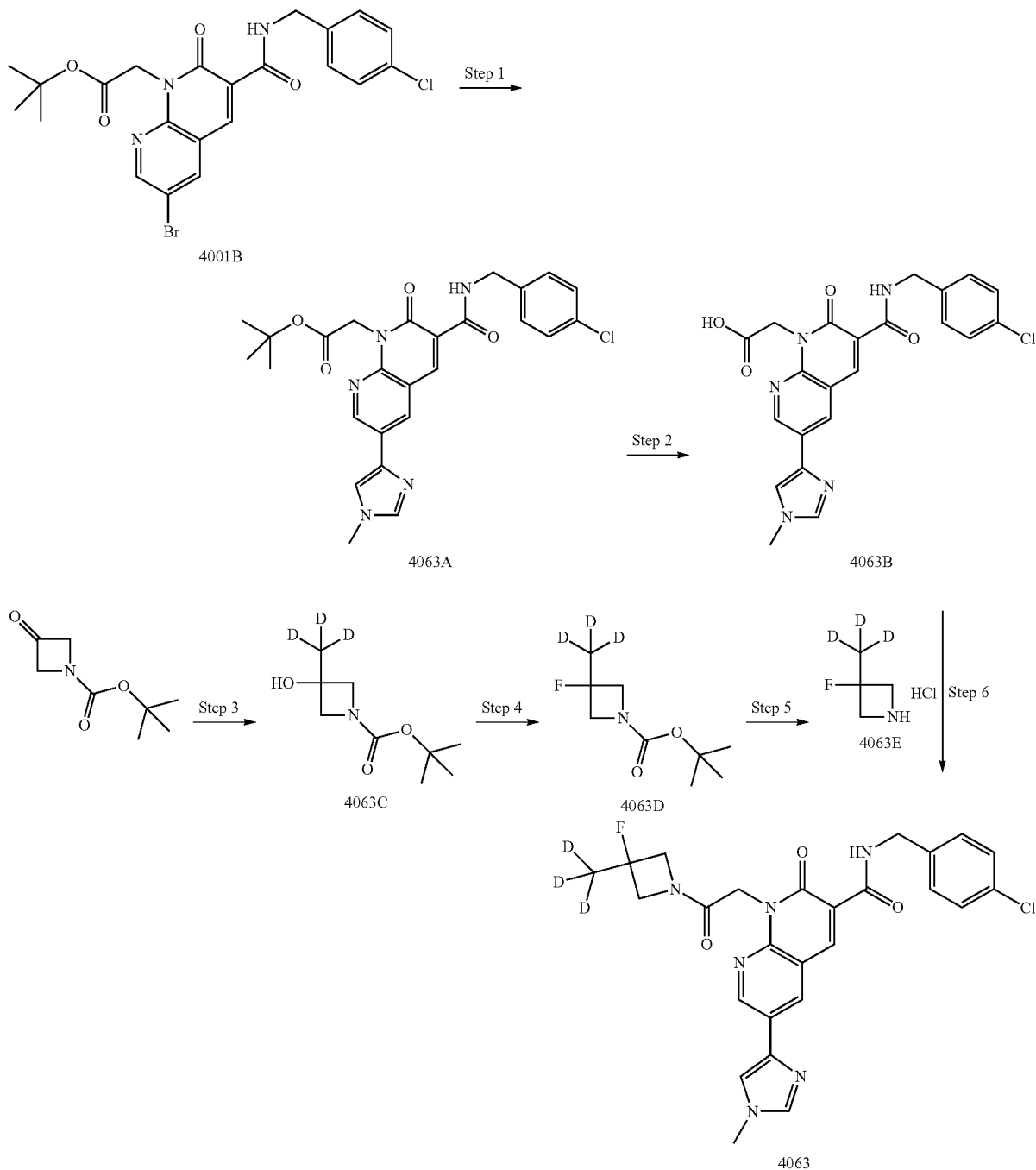

Step 1: N-methyl-4-(tributylstannyl) imidazole (Aldrich) (457 mg, 1.23 mmol, 1.25 eq) is charged in a microwave vial and a degassed solution of intermediate 4001B (500 mg, 0.987 mmol) in DMF (12 mL) is added. (Tri-t-butylphosphine)palladium (0) (137 mg, 0.118 mmol, 0.12 eq) is added and the vial is sealed and warmed in a microwave oven at 130°

Step 2: Intermediate 4063A (300 mg, 0.591 mmol) is charged in a round-bottom flask and dissolved in DCM (5 mL) and TFA (1.0 m). The solution is stirred at RT for 1 h and concentrated under reduced pressure. The residue is suspended in toluene and this mixture is concentrated under reduced pressure. The residue is dissolved in a saturated aqueous NaHCO₃ solution and washed with EtOAc. The aqueous phase is acidified to pH ~5 with 6 N HCl and washed with EtOAc. The combined organic layers are dried over MgSO₄, filtered and concentrated under reduced pressure to provide intermediate 4063B.

Step 3: To a solution of tert-butyl 3-oxoazetidine-1-carboxylate (CNH-Tech) (5.00 g, 29.2 mmol) in anhydrous THF (100 mL) is added a 1.00 M solution of CD₃MgI in ether (Aldrich) (250 mL, 250 mmol, 8.56 eq) at −78° C. The reaction mixture is stirred for 2 h at −78° C. and a saturated aqueous NH₄Cl solution is added. The mixture is washed with EtOAc. The combined organic layers are dried over Na₂SO₄, filtered and concentrated under reduced pressure. The residue is triturated in petroleum ether to afford intermediate 4063C.

Step 4: To a solution of intermediate 4063C (2.00 g, 10.7 mmol) in DCM (25 mL) is added diethylaminosulfur trifluoride (2.58 g, 16.0 mmol, 1.50 eq) at −78° C. The reaction mixture is stirred for 1 h at −78° C. and for 16 h at RT. A saturated aqueous NaHCO₃ solution is added until neutral pH is observed. The reaction mixture is washed with DCM and the combined organic layers are washed with brine. The organic layers are dried over Na₂SO₄, filtered and concentrated under reduced pressure. The residue is purified by flash chromatography to afford intermediate 4063D.

Step 5: Intermediate 4063D (5.50 g, 28.6 mmol) is charged in a round-bottom flask and dissolved in ether (50 mL) and DCM (10 mL). At 0° C., hydrochloric acid gas is passed through the solution until complete conversion is observed. The solution is concentrated under reduced pressure and the residue is triturated in ethanol/petroleum ether to afford intermediate 4063E.

Step 6: Compound 4063 is prepared analogously to compound 4057, except that intermediate 4063E is reacted with intermediate 4063B.

Synthesis of Compound 4064

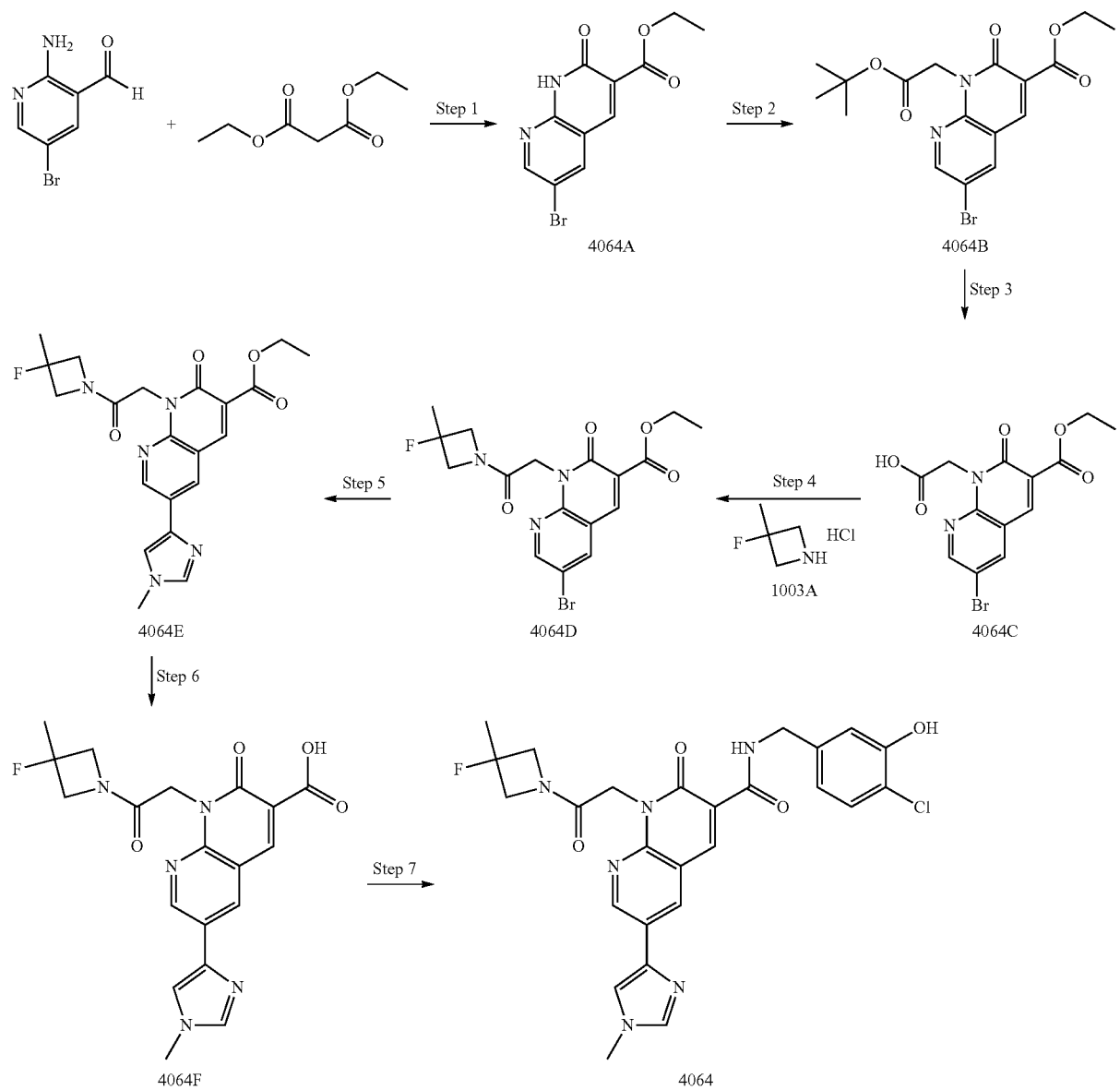

Step 1: Intermediate 4064A is prepared analogously to compound 2001A, except that 2-amino-5-bromonicotinaldehyde (Apollo-Inter) is reacted with diethylmalonate.

Step 2: Intermediate 4064B is prepared analogously to intermediate 2001B.

Step 3: Intermediate 4064C is prepared analogously to intermediate 2001C.

Step 4: Intermediate 4064D is prepared analogously to intermediate 2001D, except that intermediate 4064C is reacted with intermediate 1003A.

Step 5: Intermediate 4064E is prepared analogously to intermediate 4063A.

Step 6: Intermediate 4064F is prepared analogously to intermediate 2001E.

Step 7: Compound 4064 is prepared analogously to compound 2001, except that intermediate 4064F is reacted with 5-(aminomethyl)-2-chlorophenol (Milestone).

Synthesis of Compound 4065

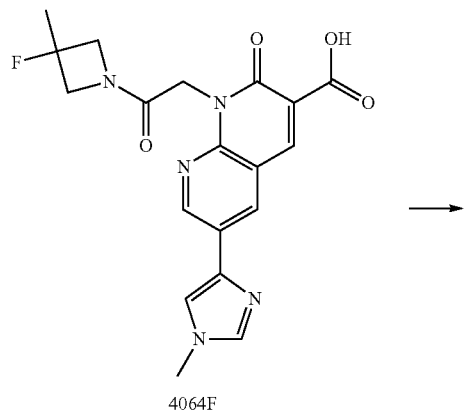

4064F

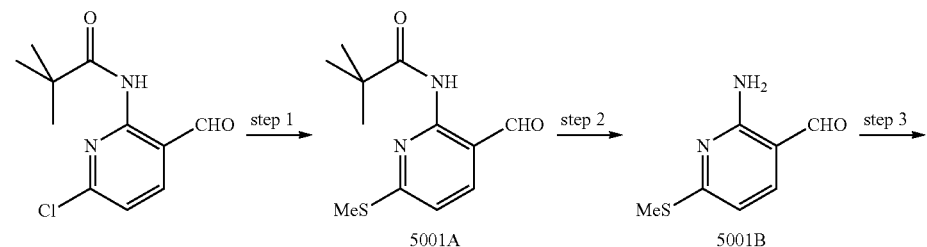

4065

Compound 4065 is prepared analogously to compound 2001, except that intermediate 4064F is reacted with 4-chloro-3-methoxybenzenemethanamine (Betapharma).

Synthesis of Compound 5001

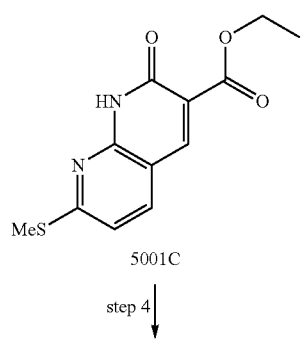

5001C step 4

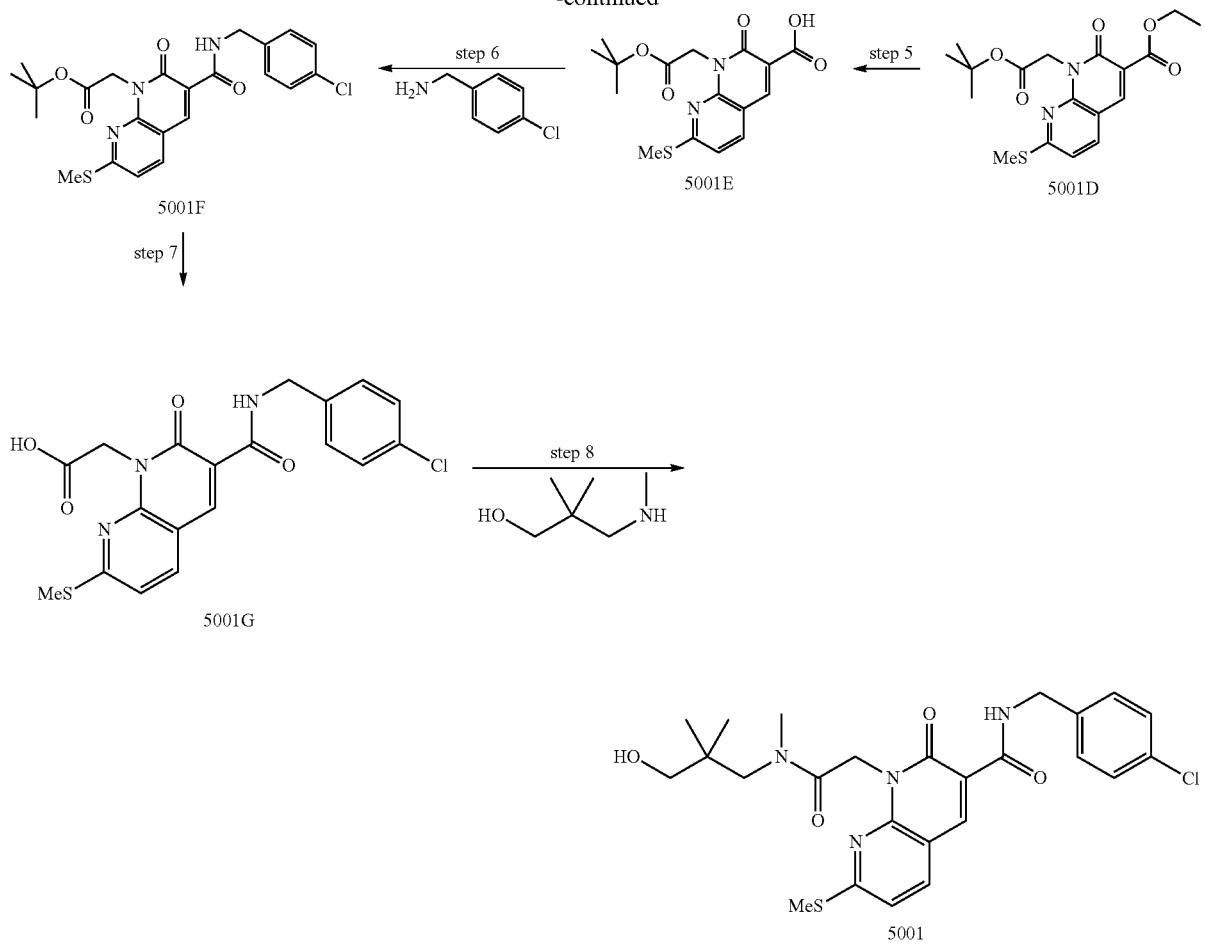

Step 1: Sodium thiomethoxide (1.37 g, 19.5 mmol, 1.50 eq) is added to N-(6-chloro-3-formyl-pyridin-2-yl)-2,2-dimethyl-propionamide (Org Process Res. Dev. 2009, 13, 555) (1.87 g, 7.79 mmol) in THF (50 mL) in a round-bottom flask and the solution is stirred at 50° C. for 2 h. The reaction mixture is diluted with EtOAc and washed with brine. The organic layer is dried over MgSO$_4$, filtered and concentrated under reduced pressure to afford intermediate 5001A.

Step 2: Intermediate 5001A (6.17 g, 29.9 mmol) is charged in a round-bottom flask, then a 2.0 M aqueous solution of potassium hydroxide (150 mL, 300 mmol, 10.0 eq) is added. The reaction mixture is stirred at 80° C. for 18 h and the solution is extracted with DCM. The organic layer is dried over MgSO$_4$, filtered and concentrated under reduced pressure to provide intermediate 5001B.

Step 3: Intermediate 5001C is prepared analogously to compound 3001D.

Step 4: Intermediate 5001D is prepared analogously to compound 2001B.

Step 5: Intermediate 5001D (5.00 g, 13.2 mmol) is dissolved in THF (55 mL) and MeOH (11 mL) in a round-bottom flask, then a 2.0 M aqueous solution of LiOH (15.2 mL, 30.4 mmol, 2.30 eq) is added. The reaction mixture is stirred at RT for 2 h, and then acidified to approximately pH=2 using a 1 M aqueous HCl solution. The resulting solid is filtered and dried under reduced pressure to provide intermediate 5001E.

Step 6: Intermediate 5001E (4.19 g, 12.0 mmol) is dissolved in DMF (40.0 mL) in a round-bottom flask, then diisopropylethylamine (6.22 mL, 35.8 mmol, 3.00 eq) and 4-chlorobenzylamine (Aldrich) (1.75 mL, 14.3 mmol, 1.20 eq) are added followed by HATU (5.23 g, 13.8 mmol, 1.15 eq). The reaction mixture is stirred at RT for 3 h. The solution is diluted with EtOAc and washed with brine (3×). The organic layer is dried over MgSO$_4$, filtered and concentrated under reduced pressure to provide intermediate 5001F.

Step 7: TFA (20.0 mL) is added to a solution of intermediate 5001F (1.30 g, 2.74 mmol) dissolved in DCM (20.0 mL) and the reaction mixture is stirred at RT for 3 h. The solution is concentrated under reduced pressure to provide intermediate 5001G.

Step 8: Intermediate 5001G (1.10 g, 2.63 mmol) is dissolved in DMF (12.0 mL) in a round-bottom flask, then triethylamine (1.10 mL, 7.90 mmol, 3.00 eq) and 2,2-dimethyl-3-(methylamino)propan-1-ol (Chembrdg-bb) (370 mg, 3.16 mmol, 1.20 eq) are added followed by TBTU (1.20 g, 3.16 mmol, 1.20 eq). The reaction mixture is stirred at RT for 2 h. Water is added and the resulting solid is filtered. The solid is dissolved in DCM and washed with brine. The organic layer is dried over MgSO$_4$, filtered and concentrated under reduced pressure to provide compound 5001 ($t_R$: 1.97, (M+H)$^+$: 517.3).

Synthesis of Compound 5002

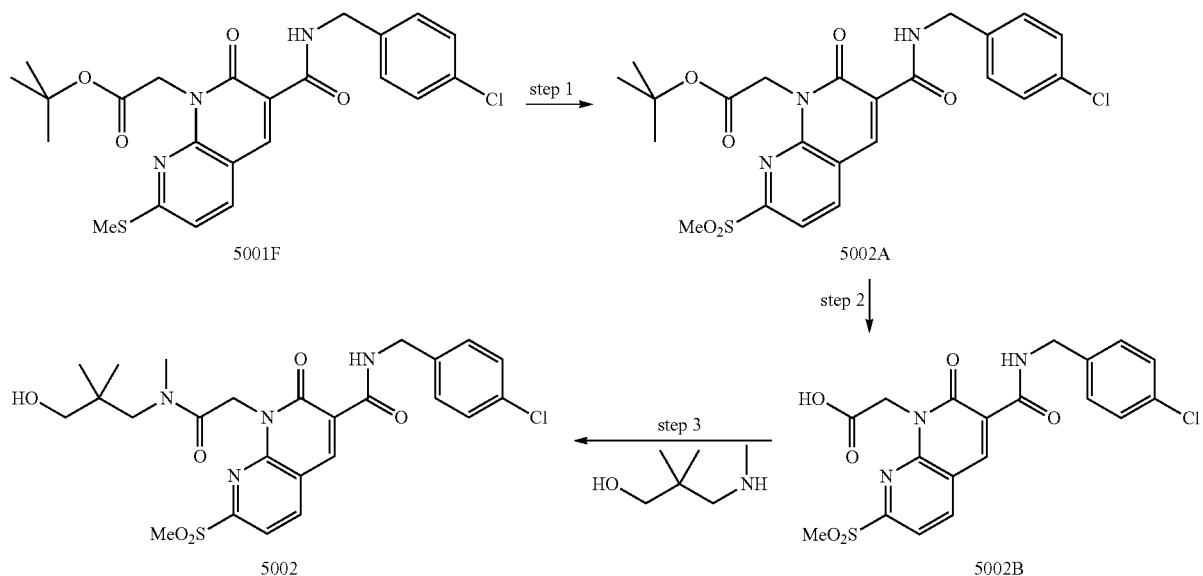

Step 1: Intermediate 5001F (2.64 g, 5.57 mmol) is suspended in acetone (60 mL) in a round-bottom flask, then oxone (10.3 g, 16.7 mmol, 3.00 eq) is added and the reaction mixture is stirred at RT for 42 h. The reaction mixture is extracted with DCM and washed with brine. The organic layer is dried over MgSO₄, filtered and concentrated under reduced pressure to provide intermediate 5002A.

Step 2: Intermediate 5002B is prepared analogously to intermediate 5001G.

Step 3: Compound 5002 ($t_R$: 1.8, (M+H)⁺: 549.3) is prepared analogously to compound 5001.

Synthesis of Compound 5003

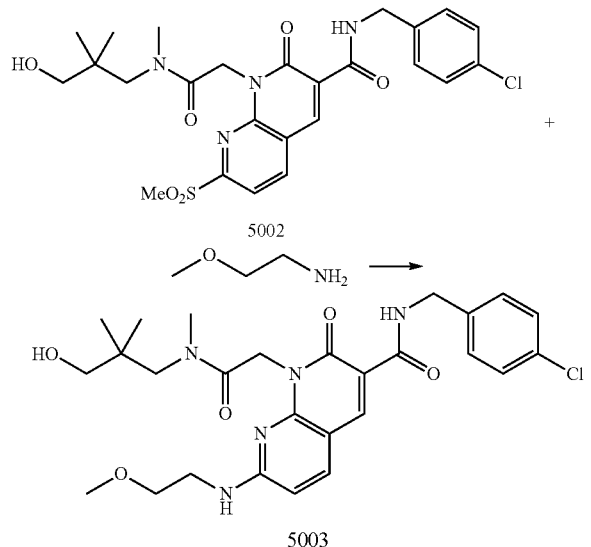

Compound 5002 (27 mg, 0.049 mmol) is charged in a vial and dissolved in DMF (0.5 mL). Diisopropylethylamine (30 µL, 0.15 mmol, 3.0 eq) is added followed by 2-methoxyethylamine (Aldrich) (15 mg, 0.20 mmol, 4.0 eq). The solution is stirred at 60° C. for 16 h, filtered and purified by preparative HPLC to provide compound 5003 ($t_R$: 5.64, (M+H)⁺: 544.3).

Synthesis of Compound 5004

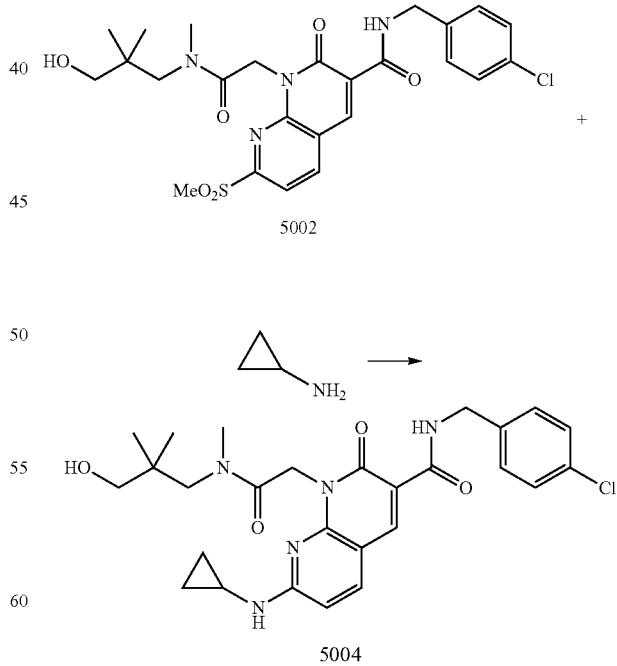

Compound 5004 ($t_R$: 6.05, (M+H)⁺: 526.3) is prepared analogously to compound 5003, except that compound 5002 is reacted with cyclopropylamine (Oakwood).

Synthesis of Compound 5005

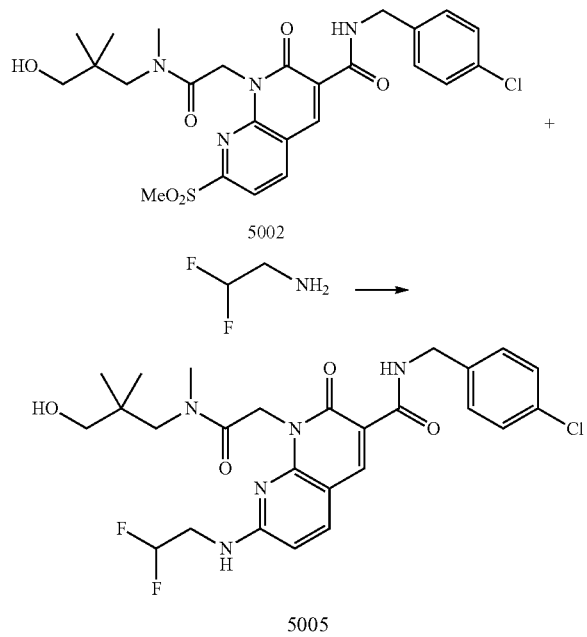

5005

Compound 5005 ($t_R$: 5.96, (M+H)$^+$: 550.2) is prepared analogously to compound 5003, except that compound 5002 is reacted with 2,2-difluoroethylamine (Matrix).

Synthesis of Compound 5006

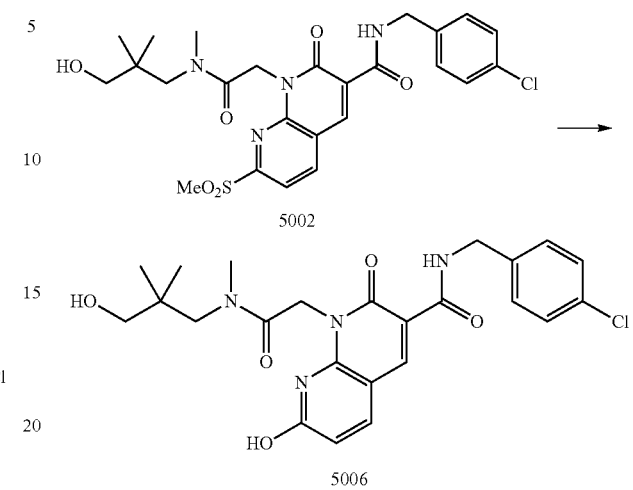

5006

Compound 5002 (50 mg, 0.091 mmol) is charged in a vial and dissolved in DMF (0.7 mL), then potassium fluoride (21 mg, 0.36 mmol, 4.0 eq) is added. The solution is stirred at 120° C. for 18 h, filtered and purified by preparative HPLC to provide compound 5006 ($t_R$: 1.84, (M+H)$^+$: 487.3).

Synthesis of Compound 5007

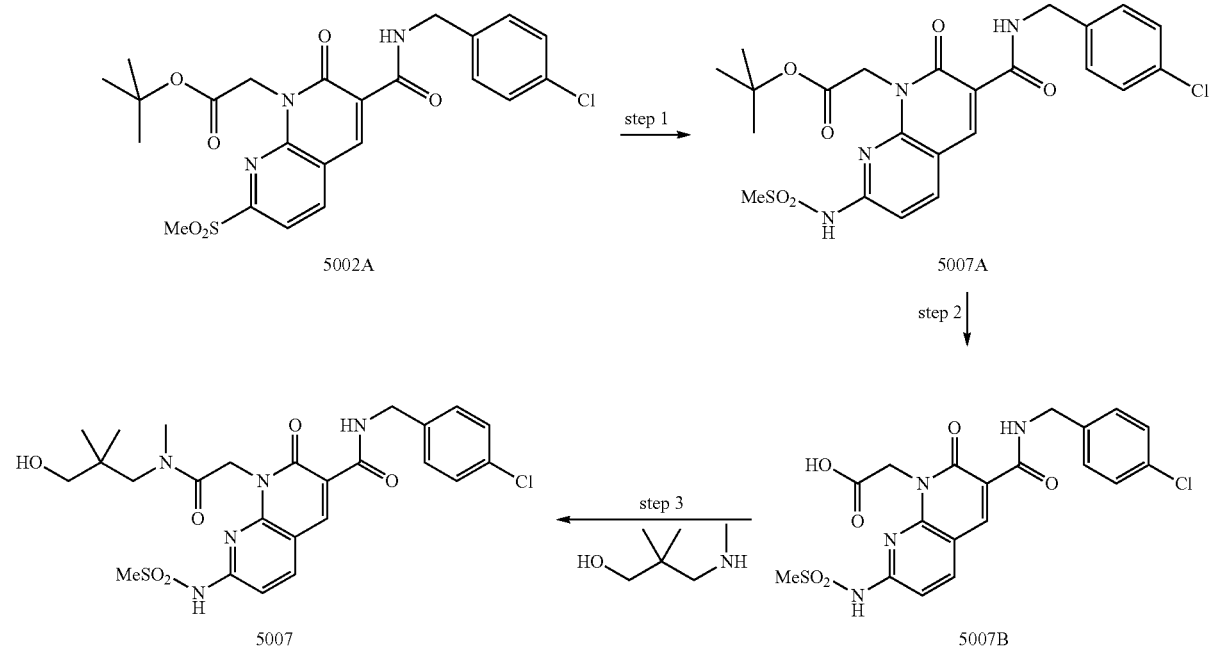

Step 1: Intermediate 5007A is prepared analogously to compound 5003, except that intermediate 5002A is reacted with methane sulfonamide (Aldrich).
Step 2: Intermediate 5007B is prepared analogously to intermediate 5001G.
Step 3: Compound 5007 ($t_R$: 1.24, (M+H)$^+$: 564) is prepared analogously to compound 5001.

Synthesis of Compound 5008

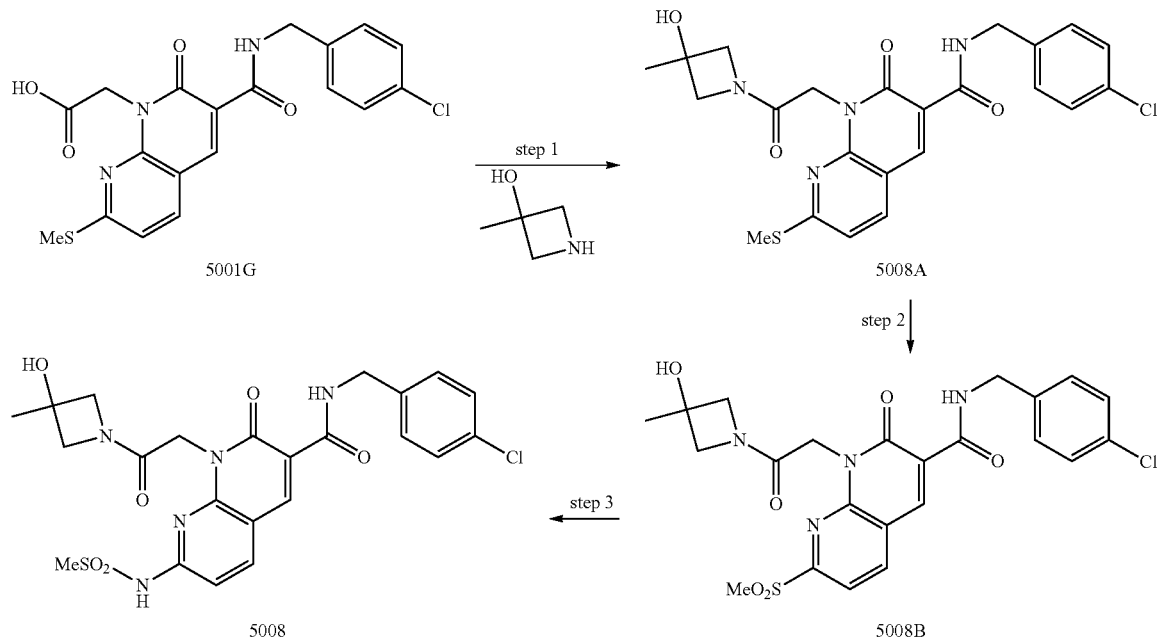

Step 1: Intermediate 5001G (177 mg, 0.422 mmol) is dissolved in DMF (1.5 mL) in a round-bottom flask, then diisopropylethylamine (290 µL, 1.69 mmol, 4.00 eq) and 3-methyl-azetidin-3-ol (Parkway) (44.5 mg, 0.506 mmol, 1.20 eq) are added followed by TBTU (163 mg, 0.506 mmol, 1.20 eq). The reaction mixture is stirred at RT for 18 h. The solution is diluted with EtOAc and washed with brine (3×). The organic layer is dried over MgSO$_4$, filtered and concentrated under reduced pressure to provide intermediate 5008A.

Step 2: Intermediate 5008A (202 mg, 0.415 mmol) is suspended in acetone (4.6 mL) in a round-bottom flask, then oxone (765 mg, 0.124 mmol, 3.00 eq) is added and the reaction mixture is stirred at RT for 42 h. The reaction mixture is extracted with DCM and washed with brine. The organic layer is dried over MgSO$_4$, filtered and concentrated under reduced pressure to provide intermediate 5008B.

Step 3: Methane sulfonamide (18 mg, 0.19 mmol, 2.0 eq) is charged in a vial and dissolved in DMF (0.65 mL). Sodium hydride (60% in oil) (7.7 mg, 0.19 mmol, 2.0 eq) is added followed by intermediate 5008B (50 mg, 0.096 mmol). The solution is stirred at RT for 2 h, filtered and purified by preparative HPLC to provide compound 5008 (t$_R$: 1.68, (M+H)$^+$: 534.2).

Synthesis of Compound 5009

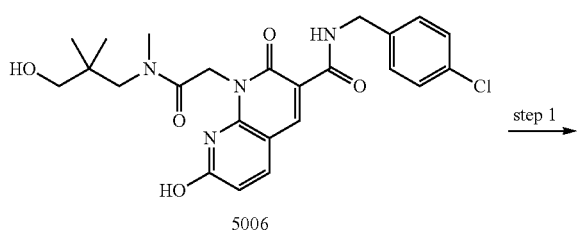

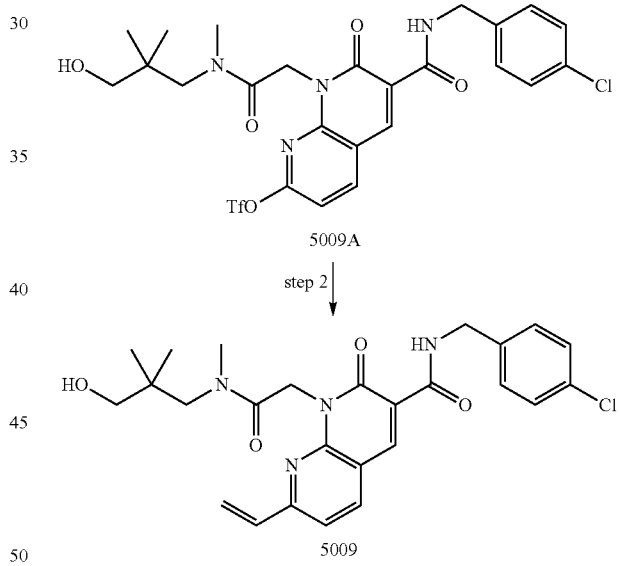

Step 1: Compound 5006 (500 mg, 1.03 mmol) is dissolved in MeCN (11 mL) in a round-bottom flask, then potassium carbonate (284 mg, 2.05 mmol, 2.00 eq) and N-phenyl trifluoromethanesulfonimide (400 mg, 1.23 mmol, 1.20 eq) are added and the reaction mixture is stirred at RT for 18 h. Following completion of the reaction, the solution is concentrated under reduced pressure and purified by flash chromatography (EtOAc/hexanes) to afford intermediate 5009A.

Step 2: Intermediate 5009A (50 mg, 0.081 mmol) is charged in a round-bottom flask with 2,4,6-trivinylcyclotriboroxane pyridine complex (Aldrich) (29 mg, 0.12 mmol, 1.50 eq) and potassium carbonate (12 mg, 0.089 mmol, 1.1 eq) then water (60 µL) and 1,2-dimethoxyethane (1.0 mL) are added. The solution is degassed by bubbling argon through the solution for 5 min, then tetrakis(triphenylphosphine) palladium(0) (9 mg, 0.008 mmol, 0.1 eq) is added. The reaction mixture is heated at 100° C. for 2.5 h. The cooled solution is diluted with DCM and washed with water (2×). The organic layer is dried over MgSO₄, filtered and concentrated under reduced pressure. The residue is purified by flash chromatography (MeOH/DCM) to afford compound 5009 (t$_R$: 1.97, (M+H)⁺: 497.3).

Synthesis of Compound 5010

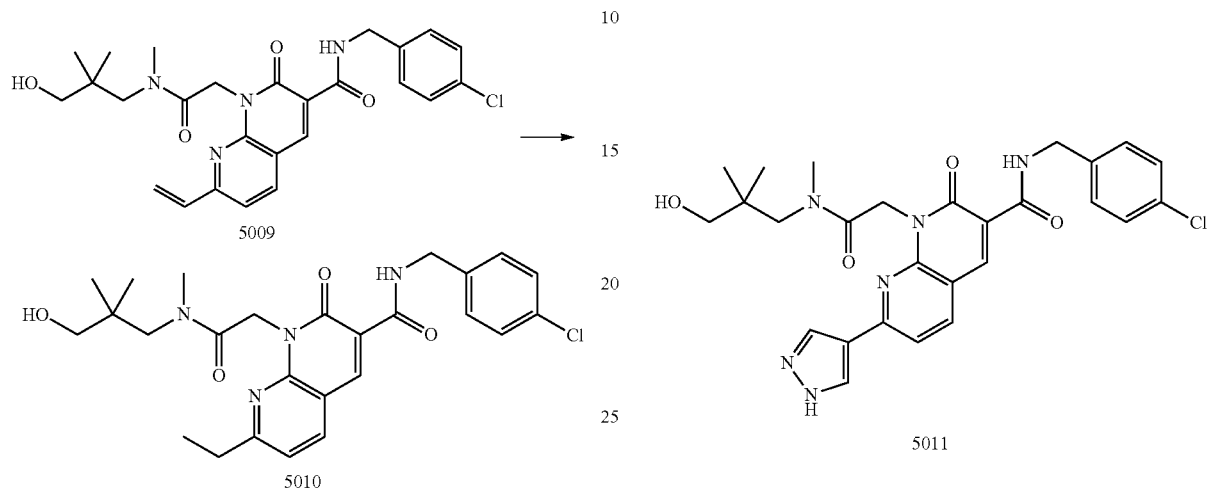

Compound 5009 (26 mg, 0.052 mmol) is charged in a round-bottom flask and dissolved in EtOAc (4 mL) and MeOH (1 mL) then palladium on charcoal (5% w/w) (10 mg, 0.005 mmol, 0.1 eq) is added. The flask is submitted to vacuum/hydrogen refill cycles (3×) and then the solution is stirred at RT under a hydrogen atmosphere (balloon) for 1 h. The solution is filtered, concentrated under reduced pressure and purified by preparative HPLC to provide compound 5010 (t$_R$: 2, (M+H)⁺: 499.3).

Synthesis of Compound 5011

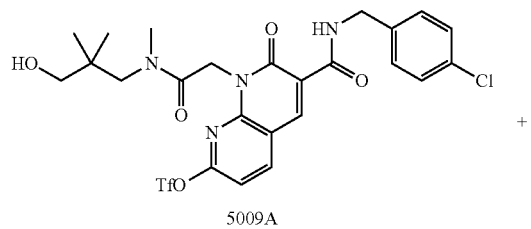

Intermediate 5009A (50 mg, 0.081 mmol) is charged in a round-bottom flask with 4,4,5,5-tetramethyl-2-(1h-pyrazol-4-yl)-1,3,2-dioxaborolane (Strem) (19 mg, 0.097 mmol, 1.20 eq) and potassium carbonate (12 mg, 0.089 mmol, 1.1 eq) then water (60 μL) and 1,2-dimethoxyethane (1.0 mL) are added. The solution is degassed by bubbling argon through the solution for 5 min, then tetrakis(triphenylphosphine) palladium(0) (9 mg, 0.008 mmol, 0.1 eq) is added. The reaction mixture is heated at 100° C. for 2.5 h. The cooled solution is diluted with DCM and washed with water (2×). The organic layer is dried over MgSO₄, filtered and concentrated under reduced pressure. The residue is purified by flash chromatography (MeOH/DCM) to afford compound 5011 (t$_R$: 1.87, (M+H)⁺: 537.3).

Synthesis of Compound 5012

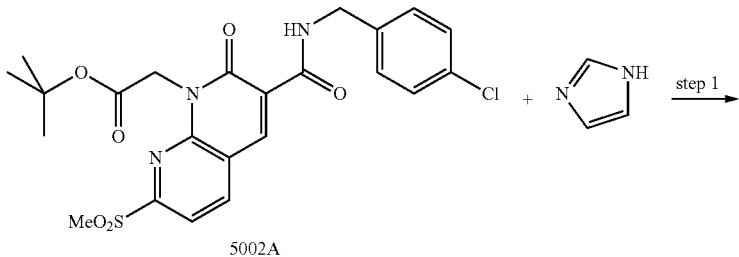

-continued

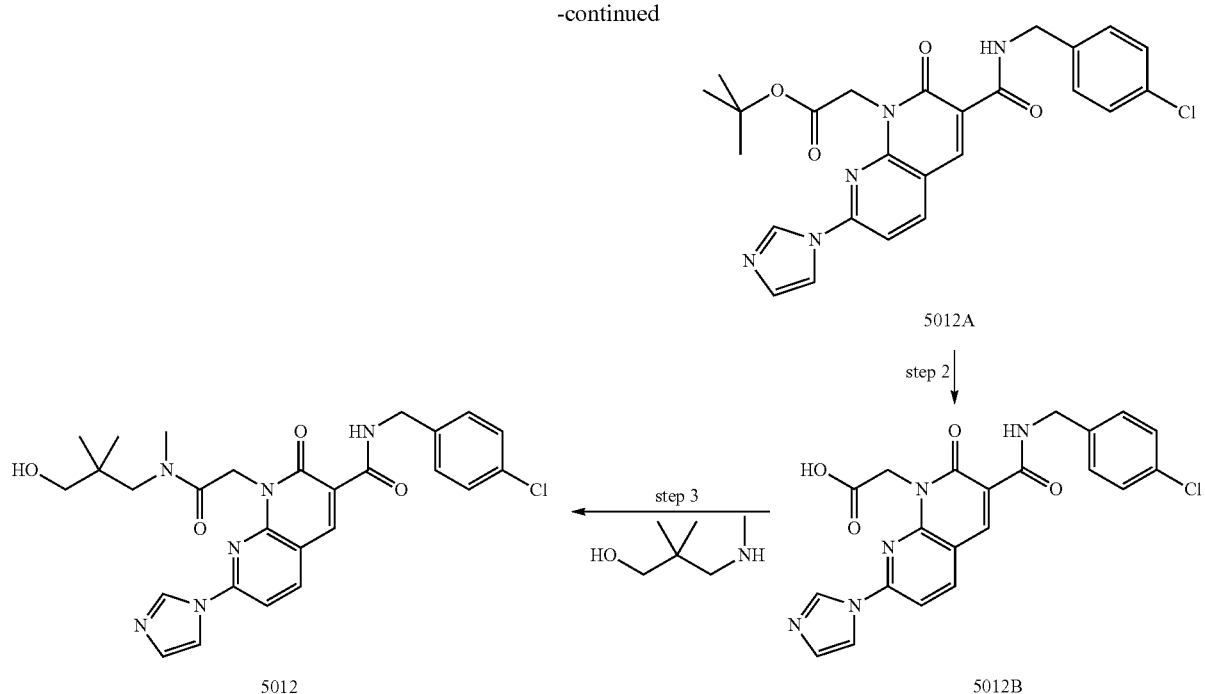

Step 1: Imidazole (16 mg, 0.24 mmol, 4.0 eq) is charged in a vial and dissolved in THF (0.60 mL). Sodium hydride (60% in oil) (9.5 mg, 0.24 mmol, 4.0 eq) is added followed by intermediate 5002A (30 mg, 0.059 mmol) and the solution is stirred at RT for 18 h. The solution is filtered and purified by preparative HPLC to provide intermediate 5012A.

Step 2: TFA (1.0 m) is added to a solution of intermediate 5012A (30 mg, 0.061 mmol) dissolved in DCM (1.0 mL) and the reaction mixture is stirred at RT for 2 h. The solution is concentrated under reduced pressure to provide intermediate 5012B.

Step 3: Intermediate 5012B (15 mg, 0.027 mmol) is dissolved in DMF (0.3 m), then diisopropylethylamine (14 μL, 0.082 mmol, 3.0 eq) and 2,2-dimethyl-3-(methylamino)propan-1-ol (Chembrdg-bb) (3.8 mg, 0.033 mmol, 1.20 eq) are added followed by TBTU (11 mg, 0.030 mmol, 1.10 eq). The reaction mixture is stirred at RT for 2 h, filtered and purified by preparative HPLC to provide compound 5012 ($t_R$: 1.76, $(M+H)^+$: 537.1/539.1).

Synthesis of Compound 5013

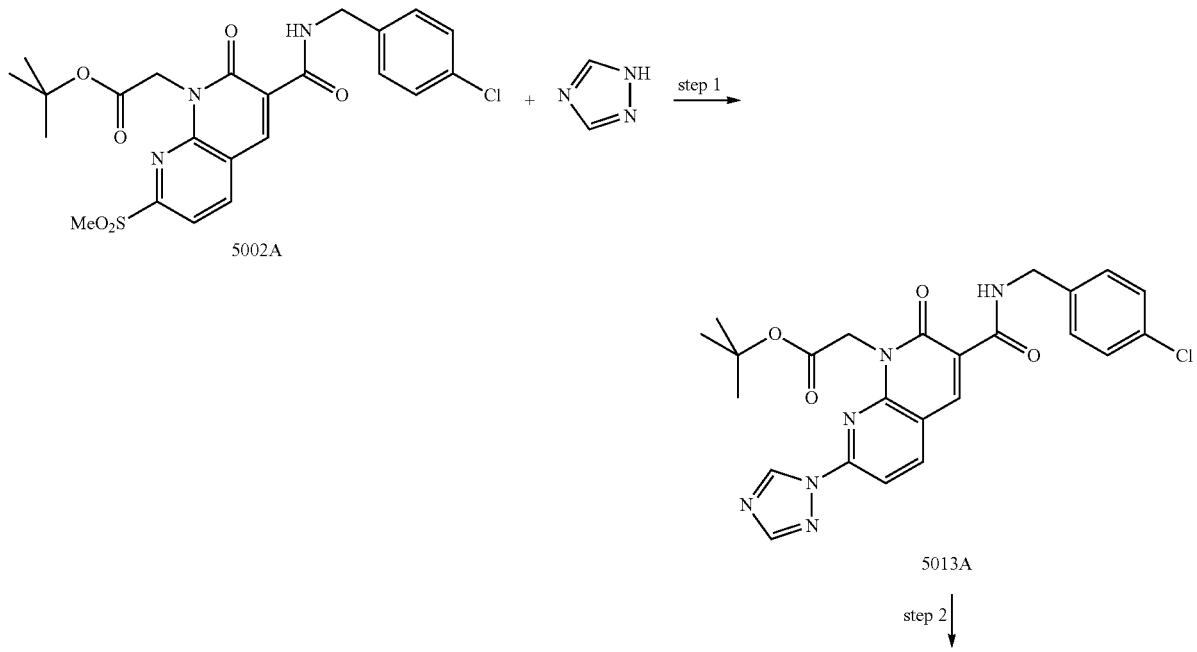

-continued

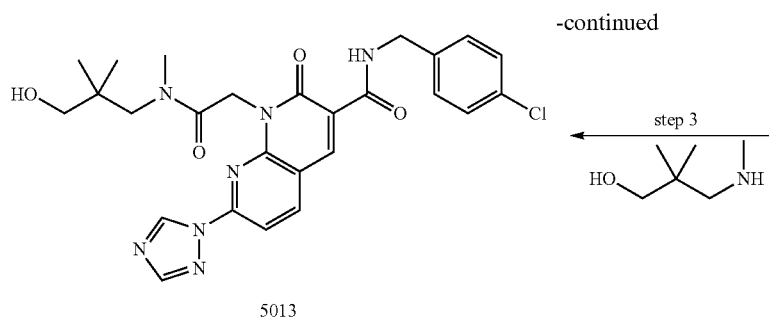
5013

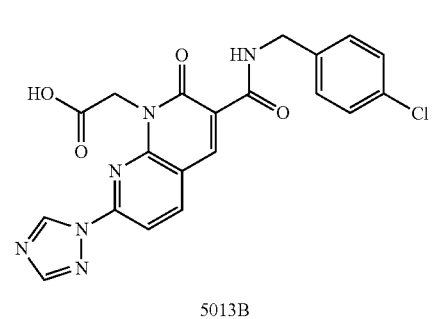
5013B

Step 1: Intermediate 5013A is prepared analogously to compound 5012A, except that intermediate 5002A is reacted with 1,2,4-triazole (Aldrich).

Step 2: Intermediate 5013B is prepared analogously to intermediate 5012B.

Step 3: Compound 5013 ($t_R$: 1.81, (M+H)$^+$: 538.3) is prepared analogously to compound 5012.

Synthesis of Compound 5014

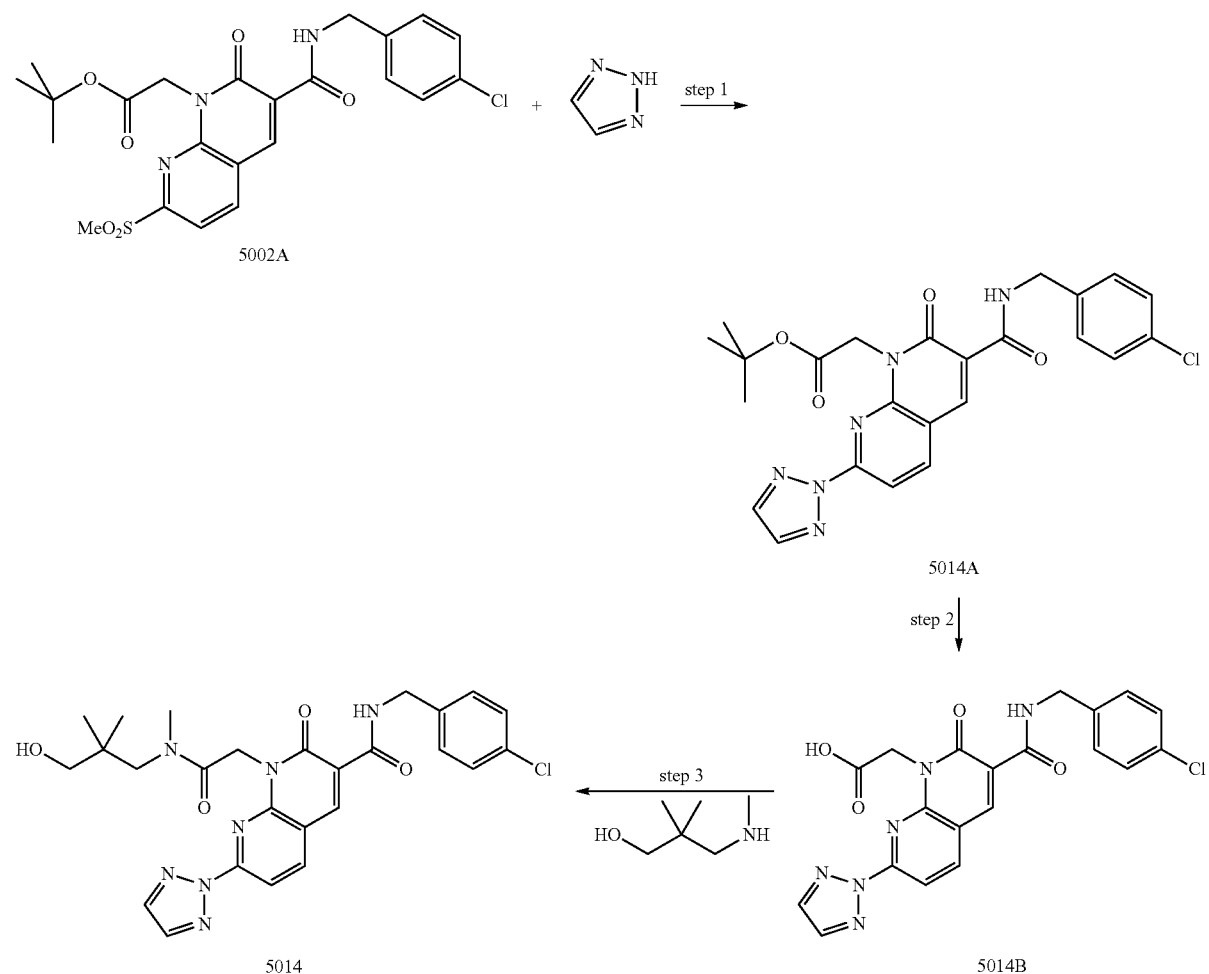

Step 1: Intermediate 5014A is prepared analogously to compound 5012A, except that intermediate 5002A is reacted with 1,2,3-triazole (Aldrich).

Step 2: Intermediate 5014B is prepared analogously to intermediate 5012B.

Step 3: Compound 5014 ($t_R$: 1.89, (M+H)$^+$: 538.3) is prepared analogously to compound 5012.

Synthesis of Compound 5015

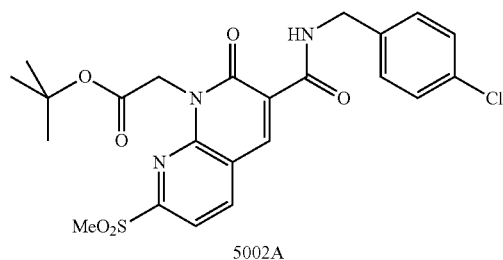

5002A

step 1

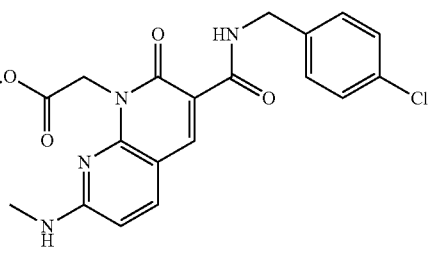

5015A

step 2

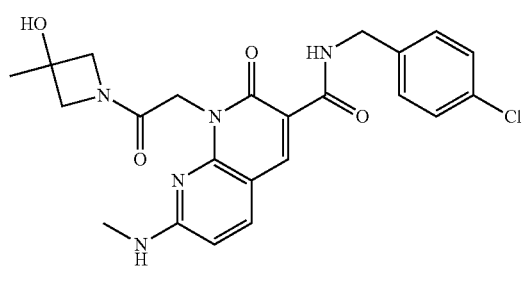

5015

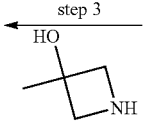
step 3

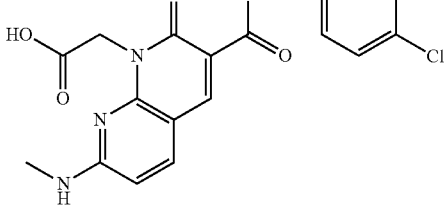

5015B

Step 1: Intermediate 5015A is prepared analogously to compound 5012A, except that intermediate 5002A is reacted with methylamine (Aldrich).

Step 2: Intermediate 5015A is prepared analogously to intermediate 5012B.

Step 3: Intermediate 5015B (56 mg, 0.11 mmol) is dissolved in DMF (0.5 mL), then diisopropylethylamine (80 μL, 0.44 mmol, 4.0 eq) and 3-methyl-azetidin-3-ol (Parkway) (12 mg, 0.13 mmol, 1.2 eq) are added followed by TBTU (42 mg, 0.131 mmol, 1.20 eq). The reaction mixture is stirred at RT for 18 h, filtered and purified by preparative HPLC to provide compound 5015 ($t_R$: 4.84, (M+H)$^+$: 470.1).

Step 1: Intermediate 5016A is prepared analogously to compound 5006.

Step 2: Intermediate 5016B is prepared analogously to intermediate 5012B.

Step 3: Intermediate 5016B (1.00 g, 2.58 mmol) is dissolved in DMF (12 mL), then triethylamine (1.08 mL, 7.74 mmol, 3.00 eq) and 3-methyl-azetidine hydrochloride (prepared analogously to the procedure in J. Med. Chem. 2008, 51, 7380, herein incorporated by reference) (335 mg, 3.10 mmol, 1.20 eq) are added followed by TBTU (1.18 g, 3.10 mmol, 1.20 eq). The reaction mixture is stirred at RT for 18 h, filtered and purified by preparative HPLC to provide compound 5016 ($t_R$: 1.86, (M+H)$^+$: 441.2).

Synthesis of Compound 5016

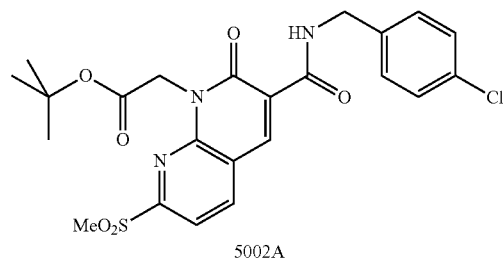

5002A

step 1

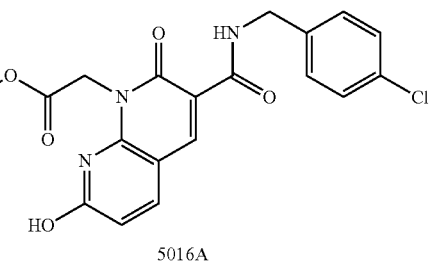

5016A

step 2

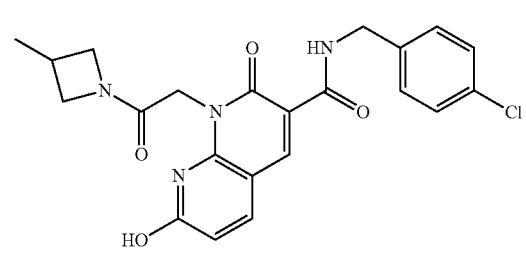

5016

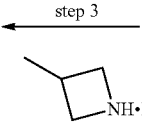
step 3

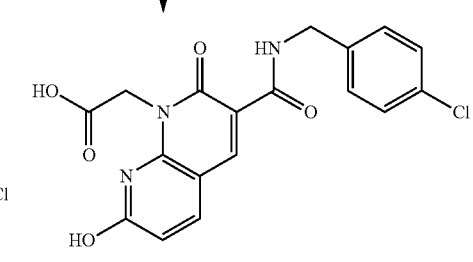

5016B

Synthesis of Compound 5017

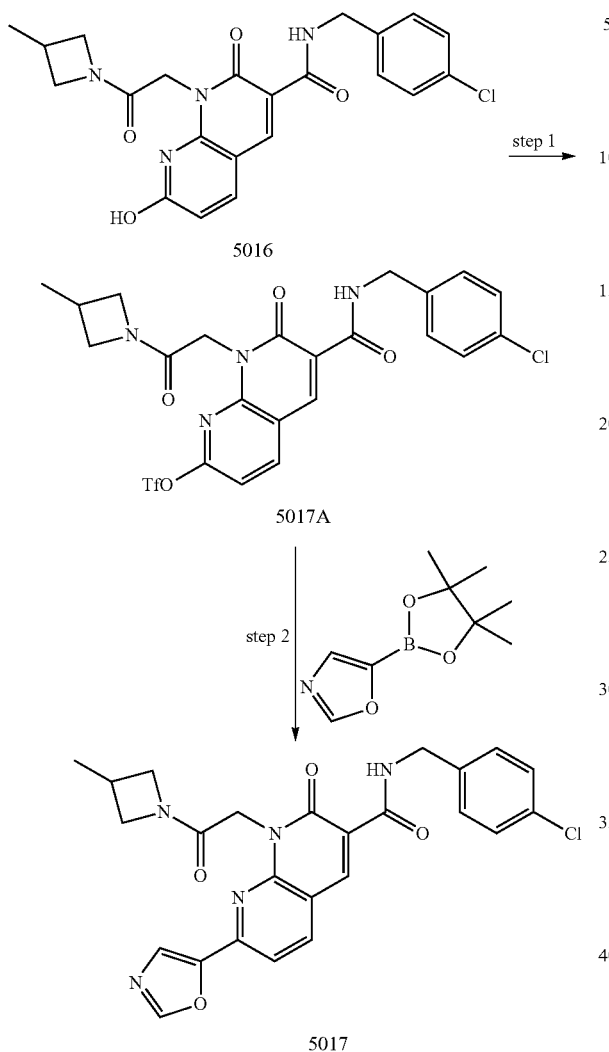

Step 1: Intermediate 5017A is prepared analogously to intermediate 5009A.

Step 2: Compound 5017 ($t_R$: 1.89, (M+H)$^+$: 492.3) is prepared analogously to compound 5011, except that intermediate 5017A is reacted with 5-(4,4,5,5-tetramethyl-1,3,2-dioxaborolan-2-yl)oxazole (Boropharm).

Synthesis of Compound 5018

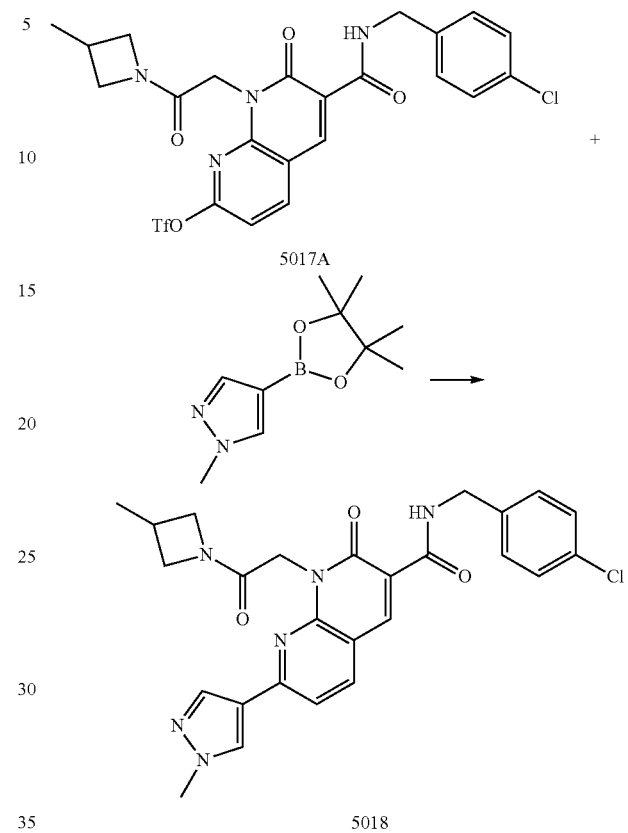

Intermediate 5017A (75 mg, 0.131 mmol) is charged in a round-bottom flask along with 1-methyl-4-(4,4,5,5-tetramethyl-1,3,2-dioxaborolan-2-yl)-1 h pyrazole (Frontier) (32.7 mg, 0.157 mmol, 1.20 eq) and potassium carbonate (19.9 mg, 0.144 mmol, 1.1 eq) then water (100 µL) and 1,2-dimethoxyethane (1.0 mL) are added. The solution is degassed by bubbling argon through the solution for 5 min, then tetrakis(triphenylphosphine)palladium(0) (15 mg, 0.013 mmol, 0.10 eq) is added. The reaction mixture is heated at 90° C. for 14 h, filtered and purified by preparative HPLC to provide compound 5018 ($t_R$: 1.92, (M+H)$^+$: 505.3).

Synthesis of Compound 5019

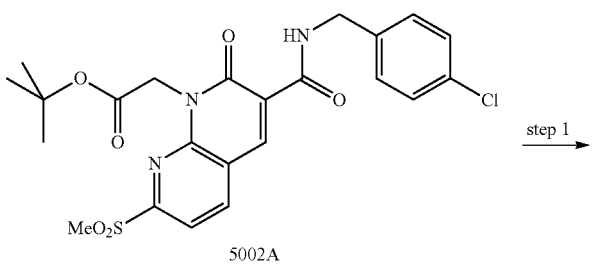

step 1

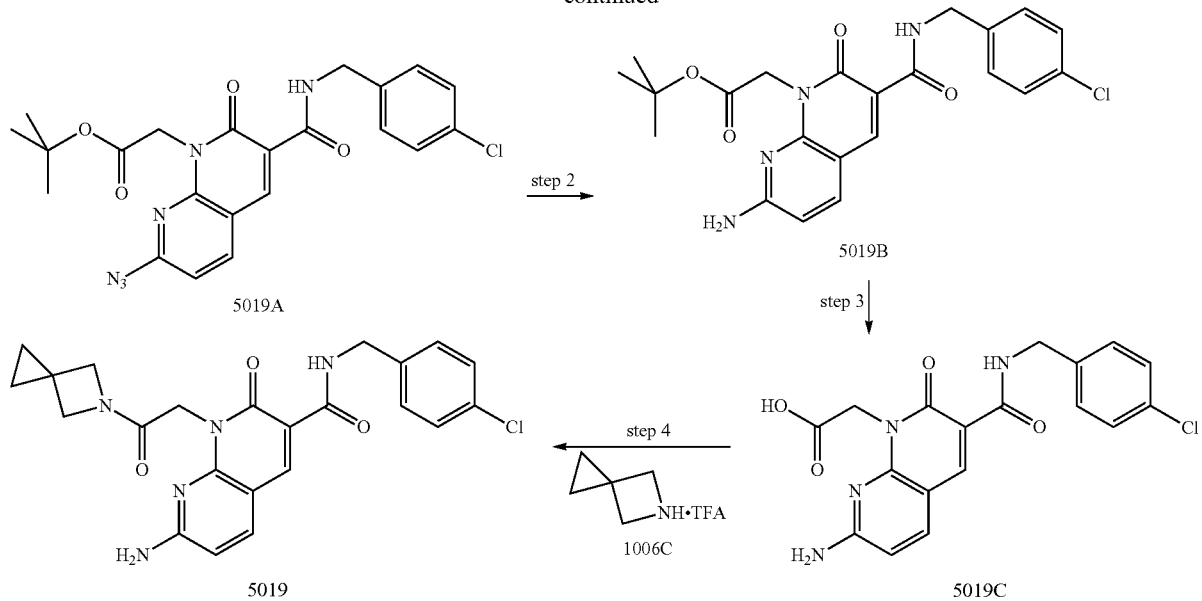

Step 1: Intermediate 5002A (553 mg, 1.09 mmol) is charged in a vial and dissolved in DMF (5.5 mL). Sodium azide (107 mg, 1.65 mmol, 1.50 eq) is added and the solution is stirred at RT. Following completion of the reaction, the solution is diluted with EtOAc and washed with water (3×) and brine (3×). The organic layer is dried over MgSO$_4$, filtered and concentrated under reduced pressure. The residue is triturated with Et$_2$O and hexanes to afford intermediate 5019A.

Step 2: Intermediate 5019A (445 mg, 0.949 mmol) is charged in a round-bottom flask then dioxane (1.8 mL) and water (0.9 mL) are added. Triphenylphosphine (372 mg, 1.42 mmol, 1.5 eq) is added and the reaction mixture is stirred at RT. Following completion of the reaction, the solution is concentrated under reduced pressure and purified by preparative HPLC to provide intermediate 5019B.

Step 3: TFA (1.0 mL) is added to a solution of intermediate 5019B (30 mg, 0.068 mmol) dissolved in DCM (1.0 mL) and the reaction mixture is stirred at RT for 2 h. The solution is concentrated under reduced pressure to provide intermediate 5019C.

Step 4: Intermediate 5019C (26 mg, 0.068 mmol) is dissolved in DMF (0.5 mL), then diisopropylethylamine (50 µL, 0.27 mmol, 4.0 eq) and intermediate 1006C (17 mg, 0.088 mmol, 1.3 eq) are added followed by TBTU (26 mg, 0.081 mmol, 1.2 eq) and the reaction mixture is stirred at RT for 18 h, filtered and purified by preparative HPLC to provide compound 5019 (t$_R$: 5.44, (M+H)$^+$: 452.2).

Synthesis of Compound 5020

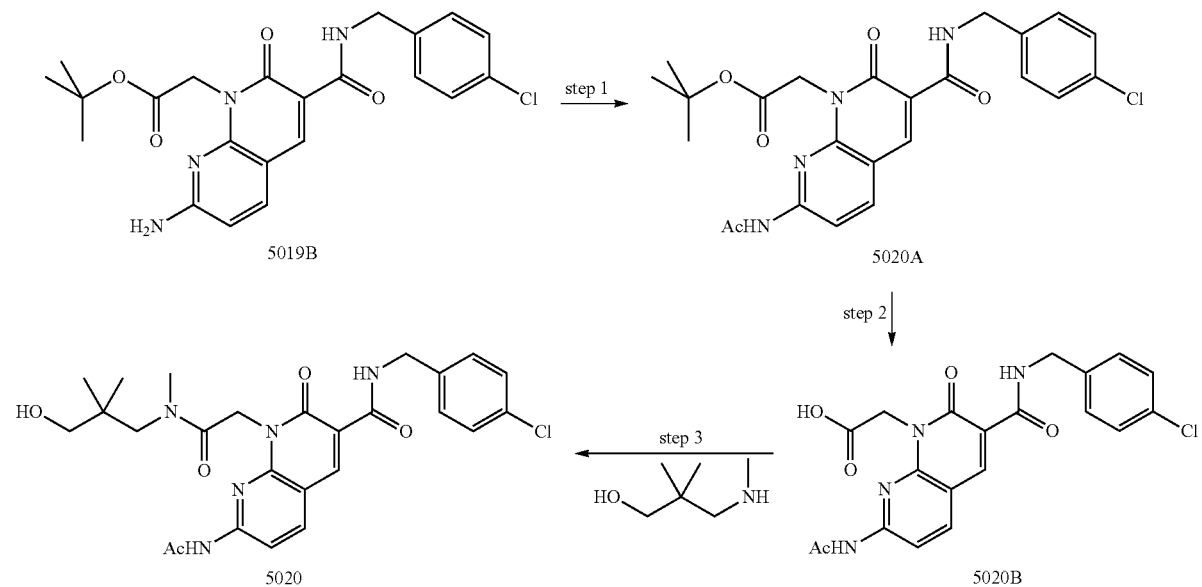

Step 1: Intermediate 5019B (44 mg, 0.099 mmol) is dissolved in THF (0.7 mL), then triethylamine (35 μL, 0.25 mmol, 2.5 eq) and 4-dimethylaminopyridine (2.4 mg, 0.020 mmol, 0.20 eq) are added followed by acetyl chloride (11 μL, 0.15 mmol, 1.50 eq). The reaction mixture is stirred at RT for 42 h, diluted with EtOAc and washed with brine (3×). The organic layer is dried over MgSO$_4$, filtered and concentrated under reduced pressure. The crude residue is purified by flash chromatography (MeOH/DCM) to provide intermediate 5020A.

Step 2: Intermediate 5020B is prepared analogously to intermediate 5012B.

Step 3: Compound 5020 (t$_R$: 1.86, (M+H)$^+$: 528.3) is prepared analogously to compound 5012.

Synthesis of Compound 5021

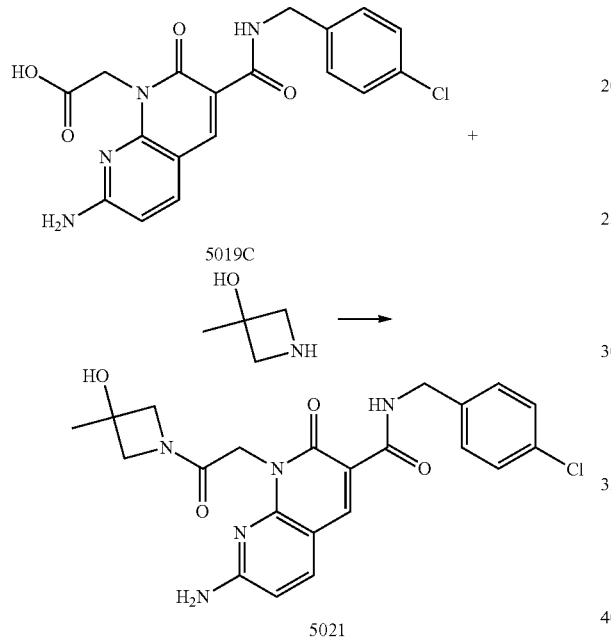

Compound 5021 (t$_R$: 1.73, (M+H)$^+$: 456.2) is prepared analogously to compound 5019, except that in step 4, intermediate 5019C is reacted with 3-methyl-azetidin-3-ol (Parkway).

Synthesis of Compound 5022

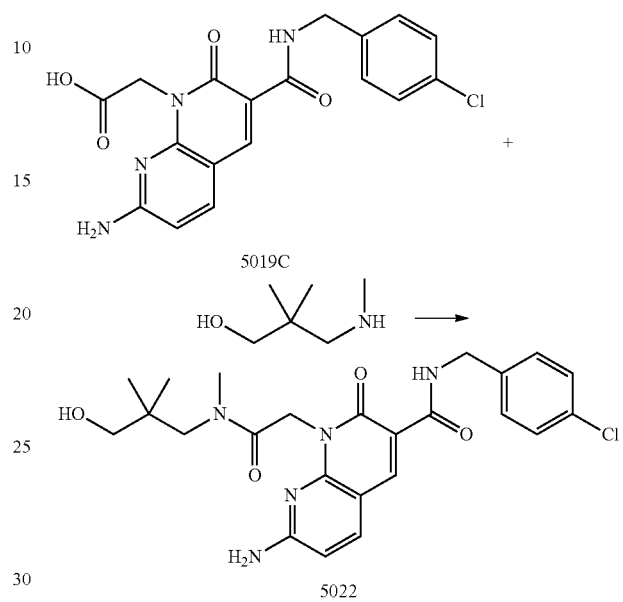

Compound 5022 (t$_R$: 1.83, (M+H)$^+$: 486.3) is prepared analogously to compound 5019, except that in step 4, intermediate 5019C is reacted with 2,2-dimethyl-3-(methylamino)propan-1-ol (Chembrdg-bb).

Synthesis of Compound 6001

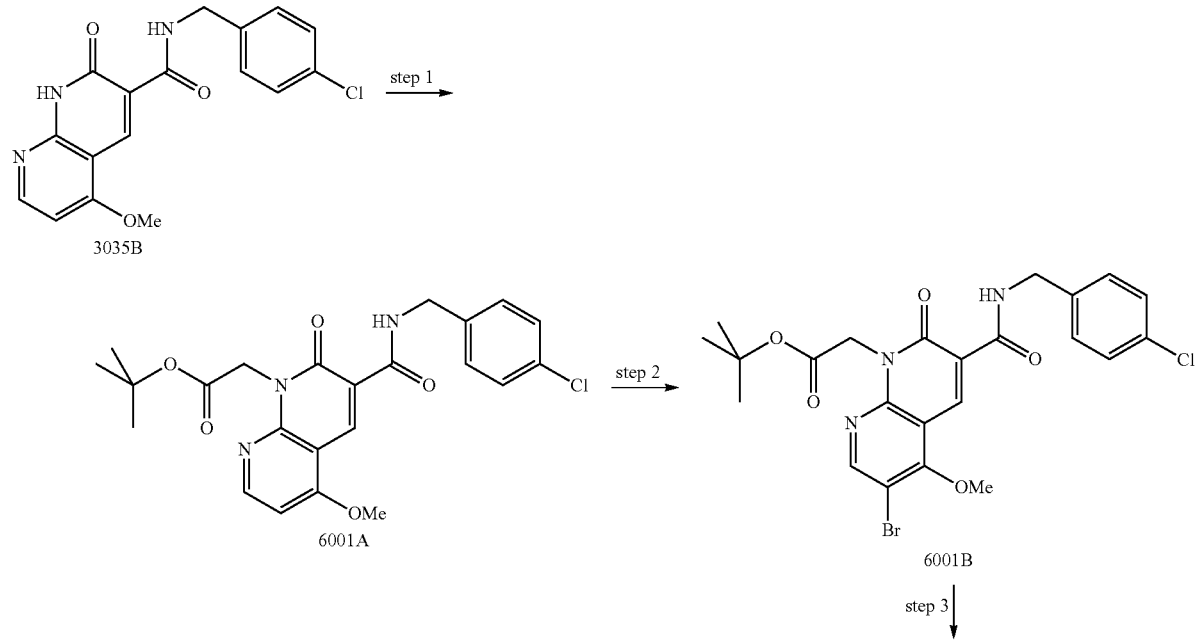

-continued

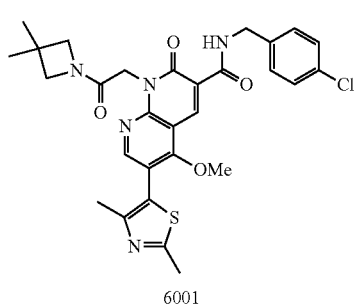
6001

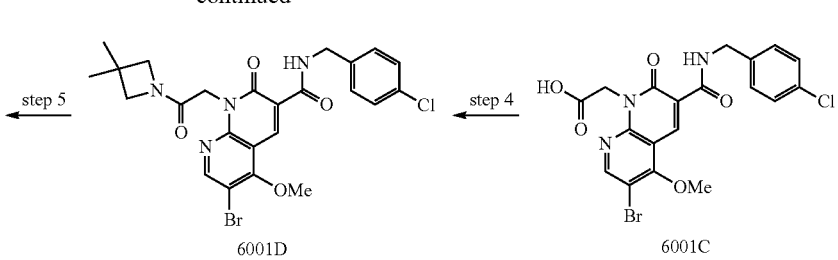

Step 1: Intermediate 3035B (10.0 g, 29.1 mmol) is charged in a round-bottom flask and suspended in DMF (10 mL). Potassium carbonate (14.1 g, 102 mmol, 3.50 eq) and tert-butyl bromoacetate (5.59 mL, 37.8 mmol, 1.30 eq) are added and the solution is stirred at RT for 18 h. The solution is diluted with EtOAc and washed with brine (3×). The organic layer is dried over MgSO$_4$, filtered and concentrated under reduced pressure. The crude mixture is purified by flash chromatography (EtOAc/hexanes) to provide intermediate 6001A.

Step 2: A 10% w/w bromine solution in DCM (20.7 mL, 40.3 mmol, 2.00 eq) is added to intermediate 6001A (9.23 g, 20.2 mmol) in DCM (200 mL). Sodium nitrate (6.85 g, 40.3 mmol, 2.00 eq) is added and the solution is stirred at RT for 4 h. The solution is diluted with EtOAc and washed with brine (3×). The organic layer is dried over MgSO$_4$, filtered and concentrated under reduced pressure to provide intermediate 6001B.

Step 3: TFA (15 mL) is added to a solution of intermediate 6001B (1.50 g, 2.79 mmol) dissolved in DCM (15 mL) and the reaction mixture is stirred at RT for 2 h. The solution is concentrated under reduced pressure to provide intermediate 6001C.

Step 4: Intermediate 6001C (1.05 g, 2.18 mmol) is dissolved in DMF (15 mL) in a round-bottom flask, then diisopropylethylamine (1.52 mL, 8.73 mmol, 4.00 eq) and 3,3-dimethyl-azetidine hydrochloride (prepared analogously to the procedure in J. Med. Chem. 2008, 51, 7380, herein incorporated by reference) (345 mg, 2.84 mmol, 1.30 eq) are added followed by HATU (1.16 g, 3.06 mmol, 1.40 eq). The reaction mixture is stirred at RT for 18 h. The solution is diluted with EtOAc and washed with brine (3×). The organic layer is dried over MgSO$_4$, filtered and concentrated under reduced pressure. The crude mixture is purified by flash chromatography (EtOAc/hexanes) to provide intermediate 6001D.

Step 5: Intermediate 6001D (51 mg, 0.093 mmol) is charged in a vial with 2,4-dimethyl-5-(4,4,5,5-tetramethyl-1,3,2-dioxaborolan-2-yl)-1,3-thiazole (CombiBlocks) (28 mg, 0.12 mmol, 1.3 eq) and potassium carbonate (39 mg, 0.28 mmol, 3.0 eq) then water (150 µL) and DMF (1.5 mL) are added. The solution is degassed by bubbling argon through the solution for 5 min, then tetrakis(triphenylphosphine) palladium(0) (16 mg, 0.014 mmol, 0.15 eq) is added. The reaction mixture is heated in a microwave oven at 110° C. for 15 min. The solution is filtered and purified by preparative HPLC to provide compound 6001 ($t_R$: 1.6, (M+H)$^+$: 580.1/582.0).

Synthesis of Compound 6002

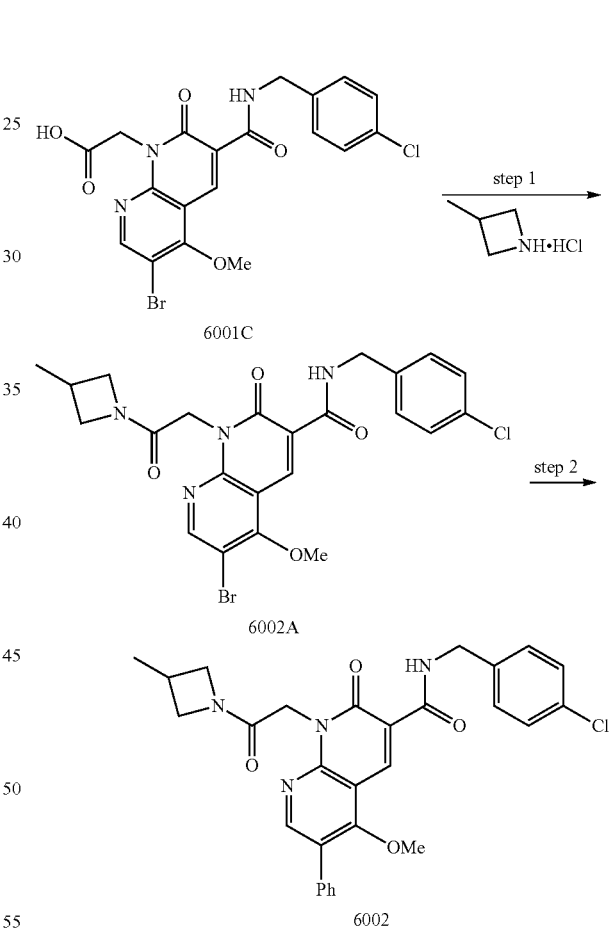

Step 1: Intermediate 6001C (2.00 g, 4.16 mmol) is dissolved in DMF (20 mL), then diisopropylethylamine (1.42 mL, 8.16 mmol, 1.96 eq) and 3-methyl-azetidine hydrochloride (prepared analogously to the procedure in J. Med. Chem. 2008, 51, 7380, herein incorporated by reference) (924 mg, 4.99 mmol, 1.20 eq) are added followed by HATU (2.06 g, 5.41 mmol, 1.30 eq). The reaction mixture is stirred at RT for 3 h. The solution is diluted with EtOAc and washed with brine (3×). The organic layer is dried over MgSO$_4$, filtered and concentrated under reduced pressure to provide intermediate 6002A.

Step 2: Intermediate 6002A (75 mg, 0.14 mmol) is charged in a vial with phenyl boronic acid (Aldrich) (21 mg, 0.18 mmol, 1.3 eq) and potassium carbonate (58 mg, 0.42 mmol, 3.0 eq) then water (150 µL) and DMF (1.5 mL) are added. The solution is degassed by bubbling argon through the solution for 5 min, then tetrakis(triphenylphosphine) palladium(0) (24 mg, 0.021 mmol, 0.15 eq) is added. The reaction mixture is heated in a microwave oven at 110° C. for 15 min. The solution is filtered and purified by preparative HPLC to provide compound 6002 ($t_R$: 1.7, (M+H)$^+$: 531.1/532.9).

Synthesis of Compound 6003

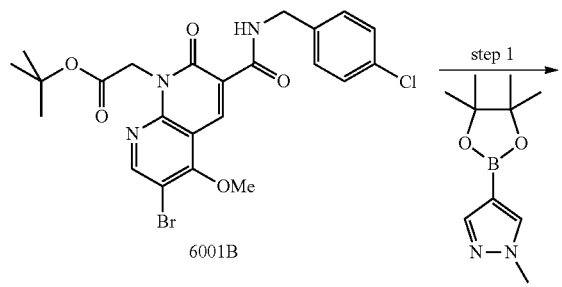
6001B

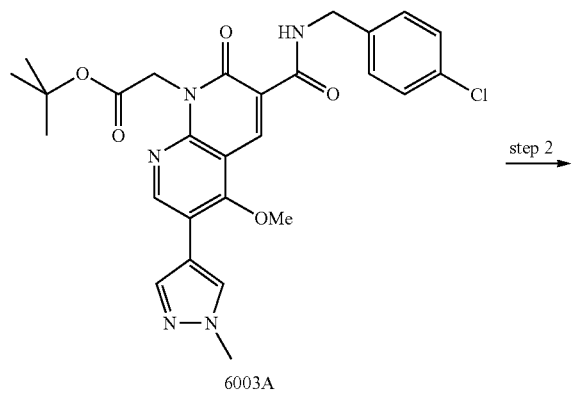
6003A

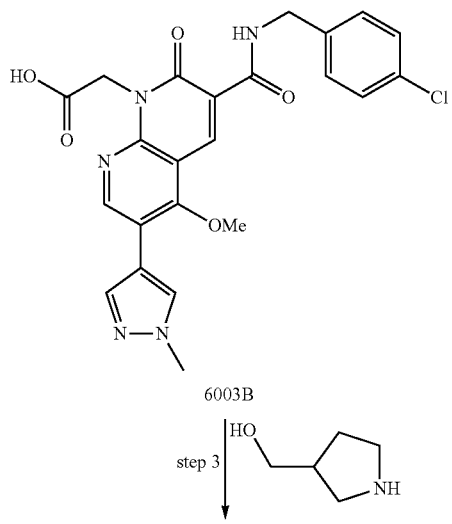
6003B

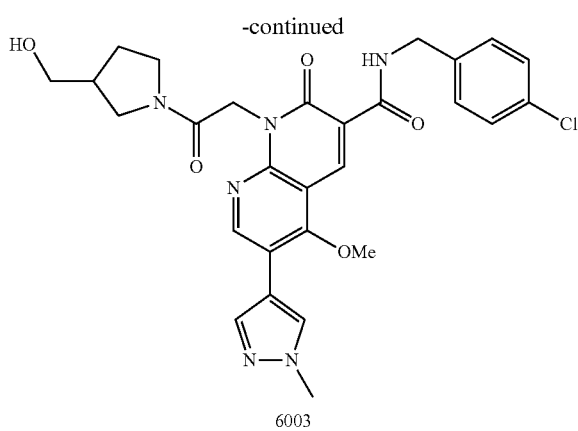
6003

Step 1: Intermediate 6001B (10.0 g, 18.6 mmol) is charged in a round-bottom flask with 1-methyl-4-(4,4,5,5-tetramethyl-1,3,2-dioxaborolan-yl-1H pyrazole (Frontier) (4.85 g, 23.3 mmol, 1.25 eq) and potassium carbonate (7.72 g, 55.9 mmol, 3.00 eq) then water (10 mL) and DMF (100 mL) are added. The solution is degassed by bubbling argon through solution for 5 min, then tetrakis(triphenylphosphine) palladium(0) (2.15 g, 1.86 mmol, 0.1 eq) is added. The reaction mixture is heated at 110° C. for 3 h. The cooled solution is diluted with EtOAc and washed with water (2×). The organic layer is dried over MgSO$_4$, filtered and concentrated under reduced pressure. The residue is purified by flash chromatography (MeOH/DCM) to afford intermediate 6003A.

Step 2: TFA (4.00 mL) is added to a solution of intermediate 6003A (380 mg, 0.706 mmol) dissolved in DCM (4.00 mL) and the reaction mixture is stirred at RT for 2 h. The solution is concentrated under reduced pressure to provide intermediate 6003B.

Step 3: Intermediate 6003B (40 mg, 0.083 mmol) is dissolved in DMF (1.5 mL), then diisopropylethylamine (58 µL, 0.33 mmol, 4.0 eq) and pyrrolidin-3-yl methanol (ChemBridge BB) (11 mg, 0.11 mmol, 1.3 eq) are added followed by HATU (44 mg, 0.12 mmol, 1.4 eq). The reaction mixture is stirred at RT for 18 h. The solution is filtered and purified by preparative HPLC to provide compound 6003 ($t_R$: 1.2, (M+H)$^+$: 565.1/567.1).

Synthesis of Compound 6004

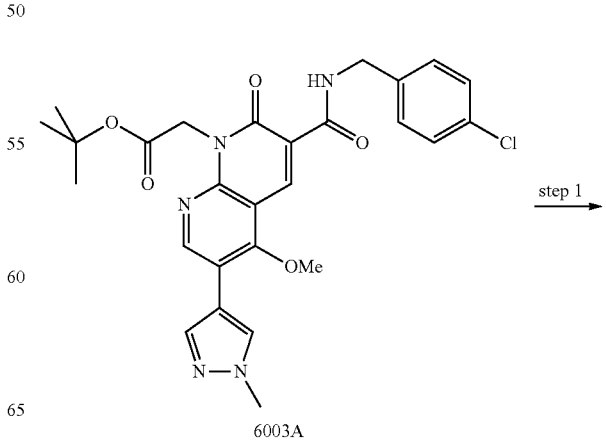
6003A

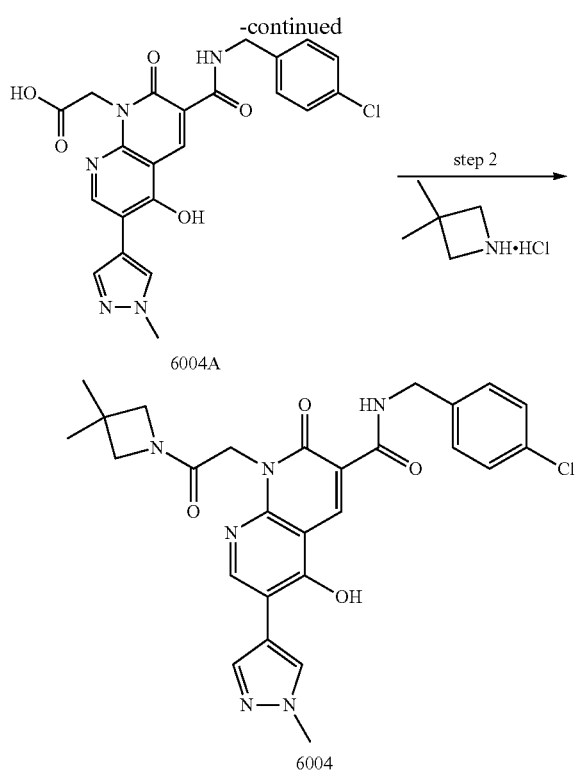

6004A

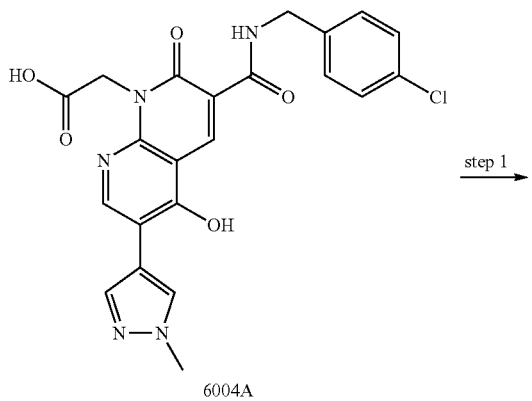

6004

Step 1: A 33% w/w solution of hydrobromic acid in AcOH (60.0 mL) is added to intermediate 6003A (4.00 g, 7.44 mmol) in a round-bottom flask and the reaction mixture is heated at 85° C. for 2 h. The reaction mixture is poured into cold water and the resulting precipitate is filtered and dried under vacuum to provide intermediate 6004A.

Step 2: Intermediate 6004A (120 mg, 0.256 mmol) is dissolved in DMF (3.0 mL), then diisopropylethylamine (156 μL, 0.897 mmol, 3.50 eq) and 3,3-dimethyl-azetidine hydrochloride (prepared analogously to the procedure in J. Med. Chem. 2008, 51, 7380, herein incorporated by reference) (40.6 mg, 0.333 mmol, 1.30 eq) are added followed by HATU (136 mg, 0.359 mmol, 1.40 eq) and the reaction mixture is stirred at RT for 1 h. The solution is filtered and purified by preparative HPLC to provide compound 6004 ($t_R$: 1.72, $(M+H)^+$: 535.2/537.2).

Synthesis of Compound 6005

-continued

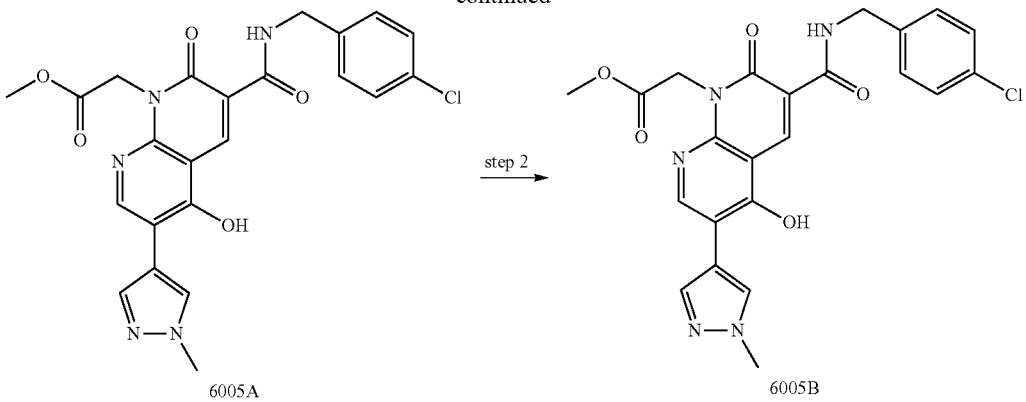

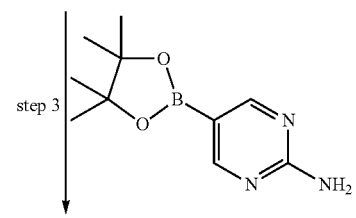

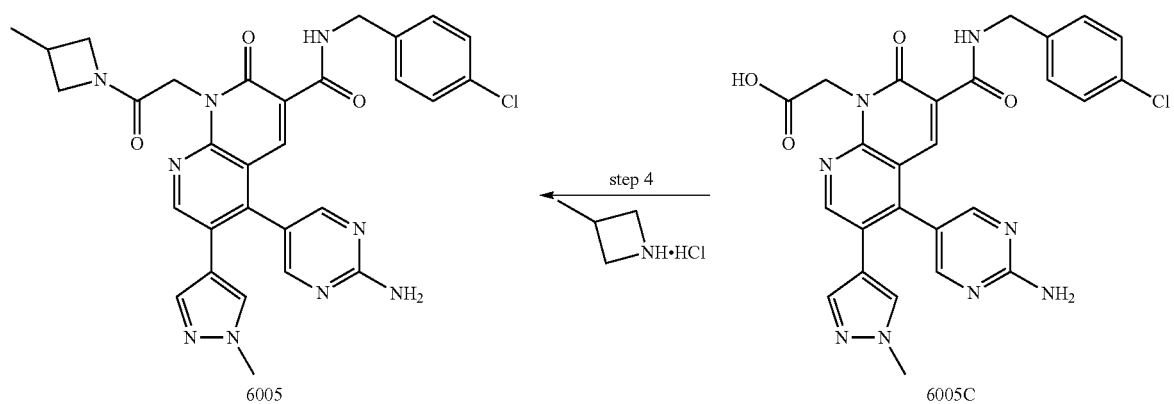

Step 1: Intermediate 6004A (1.71 g, 3.65 mmol) is charged in a round-bottom flask and dissolved in MeOH (100 mL). Concentrated HCl (1.00 mL) is added and the solution is heated at reflux for 18 h. The resulting solid is filtered, washed with MeOH and dried under vacuum to provide intermediate 6005A.

Step 2: Intermediate 6005A (1.60 g, 3.32 mmol) is charged in a round-bottom flask and phosphorus oxychloride (30.0 mL, 322 mmol, 97.0 eq) is added. The solution is stirred at RT for 24 h, and then concentrated under reduced pressure, diluted with EtOAc and washed with brine (3×). The organic layer is dried over MgSO$_4$, filtered and concentrated under reduced pressure. The residue is triturated with Et$_2$O to provide intermediate 6005B.

Step 3: Intermediate 6005B (300 mg, 0.600 mmol) is charged in a round-bottom flask with 2-aminopyrimidine-5-boronic acid, pinacol ester (Frontier) (199 mg, 0.900 mmol, 1.50 eq) and potassium carbonate (249 mg, 1.80 mmol, 3.00 eq) then water (400 µL) and DMF (4 mL) are added. The solution is degassed by bubbling argon through the solution for 5 min, then tetrakis(triphenylphosphine) palladium(0) (48.5 mg, 0.0420 mmol, 0.0700 eq) is added. The reaction mixture is heated in a microwave oven at 100° C. for 7 h. The cooled solution is diluted with EtOAc and washed with water (2×). The organic layer is dried over MgSO$_4$, and the solution is filtered and concentrated under reduced pressure. The crude mixture is dissolved in MeOH (2 mL) and THF (4 mL), then a 1.0 M aqueous solution of NaOH (2.00 mL, 2.00 mmol, 3.33 eq) is added. The solution is stirred at RT for 16 h. The reaction mixture is concentrated under reduced pressure, diluted with water and washed with Et$_2$O. The aqueous layer is neutralized to approximately pH=7 with a 1.0 M aqueous solution of HCl. The resulting precipitate is filtered and dried under vacuum to afford intermediate 6005C.

Step 4: Intermediate 6005C (60 mg, 0.11 mmol) is dissolved in DMF (2.0 mL), then diisopropylethylamine (67 µL, 0.39 mmol, 3.5 eq) and 3-methyl-azetidine hydrochloride (prepared analogously to the procedure in J. Med. Chem. 2008, 51, 7380, herein incorporated by reference) (18 mg, 0.17 mmol, 1.5 eq) are added followed by HATU (59 mg, 0.15 mmol, 1.4 eq). The reaction mixture is stirred at RT for 30 min, and then filtered and purified by preparative HPLC to provide compound 6005 ($t_R$: 1.73, (M+H)$^+$: 598.2, 600.2).

Synthesis of Compound 6006

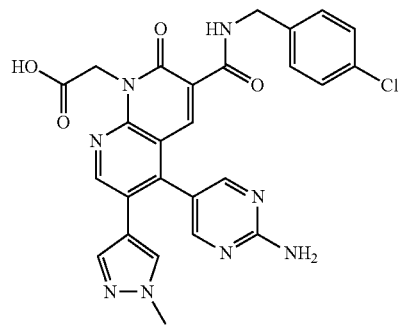

6005C

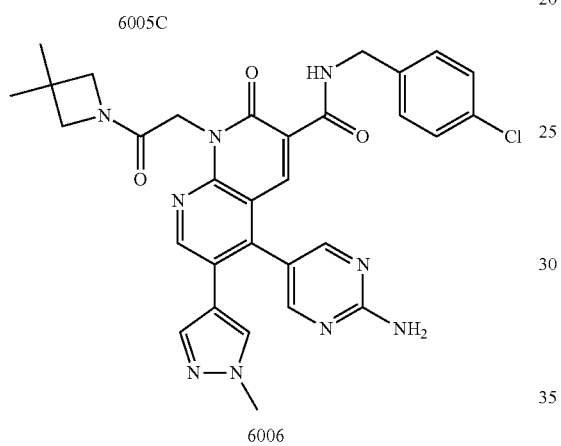

6006

Intermediate 6005C (60 mg, 0.11 mmol) is dissolved in DMF (2.0 mL), then diisopropylethylamine (67 µL, 0.39 mmol, 3.5 eq) and 3,3-dimethyl-azetidine hydrochloride (J. Med. Chem. 2008, 51, 7380) (20 mg, 0.17 mmol, 1.5 eq) are added followed by HATU (59 mg, 0.15 mmol, 1.4 eq). The reaction mixture is stirred at RT for 30 min, and then filtered and purified by preparative HPLC to provide compound 6006 ($t_R$: 1.81, (M+H)$^+$: 612.2/614.2).

Synthesis of Compound 6007

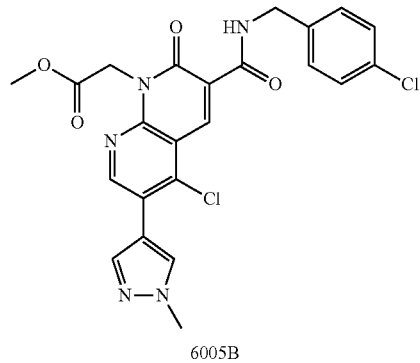

6005B

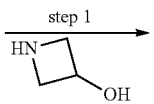

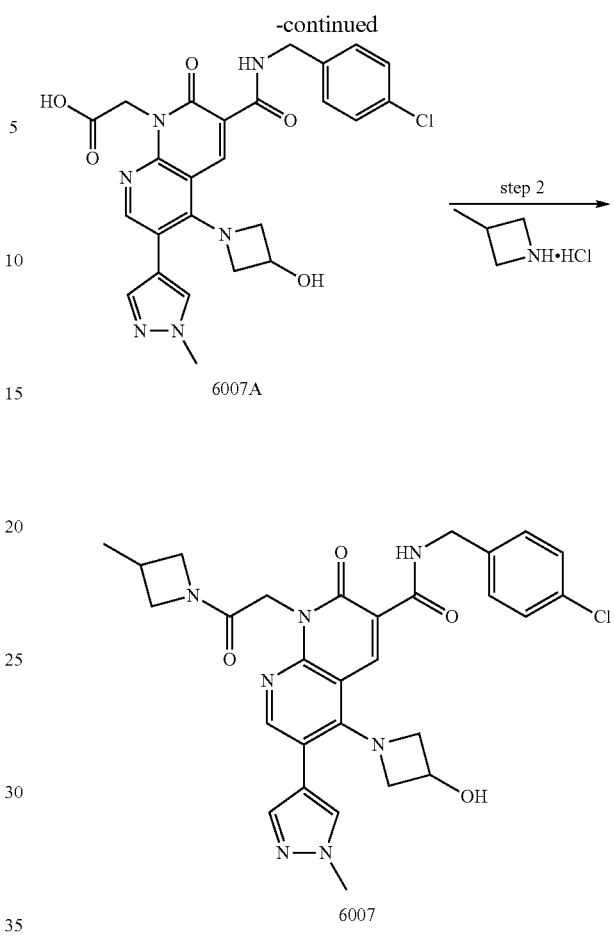

6007A

6007

Step 1: Intermediate 6005B (300 mg, 0.600 mmol) is charged in a vial and suspended in DMF (4 mL). Diisopropylethylamine (313 µL, 1.80 mmol, 3.00 eq) and 3-azetidinol (Chembrdg-bb) (98.5 mg, 0.900 mmol, 1.50 eq) are added and the solution is warmed to 70° C. for 18 h. The cooled solution is diluted with EtOAc and washed with water (2×). The organic layer is dried over MgSO$_4$, and the solution is filtered and concentrated under reduced pressure. The crude mixture is dissolved in MeOH (2 mL) and THF (4 mL), then a 1.0 M aqueous solution of NaOH (2.00 mL, 2.00 mmol, 3.33 eq) is added and solution is stirred at RT for 16 h. The reaction mixture is concentrated under reduced pressure, diluted with water and washed with Et$_2$O. The aqueous layer is neutralized to approximately pH=7 with a 1.0 M aqueous solution of HCl. The resulting precipitate is filtered and dried under vacuum to afford intermediate 6007A.

Step 2: Intermediate 6007A (56 mg, 0.11 mmol) is dissolved in DMF (2.0 mL), then diisopropylethylamine (65 µL, 0.38 mmol, 3.5 eq) and 3-methyl-azetidine hydrochloride (prepared analogously to the procedure in J. Med. Chem. 2008, 51, 7380, herein incorporated by reference) (18 mg, 0.16 mmol, 1.5 eq) are added followed by HATU (57 mg, 0.15 mmol, 1.5 eq). The reaction mixture is stirred at RT for 30

Synthesis of Compound 6008

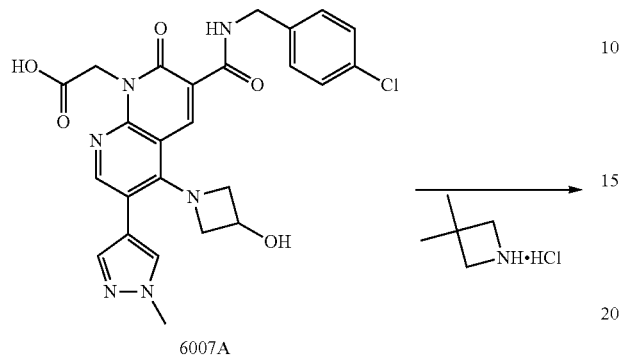

6007A

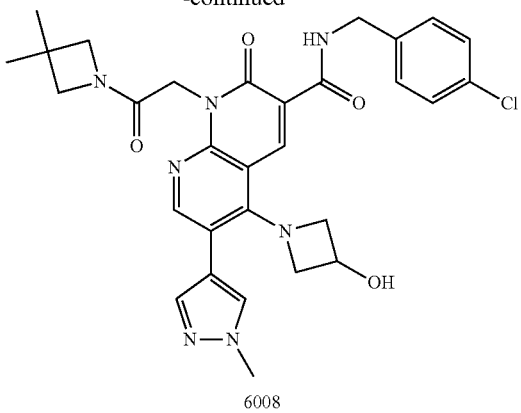

6008

Intermediate 6007A (56 mg, 0.11 mmol) is dissolved in DMF (2.0 mL), then diisopropylethylamine (65 μL, 0.38 mmol, 3.5 eq) and 3,3-dimethyl-azetidine hydrochloride (J. Med. Chem. 2008, 51, 7380) (20 mg, 0.16 mmol, 1.5 eq) are added followed by HATU (57 mg, 0.15 mmol, 1.5 eq) and the reaction mixture is stirred at RT for 30 min. The solution is filtered and purified by preparative HPLC to provide compound 6008 ($t_R$: 1.89, (M+H)$^+$: 590.1/592.1).

Synthesis of Compound 6009

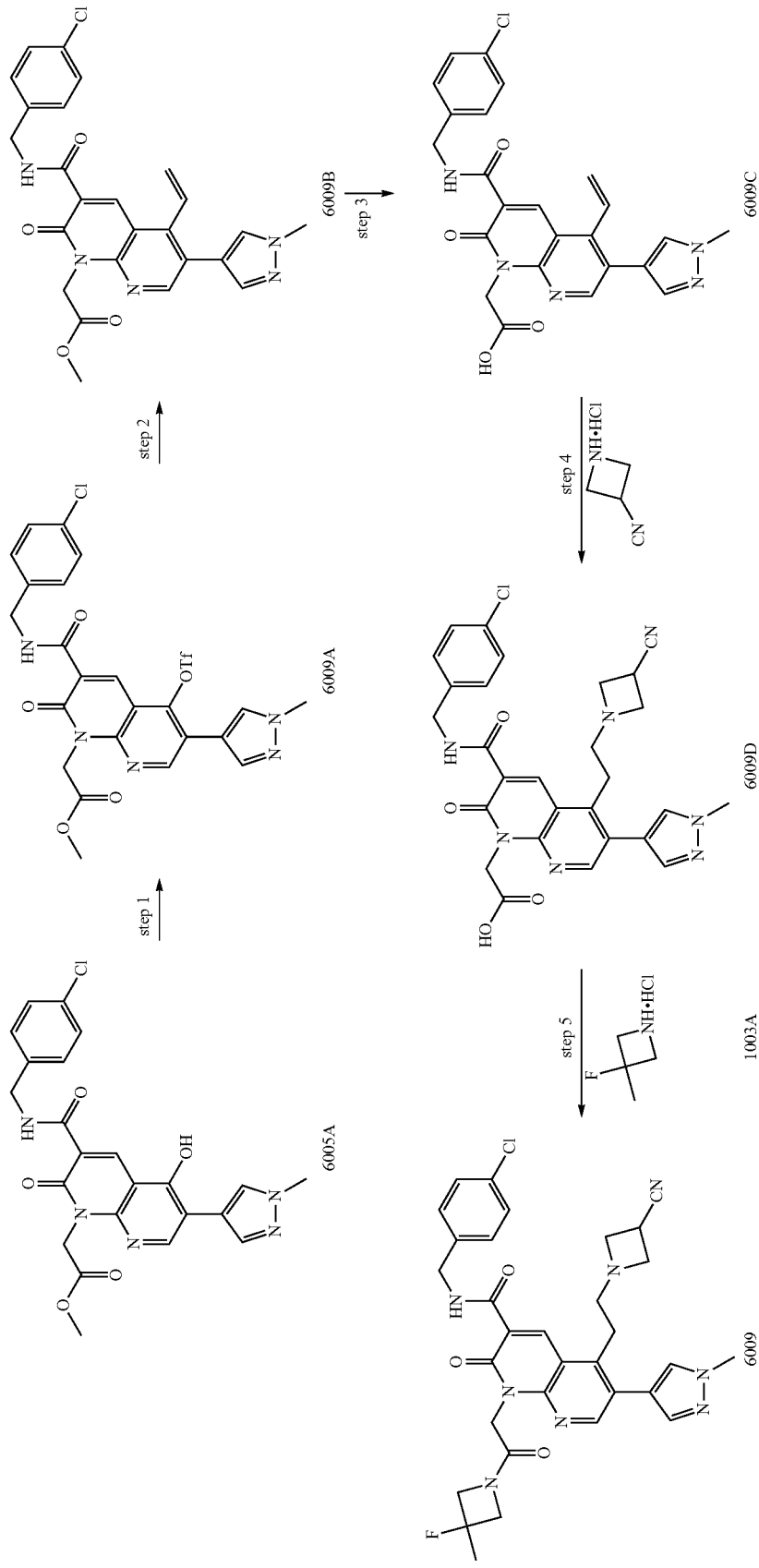

Step 1: Intermediate 6005A (1.20 g, 2.49 mmol) is dissolved in MeCN (80 mL) in a round-bottom flask, then potassium carbonate (688 mg, 4.98 mmol, 2.00 eq) and N-phenyl trifluoromethanesulfonimide (1.33 g, 3.74 mmol, 1.50 eq) are added. The reaction mixture is stirred at RT for 18 h. Following completion of the reaction, the solution is concentrated under reduced pressure and purified by flash chromatography (EtOAc/hexanes) to afford intermediate 6009A.

Step 2: Intermediate 6009A (1.40 g, 2.28 mmol) is charged in a round-bottom flask with 2,4,6-trivinylcyclotriboroxane pyridine complex (Aldrich) (823 mg, 3.42 mmol, 1.50 eq) and potassium carbonate (346 mg, 2.51 mmol, 1.10 eq) then water (4.2 mL) and 1,2-dimethoxyethane (28 mL) are added. The reaction is degassed by bubbling argon through the solution for 5 min, then tetrakis(triphenylphosphine) palladium(0) (263 mg, 0.228 mmol, 0.100 eq) is added. The reaction mixture is heated at 90° C. for 2.5 h. The cooled solution is diluted with DCM and washed with water (2×). The organic layer is dried over $MgSO_4$, filtered and concentrated under reduced pressure. The residue is purified by flash chromatography (MeOH/DCM) to afford intermediate 6009B.

Step 3: Intermediate 6009B (962 mg, 1.96 mmol) is dissolved in MeOH (5 mL) and THF (10 mL), then a 1.0 M aqueous solution of NaOH (3.92 mL, 3.92 mmol, 2.00 eq) is added. The solution is stirred at RT for 16 h. The reaction mixture is concentrated under reduced pressure, diluted with water and washed with $Et_2O$. The aqueous layer is neutralized to approximately pH=7 with a 1.0 M aqueous solution of HCl. The resulting precipitate is filtered and dried under vacuum to afford intermediate 6009C.

Step 4: Intermediate 6009C (50 mg, 0.11 mmol) is charged in a round-bottom flask and suspended in EtOH (1.0 mL). Diisopropylethylamine (48 mg, 0.26 mmol, 2.5 eq) and azetidine-3-carbonitrile hydrochloride (Fluorochem) (19 mg, 0.16 mmol, 1.5 eq) are added and the solution is heated at 100° C. for 18 h. The solution is diluted with EtOAc and washed with brine (3×). The organic layer is dried over $MgSO_4$, filtered and concentrated under reduced pressure. The crude mixture is purified by flash chromatography (EtOAc/hexanes) to provide intermediate 6009D.

Step 5: Intermediate 6009D (40 mg, 0.071 mmol) is dissolved in DMF (1.0 mL), then diisopropylethylamine (33 μL, 0.18 mmol, 2.5 eq) and intermediate 1003A (13 mg, 0.11 mmol, 1.5 eq) are added followed by HATU (41 mg, 0.11 mmol, 1.5 eq). The reaction mixture is stirred at RT for 18 h, filtered and purified by preparative HPLC to provide compound 6009 ($t_R$: 1.77, $(M+H)^+$: 631.2).

Synthesis of Compound 6010

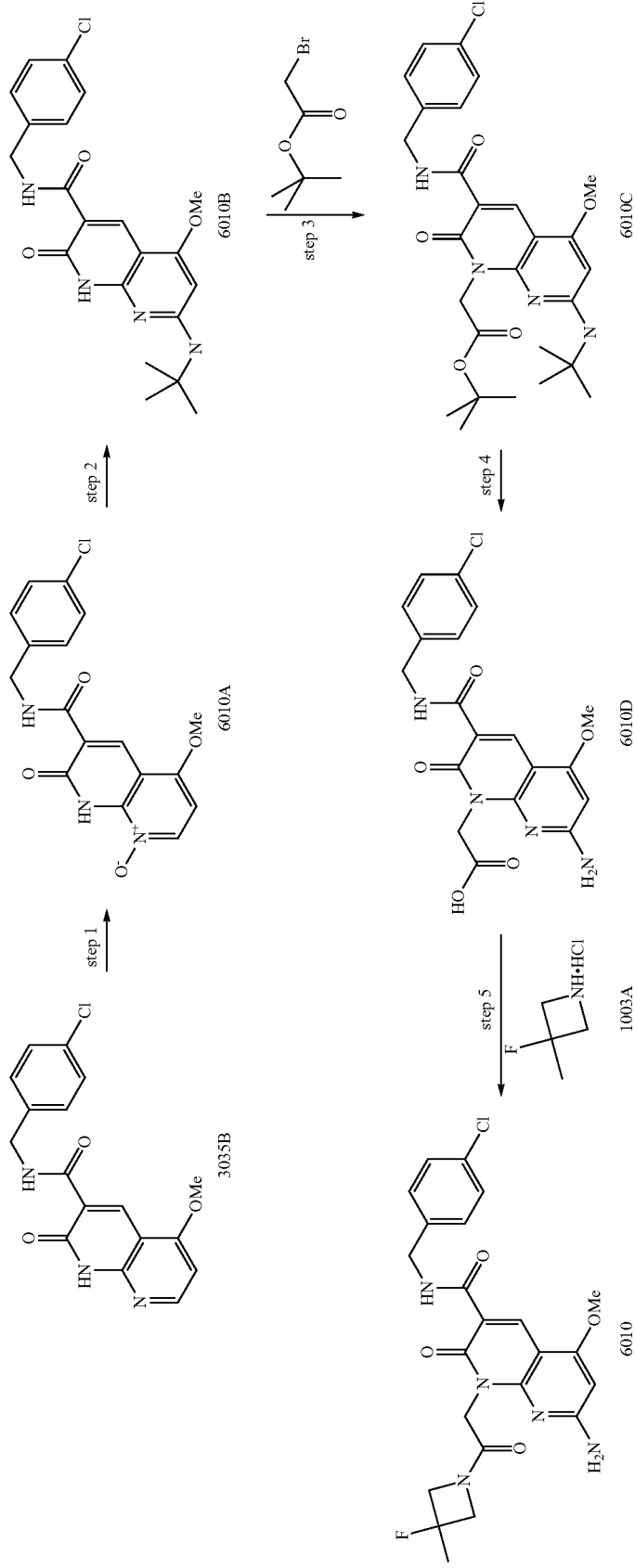

Step 1: A solution of m-CPBA (110 mg, 0.495 mmol, 1.70 eq) in AcOH (1.0 mL) is added to intermediate 3035B (100 mg, 0.291 mmol) in AcOH (1.0 mL) and the solution is stirred at 55° C. for 18 h. Water is added and the resulting solid is filtered. The filtrate is concentrated under reduced pressure. The crude residue is dissolved in DCM and washed with a saturated aqueous solution of sodium bicarbonate. The organic layer is dried over MgSO$_4$, filtered and concentrated under reduced pressure to provide intermediate 6010A.

Step 2: Intermediate 6010A (755 mg, 2.10 mmol) is charged in a round-bottom flask with tert-butylamine (Aldrich) (1.10 mL, 10.5 mmol, 5.00 eq) and dissolved in trifluorotoluene (23 mL). The solution is cooled in an ice bath (0° C.) and p-toluenesulfonic anhydride (1.37 g, 4.20 mmol, 2.00 eq) is added over a 5 min period. The ice bath is removed after the addition and the solution is stirred at RT for 30 min. The crude mixture is dissolved in DCM and washed with a saturated aqueous solution of sodium bicarbonate. The organic layer is dried over MgSO$_4$, filtered and concentrated under reduced pressure. The crude mixture is purified by flash chromatography (EtOAc/hexanes) to provide intermediate 6010B.

Step 3: Intermediate 6010B (50 mg, 0.12 mmol) is charged in a vial and suspended in DMF (2 mL). Potassium carbonate (50 mg, 0.36 mmol, 3.00 eq) and tert-butyl bromoacetate (31 mg, 0.16 mmol, 1.3 eq) are added and the solution is stirred at RT for 18 h. The solution is diluted with EtOAc and washed with brine (3×). The organic layer is dried over MgSO$_4$, filtered and concentrated under reduced pressure. The crude mixture is purified by flash chromatography (EtOAc/hexanes) to provide intermediate 6010C.

Step 4: Intermediate 6010C (365 mg, 0.690 mmol) is dissolved in TFA (5.0 mL) and the reaction mixture is warmed to 70° C. for 20 h. The solution is concentrated under reduced pressure to provide intermediate 6010D.

Step 5: Intermediate 6010D (62 mg, 0.15 mmol) is dissolved in DMF (2.0 mL), then diisopropylethylamine (130 μL, 0.74 mmol, 5.0 eq) and intermediate 1003A (37 mg, 0.30 mmol, 2.0 eq) are added followed by HATU (70 mg, 0.17 mmol, 1.20 eq). The reaction mixture is stirred at RT for 40 min, filtered and purified by preparative HPLC to provide compound 6010 ($t_R$: 1.78, (M+H)$^+$: 488.2/490.1).

Synthesis of Compound 6011

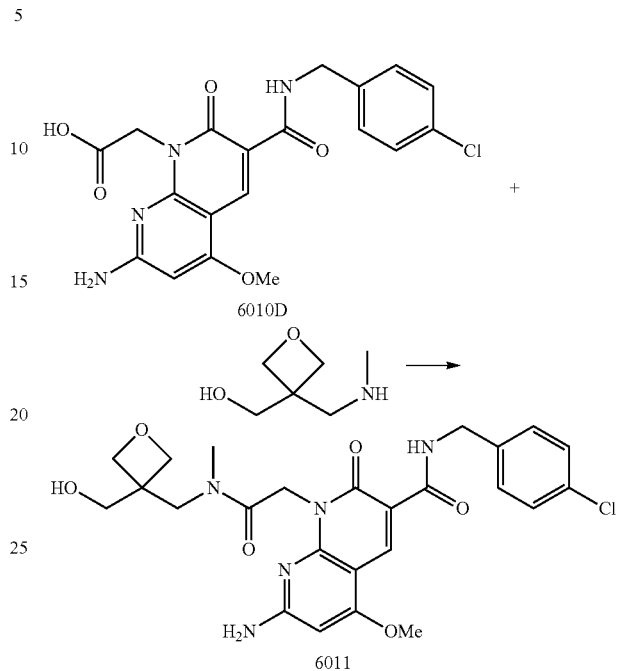

Intermediate 6010D (62 mg, 0.15 mmol) is dissolved in DMF (2.0 mL), then diisopropylethylamine (130 μL, 0.74 mmol, 5.0 eq) and intermediate 1010A (39 mg, 0.30 mmol, 2.0 eq) are added followed by HATU (70 mg, 0.17 mmol, 1.20 eq). The reaction mixture is stirred at RT for 40 min, filtered and purified by preparative HPLC to provide compound 6011 ($t_R$: 1.65, (M+H)$^+$: 530.3/532.2).

Synthesis of 6012

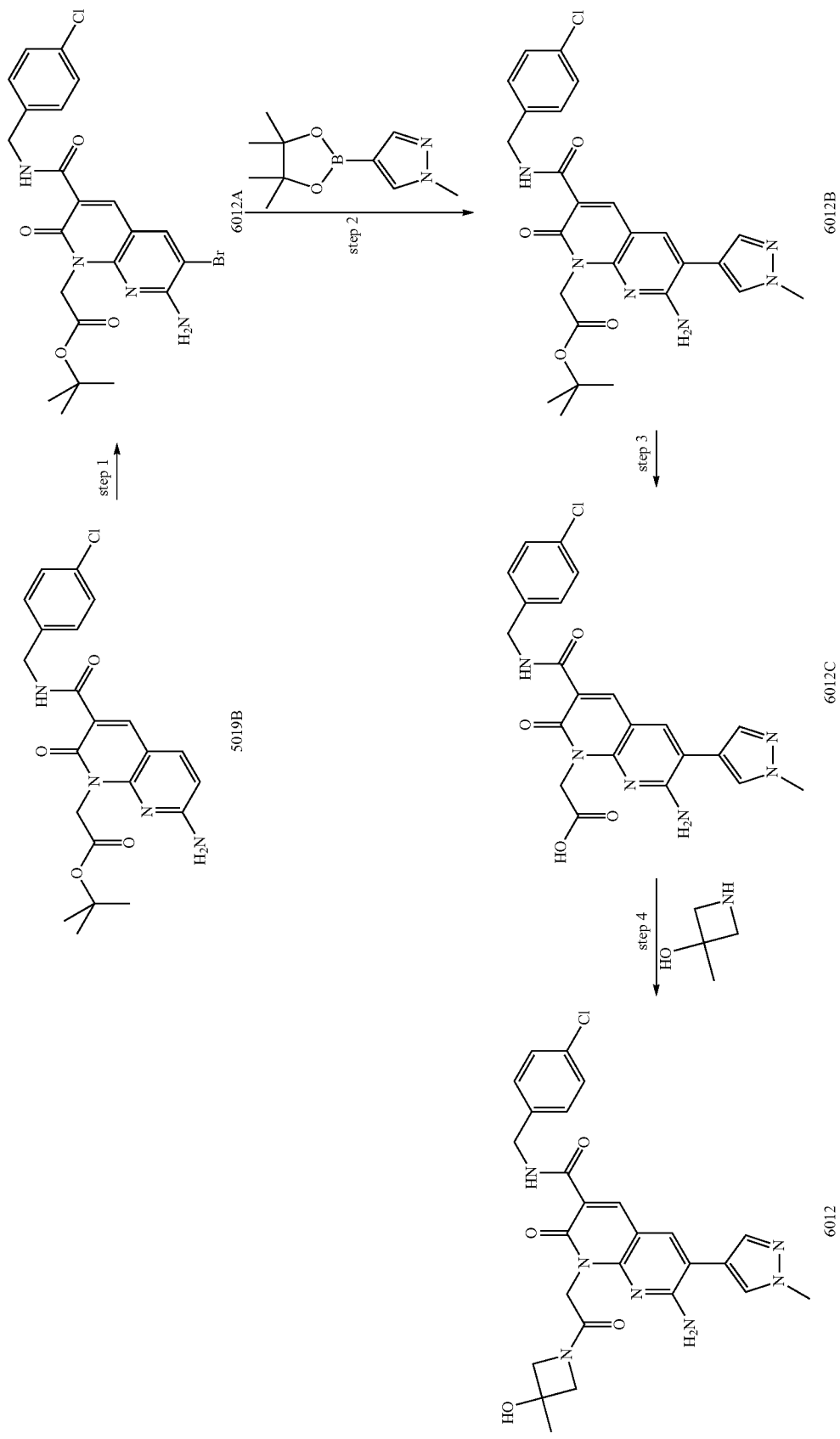

Step 1: A solution of bromine (140 µL, 2.71 mmol, 1.20 eq) in DCM (14 mL) is added to intermediate 5019B (1.00 g, 2.26 mmol) in DCM (14 mL) and the solution is stirred at RT for 18 h. The solution is diluted with DCM and washed with brine (3×). The organic layer is dried over MgSO$_4$, filtered and concentrated under reduced pressure to provide intermediate 6012A.

Step 2: Intermediate 6012A (275 mg, 0.527 mmol) is charged in a microwave vial with 1-methyl-4-(4,4,5,5-tetramethyl-1,3,2-dioxaborolan-yl-1H pyrazole (Frontier) (143 mg, 0.685 mmol, 1.30 eq) and potassium carbonate (220 mg, 1.58 mmol, 3.00 eq) then water (0.80 mL) and DMF (5.0 mL) are added. The solution is degassed by bubbling argon through the solution for 5 min, then tetrakis(triphenylphosphine) palladium(0) (83.0 mg, 0.0790 mmol, 0.150 eq) is added. The reaction mixture is heated in a microwave oven at 125° C. for 20 min. The cooled solution is diluted with EtOAc and washed with water (2×). The organic layer is dried over MgSO$_4$, filtered and concentrated under reduced pressure. The residue is purified by flash chromatography (MeOH/DCM) to afford intermediate 6012B.

Step 3: TFA (3.0 mL) is added to a solution of intermediate 6012B (307 mg, 0.588 mmol) dissolved in DCM (3.0 mL) and the reaction mixture is stirred at RT for 2 h. The solution is concentrated under reduced pressure to provide intermediate 6012C.

Step 4: Intermediate 6012C (50 mg, 0.086 mmol) is dissolved in DMF (0.5 mL), then diisopropylethylamine (60 µL, 0.35 mmol, 4.0 eq) and 3-methyl-azetidin-3-ol (Parkway) (14 mg, 0.11 mmol, 1.3 eq) are added followed by TBTU (33 mg, 0.10 mmol, 1.2 eq). The reaction mixture is stirred at RT for 18 h, filtered and purified by preparative HPLC to provide compound 6012 ($t_R$: 4.84, (M+H)$^+$: 536.1).

Synthesis of 6013

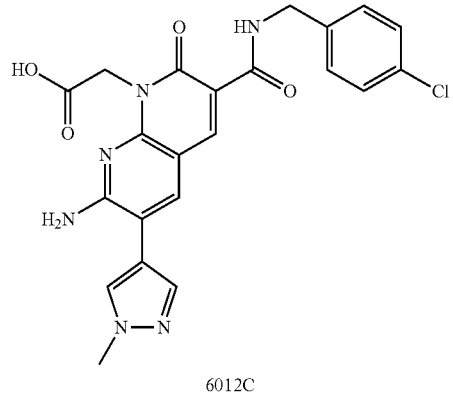

6012C

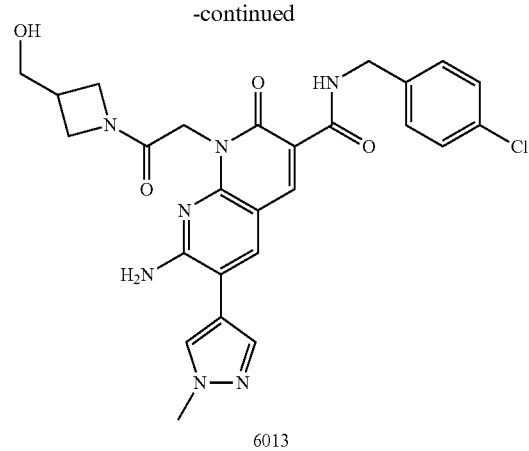

6013

Intermediate 6012C (50 mg, 0.086 mmol) is dissolved in DMF (0.5 mL), then diisopropylethylamine (60 µL, 0.35 mmol, 4.0 eq) and azetidin-3-yl methanol hydrochloride (Parkway) (14 mg, 0.11 mmol, 1.3 eq) are added followed by TBTU (33 mg, 0.10 mmol, 1.2 eq). The reaction mixture is stirred at RT for 18 h, filtered and purified by preparative HPLC to provide compound 6013 ($t_R$: 4.73, (M+H)$^+$: 536.1).

Synthesis of 6014

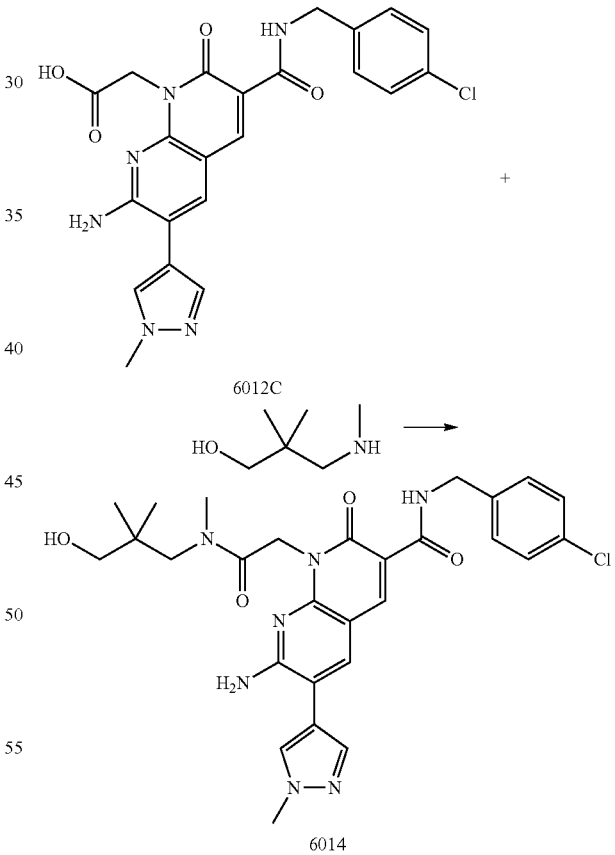

6014

Intermediate 6012C (50 mg, 0.086 mmol) is dissolved in DMF (0.5 mL), then diisopropylethylamine (60 µL, 0.35 mmol, 4.0 eq) and 2,2-dimethyl-3-(methylamino)propan-1-ol (Chembridge-BB) (10 mg, 0.11 mmol, 1.3 eq) are added followed by TBTU (33 mg, 0.10 mmol, 1.2 eq). The reaction mixture is stirred at RT for 18 h, filtered and purified by preparative HPLC to provide compound 6014 ($t_R$: 5.49, (M+H)$^+$: 566.2).

Synthesis of 6015

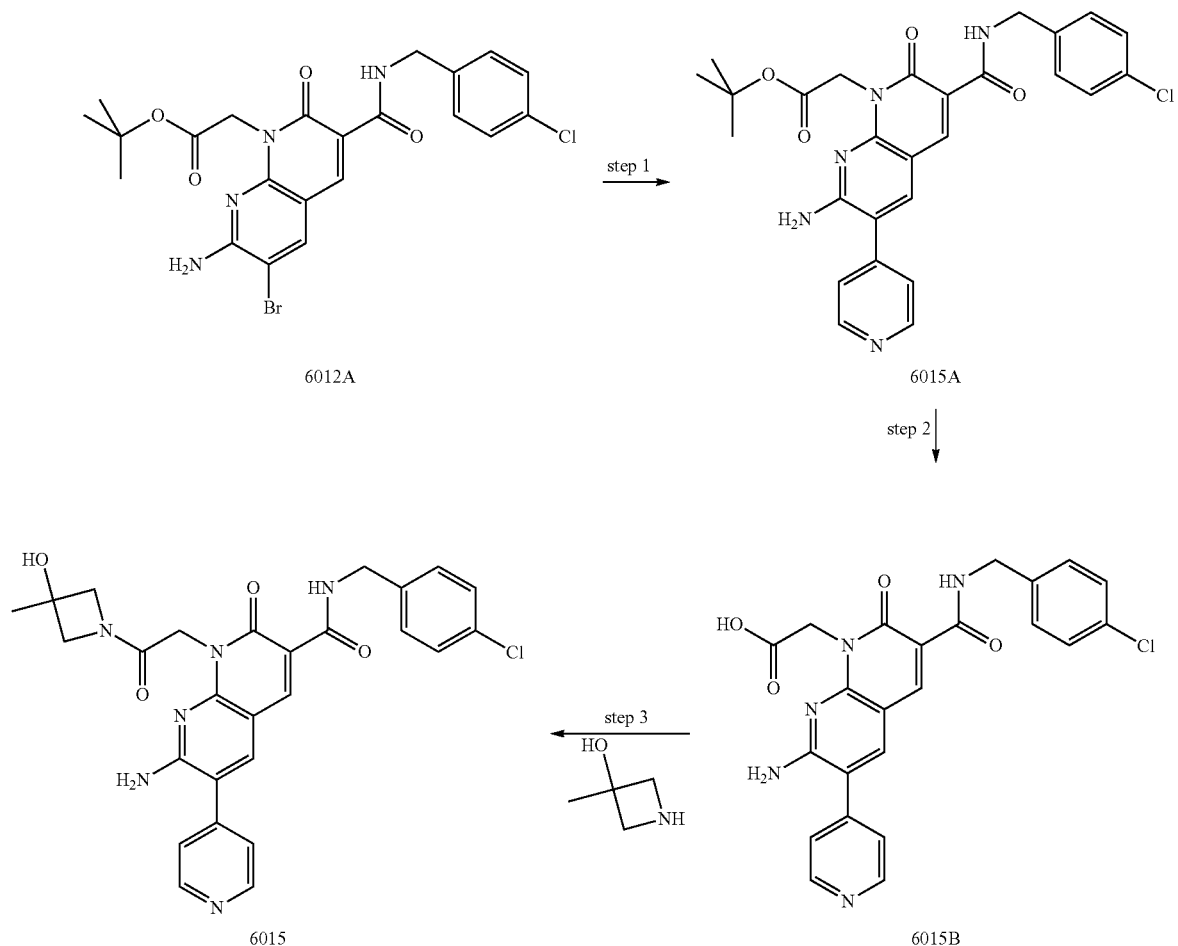

Step 1: Intermediate 6012A (240 mg, 0.460 mmol) is charged in a microwave vial with pyridine 4-boronic acid (Aaronchem) (73.5 mg, 0.598 mmol, 1.30 eq) and potassium carbonate (190 mg, 1.38 mmol, 3.00 eq) then water (0.20 mL) and DMF (2.0 mL) are added. The reaction is degassed by bubbling argon through the solution for 5 min, then bis[(tri-tert-butyl)phosphine]palladium(0) (35.2 mg, 0.0690 mmol, 0.150 eq) is added. The reaction mixture is heated in a microwave oven at 125° C. for 10 min. The cooled solution is diluted with EtOAc and washed with water (2×). The organic layer is dried over MgSO$_4$, filtered and concentrated under reduced pressure. The residue is purified by flash chromatography (MeOH/DCM) to afford intermediate 6015A.

Step 2: TFA (3.0 mL) is added to a solution of intermediate 6015A (239 mg, 0.460 mmol) dissolved in DCM (3.0 mL) and the reaction mixture is stirred at RT for 18 h. The solution is concentrated under reduced pressure to provide intermediate 6015B.

Step 3: Intermediate 6015B (53 mg, 0.092 mmol) is dissolved in DMF (0.5 mL), then diisopropylethylamine (60 µL, 0.37 mmol, 4.0 eq) and 3-methyl-azetidin-3-ol (Parkway) (15 mg, 0.12 mmol, 1.3 eq) are added followed by TBTU (35 mg, 0.11 mmol, 1.2 eq). The reaction mixture is stirred at RT for 18 h, filtered and purified by preparative HPLC to provide compound 6015 ($t_R$: 3.98, (M+H)$^+$: 533.1).

Synthesis of 6016

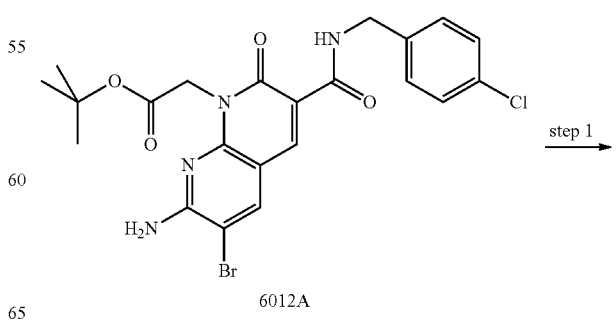

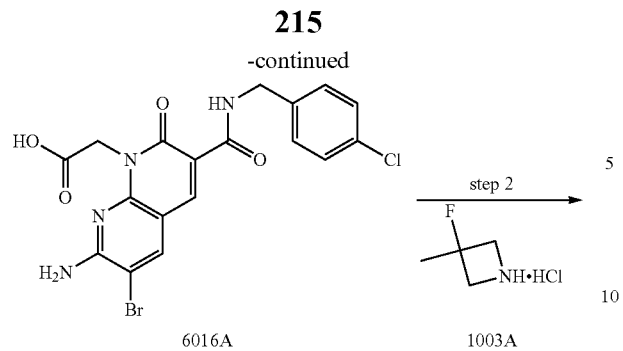

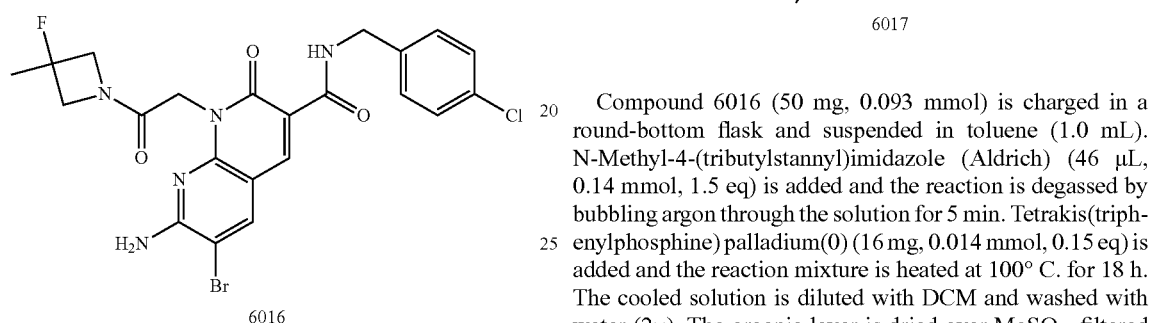

Step 1: TFA (3.0 mL) is added to a solution of intermediate 6012A (113 mg, 0.217 mmol) dissolved in DCM (3.0 mL) and the reaction mixture is stirred at RT for 3 h. The solution is concentrated under reduced pressure to provide intermediate 6016A.

Step 2: Intermediate 6016A (63 mg, 0.11 mmol) is dissolved in DMF (1.0 mL), then diisopropylethylamine (80 μL, 0.43 mmol, 4.0 eq) and intermediate 1003A (17 mg, 0.14 mmol, 1.3 eq) are added followed by TBTU (42 mg, 0.13 mmol, 1.2 eq). The reaction mixture is stirred at RT for 18 h, filtered and purified by preparative HPLC to provide compound 6016 ($t_R$: 5.79, (M+H)$^+$: 536.0/538.0)

Synthesis of 6017

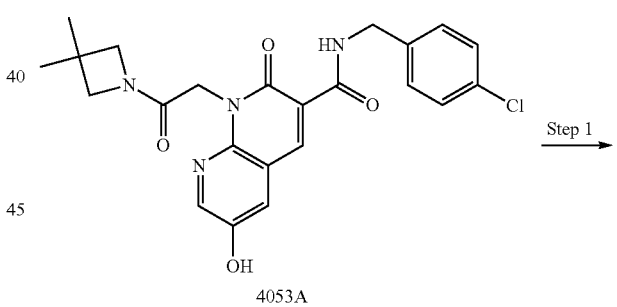

Compound 6016 (50 mg, 0.093 mmol) is charged in a round-bottom flask and suspended in toluene (1.0 mL). N-Methyl-4-(tributylstannyl)imidazole (Aldrich) (46 μL, 0.14 mmol, 1.5 eq) is added and the reaction is degassed by bubbling argon through the solution for 5 min. Tetrakis(triphenylphosphine)palladium(0) (16 mg, 0.014 mmol, 0.15 eq) is added and the reaction mixture is heated at 100° C. for 18 h. The cooled solution is diluted with DCM and washed with water (2×). The organic layer is dried over MgSO$_4$, filtered and concentrated under reduced pressure. The residue is purified by preparative HPLC to provide compound 6017 ($t_R$: 4.47, (M+H)$^+$: 538.3).

Synthesis of Compound 6018

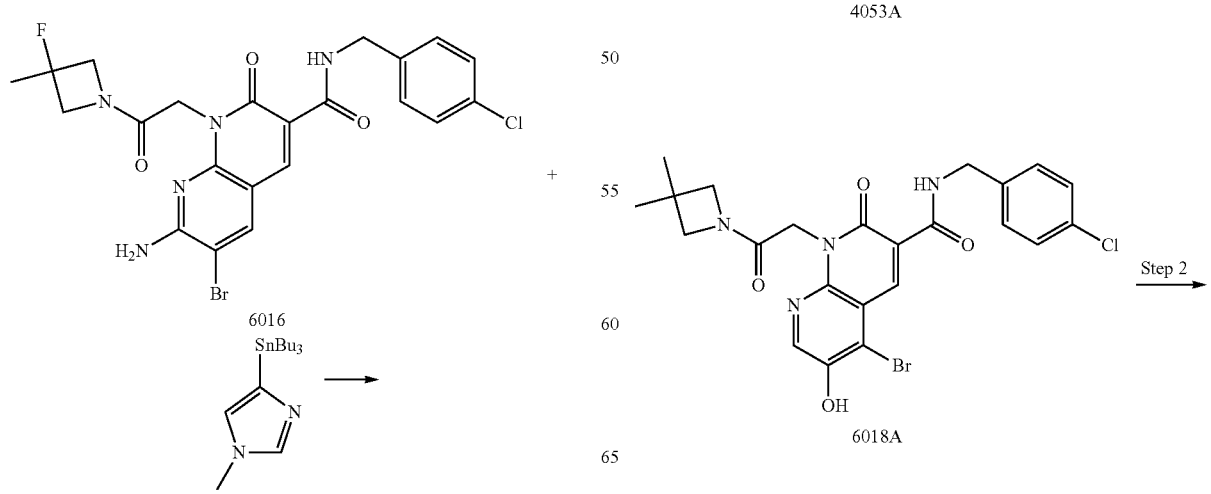

-continued

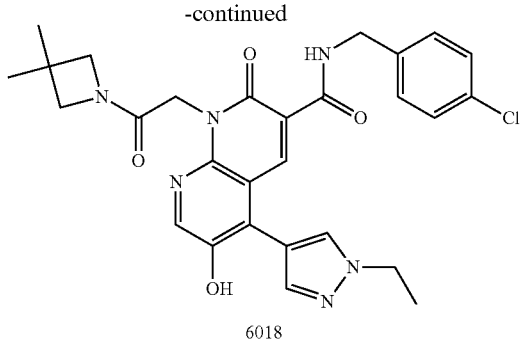

6018

Step 1: Intermediate 4053A (325 mg, 0.434 mmol) is charged in a round-bottom flask and dissolved in DCM (2.4 mL). A solution of bromine (75.0 mg, 0.470 mmol, 1.10 eq) in DCM (2.4 mL) is added and the resulting solution is stirred for 1 h at RT. The reaction mixture is diluted with EtOAc and washed with a saturated aqueous $Na_2S_2O_3$ solution. The organic layer is dried over $MgSO_4$, filtered and concentrated under reduced pressure to provide intermediate 6018A.

Step 2: Intermediate 6018A (230 mg, 0.129 mmol), 1-ethyl-1H-pyrazole-4-boronic acid pinacol ester (Combi-Blocks) (143 mg, 0.646 mmol, 5.00 eq), potassium carbonate (179 mg, 1.29 mmol, 10.0 eq) and palladium (0) tetrakis (triphenylphosphine) (75 mg, 0.064 mmol, 0.50 eq) are charged in a microwave vial and DMF (8.0 mL) and water (0.80 mL) are added. The vial is purged with argon, sealed and warmed in a microwave oven at 125° C. for 10 min. The reaction mixture is diluted with EtOAc and washed with water. The organic layer is dried over $MgSO_4$, filtered and concentrated under reduced pressure. The residue is purified by preparative HPLC to provide compound 6018 ($t_R$: 1.36, $(M+H)^+$: 549.0/551.0).

Synthesis of Compound 6019

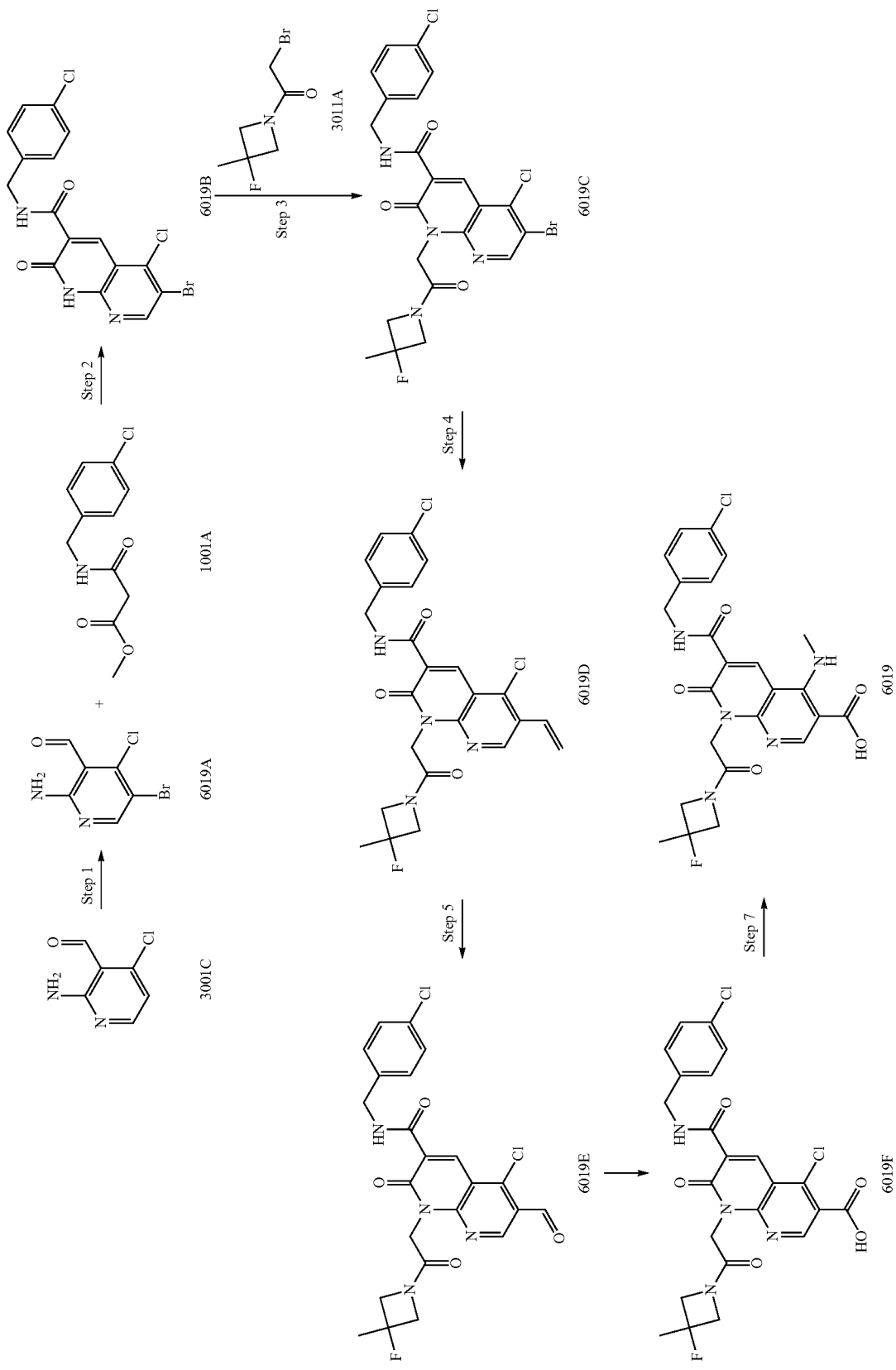

Step 1: Intermediate 3001C (175 mg, 1.12 mmol) is charged in a round-bottom flask and dissolved in MeCN (5.0 mL). N-bromosuccinimide (298 mg, 1.68 mmol, 1.50 eq) is added and the reaction mixture is stirred for 24 h at RT. The reaction mixture is concentrated under reduced pressure and the residue is dissolved in DCM. The organic solution is washed with a saturated aqueous $NaHCO_3$ solution. The organic layer is dried over $MgSO_4$, filtered and concentrated under reduced pressure to provide intermediate 6019A.

Step 2: Intermediate 6019A (150 mg, 0.637 mmol) and intermediate 1001A (154 g, 0.637 mmol, 1.00 eq) are charged in a round-bottom flask and dissolved in THF (10 mL). A 1.0 M solution of titanium(IV) chloride in DCM (0.637 mL, 0.637 mmol, 1.00 eq) is added and the solution is stirred at RT for 4 h. The resulting solid is collected by filtration, washed with water and MeOH and dried under vacuum to afford intermediate 6019B.

Step 3: Intermediate 6019C is prepared analogously to intermediate 3001E, except that intermediate 6019B is reacted with intermediate 3011A.

Step 4: Intermediate 6019D is prepared analogously to intermediate 4019A.

Step 5: Intermediate 6019E is prepared analogously to intermediate 4019B.

Step 6: Intermediate 6019E (725 mg, 1.44 mmol) is charged in a round-bottom flask and dissolved in t-BuOH (14.0 mL). Sodium phosphate monobasic (2.97 g, 21.5 mmol, 15.0 eq), 2-methylbutene (2.00 M solution in THF) (4.45 mL, 8.90 mmol, 6.20 eq), sodium chlorite (649 mg, 5.74 mmol, 4.00 eq) and water (11.5 mL) are added and the reaction mixture is stirred for 2 h at RT. The reaction mixture is diluted with water, basified with 10 M NaOH and washed with EtOAc. The aqueous layer is acidified to approximately pH=2 with concentrated HCl and washed with DCM. The organic layer is washed with brine, dried over $MgSO_4$, filtered and concentrated under reduced pressure to provide intermediate 6019F.

Step 7: Intermediate 6019F (50 mg, 0.096 mmol) is charged in a round-bottom flask and dissolved in NMP (1.10 mL). 2.0 M methylamine in THF (Aldrich) (0.14 mL. 0.29 mmol, 3.0 eq) and diisopropylethylamine (53 µL, 0.29 mmol, 3.0 eq) are added and the reaction mixture is stirred at 70° C. for 12 h. The reaction mixture is filtered and purified by preparative HPLC to provide compound 6019 ($t_R$: 1.63, $(M+H)^+$: 516.3).

Synthesis of Compound 6020

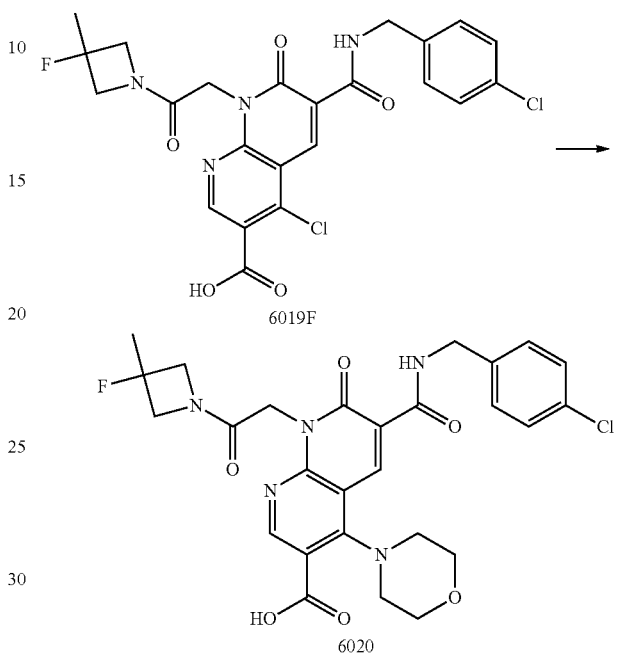

Compound 6020 ($t_R$: 1.56, $(M+H)^+$: 572.4) is prepared analogously to compound 6019, except that in step 7, intermediate 6019F is reacted with morpholine (Aldrich).

Synthesis of Compound 6021

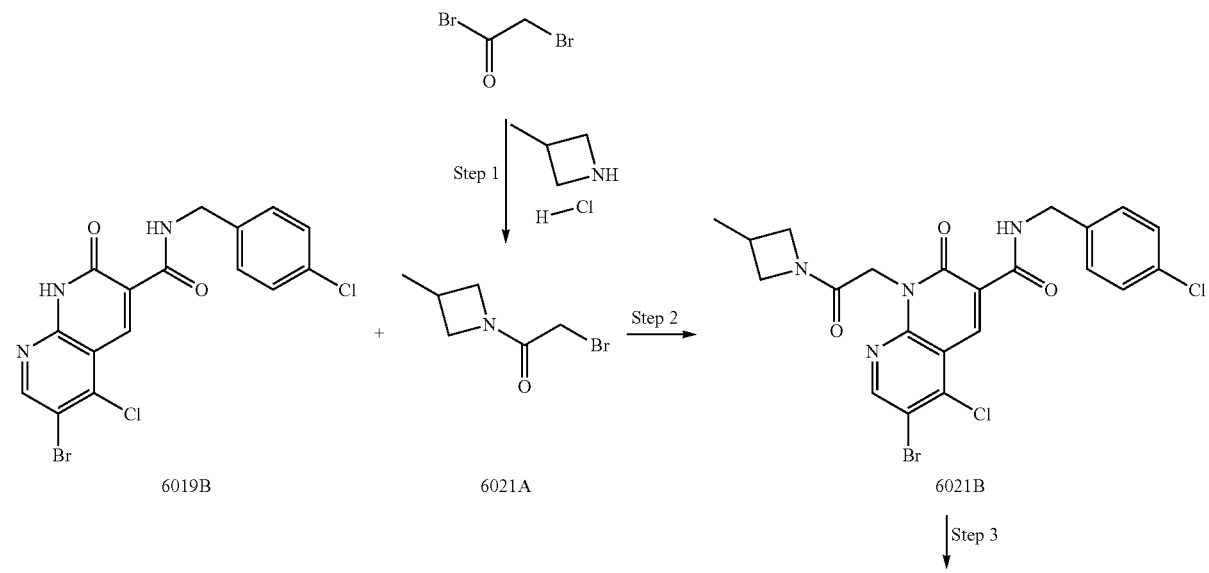

-continued

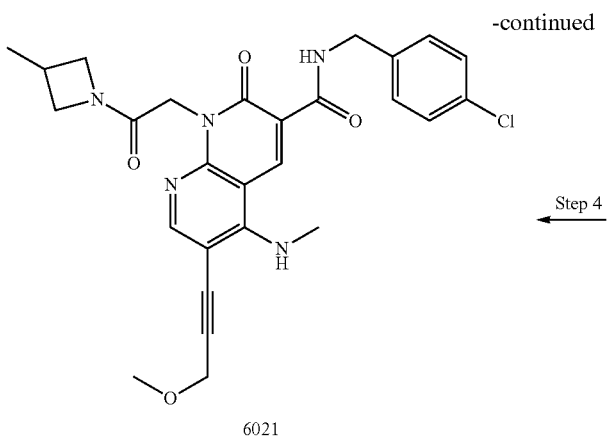

6021

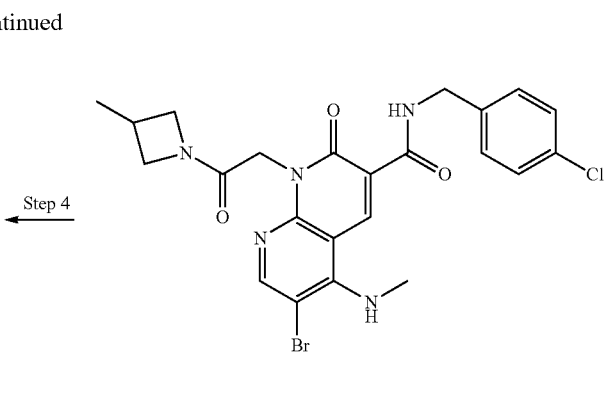

6021C

Step 1: Intermediate 6021A is prepared analogously to intermediate 3001F, but using 3-methyl-azetidine hydrochloride instead of 3,3-dimethyl-azetidine hydrochloride (prepared analogously to the procedure in J. Med. Chem. 2008, 51, 7380, herein incorporated by reference).

Step 2: Intermediate 6021B is prepared analogously to intermediate 3001E, except that intermediate 6019B is reacted with intermediate 6021A.

Step 3: Intermediate 6021B (500 mg, 0.929 mmol) is charged in a pressure vessel and 2.00 M methylamine in THF (2.32 mL, 4.65 mmol, 5.00 eq) is added. The vessel is sealed and heated at 70° C. for 4 h. The mixture is cooled to RT and concentrated under reduced pressure. The residue is purified by flash chromatography (100% DCM to 20% MeOH in DCM) to provide intermediate 6021C.

Step 4: Intermediate 6021C (90 mg, 0.17 mmol) is charged in a vial and dissolved in DMF (2.0 mL). Copper(I) iodide (6.4 mg, 0.034 mmol, 0.20 eq), triethylamine (0.12 mL, 0.85 mmol, 5.0 eq), methyl propargyl ether (Aldrich) (30 mg, 0.42 mmol, 2.5 eq) and palladium (0) tetrakis(triphenylphosphine) (20 mg, 0.017 mmol, 0.10 eq) are added and the reaction mixture is degassed with argon. The vial is sealed and heated at 100° C. for 3 days. The reaction mixture is diluted with EtOAc and washed with water. The organic layer is dried over $MgSO_4$, filtered and concentrated under reduced pressure. The residue is purified by preparative HPLC to provide compound 6021 ($t_R$: 1.98, $(M+H)^+$: 522.3/524.3).

Synthesis of Compound 6022

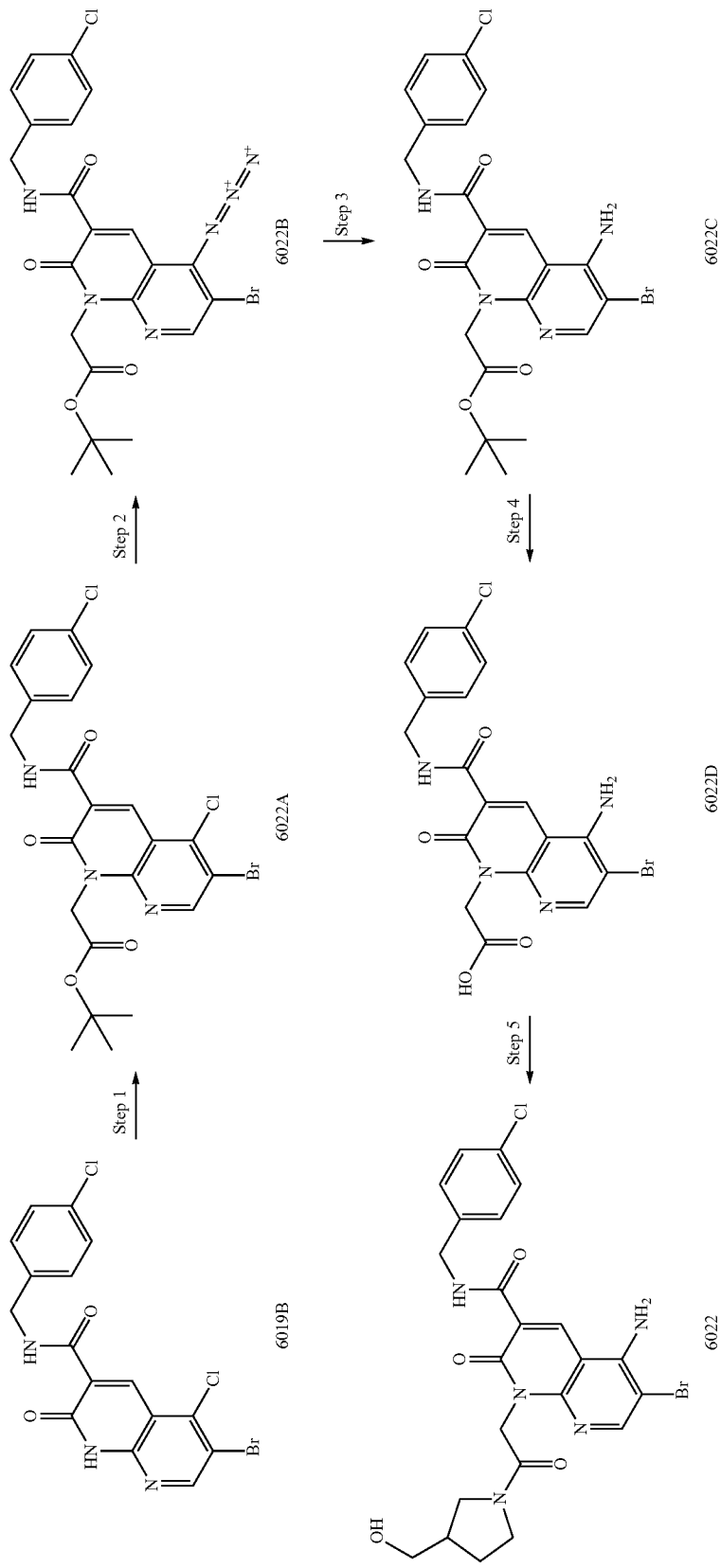

Step 1: Intermediate 6019B (3.00 g, 7.02 mmol) is charged in a round-bottom flask and suspended in DMF (50 mL). Potassium carbonate (2.94 g, 21.2 mmol, 3.03 eq) and t-butyl bromoacetate (1.30 mL, 8.78 mmol, 1.25 eq) are added and the solution is stirred at RT for 16 h. The solution is diluted with EtOAc and washed with brine. The organic layer is dried over MgSO₄, filtered and concentrated under reduced pressure. The residue is purified by trituration in methyl t-butyl ether to provide intermediate 6022A.

Step 2: Intermediate 6022A (2.00 g, 3.70 mmol) is charged in a round-bottom flask and dissolved in DMF (25.0 mL). Sodium azide (360 mg, 5.54 mmol, 1.50 eq) is added and the reaction mixture is stirred for 16 h at RT. The solution is added to water and the resulting solid is collected by filtration. The solid is washed with water and dried under vacuum to afford intermediate 6022B.

Step 3: Intermediate 6022B (500 mg, 0.913 mmol) is charged in a round-bottom flask and suspended in 1,4-dioxane (5.0 mL) and water (0.33 mL). Tris(carboxyethyl)phosphine hydrochloride (392 mg, 1.37 mmol, 1.50 eq) is added and the reaction mixture is stirred for 16 h at RT. A 1 M sodium dihydrogen phosphate solution is added and the reaction mixture is stirred for 15 min at RT. Water is added and the resulting solid is collected by filtration. The solid is washed with water and dried under vacuum to afford intermediate 6022C.

Step 4: Intermediate 6022C (490 mg, 0.939 mmol) is charged in a round-bottom flask and dissolved in TFA (15.0 mL). The solution is stirred at RT for 2 h and concentrated. The residue is suspended in toluene and concentrated under reduced pressure to provide intermediate 6022D.

Step 5: Intermediate 6022D (50 mg, 0.086 mmol) is charged in a vial and dissolved in DMF (1 mL). Triethylamine (39 µL, 0.27 mmol, 3.1 eq) and pyrrolidin-3-yl-methanol (Chembrdg-bb) (10 mg, 0.10 mmol, 1.2 eq) are added followed by HATU (52 mg, 0.14 mmol, 1.6 eq) and the solution is stirred at RT for 12 h. Following completion of the reaction, the solution is filtered and purified by preparative HPLC to provide compound 6022 ($t_R$: 1.79, (M+H)⁺: 550.1).

Synthesis of Compound 6023

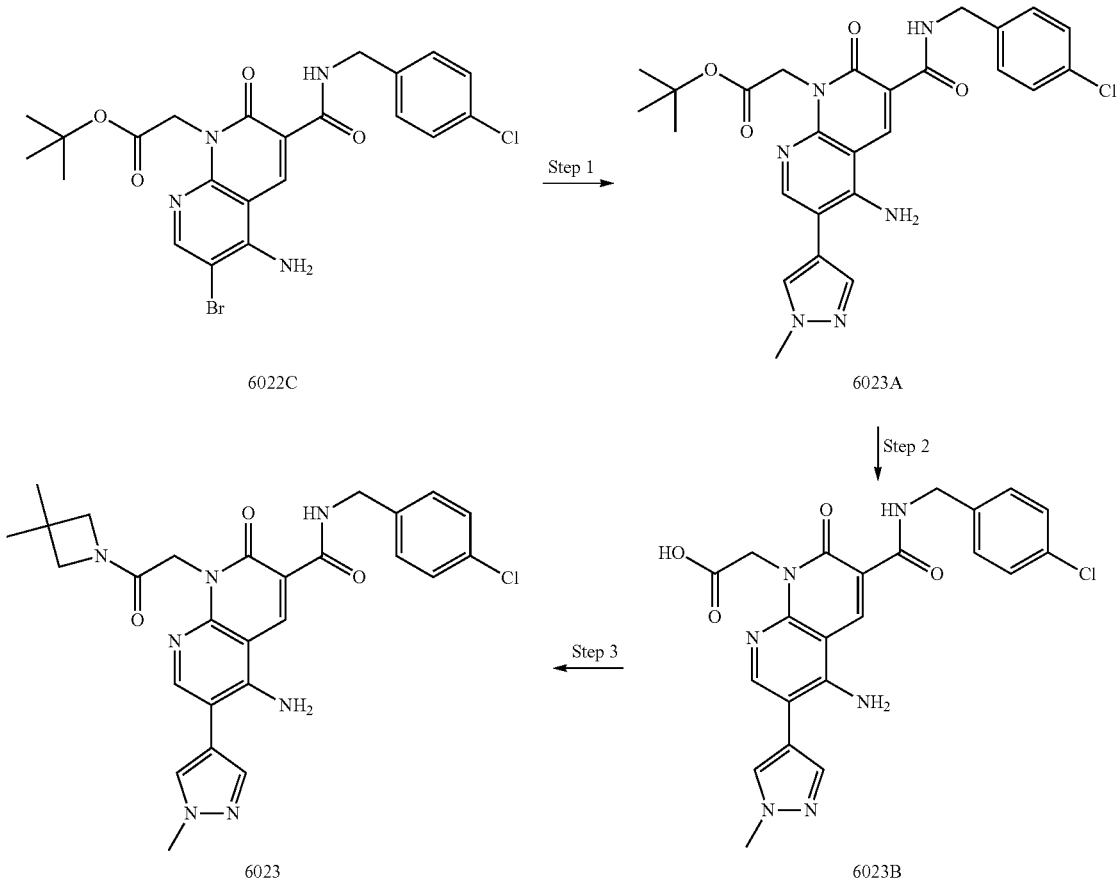

Step 1: Intermediate 6022C (45 mg, 0.086 mmol), 1-methyl-4-(4,4,5,5-tetramethyl-1,3,2-dioxaborolan-2-yl)-1H pyrazole (Frontier) (23 mg, 0.11 mmol, 1.3 eq), potassium carbonate (36 mg, 0.26 mmol, 3.0 eq) and bis(tri-t-butylphosphine)palladium (0) (8.8 mg, 0.017 mmol, 0.20 eq) are charged in a microwave vial and DMF (1.0 mL) and water (0.10 mL) are added. The vial is purged with argon, sealed and warmed in a microwave oven at 125° C. for 10 min. The reaction mixture is diluted with DCM and washed with water and brine. The organic layer is dried over MgSO₄, filtered and concentrated under reduced pressure. The residue is purified by flash chromatography (100% DCM to 5% MeOH in DCM) to provide intermediate 6023A.

Step 2: Intermediate 6023B is prepared analogously to intermediate 6022D.

Step 3: Compound 6023 ($t_R$: 1.92, (M+H)⁺: 534.3) is prepared analogously to compound 6022, except that intermediate 6023B is reacted with 3,3-dimethyl-azetidine hydrochloride (prepared analogously to the procedure in J. Med. Chem. 2008, 51, 7380, herein incorporated by reference).

Synthesis of Compound 6024

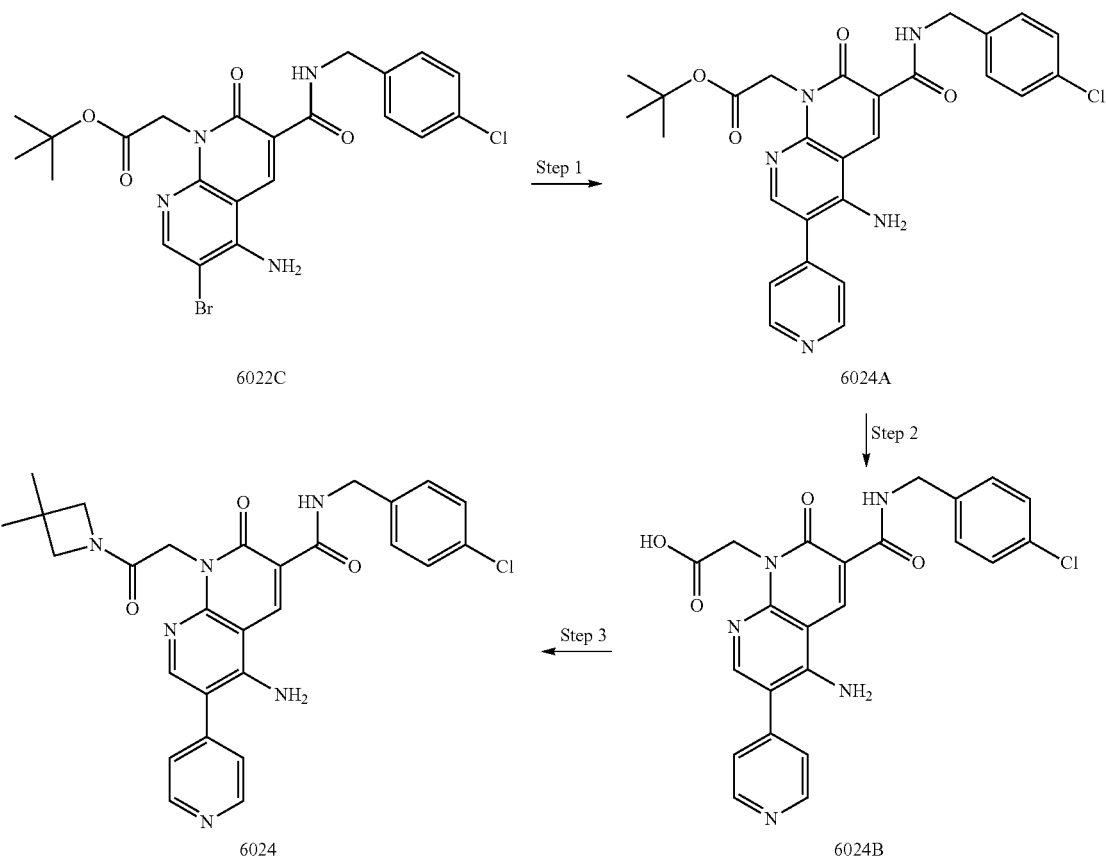 [SMILES: CC(C)(C)OC(=O)Cn1c(=O)c(C(=O)NCc2ccc(Cl)cc2)cc2c(N)c(Br)cnc21 ; CC(C)(C)OC(=O)Cn1c(=O)c(C(=O)NCc2ccc(Cl)cc2)cc2c(N)c(-c3ccncc3)cnc21 ; CC1(C)CN(C(=O)Cn2c(=O)c(C(=O)NCc3ccc(Cl)cc3)cc3c(N)c(-c4ccncc4)cnc32)C1 ; Nc1c(-c2ccncc2)cnc2c1cc(C(=O)NCc1ccc(Cl)cc1)c(=O)n2CC(=O)O]

Step 1: Intermediate 6024A is prepared analogously to intermediate 6023A, except that intermediate 6022C is reacted with 4-(4,4,5,5-tetramethyl-1,3,2-dioxaborolan-2-yl)pyridine (Aldrich).

Step 2: Intermediate 6024B is prepared analogously to intermediate 6022D.

Step 3: Compound 6024 ($t_R$: 1.94, $(M+H)^+$: 531.2) is prepared analogously to compound 6022, except that intermediate 6024B is reacted with 3,3-dimethyl-azetidine hydrochloride (prepared analogously to the procedure described in J. Med. Chem. 2008, 51, 7380, herein incorporated by reference).

Synthesis of Compound 7001

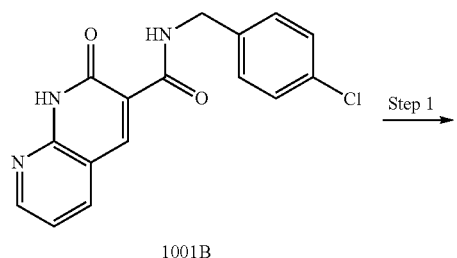

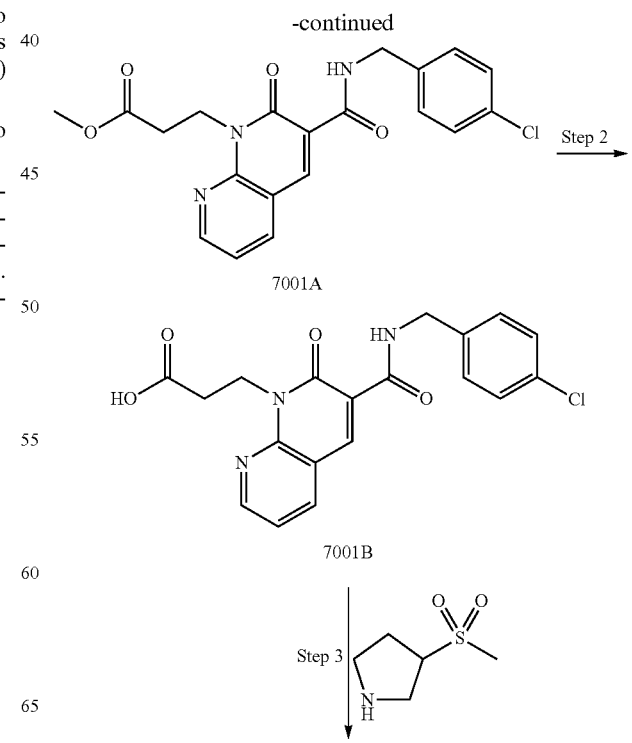

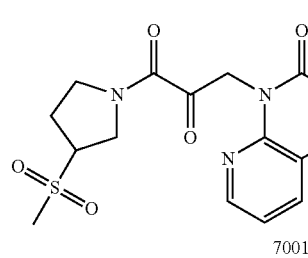

7001

Step 1: Intermediate 1001B (7.00 g, 22.3 mmol) is charged in a round-bottom flask and suspended in DMF (70 mL). Potassium carbonate (6.17 g, 44.6 mmol, 2.00 eq) and methyl 3-bromopropionate (4.47 g, 26.8 mmol, 1.20 eq) are added and the solution is stirred at 120° C. for 20 h. Methyl 3-bromopropionate (2.24 g, 13.4 mmol, 0.600 eq) is added and heating is continued for 16 h. The reaction mixture is diluted with EtOAc and washed with water. The organic layer is dried over $Na_2SO_4$, filtered and concentrated to provide intermediate 7001A.

Step 2: Intermediate 7001A (7.04 g, 17.6 mmol) is charged in a round-bottom flask and suspended in THF (120 mL). MeOH (120 mL) and NaOH 1.00 N (66.9 mL, 66.9 mmol, 3.80 eq) are added and the solution is stirred at RT for 16 h. The reaction mixture is concentrated and the residue is dissolved in EtOAc. The organic solution is washed with 1 N HCl, dried over $MgSO_4$, filtered and concentrated to provide intermediate 7001B.

Step 3: Intermediate 7001B (32 mg, 0.082 mmol) is charged in a vial and dissolved in 1-methyl-2-pyrrolidinone (1 mL). Diisopropylethylamine (41 µL, 0.23 mmol, 2.9 eq) and 3-(methanesulfonyl)pyrrolidine (Chem-Impex) (25 mg, 0.16 mmol, 2.0 eq) are added followed by TBTU (44 mg, 0.12 mmol, 1.4 eq) and the solution is stirred at RT for 2 h. Following completion of the reaction, the solution is filtered and purified by preparative HPLC to provide compound 7001 ($t_R$: 1.62, (M+H)$^+$: 517.1).

Synthesis of Compound 7002

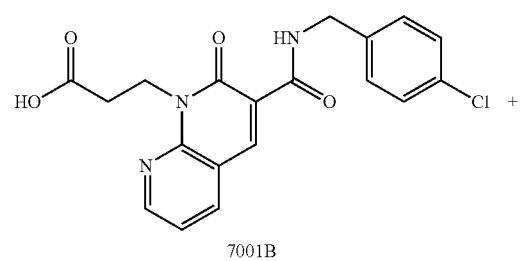

7001B

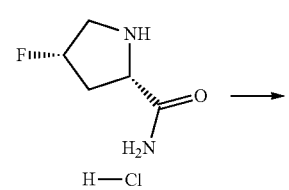

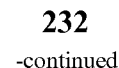

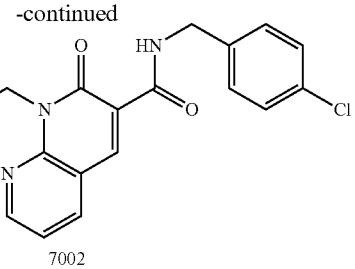

7002

Compound 7002 ($t_R$: 1.64, (M+H)$^+$: 500.2) is prepared analogously to compound 7001, except that in step 3, intermediate 7001B is reacted with 4-cis-fluoro-L-prolinamide hydrochloride (Chem-Impex).

Synthesis of Compound 7003

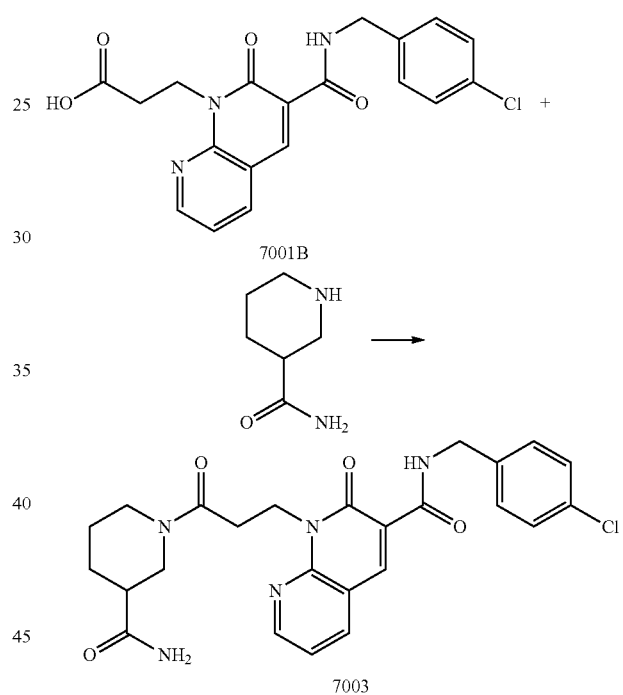

7003

Compound 7003 ($t_R$: 1.75, (M+H)$^+$: 496.3) is prepared analogously to compound 7001, except that in step 3, intermediate 7001B is reacted with nipecotamide (Aldrich).

Synthesis of Compound 7004

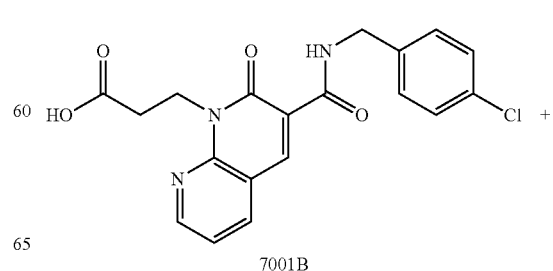

7001B

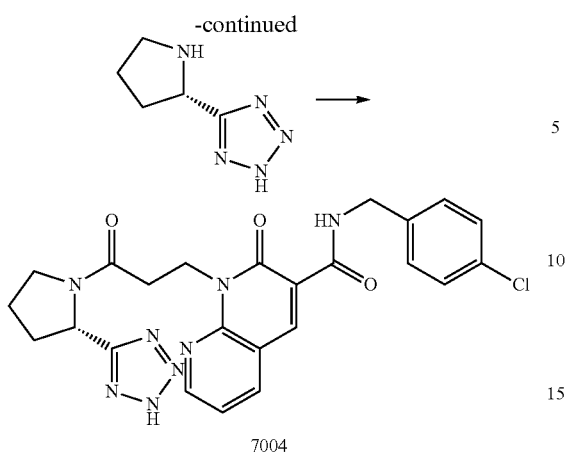

7004

Compound 7004 ($t_R$: 1.5, (M+H)$^+$: 507.2) is prepared analogously to compound 7001, except that in step 3, intermediate 7001B is reacted with (S)-5-(pyrrolidin-2-yl)-1H-tetrazole (Aldrich).

Synthesis of Compound 7005

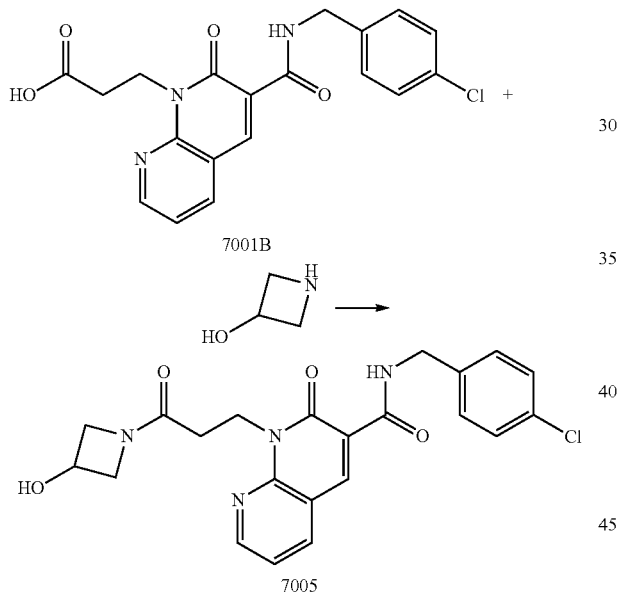

7005

Compound 7005 ($t_R$: 1.63, (M+H)$^+$: 441.2/443.1) is prepared analogously to compound 7001, except that in step 3, intermediate 7001B is reacted with 3-azetidinol (Chembrdg-bb).

Synthesis of Compound 7006

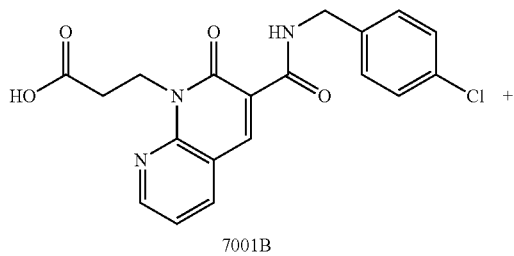

7001B

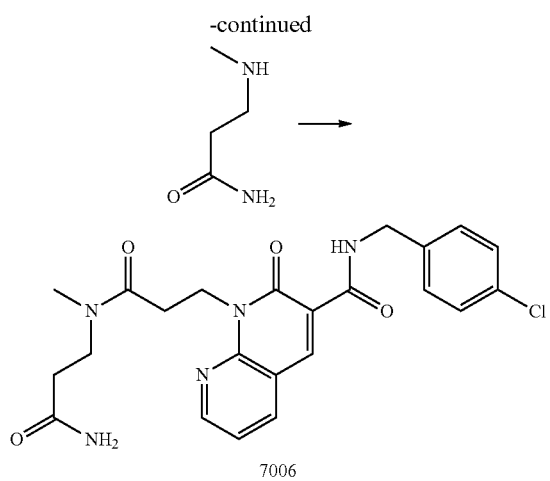

7006

Compound 7006 ($t_R$: 1.61, (M+H)$^+$: 470.1) is prepared analogously to compound 7001, except that in step 3, intermediate 7001B is reacted with 3-(methylamino)propanamide hydrochloride (Matrix).

Synthesis of Compound 7007

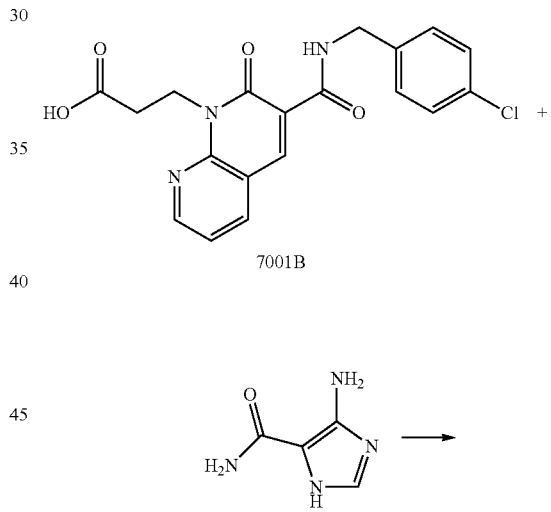

7007

Compound 7007 ($t_R$: 1.64, (M+H)$^+$: 494.2) is prepared analogously to compound 7001, except that in step 3, intermediate 7001B is reacted with 4-amino-5-imidazolecarboxamide hydrochloride (Acros).

Synthesis of Compound 7008

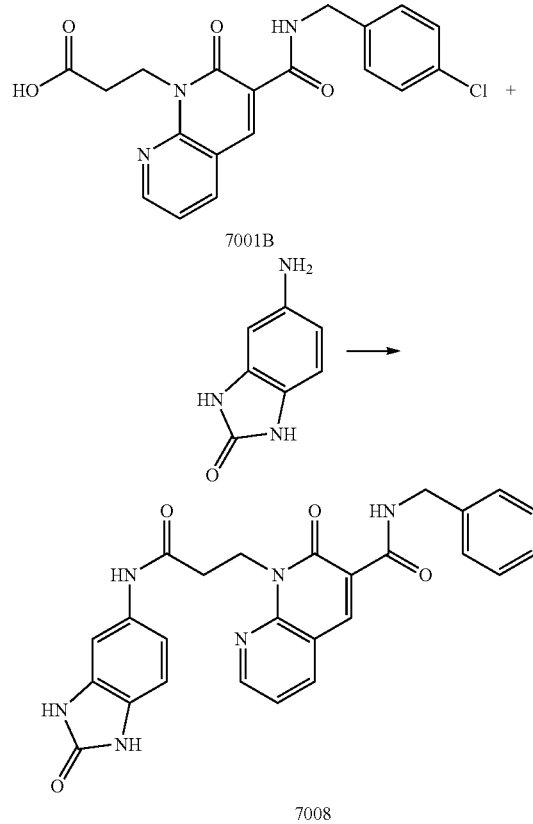

Compound 7008 ($t_R$: 1.66, (M+H)$^+$: 517.1) is prepared analogously to compound 7001, except that in step 3, intermediate 7001B is reacted with 5-aminobenzimidazolone (Pfaltz-Bauer).

Synthesis of Compound 7009

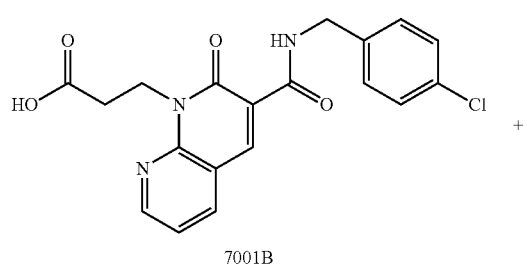

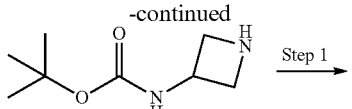

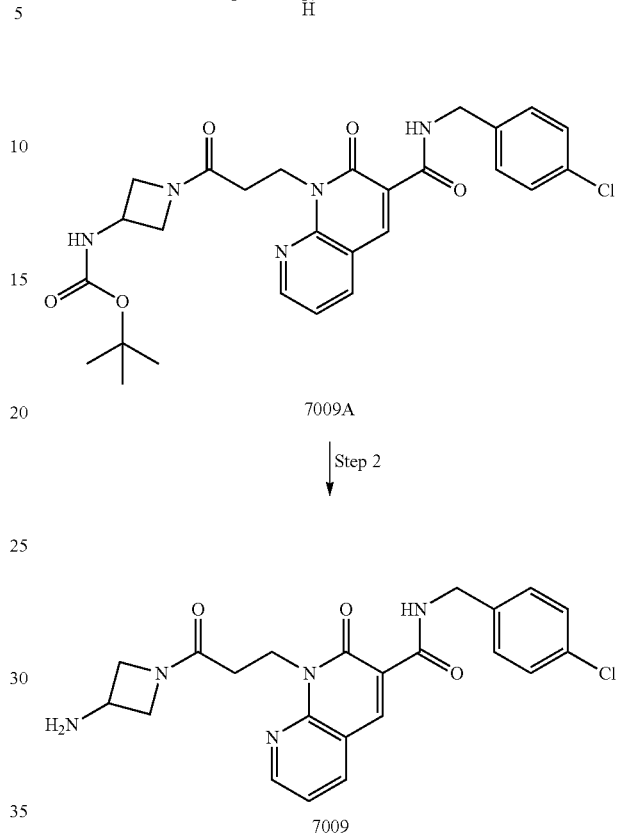

Step 1: Intermediate 7009A is prepared analogously to compound 7001, except that in step 3, intermediate 7001B is reacted with 3-N-boc-amino-azetidine (Betapharma).

Step 2: Intermediate 7009A (7.8 mg, 0.014 mmol) is charged in a vial and dissolved in DCM (0.20 mL). TFA (5.6 mL, 0.072 mmol, 5.0 eq) is added and the solution is stirred at RT for 16 h. The reaction mixture is concentrated and the residue is dissolved in DCM and washed with a saturated NaHCO$_3$ aqueous solution. The organic layer is dried over MgSO$_4$, filtered and concentrated to provide compound 7009 ($t_R$: 1.59, (M+H)$^+$: 440.1).

Synthesis of Compound 7010

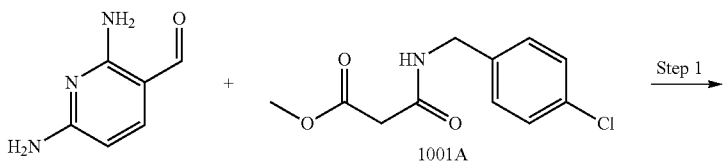

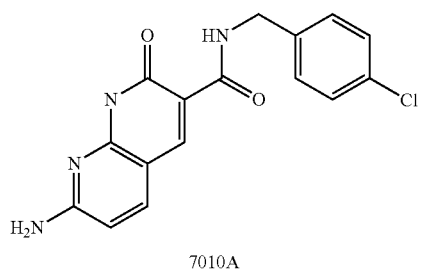

7010A

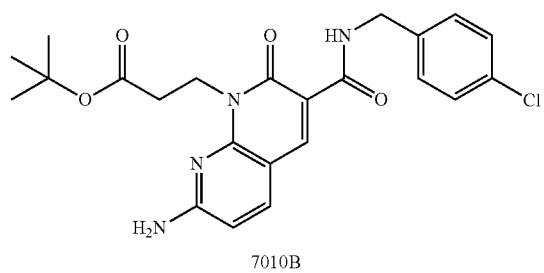

7010B

-continued

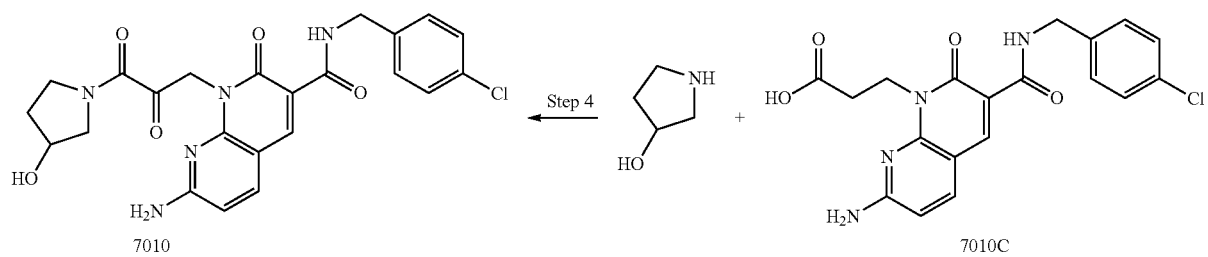

Step 1: 2,6-Diamino-pyridine-3-carbaldehyde (prepared analogously to the procedure in J. Am. Chem. Soc. 2002, 124, 13757, herein incorporated by reference) (1.90 g, 13.9 mmol) and intermediate 1001A (4.02 g, 16.6 mmol, 1.20 eq) are charged in a microwave vial and EtOH (14 mL) is added. Piperidine (3.43 mL, 34.6 mmol, 2.50 eq) is added and vial is sealed and warmed in a microwave oven at 120° C. for 30 min. The cooled solution is diluted with Et$_2$O and sonicated. The resulting solid is filtered and dried under vacuum to afford intermediate 7010A.

Step 2: Intermediate 7010A (600 mg, 1.83 mmol) is charged in a round-bottom flask and suspended in DMF (5.0 mL). Potassium carbonate (415 mg, 3.00 mmol, 1.64 eq) and t-butyl 3-bromopropionate (305 µL, 1.83 mmol, 1.00 eq) are added and the solution is stirred at 130° C. for 3 h. The reaction mixture is then diluted with EtOAc and washed with water and brine. The organic layer is dried over MgSO$_4$, filtered and concentrated to provide intermediate 7010B.

Step 3: Intermediate 7010B (150 mg, 0.328 mmol) is charged in a round-bottom flask and dissolved in TFA (1.0 mL). The solution is stirred at RT for 1 h and concentrated. The residue is suspended in toluene and re-concentrated under reduced pressure to provide intermediate 7010C.

Step 4: Intermediate 7010C (131 mg, 0.328 mmol) is charged in a vial and dissolved in DMF (2.0 mL). Diisopropylethylamine (306 µL, 1.73 mmol, 5.26 eq) and DL-3-pyrrolidinol (TCI-Europe) (43 mg, 0.50 mmol, 1.5 eq) are added followed by HATU (167 mg, 0.440 mmol, 1.34 eq). The solution is stirred at RT for 1 h. Following completion of the reaction, the solution is filtered and purified by preparative HPLC to provide compound 7010 (t$_R$: 1.73, (M+H)$^+$: 470.2/472.2).

Synthesis of Compound 7011

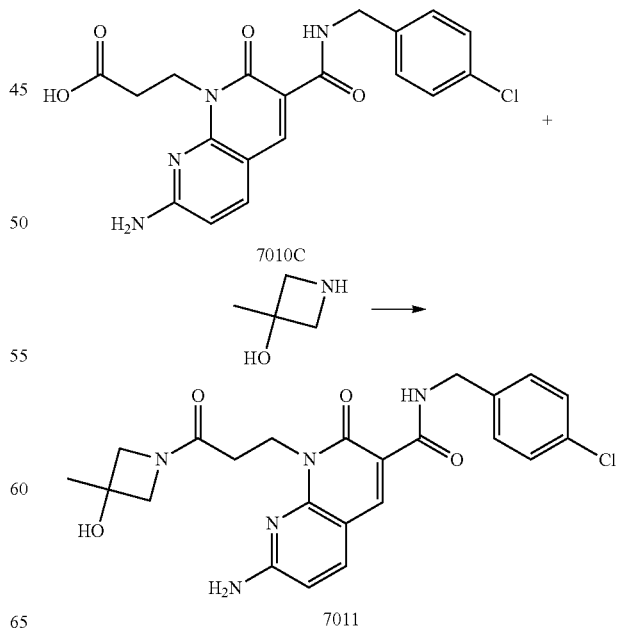

7011

Compound 7011 ($t_R$: 1.76, (M+H)$^+$: 470.2/472.2) is prepared analogously to compound 7010, except that in step 4, intermediate 7010C is reacted with 3-methyl-azetidin-3-ol (Parkway).

Synthesis of Compound 7012

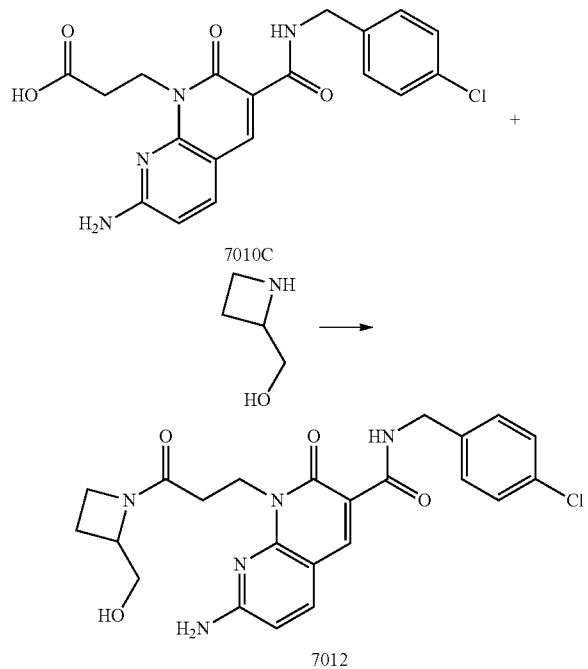

Compound 7012 ($t_R$: 1.67, (M+H)$^+$: 470.2/472.2) is prepared analogously to compound 7010, except that in step 4, intermediate 7010C is reacted with azetidin-2-ylmethanol (Amatek).

Example A

Expression Vector, Protein Expression and Purification

The codon optimized UL54 HCMV polymerase gene for expression in insect cells is obtained from DNA 2.0 (Menlo Park, Calif.) and subcloned in 3' of the Glutathione-S-transferase (GST) gene in a pFastBac-derived vector. Bacmids and baculoviruses are generated and expression performed in Sf21 insect cells cultured in SF900 II SFM media. Infection using the baculoviruses is performed using an MOI of 5-10 and the cells are harvested 48 h post-infection and frozen.
Reagents and Materials (Equivalents are Acceptable):

| Product | Company | Catalog # | Storage |
|---|---|---|---|
| SF900 II SFM media | Invitrogen | 10902104 | 4° C. |
| Tris | Sigma | T1503 | RT |
| TCEP | Thermo Fisher Scientific | 77720 | 4° C. |
| EDTA | Ambion | AM9262 | RT |
| NaCl | Sigma | S6191 | RT |
| Glycerol | Thermo Fisher Scientific | BP229-4 | RT |
| PMSF | VWR | PB0425 | RT |
| Leupeptin | Cedarlane | N-1000.0025 | −20° C. |
| Antipain | MP Biomedicals | 152843 | −20° C. |
| Pepstatin A | MP Biomedicals | 195368 | −20° C. |

-continued

| Product | Company | Catalog # | Storage |
|---|---|---|---|
| Glutathione | Thermo Fisher Scientific | BP229-4 | RT |
| Glutathione Sepharose 4B | GE Healthcare | 17-0756-05 | 4° C. |
| HiTrap DEAE-Sepharose FF dolumn | GE Healthcare | 17-5055-01 | 4° C. |

All purification procedures are performed at 4° C. The cell pellet from 1 L of culture (1×10$^9$ cells) is resuspended in 25 mL of 50 mM Tris pH 7.5, 1 mM TCEP, 0.1 mM EDTA, 150 mM NaCl, 10% Glycerol, 1 mM PMSF, 2 μg/mL Leupeptin, 2 μg/mL Antipain, 2 μg/mL Pepstatin A. The solution is homogenized using a Dounce tissue grinder. Following homogenization, the volume is increased to 40 mL followed by centrifugation at 750×g for 5 min to remove nuclei. The supernatant is then transferred and 3 cc of 50% slurry of glutathione-sepharose 4B resin is added and the mixture is incubated on a rotator for 1 h. The slurry is centrifuged at 500 g for 5 min. The supernatant is discarded and the pellet is resuspended in 10× volume of wash buffer (50 mM Tris pH 7.5, 1 mM TCEP, 0.1 mM EDTA, 150 mM NaCl, 10% Glycerol) and incubated for 5 min. The slurry is centrifuged at 500 g for 5 min and the supernatant is discarded. The wash step is performed 5 times. The elution is performed by adding 1.5 volume of elution buffer (50 mM Tris pH 7.5, 1 mM TCEP, 0.1 mM EDTA, 150 mM NaCl, 10% Glycerol, 20 mM glutathione) and then incubating on a rotator for 15 min. The slurry is centrifuged at 500 g for 5 min and the supernatant is removed and kept. The elution step is performed four times. The supernatant are pooled and centrifuged at 500×g for 5 min to remove resin particles and are frozen at −80° C.

The frozen protein is thawed and the NaCl concentration reduced to 37.5 mM by the addition of 3 volumes of DEAE buffer A (50 mM Tris pH 7.5, 1 mM TCEP, 0.1 mM EDTA, 10% Glycerol). The protein is loaded on a HiTrap DEAE-Sepharose FF column and eluted using a gradient with DEAE buffer B (50 mM Tris pH 7.5, 1 mM TCEP, 0.1 mM EDTA, 10% Glycerol, 1 M NaCl). UL54 eluted at 140 mM NaCl. The DEAE fractions are pooled, frozen and stored at −80° C. The protein concentration is determined by OD$_{280}$ (A$_{280}$=1.03 mg/mL).

Example B

HCMV Polymerase Scintillation Proximity Assay

This radiometric assay is used to determine the enzymatic activity of purified recombinant HCMV polymerase (UL54) using a biotinylated oligo(dT) primed to poly(dA) template. Recombinant HCMV polymerase from strain AD169 is produced as a GST-fusion protein using a Baculovirus/Sf21 insect cells system. The enzymatic activity is measured by incorporating $^3$H-dTTP in the nascent complementary strand and revealed using streptavidin-coated SPA beads.
Reagents and Materials (Equivalents are Acceptable):

| Product | Company | Catalog # | Storage |
|---|---|---|---|
| 384 well plate Lumitrac 200 | Greiner | 781075 | RT |
| 1M Hepes | Invitrogen | 15630-080 | 4° C. |
| 10 mg/mL BSA | New England Biolabs | B9001S | −20° C. |
| 0.5M TCEP pH 7.0 | Thermo Fisher Scientific | 77720 | 4° C. |

-continued

| Product | Company | Catalog # | Storage |
|---|---|---|---|
| 0.5M EDTA pH 8.0 | Ambion | AM9262 | RT |
| DMSO | VWR (EMD Chemicals) | CAMX1457-6 | RT |
| KCl | Sigma | P9541 | RT |
| NaCl | Sigma | S6191 | RT |
| MgCl$_2$ | VWR (EMD Chemicals) | CAMX0045-1 | RT |
| CsCl | Sigma | C4036 | RT |
| Glycerol | Thermo Fisher Scientific | BP229-4 | RT |
| Poly(dA) template | Midland | P-2002 | −20° C. |
| Oligo(dT) primer | Integrated DNA Technologies | custom synthesis (BioTEG-dT19) | −20° C. |
| 100 mM dTTP | New England Biolabs | N0446S | −20° C. |
| $^3$H-dTTP 2.5 mCi/mL | Perkin-Elmer | NET520A001MC or NET221A001MC | −80° C. |
| SPA beads | Perkin-Elmer | RPNQ0007 | 4° C. |
| TopSeal-Adhesive sealing film | PerkinElmer | 6005185 | RT |
| GST-UL54 | Purified as described in Example A | | −80° C. |

Preparation of Compounds:

Serial dilutions of the DMSO stock compound solution are performed using DMSO in columns 2-11 and 14-23. DMSO alone is present in columns 1, 12, 13 and 24. The DMSO serial dilutions are diluted using 10 mM Hepes pH 7.5, 25 mM KCl, 5 mM MgCl$_2$, 1 mM TCEP to obtain a 15% DMSO concentration (3×). 10 μL per well of the 15% DMSO serial dilution compound solution is added to the assay plate. The plate is centrifuged at 200×g for 30 sec.

Polymerase Scintillation Proximity Assay:

The assay conditions are the following: 10 mM HEPES pH 7.5, 25 mM KCl, 7.5 mM NaCl, 5 mM MgCl$_2$, 0.2 mg BSA/mL, 1 mM TCEP, 1.5% glycerol, 2 μM dTTP, 90 nM $^3$H-dTTP (minor variations in concentration are possible due to specific activity of stock), 26 nM Poly(dA)/190 nM BioTEG-dT19; 5% DMSO. The assay volume is 30 μL. Each reagent is added at a 3× conc.: 10 μL a+10 μL b+10 μL c; a: compound diluted in 10 mM Hepes pH 7.5, 25 mM KCl, 5 mM MgCl$_2$, 1 mM TCEP with 15% DMSO; b: enzyme (GST-UL54) in 10 mM Hepes pH 7.5, 25 mM KCl, 5 mM MgCl$_2$, 22.5 mM NaCl, 4.5% Glycerol, 0.6 mg BSA/mL, 1 mM TCEP w/o DMSO (1 nM GST-UL54 is present in the assay); c: substrate in 10 mM Hepes pH 7.5, 25 mM KCl, 5 mM MgCl$_2$, 1 mM TCEP, 6 μM dTTP, 270 nM $^3$H-dTTP, 78 nM Poly(dA)/570 nM BioTEG-dT19 w/o DMSO. To perform the assay, 10 μL enzyme solution is added to columns 2-12 and 14-24. The enzyme is substituted by the blank solution (b solution without enzyme) for columns 1 and 13 (blanks). The plate is centrifuged at 200×g for 30 sec. 10 μL of substrate solution is added to each well. The plate is centrifuged at 200×g for 30 sec. The plates are incubated at 37° C. for 40 min. To stop the reaction, 25 μL of SPA beads (5 mg/mL in 0.5 M EDTA) are added and mixed by pipetting up and down. The plates are incubated at RT for at least 15 min. 35 μL of 5 M CsCl is added to the bottom of each well. TopSeal is applied to the plate and the plate is incubated at RT for at least 90 min prior to reading. The signal is read on TopCount plate reader (Perkin-Elmer) or equivalent.

Example C

HCMV Polymerase LANCE TR-FRET Assay

This non-radiometric assay determines the enzymatic activity of purified recombinant HCMV polymerase (UL54) using a Digoxigenin-labeled oligonucleotide priming a heteropolymeric template. The enzymatic activity is determined by incorporating Biotin-dUTP in the nascent complementary strand. The signal is generated by Fluorescence Resonance Energy Transfer from the donor (Anti-Digoxigenin-Europium Chelate binding with the primer) to the acceptor Streptavidin-AlloPhycoCyanin (SA-APC) binding to the biotin of the labeled nucleotides incorporated in proximity. Reagents and Materials (Equivalents are Acceptable):

| Product | Company | Catalog # | Storage |
|---|---|---|---|
| 384-well white PP | SeaHorse | S30033W | RT |
| 1M Hepes | Invitrogen | 15630-080 | 4° C. |
| 10 mg/mL BSA | New England Biolabs | B9001S | −20° C. |
| 0.5M TCEP pH 7.0 | Thermo Fisher Scientific | 77720 | 4° C. |
| 0.5M EDTA pH 8.0 | Ambion | AM9262 | RT |
| DMSO | VWR (EMD Chemicals) | CAMX1457-6 | RT |
| KCl | Sigma | P9541 | RT |
| NaCl | Sigma | S6191 | RT |
| MgCl$_2$ | VWR (EMD Chemicals) | CAMX0045-1 | RT |
| Glycerol | Thermo Fisher Scientific | BP229-4 | RT |
| Tris | Sigma | T1503 | RT |
| 10% Tween-20 | Bio-Rad | 161-0781 | RT |
| Heteropolymeric template | Integrated DNA Technologies | Custom | −20° C. |
| Digoxigenin-labeled primer | Integrated DNA Technologies | Custom | −20° C. |
| 100 mM Deoxynucleotide Solution | New England Biolabs | N0446S | −20° C. |
| 1 mM Biotin-16-dUTP | Roche | 11093070910 | −20° C. |
| Streptavidin-APC | PerkinElmer | CR130-100 | 4° C. |
| Anti-Dig-Europium | PerkinElmer | Custom | 4° C. |
| GST-UL54 | Purified as described in Example A | | −80° C. |

Preparation of Compounds:

Serial dilutions of the DMSO stock compound solution are performed using DMSO in columns 2-11 and 14-23. DMSO alone is present in columns 1, 12, 13 and 24. Three μL of the DMSO serial dilutions is transferred and diluted using 21 μL of compound dilution buffer (10 mM Hepes pH 7.5, 25 mM KCl, 5 mM MgCl$_2$, 1 mM TCEP) to obtain 12.5% DMSO. 4 μL per well of the 12.5% DMSO serial dilution compound solution is added to the assay plate. The plate is centrifuged at 200×g for 30 sec.

LANCE TR-FRET Assay:

The assay conditions are the following: 10 mM HEPES pH 7.5, 25 mM KCl, 7.5 mM NaCl, 5 mM MgCl$_2$, 0.2 mg BSA/mL, 1 mM TCEP, 1.5% glycerol, 5% DMSO, 235 nM dATP, 350 nM dCTP, 350 nM dGTP, 235 nM dTTP, 12 nM biotin-16-dUTP, 23.5 nM Dig-primer/template, 2 nM GST-UL54. The assay volume is 10 μL. Each reagent is added as follow: 4 μL a+3 μL b+3 μL c; a: compound diluted in compound dilution buffer to obtain 12.5% DMSO; b: enzyme (GST-UL54) in 10 mM Hepes pH 7.5, 25 mM KCl, 5 mM MgCl$_2$, 25 mM NaCl, 5% Glycerol, 0.67 mg BSA/mL, 1 mM TCEP w/o DMSO (2 nM GST-UL54 is present in the assay); c: substrate in 10 mM HEPES pH 7.5, 25 mM KCl, 5 mM MgCl$_2$, 1 mM TCEP, 783 nM dATP, 1166 nM dCTP, 1166 nM dGTP, 783 nM dTTP, 40 nM biotin-16-dUTP, 78 nM Dig-primer (5'-/Dig/AGC TCG TTT AGT GAA CC-3')/template (5'-GAG GTC AAA ACA GCG TGG ATG GCG TCT CCA GGC GAT CTG ACG GTT CAC TAA ACG AGC T-3') w/o DMSO. The primer and template are annealed in 10 mM Tris-HCl pH 7.5, 50 mM NaCl at a respective concentration of 50 μM. They are incubated at 95° C. for 5 min in a dry batch block. The block is removed from the dry bath and allowed to cool to RT. Aliquots are made and stored at −20° C.

To perform the assay, 3 μL of the enzyme solution is added to columns 2-12 and 14-24. The enzyme is substituted by the blank solution (b solution without enzyme) for columns 1 and 13 (blanks). The plate is centrifuged at 200×g for 30 sec. 3 μL of substrate solution is added to each well. The plate is centrifuged at 200×g for 30 sec. Plates are incubated at 37° C. for 30 min. 5 μL of conjugate solution is added (25 mM Hepes pH 7.5, 0.1 M NaCl, 0.25% Tween-20, 1 mg/mL BSA, 12 mM EDTA, 24 nM Sreptavidin-APC, 342 ng/mL Anti-Dig-Europium). The plates are incubated at RT for at least 120 min. The signal is read on the Envision plate reader (Perkin-Elmer) or equivalent.

All compounds of the invention are tested in the assay described in Examples B and/or C and show $IC_{50}$ values in the range of 40 μM or less. Representative data is shown in the table below:

| Cmpd # | Example C ($IC_{50}$ nM) | Example B ($IC_{50}$ nM) |
| --- | --- | --- |
| 1006 | 280 | |
| 1008 | 220 | |
| 1028 | 5600 | |
| 1029 | 6200 | |
| 1030 | 10000 | |
| 1032 | 17000 | |
| 1043 | | 16000 |
| 2008 | | 14000 |
| 2009 | | 38000 |
| 3008 | 200 | |
| 3019 | 50 | |
| 3025 | 280 | |
| 3027 | 71 | |
| 3034 | 200 | |
| 3038 | 62 | |
| 3043 | 280 | |
| 4005 | 65 | |
| 4012 | 30 | |
| 4017 | 180 | |
| 4018 | 190 | |
| 4020 | 65 | |
| 4024 | 74 | |
| 4034 | 120 | |
| 4038 | 320 | |
| 4040 | 130 | |
| 4056 | 170 | |
| 4062 | 59 | |
| 4065 | 400 | |
| 5004 | 970 | |
| 5011 | 1000 | |
| 5015 | 120 | |
| 6001 | 1200 | |
| 6003 | 140 | |
| 6005 | 120 | |
| 6008 | 180 | |
| 6011 | 22 | |
| 6012 | 110 | |
| 6017 | 77 | |
| 6018 | 160 | |
| 6022 | 83 | |
| 7002 | 210 | |
| 7006 | | |

Each reference, including all patents, patent applications, and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I):

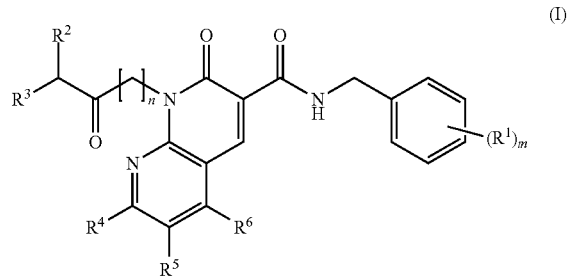

wherein m is 1, 2 or 3;

n is 1, 2 or 3;

$R^1$ is halo, —CN, $(C_{1-6})$alkyl, OH, —O—$(C_{1-6})$alkyl, $(C_{1-6})$haloalkyl or nitro;

$R^2$ is H or $(C_{1-6})$alkyl optionally substituted with halo, —CN, $(C_{1-6})$alkyl, $(C_{1-6})$haloalkyl, —$(C_{3-7})$cycloalkyl, —O—$(C_{1-6})$alkyl, OH, —NH_2, —NH$(C_{1-6})$alkyl or —N$((C_{1-6})$alkyl$)_2$;

$R^3$ is H, $(C_{1-6})$alkyl, $(C_{3-7})$cycloalkyl, aryl, heterocyclyl, heteroaryl, —$(C_{1-6})$alkyl-$(C_{3-7})$cycloalkyl, —$(C_{1-6})$alkyl-aryl, —$(C_{1-6})$alkyl-heterocyclyl or —$(C_{1-6})$alkyl-heteroaryl, wherein each said alkyl, cycloalkyl, aryl, heterocyclyl and heteroaryl, either alone or in combination with another radical, is optionally mono-, di-, or tri-substituted with $R^{32}$;

or $R^2$ and $R^3$, together with the N to which they are attached, are linked to form a heterocyclyl or heteroaryl; wherein each said heterocyclyl and heteroaryl are optionally mono-, di-, or tri-substituted with $R^{32}$;

$R^{32}$ is each independently selected from the group consisting of $R^{33}$, halo, oxo, —CN, OH, SH, —COOH, —O—$(C_{1-6})$alkyl, —S—$(C_{1-6})$alkyl, $(C_{3-7})$cycloalkyl, $(C_{1-6})$haloalkyl, —C(=O)—$(C_{1-6})$alkyl, —C(=O)—O—$(C_{1-6})$alkyl, —SO_2NH_2, —SO_2—NH$(C_{1-6})$alkyl, —SO_2—N$((C_{1-6})$alkyl$)_2$, —SO$(C_{1-6})$alkyl, —SO_2$(C_{1-6})$alkyl, —C(=O)—NH_2, —C(=O)—NH$(C_{1-6})$alkyl, —C(=O)—N$((C_{1-6})$alkyl$)_2$, —C(=O)—NH—SO_2$(C_{1-6})$alkyl, —SO_2—NH—C(=O)—$(C_{1-6})$alkyl, —NH_2, —NH$(C_{1-6})$alkyl, —N$((C_{1-6})$alkyl$)_2$, —NH$(C_{3-7})$cycloalkyl, —N$((C_{1-6})$alkyl$)(C_{3-7})$cycloalkyl, —NH—C(=O)$(C_{1-6})$alkyl, —NH—C(=O)—O$(C_{1-6})$alkyl, heterocyclyl (optionally substituted with $(C_{1-6})$alkyl) and heteroaryl (optionally substituted with $(C_{1-6})$alkyl);

$R^{33}$ is $(C_{1-6})$alkyl optionally mono-or di-substituted with OH, —O—$(C_{1-6})$alkyl, —NH_2, —NH$(C_{1-6})$alkyl or —N$((C_{1-6})$alkyl$)_2$;

$R^4$, $R^5$ and $R^6$ are each independently selected from the group consisting of halo, —CN, nitro, $R^{42}$, —C(=O)—$R^{42}$, —C(=O)O$R^{42}$, —O$R^{42}$, —S$R^{42}$, —SO$R^{42}$, —SO_2$R^{42}$, —N$(R^{43})R^{42}$, —$(C_{1-6})$alkyl—N$(R^{43})R^{42}$, —C(=O)—N$(R^{43})R^{42}$, —N$(R^{43})$—C(=O)$R^{42}$, —N$(R^{43})$—C(=O)—O$R^{42}$, —O—C(=O)—N$(R^{43})R^{42}$, —C(=O)—N(H)—SO_2$R^{42}$, —SO_2—N(H)—C(=O)$R^{42}$, —N$(R^{43})$—SO_2$R^{42}$ and —SO_2—N$(R^{43})R^{42}$;

$R^{42}$ is each independently selected from the group consisting of H, $(C_{1-6})$alkyl, $(C_{2-6})$alkenyl, $(C_{2-6})$alkynyl, —$(C_{1-6})$alkyl-$(C_{3-7})$cycloalkyl, —$(C_{1-6})$alkyl-aryl, —$(C_{1-6})$alkyl-heterocyclyl, —$(C_{1-6})$alkyl-heteroaryl, ($C_{3-7}$)cycloalkyl, aryl, heterocyclyl and heteroaryl, wherein each said alkyl, alkenyl, alkynyl, cycloalkyl, aryl, heterocyclyl and heteroaryl, either alone or in combination with another radical, is optionally substituted with 1 to 3 substituents each independently selected from the group consisting of: oxo, halo, —CN, OH, —COOH, —O—($C_{1-6}$)alkyl, —S—($C_{1-6}$)alkyl, ($C_{3-7}$)cycloalkyl, —O—($C_{3-7}$)cycloalkyl, ($C_{1-6}$)haloalkyl, —C(=O)—O—($C_{1-6}$)alkyl, —$SO_2NH_2$, —$SO_2$—NH($C_{1-6}$)alkyl, —$SO_2$—N(($C_{1-6}$)alkyl)$_2$, —SO($C_{1-6}$)alkyl, —$SO_2$($C_{1-6}$)alkyl, —C(=O)—$NH_2$, —C(=O)—NH($C_{1-6}$)alkyl, —C(=O)—N(($C_{1-6}$)alkyl)$_2$, —$NH_2$, —NH($C_{1-6}$)alkyl, —N(($C_{1-6}$)alkyl)$_2$, —NH—C(=O)($C_{1-6}$)alkyl, —NH—C(=O)—O—($C_{1-6}$)alkyl, —C(=O)—N(H)—$SO_2$($C_{1-6}$)alkyl, —$SO_2$—N(H)—C(=O)($C_{1-6}$)alkyl, and ($C_{1-6}$)alkyl optionally mono-or di-substituted with OH, —O—($C_{1-6}$)alkyl, —S—($C_{1-6}$)alkyl, —SO($C_{1-6}$)alkyl, —$SO_2$($C_{1-6}$)alkyl, —$NH_2$, —NH($C_{1-6}$)alkyl, —N(($C_{1-6}$)alkyl)$_2$, —C(=O)-heterocyclyl, —C(=O)-heteroaryl, aryl, heterocyclyl or heteroaryl;

$R^{43}$ is H, ($C_{1-6}$)haloalkyl or ($C_{1-6}$)alkyl optionally mono-or di-substituted with OH, —O—($C_{1-6}$)alkyl, or —O—($C_{3-7}$)cycloalkyl;

or a salt thereof.

2. The compound according to claim 1, or a pharmaceutically acceptable salt thereof, wherein n is 1 or 2.

3. The compound according to claim 2, or a pharmaceutically acceptable salt thereof, wherein n is 1.

4. The compound according to claim 1, or a pharmaceutically acceptable salt thereof, wherein $R^1$ is F, Cl, Br, —CN, ($C_{1-3}$) alkyl, OH, —O—($C_{1-3}$)alkyl, ($C_{1-3}$)halo alkyl or nitro.

5. The compound according to claim 4, or a pharmaceutically acceptable salt thereof, wherein $R^1$ is F, Cl, Br, —CN, OH or —O—($C_{1-3}$)alkyl.

6. The compound according to claim 1, or a pharmaceutically acceptable salt thereof, wherein m is 1 or 2.

7. The compound according to claim 6, or a pharmaceutically acceptable salt thereof, wherein m is 1.

8. The compound according to claim 1, or a pharmaceutically acceptable salt thereof, wherein $R^2$ is H or ($C_{1-6}$)alkyl;

$R^3$ is H, ($C_{1-6}$)alkyl, ($C_{3-7}$)cycloalkyl, aryl, heterocyclyl, heteroaryl, —($C_{1-6}$)alkyl-($C_{3-7}$)cycloalkyl, —($C_{1-6}$)alkyl-aryl, —($C_{1-6}$)alkyl-heterocyclyl or —($C_{1-6}$)alkyl-heteroaryl, wherein each said alkyl, cycloalkyl, aryl, heterocyclyl and heteroaryl, either alone or in combination with another radical, is optionally mono-, di-, or tri-substituted with $R^{32}$;

or $R^2$ and $R^3$, together with the N to which they are attached, are linked to form a heterocyclyl; wherein said heterocyclyl is optionally mono-, di-, or tri-substituted with $R^{32}$;

$R^{32}$ is each independently selected from the group consisting of $R^{33}$, halo, oxo, —CN, OH, —COOH, —O—($C_{1-6}$)alkyl, ($C_{3-7}$)cycloalkyl, ($C_{1-6}$)haloalkyl, —C(=O)—O—($C_{1-6}$)alkyl, —$SO_2NH_2$, —$SO_2$—NH($C_{1-6}$)alkyl, —$SO_2$—N(($C_{1-6}$)alkyl)$_2$, —SO($C_{1-6}$)alkyl, —$SO_2$($C_{1-6}$)alkyl, —C(=O)—$NH_2$, —C(=O)—NH($C_{1-6}$)alkyl, —C(=O)—N(($C_{1-6}$)alkyl)$_2$, —C(=O)—NH—$SO_2$($C_{1-6}$)alkyl, —$SO_2$—NH—C(=O)—($C_{1-6}$)alkyl, heterocyclyl (optionally substituted with ($C_{1-6}$)alkyl) and heteroaryl (optionally substituted with ($C_{1-6}$)alkyl);

$R^{33}$ is ($C_{1-6}$)alkyl optionally mono-or di-substituted with OH, —O—($C_{1-6}$)alkyl, —$NH_2$, —NH($C_{1-6}$)alkyl or —N(($C_{1-6}$)alkyl)$_2$.

9. The compound according to claim 8, or a pharmaceutically acceptable salt thereof, wherein $R^2$ and $R^3$, together with the N to which they are attached, are linked to form a heterocyclyl; wherein said heterocyclyl is optionally mono-, di-, or tri-substituted with $R^{32}$;

$R^{32}$ is each independently selected from the group consisting of $R^{33}$, halo, oxo, —CN, OH, —COOH, —O—($C_{1-6}$)alkyl, ($C_{3-7}$)cycloalkyl, ($C_{1-6}$)haloalkyl, —C(=O)—O—($C_{1-6}$)alkyl, —$SO_2NH_2$, —$SO_2$—NH($C_{1-6}$)alkyl, —$SO_2$—N(($C_{1-6}$)alkyl)$_2$, —SO($C_{1-6}$)alkyl, —$SO_2$($C_{1-6}$)alkyl, —C(=O)—$NH_2$, —C(=O)—NH($C_{1-6}$)alkyl, —C(=O)—N(($C_{1-6}$)alkyl)$_2$, —C(=O)—NH—$SO_2$($C_{1-6}$)alkyl, —$SO_2$—NH—C(=O)—($C_{1-6}$)alkyl, heterocyclyl (optionally substituted with ($C_{1-6}$)alkyl) and heteroaryl (optionally substituted with ($C_{1-6}$)alkyl);

$R^{33}$ is ($C_{1-6}$)alkyl optionally mono-or di-substituted with OH, —O—($C_{1-6}$)alkyl, —$NH_2$, —NH($C_{1-6}$)alkyl or —N(($C_{1-6}$)alkyl)$_2$.

10. The compound according to claim 9, or a pharmaceutically acceptable salt thereof, wherein $R^2$ and $R^3$, together with the N to which they are attached, are linked to form a heterocyclyl; wherein each said heterocyclyl is optionally mono-or di-substituted with $R^{32}$;

$R^{32}$ is each independently selected from the group consisting of $R^{33}$, halo, oxo, —CN, OH, ($C_{1-6}$)haloalkyl, heterocyclyl (optionally substituted with ($C_{1-6}$)alkyl) and heteroaryl (optionally substituted with ($C_{1-6}$)alkyl);

$R^{33}$ is ($C_{1-6}$)alkyl optionally mono-or di-substituted with OH or —O—($C_{1-6}$)alkyl.

11. The compound according to claim 1, or a pharmaceutically acceptable salt thereof, wherein $R^4$, $R^5$ and $R^6$ are each independently selected from the group consisting of halo, —CN, nitro, $R^{42}$, —$O^{42}$, —$SR^{42}$, —$SOR^{42}$, —$SO_2R^{42}$, —N($R^{43}$)$R^{42}$, —($C_{1-3}$)alkyl-N($R^{43}$)$R^{42}$, —C(=O)—N($R^{43}$)$R^{42}$, —N($R_{43}$)—C(=O)$R_{42}$ and —N($R^{43}$)—$SO_2R^{42}$;

$R^{42}$ is each independently selected from the group consisting of H, ($C_{1-6}$)alkyl, ($C^{2-6}$)alkenyl, —($C_{1-3}$)alkyl-($C_{3-7}$)cycloalkyl, —($C_{1-3}$)alkyl-aryl, —($C_{1-3}$)alkyl-heterocyclyl, —($C_{1-3}$)alkyl-heteroaryl, ($C_{3-7}$)cycloalkyl, aryl, heterocyclyl and heteroaryl, wherein each said alkyl, cycloalkyl, aryl, heterocyclyl and heteroaryl, either alone or in combination with another radical, is optionally substituted with 1 to 2 substituents each independently selected from the group consisting of: oxo, halo, —CN, OH, —COOH, —O—($C_{1-3}$)alkyl, ($C_{1-3}$)haloalkyl, —$SO_2NH_2$, —$SO_2$—NH($C_{1-3}$)alkyl, —$SO_2$—N(($C_{1-3}$)alkyl)$_2$, —$NH_2$, —NH($C_{1-3}$)alkyl, —N(($C_{1-3}$)alkyl)$_2$, —NH—C(=O)($C_{1-3}$)alkyl and ($C_{1-6}$)alkyl optionally mono-or di-substituted with OH, —O—($C_{1-6}$)alkyl, —S—($C_{1-3}$)alkyl, —SO($C_{1-3}$)alkyl, —$SO_2$($C_{1-3}$)alkyl, —C(=O)-heterocyclyl, —C(=O)—heteroaryl, aryl, heterocyclyl or heteroaryl;

$R^{43}$ is H, ($C_{1-3}$)haloalkyl or ($C_{1-3}$)alkyl optionally mono-or di-substituted with OH or —O—($C_{1-3}$)alkyl.

12. The compound according to claim 11, or a pharmaceutically acceptable salt thereof, wherein $R^4$, $R^5$ and $R^6$ are each independently selected from the group consisting of $R^{42}$ and —N($R^{43}$)$R^{42}$;

$R^{42}$ is each independently selected from the group consisting of H, ($C_{1-6}$)alkyl, —($C_{1-3}$)alkyl-heterocyclyl, —($C_{1-3}$)alkyl-heteroaryl, heterocyclyl and heteroaryl, wherein each said alkyl, heterocyclyl and heteroaryl, either alone or in combination with another radical, is optionally substituted with 1 to 2 substituents each independently selected from the group consisting of: halo, oxo, —CN, OH, —COOH, —O—($C_{1-3}$)alkyl, ($C_{1-3}$)

haloalkyl, —SO$_2$NH$_2$, —SO$_2$—NH(C$_{1-3}$)alkyl, —SO$_2$—N((C$_{1-3}$)alkyl)$_2$, —NH$_2$, —NH(C$_{1-3}$)alkyl, —N((C$_{1-3}$)alkyl)$_2$, —NH—C(=O)(C$_{1-3}$)alkyl and (C$_{1-6}$)alkyl;

R$^{43}$ is H or (C$_{1-3}$)alkyl optionally mono-or di-substituted with OH or —O—(C$_{1-3}$)alkyl.

13. The compound according to claim 12, or a pharmaceutically acceptable salt thereof, wherein two of R$^4$, R$^5$ and R$^6$ are H; and one of R$^4$, R$^5$ and R$^6$ are each independently selected from the group consisting of R$^{42}$ and —N(R$^{43}$R$^{42}$;;
R$^{42}$ is each independently selected from the group consisting of H, (C$_{1-6}$)alkyl, —(C$_{1-3}$)alkyl-heterocyclyl, —(C$_{1-3}$)alkyl-heteroaryl, heterocyclyl and heteroaryl, wherein each said alkyl, heterocyclyl and heteroaryl, either alone or in combination with another radical, is optionally substituted with 1 to 2 substituents each independently selected from the group consisting of: halo, oxo, —CN, OH, —COOH, —O—(C$_{1-3}$)alkyl, (C$_{1-3}$)haloalkyl, —SO$_2$NH$_2$, —SO$_2$—NH(C$_{1-3}$)alkyl, —SO$_2$—N((C$_{1-3}$)alkyl)$_2$, —NH$_2$, —NH(C$_{1-3}$)alkyl, —N((C$_{1-3}$)alkyl)$_2$, —NH—C(=O)(C$_{1-3}$)alkyl and (C$_{1-6}$)alkyl;

R$^{43}$ is H or (C$_{1-3}$)alkyl optionally mono-or di-substituted with OH or —O—(C$_{1-3}$)alkyl.

14. The compound according to claim 1, or a pharmaceutically acceptable salt thereof, as a medicament.

15. A pharmaceutical composition comprising a compound of formula (I) according to claim 1, or a pharmaceutically acceptable salt thereof, and a pharmaceutically acceptable carrier.

16. The pharmaceutical composition according to claim 15, further comprising a therapeutically effective amount of at least one other antiviral agent.

17. A method of treating CMV disease and/or infection in a human being by administering to the human being an anti-CMV virally effective amount of a compound according to claim 1, or a pharmaceutically acceptable salt thereof.

18. A method of treating CMV disease and/or infection in a human being by administering to the human being an anti-CMV virally effective amount of a compound according to claim 1, or a pharmaceutically acceptable salt thereof, and a pharmaceutically acceptable carrier.

19. A method of treating CMV disease and/or infection in a human being by administering to the human being an anti-CMV virally effective amount of a compound according to claim 1, or a pharmaceutically acceptable salt thereof, in combination with at least one other antiviral agent, administered together or separately.

20. An article of manufacture comprising a composition effective to treat CMV disease and/or infection; and packaging material comprising a label which indicates that the composition can be used to treat disease and/or infection by CMV; wherein the composition comprises a compound of formula (I) according to claim 1, or a pharmaceutically acceptable salt thereof.

21. A method of inhibiting the replication of CMV comprising exposing the virus to an effective amount of the compound of formula (I) according to claim 1, or a salt thereof, under conditions where replication of CMV is inhibited.

* * * * *